US008110570B2

(12) United States Patent
Anderson et al.

(10) Patent No.: US 8,110,570 B2
(45) Date of Patent: Feb. 7, 2012

(54) MODULATORS OF ACETYL-COENZYME A CARBOXYLASE AND METHODS OF USE THEREOF

(75) Inventors: Richard Anderson, Palo Alto, CA (US); Steven Breazeale, Durham, NC (US); Tedd Elich, Durham, NC (US); Shy-Fuh Lee, Sunnyvale, CA (US)

(73) Assignee: Cropsolution, Inc., Morrisville, NC (US)

( * ) Notice: Subject to any disclaimer, the term of this patent is extended or adjusted under 35 U.S.C. 154(b) by 281 days.

(21) Appl. No.: 12/501,717

(22) Filed: Jul. 13, 2009

(65) Prior Publication Data

US 2010/0009982 A1     Jan. 14, 2010

Related U.S. Application Data

(60) Provisional application No. 61/080,504, filed on Jul. 14, 2008, provisional application No. 61/120,599, filed on Dec. 8, 2008.

(51) Int. Cl.
*C07D 413/04* (2006.01)
*A61K 31/537* (2006.01)

(52) U.S. Cl. ...................... 514/230.5; 544/71

(58) Field of Classification Search .................... 544/71; 514/230.5
See application file for complete search history.

(56) References Cited

U.S. PATENT DOCUMENTS

| 5,206,240 | A | 4/1993 | Baldwin et al. |
| 6,911,449 | B2 | 6/2005 | VanZandt et al. |
| 2007/0021453 | A1 | 1/2007 | Yamakawa et al. |
| 2008/0171761 | A1 | 7/2008 | Iino et al. |

FOREIGN PATENT DOCUMENTS

| JP | 2005119987 A | 5/2005 |
| WO | WO 2004/092179 A1 | 10/2004 |
| WO | WO 2008/020607 A1 | 2/2008 |
| WO | WO 2008/065508 A1 | 6/2008 |
| WO | WO 2008/088692 A2 | 7/2008 |
| WO | WO 2008/102749 A1 | 8/2008 |

OTHER PUBLICATIONS

International Search Report and Written Opinion of International Application No. PCT/US09/04062, mailed Sep. 21, 2009 (11 pages).
Database Search Report dated May 27, 2008; Science IP Search Results (16 pages).
Database Search Report dated Jun. 29, 2009; Science IP Search Results (69 pages).

Elliott et al. "4-Oxospiro[benzopyran-2,4'-piperidines] as Class III Antiarrhythmic Agents. Pharmacological Studies on 3,4-Dihydro-1'-[2-(benzofurazan-5-yl)-ethyl]-6-methanesulfonamidospiro[(2H)-1-benzopyran-2,4'-piperidin]-4-one (L-691,121)" *J Med Chem* 35:3973-3976 (1992).
Shinde et al. "Synthesis of Spiro[chroman-2-4'-piperidin]-4-one Derivatives as Acetyl-CoA Carboxylase Inhibitors" *Bioorganic & Medicinal Chemistry Letters* 19:949-953 (2009).
Chamberlain and Crawford, "In vitro and in vivo Antagonism of Pathogenic Turfgrass Fungi by *Streptomyces hygroscopicus* Strains YCED9 and WYE53" *Journal of Industrial Microbiology & Biotechnology* 23:641-646 (1999).
Davis et al. "Powdery Mildew on Vegetables. Integrated Pest Management for Home Gardeners" Pest Notes, Publication 7406, University of California Agriculture and Natural Resources (2008) (3 pages).
Data sheet for Decree, Botrytis Fungicide for Preventative Control, Post-Harvest Spray Applications, by SePRO Turf&Ornamental Corporation, Carmel, IN (2004)(2 pages).
Gasior et al. "Neuroprotective and Disease-Modifying Effects of the Ketogenic Diet" *Behavioural Pharmacology* 17:431-439 (2006).
Henderson et al. "Study of the Ketogenic Agent AC-1202 in mild to Moderate Alzheimer's Disease: a Randomized, Double-Blind, Placebo-Controlled, Multicenter Trial" *Nutrition & Metabolism* 6(31):1-25 (2009).
Reger et al. "Efefcts of β-Hydroxybutyrate on Cognition in Memory-Impaired Adults" *Neurobiology of Aging* 25:311-314 (2004).
Specimen Label for 3336$^G$, Turf & Ornamental Systemic Fungicide, marketed by Cleary Chemical Corporation, Dayton, NJ (2007) (4 pages).

*Primary Examiner* — Kahsay T Habte
(74) *Attorney, Agent, or Firm* — Myers Bigel Sibley & Sajovec, P.A.

(57) ABSTRACT

The present invention provides compounds of formula I:

along with methods of use of these compounds as pharmaceuticals, particularly in the treatment of obesity, metabolic syndrome, atherosclerosis, cardiovascular disease, insulin resistance, diseases associated with reduced neuronal metabolism, and cancer as well as the use of these compounds for treatment of pathogens of humans and animals, and for the control of agricultural pests, particularly fungi, weeds and insects.

38 Claims, No Drawings

MODULATORS OF ACETYL-COENZYME A CARBOXYLASE AND METHODS OF USE THEREOF

STATEMENT OF PRIORITY

This application claims the benefit, under 35 U.S.C. §119(e), of U.S. Provisional Application No. 61/080,504; filed Jul. 14, 2008, and U.S. Provisional Application No. 61/120,599; filed Dec. 8, 2008, the entire contents of each of which are incorporated by reference herein.

STATEMENT OF GOVERNMENT SUPPORT

This invention was made with Government support under grant number DK68962 from the National Institutes of Health. The Government has certain rights in this invention.

FIELD OF THE INVENTION

The present invention concerns certain spirocyclic amides, compositions thereof, and methods of use thereof as pharmaceuticals, particularly in the treatment of obesity, metabolic syndrome, atherosclerosis, cardiovascular disease, insulin resistance, e.g., type II or adult-onset diabetes, diseases associated with reduced neuronal metabolism, and cancer such as breast cancer, uterine cancer, ovarian cancer, colon cancer, prostate cancer, liver cancer, and endometrial cancer, as well as the use thereof for the control of agricultural pests, particularly fungal pests, weedy pests and insect pests, as well as the use thereof for treatment of pathogens of humans and animals.

BACKGROUND OF THE INVENTION

Acetyl CoA carboxylase (ACC) catalyzes the first committed step in fatty acid biosynthesis, and therefore is an essential enzyme in most organisms. This makes ACC an attractive agrochemical target and ACC is chemically validated as a fungicide, herbicide, and insecticide target as described in more detail in Elich et al., U.S. Patent Application Publication No. 2004/0086994. Additionally, ACC plays a crucial role in the metabolism of fatty acids in mammals and therefore has been used as a target for drug development against obesity, diabetes, cancer and other diseases (Abu-Elheiga, L. et al., *Science* 291, 2613-2616 (2001); Alberts, A. W., and Vagelos, P. R. Acyl-CoA Carboxylases. In *The Enzymes*, P. D. Boyer, ed. (New York, Academic Press), pp. 37-82 (1972); Cronan Jr., J. E., and Waldrop, G. L., *Prog Lipid Res* 41, 407-435 (2002); Harwood Jr., H. J. et al., *J Biol Chem* 278, 37099-37111 (2003); Wakil, S. J. et al., *Ann Rev Biochem* 52, 537-579 (1983); Zhang, H. et al., *Structure* 12, 1683-1691 (2004); Zhang, H. et al., *Proc Natl Acad Sci USA* 101, 5910-5915 (2004); Zhang, H. et al., *Science* 299, 2064-2067 (2003)). ACCs catalyze the carboxylation of acetyl-CoA to produce malonyl-CoA. Mammals have two isoforms of ACC, ACC1 and ACC2. ACC1 is present in the cytosol of liver and adipose tissues and controls the committed step in the biosynthesis of long-chain fatty acids. In comparison, ACC2 is associated with the outer membrane of mitochondria in the heart and muscle. Its malonyl-CoA product is a potent inhibitor of carnitine palmitoyltransferase I, which facilitates the transport of long-chain acyl-CoAs into the mitochondria for oxidation (McGarry, J. D. et al., *Eur J Biochem* 244, 1-14 (1997); Ramsay, R. R. et al., *Biochim Biophys Acta* 1546, 21-43 (2001)). The importance of ACCs for drug discovery is underscored by the observations that mice lacking ACC2 have elevated fatty acid oxidation, reduced body fat and body weight (Abu-Elheiga, L. et al., *Proc Natl Acad Sci USA* 100, 10207-10212 (2003); Lenhard, J. M. et al., *Advanced Drug Delivery Reviews* 54, 1199-1212 (2002)).

Additionally, it is well known that de novo lipogenesis is required for the growth of many tumor cells and that ACC is upregulated in many cancer cells (Milgraum et al., *Clin Cancer Res* 3:2115-20 (1997); Swinnen et al., *Int J Cancer* 88:176-9 (2000); Zhan et al., *Clin Cancer Res* 14:5735-5742 (2008)). The importance of ACC as an anti-cancer target is underscored by the observations that the ACC inhibitor soraphen induces growth arrest and selective cytotoxicity in cancer cells (Beckers et al., *Cancer Res* 67:8180-8187 (2007)), and that RNA interference-mediated down-regulation of ACC inhibited growth and induced apoptosis in breast cancer cells (Chajes et al., *Cancer Res* 66:5287-5294 (2006)) and in HCT-116, PC-3, and A2780 cancer cells (Zhan et al., *Clin Cancer Res* 14:5735-5742 (2008)).

Diseases including, but not limited to, Alzheimer's Disease, Parkinson Disease, Huntington's Disease, epilepsy and Mild Cognitive Impairment are associated with reduced neuronal metabolism. Inhibition of ACC leads to increases in fatty acid oxidation and corresponding increases in blood ketone body levels that can provide an alternative energy source for neuronal cells with compromised metabolism. For example, in the brain, blood glucose provides the typical source of energy; however, under some circumstances ketone bodies can provide an alternative energy source. Alzheimer's Disease appears to result from a decreased metabolic rate in the brain due to a reduction in glucose utilization. Induction of ketosis by oral administration of medium chain triglycerides improves the cognitive performance of probable mild to moderate Alzheimer's disease subjects (U.S. Pat. No. 6,835,750) and elevation of serum ketone body levels in Alzheimer's Disease patients raises cognitive scores (Reger et al. Neurobiol. Aging 3:311-314 (2004)).

SUMMARY OF THE INVENTION

Some aspects of the present invention provide compounds which act as modulators of Acetyl CoA carboxylase (ACC).

Thus, a particular aspect of the invention is a compound of formula I:

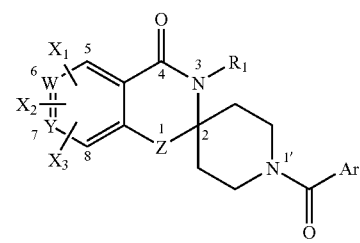

wherein:

$R_1$ is hydrogen or alkyl, wherein the alkyl may be optionally substituted with halogen, hydroxyl, alkoxy, haloalkoxy, cyano, amino, alkylamino, dialkylamino, alkylthio, alkylsulfinyl, alkylsulfonyl, acyl, alkoxycarbonyl, aryl or heteroaryl, where aryl or heteroaryl may be further optionally substituted with one to three $R_2$;

Ar is aryl or heteroaryl, each of which may be optionally substituted from one to three times by: halogen, hydroxyl, alkyl, haloalkyl, alkoxy, alkenyloxy, alkynyloxy, haloalkoxy, cyano, amino, alkylamino, dialkylamino, alkylthio, alkylsulfinyl, alkylsulfonyl, acyl, alkoxycarbonyl, aryl or heteroaryl, where aryl or heteroaryl may be further optionally substituted with one to three $R_2$;

W and Y each independently are N or CH;

Z is O, S, or $NR_3$;

$R_3$ is hydrogen or alkyl, wherein the alkyl may be optionally substituted with halogen, hydroxyl, alkoxy, haloalkoxy, cyano, amino, alkylamino, alkylthio, alkylsulfinyl, alkylsulfonyl, acyl, alkoxycarbonyl, aryl or heteroaryl, where aryl or heteroaryl may be further optionally substituted with one to three $R_2$;

each $R_2$ is independently halogen, hydroxyl, alkyl, haloalkyl, alkoxy, haloalkoxy, cyano, alkylthio, alkylsulfinyl, alkylsulfonyl, acyl, or alkoxycarbonyl;

$X_1$, $X_2$, and $X_3$ are each independently hydrogen, halogen, hydroxyl, alkyl, haloalkyl, alkoxy, haloalkoxy, alkenyl, haloalkenyl, alkenyloxy, haloalkenyloxy, alkynyl, haloalkynyl, alkynyloxy, haloalkynyloxy, cyano, $R_5R_6N-$, alkylthio, alkylsulfinyl, alkylsulfonyl, aminosulfonyl, carbamoylamino, acyl, acylamino, carboxy, alkoxycarbonyl, arylalkoxycarbonyl, alkylaminocarbonyl, dialkylaminocarbonyl, carboxyalkoxy, alkoxycarbonylalkoxy, alkylaminocarbonyloxy, dialkylaminocarbonyl, aryl, heteroaryl, arylalkyl, or heteroarylalkyl, where aryl, heteroaryl, arylalkyl, or heteroarylalkyl may be optionally substituted with one to three $R_4$;

or when W and Y are both CH, $X_1$ and $X_2$ taken together on adjacent carbon atoms form a 3- to 5-membered bridged ring comprised of moieties selected from methylene, substituted methylene, $-CH=$, $-C(R_4)=$, $C=O$, $-N=$, NH, O, or $S(O)_n$;

each $R_4$ is independently halogen, hydroxyl, alkyl, haloalkyl, alkoxy, haloalkoxy, alkenyl, alkynyl, cyano, amino, alkylamino, dialkylamino, alkylthio, alkylsulfinyl, alkylsulfonyl, aminosulfonyl, carbamoylamino, acyl, acylamino, carboxy, alkoxycarbonyl, arylalkoxycarbonyl, alkylaminocarbonyl, dialkylaminocarbonyl, alkylaminocarbonyloxy, or dialkylaminocarbonyloxy;

each $R_5$ and $R_6$ are independently hydrogen, alkyl, arylalkyl, alkoxyalkyl, hydroxyalkyl; or taken together to form a 5- or 6-member heterocycle containing 2-5 C-atoms, 0-1 O-atom, 0-1 S-atom, and 1-3 N-atoms, which heterocycle may be optionally substituted on a C-atom or N-atom by alkyl, acyl, alkoxycarbonyl, or alkylsulfonyl;

n is 0, 1, or 2;

or a pharmaceutically or agriculturally acceptable salt thereof.

Any of the R groups or substituents thereof may be excluded from a particular compound. Thus, in some embodiments, the compounds of formula I are subject to the proviso that when $R_1$ is H, Z is O, W and Y are CH, $X_1$ is H, and Ar is phenyl, then $X_2$ and $X_3$ cannot be taken together at the 7,8-positions of the benzoxazinone to form a fused phenyl ring;

when $R_1$ is H, Z is O, W and Y are CH, $X_1$ and $X_2$ and $X_3$ are all H, then Ar cannot be 2-fluorophenyl, 4-aminocarbonyl-2-fluorophenyl, 4-amino-5-chloro-methoxyphenyl, 4-(3-thietanyloxy)phenyl, 3-pyridyl, 2-pyrazinyl, 2,3-dihydro-1-methylsulfonyl-1H-indol-5-yl, 2,3-dihydro-1-(2-methoxyethyl)-2-oxo-1H-benzimidazol-5-yl, 2,3-dihydro-1,3-dimethyl-2-oxo-1H-benzimidazol-5-yl, 2,3-dihydro-3-oxo-2H-1,4-benzoxazin-6-yl, 2,3-dihydro-2-(2-methylpropyl)-3-oxo-1H-isoindol-4-yl, or 4-(3,5-dimethylpyrazol-1-yl)phenyl;

when $R_1$ is H, Z is NH, W and Y are CH, and $X_1$ and $X_2$ and $X_3$ are independently H, methyl or halogen, then Ar cannot be phenyl, 2-methylphenyl, 4-methylphenyl, 4-ethylphenyl, 4-n-butylphenyl, 4-n-pentylphenyl, 4-n-hexylphenyl, 4-tert-butylphenyl, 4-phenylphenyl, 4-trifluoromethylphenyl, 3,5-bis-trifluoromethylphenyl, 2-bromophenyl, 3-bromophenyl, 2-chlorophenyl, 3-chlorophenyl, 4-chlorophenyl, 2,4-dichlorophenyl, 3,4-dichlorophenyl, 3,5-dichlorophenyl, 2-fluorophenyl, 3-fluorophenyl, 4-fluorophenyl, 2-methoxyphenyl, 3-methoxyphenyl, 4-methoxyphenyl, 3,4-dimethoxyphenyl, 3,5-dimethoxyphenyl, 2,6-dimethoxyphenyl, 4-allyloxyphenyl, 4-n-butoxyphenyl, 3,4-methylenedioxyphenyl, 3-nitrophenyl, 4-nitrophenyl, 4-methyl-3-nitrophenyl, 1-naphthyl, 2-naphthyl, 2-pyridyl, 3-pyridyl, 2-pyrazinyl, 5-methyl-2-pyrazinyl, 4-(3,5-dimethylpyrazol-1-yl)phenyl, 8-quinolinyl, 1-isoquinolinyl, 4-(1-piperidinylmethyl)phenyl, 4-(4-methyl-1-piperidinyl)phenyl, or 1-methyl-9H-pyrido[3,4-b]indol-3-yl;

when $R_1$ is H, Z is O, W and Y are CH, and $X_1$ and $X_2$ and $X_3$ are all H, or $X_1$ is 6-bromo and $X_2$ and $X_3$ are H, then Ar cannot be 2-amino-1-benzothiophene-3-yl or 2-(3-ethylureido)-1-benzothiophene-3-yl; or when $R_1$ is H, Z is NH, W and Y are CH, and $X_1$ and $X_2$ and $X_3$ are all H, then Ar cannot be 2-amino-1-benzothiophene-3-yl or 2-(3-ethylureido)-1-benzothiophene-3-yl.

The present invention relates to the identification of acetyl CoA carboxylase (ACC) modulators, pharmaceutical and agricultural compositions containing such modulators, and the use of such modulators. Thus, in some aspects of the present invention, the compounds and compositions described herein are used in pharmaceutical applications, for example, in the treatment of obesity, metabolic syndrome, atherosclerosis, cardiovascular disease, insulin resistance, e.g., type II or adult-onset diabetes, diseases associated with reduced neuronal metabolism (e.g., Alzheimer's disease, Mild Cognitive Impairment, Parkinson's disease, Huntington's disease, epilepsy), cancer, including breast cancer, uterine cancer, ovarian cancer, colon cancer, prostate cancer, liver cancer, and endometrial cancer, in human or animal subjects. In other aspects of the invention, the compounds and compositions described herein also have utility as human and animal antifungal compounds. Further aspects of the invention include the use of the aforementioned compounds and compositions as crop protection agents to combat or prevent fungal infestations (fungicides), or to control other pests such as weeds, insects, or acarids that are harmful to crops (insecticides and herbicides).

A further aspect of the present invention provides the use of a compound as described herein for the manufacture of a medicament for treating fungal infection, obesity, metabolic syndrome, atherosclerosis, cardiovascular disease, insulin resistance, e.g., type II or adult-onset diabetes, diseases associated with reduced neuronal metabolism (e.g., Alzheimer's disease, Mild Cognitive Impairment, Parkinson's disease, Huntington's disease, epilepsy), cancer, including breast cancer, uterine cancer, ovarian cancer, colon cancer, prostate cancer, liver cancer and endometrial cancer in a subject.

These and other aspects of the invention will be set forth in more detail in the description of the invention that follows.

DETAILED DESCRIPTION OF THE PREFERRED EMBODIMENTS

The present invention will now be described with reference to the accompanying drawings, in which representative embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety.

Definitions

As used herein, "a," "an" or "the" can mean one or more than one. For example, a cell can mean a single cell or a multiplicity of cells.

As used herein, "and/or" refers to and encompasses any and all possible combinations of one or more of the associated listed items, as well as the lack of combinations when interpreted in the alternative (or).

Further, the term "about," as used herein when referring to a measurable value such as an amount of a compound or agent, dose, time, temperature, and the like, is meant to encompass variations of ±20%, ±10%, ±5%, ±1%, ±0.5%, or even ±0.1% of the specified amount.

"Alkyl" as used herein refers to a saturated hydrocarbon radical which may be straight-chain or branched-chain (for example, ethyl, isopropyl, t-amyl, or 2,5-dimethylhexyl) or cyclic (for example cyclobutyl, cyclopropyl or cyclopentyl) and contains from 1 to 24 carbon atoms. This definition applies both when the term is used alone and when it is used as part of a compound term, such as "haloalkyl" and similar terms. In some embodiments, preferred alkyl groups are those containing 1 to 4 carbon atoms, which are also referred to as "lower alkyl." In some embodiments preferred alkyl groups are those containing 5 or 6 to 24 carbon atoms, which may also be referred to as "higher alkyl".

"Alkenyl," as used herein, refers to a straight or branched chain hydrocarbon containing from 2 to 24 carbons and containing at least one carbon-carbon double bond formed by the removal of two hydrogens. This definition applies both when the term is used alone and when it is used as part of a compound term, such as "haloalkenyl" and similar terms. Representative examples of "alkenyl" include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl and the like. "Lower alkenyl" as used herein, is a subset of alkenyl and refers to a straight or branched chain hydrocarbon group containing from 1 to 4 carbon atoms.

"Alkynyl," as used herein, refers to a straight or branched chain hydrocarbon group containing from 2 to 24 carbon atoms and containing at least one carbon-carbon triple bond. This definition applies both when the term is used alone and when it is used as part of a compound term, such as "haioalkynyl" and similar terms. Representative examples of alkynyl include, but are not limited, to acetylenyl, 1-propynyl, 2-propynyl, 3-butynyl, 2-pentynyl, 1-butynyl and the like. "Lower alkynyl" as used herein, is a subset of alkyl and refers to a straight or branched chain hydrocarbon group containing from 1 to 4 carbon atoms.

"Alkoxy" refers to an alkyl radical as described above which also bears an oxygen substituent which is capable of covalent attachment to another hydrocarbon radical (such as, for example, methoxy, ethoxy and t-butoxy). This definition applies both when the term is used alone and when it is used as part of a compound term, such as "haloalkoxy" and similar terms.

"Alkenyloxy" refers to an alkenyl group as described above which also bears an oxygen substituent which is capable of covalent attachment to another hydrocarbon radical (such as, for example, allyloxy and 2-butenyloxy). This definition applies both when the term is used alone and when it is used as part of a compound term, such as "haloalkenyloxy" and similar terms.

"Alkynyloxy" refers to an alkynyl group as described above which also bears an oxygen substituent which is capable of covalent attachment to another hydrocarbon radical (such as, for example, propargyloxy and 3-butynyloxy). This definition applies both when the term is used alone and when it is used as part of a compound term, such as "haloalkynyloxy" and similar terms.

"Alkylthio" as used herein refers to an alkyl group, as defined herein, appended to the parent molecular moiety through a thio moiety, as defined herein. Representative examples of alkylthio include, but are not limited, methylthio, ethylthio, tert-butylthio, hexylthio, and the like.

"Aryl" or "aromatic ring moiety" refers to an aromatic substituent which may be a single ring or multiple rings which are fused together, linked covalently or linked to a common group such as an ethylene or methylene moiety. The aromatic rings may each contain heteroatoms and hence "aryl" encompasses "heteroaryl" as used herein. Representative examples of aryl include, azulenyl, indanyl, indenyl, naphthyl, phenyl, tetrahydronaphthyl, biphenyl, diphenylmethyl, 2,2-diphenyl-1-ethyl, thienyl, pyridyl and quinoxaloyl. "Aryl" means substituted or unsubstituted aryl unless otherwise indicated and hence the aryl moieties may be optionally substituted with halogen atoms, or other groups such as nitro, carboxyl, alkoxy, phenoxy and the like. Additionally, the aryl radicals may be attached to other moieties at any position on the aryl radical which would otherwise be occupied by a hydrogen atom (such as, for example, 2-pyridyl, 3-pyridyl and 4-pyridyl).

"Heteroaryl" means a cyclic, aromatic hydrocarbon in which one or more carbon atoms have been replaced with heteroatoms. If the heteroaryl group contains more than one heteroatom, the heteroatoms may be the same or different. Examples of heteroaryl groups include pyridyl, pyrimidinyl, imidazolyl, thienyl, furyl, pyrazinyl, pyrrolyl, pyranyl, isobenzofuranyl, chromenyl, xanthenyl, indolyl, isoindolyl, indolizinyl, triazolyl, pyridazinyl, indazolyl, purinyl, quinolizinyl, isoquinolyl, quinolyl, quinazolinyl, phthalazinyl, naphthyridinyl, quinoxalinyl, isothiazolyl, benzo[b]thienyl, thieno[d]pyrimidinyl, pyrazolo[d]pyrimidinyl, thieno[b]pyridyl, and thieno[c]pyridyl. Preferred heteroaryl groups are six, nine and ten membered rings and contain from one to four heteroatoms independently selected from O, N, and S. The heteroaryl group, including each heteroatom, can be unsubstituted or substituted with from 1 to 4 substituents, as chemically feasible. For example, the heteroatom S may be substituted with one or two oxo groups, which may be shown as =O.

"Cyano" as used herein refers to a —CN group.

"Halo" or "halogen," as used herein, refers to —Cl, —Br, —I or —F.

"Haloalkyl," as used herein, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, 2-chloro-3-fluoropentyl, and the like.

"Hydroxy," as used herein, refers to an —OH group.
"Nitro," as used herein, refers to a —NO$_2$ group.
"Oxy," as used herein, refers to a —O— moiety.
"Thio," as used herein, refers to a —S— moiety.
"Organic base" as used herein includes, but is not limited to, triethylamine, triisobutylamine, trioctylamine, triisodecylamine, diethanolamine, triethanolamine, pyridine, morpholine, and mixtures thereof. A preferred category of organic bases is organic amines.

"Inorganic base" as used herein includes, but is not limited to, sodium carbonate, sodium bicarbonate, potassium carbonate, and mixtures thereof.

"Inert solvent" as used herein includes any suitable inert solvent, such as tetrahydrofuran, N-methylpyrrolidone, dimethylformamide, toluene, dimethyl ether, methyl t-butyl ether and dioxane, methylene chloride, chloroform, 1,2-dichloroethane, and mixtures thereof.

"Protic solvent" as used herein may be any suitable protic solvent including, but not limited to, methanol, ethanol, isopropanol, n-butanol, ethylene glycol, methyl Cellosolve, ethyl Cellosolve, cyclohexanol, glycerol, diethylene glycol, triethanolamine, polyethylene glycol, sec-butanol, n-propanol and tert-butanol.

"Pharmaceutically acceptable salt" means a salt, the cation or anion of which is known and accepted in the art, for the formation of salts for pharmaceutical use. Preferably the salts are water soluble.

"Agriculturally acceptable salt" means a salt, the cation or anion of which is known and accepted in the art, for the formation of salts for agricultural or horticultural use. Preferably the salts are water soluble.

"Prodrug" as used herein means a pharmacological compound or composition that is administered in an inactive form or a significantly less active form than the active form and which undergoes a conversion to an active form of the compound within a biological system.

When used in a therapeutic context, an "effective" amount is an amount sufficient to provide some improvement or benefit to the subject, e.g., an amount that provides some alleviation, mitigation or decrease in at least one clinical symptom, a delay or reduction in the progression of the disorder, and/or prevention or delay of the onset of the disorder. Those skilled in the art will appreciate that the therapeutic effects need not be complete or curative, as long as some benefit is provided to the subject.

By the term "treat," "treating" or "treatment of" (or grammatically equivalent terms) it is meant that the severity of the subject's condition is reduced or at least partially improved or ameliorated and/or that some alleviation, mitigation or decrease in at least one clinical symptom is achieved and/or there is a delay in the progression of the condition and/or prevention or delay of the onset of a disease or disorder. The terms "treat," "treats," "treating," or "treatment of" and the like also include prophylactic treatment of the subject. As used herein, the terms "prevent," "prevents," or "prevention" (and grammatical equivalents thereof) are not meant to imply complete abolition of disease and encompass any type of prophylactic action that reduces the incidence of the condition, delays the onset and/or progression of the condition, and/or reduces the symptoms associated with the condition. Thus, unless the context indicates otherwise, the terms "treat," "treating" or "treatment of" (or grammatically equivalent terms) refer to both prophylactic and therapeutic regimens.

Compounds of Formula I may exist in different stable conformational forms that may be separable. Torsional asymmetry due to restricted rotation about an asymmetric single bond, for example because of steric hindrance or ring strain, may allow separation of different conformers. The compounds of this invention include each conformational isomer of Formula I and mixtures thereof.

The disclosures of all U.S. Patent references cited herein are to be incorporated herein in their entirety as if fully set forth.

2. Compounds.
A. General.
The compounds of this invention are represented by formula I:

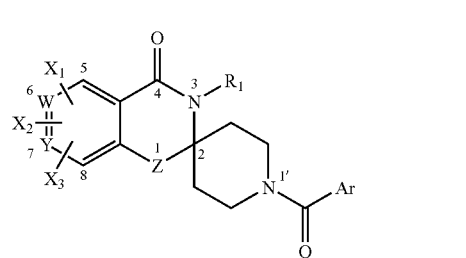

wherein:

$R_1$ is hydrogen or alkyl, wherein the alkyl may be optionally substituted with halogen, hydroxyl, alkoxy, haloalkoxy, cyano, amino, alkylamino, dialkylamino, alkylthio, alkylsulfinyl, alkylsulfonyl, acyl, alkoxycarbonyl, aryl or heteroaryl, the last two of which may be further optionally substituted with one to three $R_2$;

Ar is aryl or heteroaryl, each of which may be optionally substituted from one to three times by: halogen, hydroxyl, alkyl, haloalkyl, alkoxy, alkenyloxy, alkynyloxy, haloalkoxy, cyano, amino, alkylamino, dialkylamino, alkylthio, alkylsulfinyl, alkylsulfonyl, acyl, alkoxycarbonyl, aryl or heteroaryl, where aryl or heteroaryl may be further optionally substituted with one to three $R_2$;

In some embodiments, Ar is aryl or heteroaryl, each of which may be optionally substituted from one to three times by: halogen, hydroxyl, alkyl, haloalkyl, alkoxy, alkenyloxy, alkynyloxy, haloalkoxy, cyano, alkylthio, alkylsulfinyl, alkylsulfonyl, acyl, alkoxycarbonyl, aryl or heteroaryl where aryl or heteroaryl may be further optionally substituted with one to three $R_2$;

W and Y each independently are N or CH;

Z is O, S, or $NR_3$;

$R_3$ is hydrogen or alkyl, wherein the alkyl may be optionally substituted with halogen, hydroxyl, alkoxy, haloalkoxy, cyano, amino, alkylamino, alkylthio, alkylsulfinyl, alkylsulfonyl, acyl, alkoxycarbonyl, aryl or heteroaryl, where aryl or heteroaryl may be further optionally substituted with one to three $R_2$;

each $R_2$ is independently halogen, hydroxyl, alkyl, haloalkyl, alkoxy, haloalkoxy, cyano, alkylthio, alkylsulfinyl, alkylsulfonyl, acyl, alkoxycarbonyl;

$X_1$, $X_2$, and $X_3$ are each independently hydrogen, halogen, hydroxyl, alkyl, haloalkyl, alkoxy, haloalkoxy, alkenyl, haloalkenyl, alkenyloxy, haloalkenyloxy, alkynyl, haloalkynyl, alkynyloxy, haloalkynyloxy, cyano, $R_5R_6N$—, alkylthio, alkylsulfinyl, alkylsulfonyl, aminosulfonyl, carbamoylamino, acyl, acylamino, carboxy, alkoxycarbonyl, arylalkoxycarbonyl, alkylaminocarbonyl, dialkylaminocarbonyl, carboxyalkoxy, alkoxycarbonylalkoxy, alkylaminocarbonyloxy, dialkylaminocarbonyl; aryl, heteroaryl, arylalkyl, or heteroarylalkyl, the last four of which may be optionally substituted with one to three $R_4$;

or when W and Y are both CH, $X_1$ and $X_2$ taken together on adjacent carbon atoms form a 3- to 5-membered bridged ring comprised of moieties selected from methylene, substituted methylene, —CH=, —$CR_4$=, C=O, —N=, NH, O, or $S(O)_n$;

each $R_4$ is independently halogen, hydroxyl, alkyl, haloalkyl, alkoxy, haloalkoxy, alkenyl, alkynyl, cyano, amino, alkylamino, dialkylamino, alkylthio, alkylsulfinyl, alkylsulfonyl, aminosulfonyl, carbamoylamino, acyl, acylamino, carboxy, alkoxycarbonyl, arylalkoxycarbonyl, alkylaminocarbonyl, dialkylaminocarbonyl, alkylaminocarbonyloxy, or dialkylaminocarbonyloxy;

each $R_5$ and $R_6$ are independently hydrogen, alkyl, arylalkyl, alkoxyalkyl, hydroxyalkyl; or taken together to form a 5- or 6-member heterocycle containing 2-5 C-atoms, 0-1 O-atom, 0-1 S-atom, and 1-3 N-atoms, which heterocycle may be optionally substituted on a C-atom or N-atom by alkyl, acyl, alkoxycarbonyl, or alkylsulfonyl;

n is 0, 1, or 2;

or a pharmaceutically or agriculturally acceptable salt thereof.

Any of the R groups or substituents thereof may be excluded from a particular compound. Thus, in some embodiments, the compounds of formula I are subject to the proviso that when $R_1$ is H, Z is O, W and Y are CH, $X_1$ is H, and Ar is phenyl, then $X_2$ and $X_3$ cannot be taken together at the 7,8-positions of the benzoxazinone to form a fused phenyl ring;

when $R_1$ is H, Z is O, W and Y are CH, $X_1$ and $X_2$ and $X_3$ are all H, then Ar cannot be 2-fluorophenyl, 4-aminocarbonyl-2-fluorophenyl, 4-amino-5-chloro-methoxyphenyl, 4-(3-thietanyloxy)phenyl, 3-pyridyl, 2-pyrazinyl, 2,3-dihydro-1-methylsulfonyl-1H-indol-5-yl, 2,3-dihydro-1-(2-methoxyethyl)-2-oxo-1H-benzimidazol-5-yl, 2,3-dihydro-1,3-dimethyl-2-oxo-1H-benzimidazol-5-yl, 3,4-dihydro-3-oxo-2H-1,4-benzoxazin-6-yl, 2,3-dihydro-2-(2-methylpropyl)-3-oxo-1H-isoindol-4-yl, or 4-(3,5-dimethylpyrazol-1-yl)phenyl;

when $R_1$ is H, Z is NH, W and Y are CH, and $X_1$ and $X_2$ and $X_3$ are independently H, methyl or halogen, then Ar cannot be phenyl, 2-methylphenyl, 4-methylphenyl, 4-ethylphenyl, 4-n-butylphenyl, 4-n-pentylphenyl, 4-n-hexylphenyl, 4-tert-butylphenyl, 4-phenylphenyl, 4-trifluoromethylphenyl, 3,5-bis-trifluoromethylphenyl, 2-bromophenyl, 3-bromophenyl, 2-chlorophenyl, 3-chlorophenyl, 4-chlorophenyl, 2,4-dichlorophenyl, 3,4-dichlorophenyl, 3,5-dichlorophenyl, 2-fluorophenyl, 3-fluorophenyl, 4-fluorophenyl, 2-methoxyphenyl, 3-methoxyphenyl, 4-methoxyphenyl, 3,4-dimethoxyphenyl, 3,5-dimethoxyphenyl, 2,6-dimethoxyphenyl, 4-allyloxyphenyl, 4-n-butoxyphenyl, 3,4-methylenedioxyphenyl, 3-nitrophenyl, 4-nitrophenyl, 4-methyl-3-nitrophenyl, 1-naphthyl, 2-naphthyl, 2-pyridyl, 3-pyridyl, 2-pyrazinyl, 5-methyl-2-pyrazinyl, 4-(3,5-dimethylpyrazol-1-yl)phenyl, 8-quinolinyl, 1-isoquinolinyl, 4-(1-piperidinylmethyl)phenyl, 4-(4-methyl-1-piperidinyl)phenyl, or 1-methyl-9H-pyrido[3,4-b]indol-3-yl;

when $R_1$ is H, Z is O, W and Y are CH, and $X_1$ and $X_2$ and $X_3$ are all H, or $X_1$ is 6-bromo and $X_2$ and $X_3$ are H, then Ar cannot be 2-amino-1-benzothiophene-3-yl or 2-(3-ethylureido)-1-benzothiophene-3-yl; or when $R_1$ is H, Z is NH, W and Y are CH, and $X_1$ and $X_2$ and $X_3$ are all H, then Ar cannot be 2-amino-1-benzothiophene-3-yl or 2-(3-ethylureido)-1-benzothiophene-3-yl.

As a reference, some of the Ar substituents named in the above provisos are set forth with their corresponding structure in Table 1.

TABLE 1

Some Ar substituents named in the above provisos set forth with their corresponding structure.

| STRUCTURE | NAME |
|---|---|
| 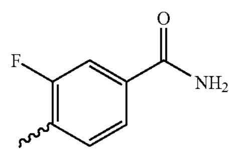 | 4-aminocarbonyl-2-fluorophenyl |
| 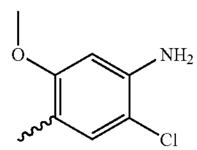 | 4-amino-5-chloro-methoxyphenyl |
| 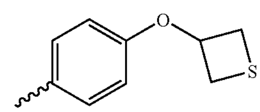 | 4-(3-thietanyloxy)-phenyl |
| 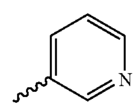 | 3-pyridyl |
| 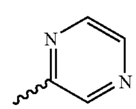 | 2-pyrazinyl |
| 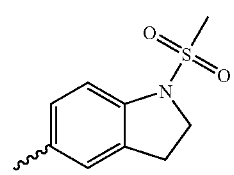 | 2,3-dihydro-1-methylsulfonyl-1H-indol-5-yl |
| 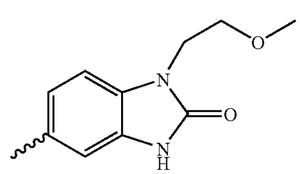 | 2,3-dihydro-1-(2-methoxyethyl)-2-oxo-1H-benzimidazol-5-yl |
| 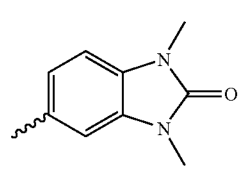 | 2,3-dihydro-1,3-dimethyl-2-oxo-1H-benzimidazol-5-yl |
| 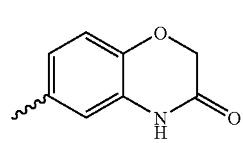 | 3,4-dihydro-3-oxo-2H-1,4-benzoxazin-6-yl |

TABLE 1-continued

Some Ar substituents named in the above provisos set forth with their corresponding structure.

| STRUCTURE | NAME |
| --- | --- |
| 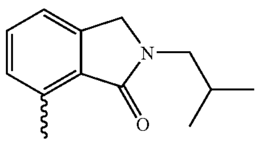 | 2,3-dihydro-2-(2-methylpropyl)-3-oxo-1H-isoindol-4-yl |
|  | 4-(3,5-dimethylpyrazol-1-yl)phenyl |
| 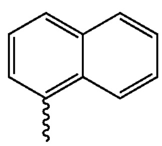 | 1-naphthyl |
| 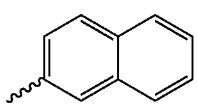 | 2-naphthyl |
| 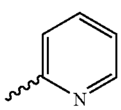 | 2-pyridyl |
| 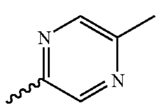 | 5-methyl-2-pyrazinyl |
|  | 4-(3,5-dimethylpyrazol-1-yl)phenyl |
| 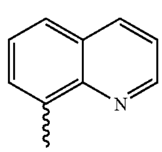 | 8-quinolinyl |
| 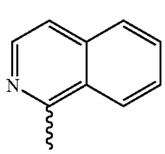 | 1-isoquinolinyl |
|  | 4-(1-piperidinylmethyl)phenyl |
|  | 4-(4-methyl-1-piperidinyl)phenyl |
|  | 1-methyl-9H-pyrido[3,4-b]indol-3yl |
|  | 2-amino-1-benzothiophen-3-yl |
|  | 2-(3-ethylureido)-1-benzothiophen-3-yl |

In some embodiments of the compound of formula I, $X_1$ is located at position 5, $X_2$ is located at position 6 and $X_3$ is located at position 7.

In some embodiments of the compound of formula I, when W and Y are both CH, $X_1$ and $X_2$ taken together on adjacent carbon atoms form a 3- to 5-membered bridged ring comprised of moieties selected from methylene, substituted methylene, —CH=, —CR$_4$=, C=O, —N=, NH, O, or S(O)$_n$, the 3- to 5-membered ring excludes the bridge atoms W and Y. Thus, when W and Y are both CH, $X_1$ and $X_2$ taken together on adjacent carbon atoms form a 3- to 5-membered bridged ring as described above, a $C_5$ to $C_7$ aryl ring is formed. In some embodiments, the $C_5$ to $C_7$ aryl ring is a phenyl ring. Thus, in some embodiments of the compound of formula I, W and Y are both CH, $X_1$ and $X_2$ are taken together on adjacent carbon atoms form a phenyl ring.

In some embodiments of the compound of formula I, $R_1$ and $R_3$ are independently selected from the group consisting of hydrogen and alkyl. In other embodiments, $R_1$ and $R_3$ are independently selected from the group consisting of hydrogen, methyl, and ethyl. In still other embodiments, Ar is aryl optionally substituted by halogen, hydroxyl, alkyl, haloalkyl, alkoxy, haloalkoxy, alkenyloxy, alkynyloxy, cyano, amino, alkylamino, dialkylamino, alkylthio, alkylsulfinyl, alkylsulfonyl, acyl, alkoxycarbonyl, aryl or heteroaryl, where the aryl or heteroaryl may be further optionally substituted with one to three $R_2$. In further embodiments, Ar is aryl optionally substituted by halogen, hydroxyl, alkyl, haloalkyl, alkoxy, haloalkoxy, alkenyloxy, alkynyloxy, cyano, alkylthio, alkylsulfinyl, alkylsulfonyl, acyl, alkoxycarbonyl, aryl or heteroaryl, where the aryl or heteroaryl may be further optionally substituted with one to three $R_2$. In still further embodiments, Ar is aryl optionally substituted by halogen, hydroxyl, alkyl, haloalkyl, alkoxy, haloalkoxy, alkenyloxy, alkynyloxy, cyano, alkylamino, dialkylamino, alkylthio, alkylsulfinyl, alkylsulfonyl, acyl, alkoxycarbonyl, aryl or heteroaryl, where the aryl or heteroaryl may be further optionally substituted with one to three $R_2$. In some embodiments, Ar is heteroaryl optionally substituted by halogen, hydroxyl, alkyl, haloalkyl, alkoxy, haloalkoxy, alkenyloxy, alkynyloxy, cyano, amino, alkylamino, dialkylamino, alkylthio, alkylsulfinyl, alkylsulfonyl, acyl, alkoxycarbonyl, aryl or heteroaryl, where aryl or heteroaryl may be further optionally substituted with one to three $R_2$. In other embodiments, Ar is heteroaryl optionally substituted by halogen, hydroxyl, alkyl, haloalkyl, alkoxy, haloalkoxy, alkenyloxy, alkynyloxy, cyano, alkylamino, dialkylamino, alkylthio, alkylsulfinyl, alkylsulfonyl, acyl, alkoxycarbonyl, aryl or heteroaryl, where aryl or heteroaryl may be further optionally substituted with one to three $R_2$. In still other embodiments, Ar is heteroaryl optionally substituted by halogen, hydroxyl, alkyl, haloalkyl, alkoxy, haloalkoxy, alkenyloxy, alkynyloxy, cyano, alkylthio, alkylsulfinyl, alkylsulfonyl, acyl, alkoxycarbonyl, aryl or heteroaryl, where aryl or heteroaryl may be further optionally substituted with one to three $R_2$. In some embodiments, W and Y are CH. In other embodiments, W is N and Y is CH. In further embodiments, W is CH and Y is N. In yet further embodiments of the compound of formula I, Z is O. In still further embodiments, Z is S. In other embodiments, Z is $NR_3$.

In some embodiments of the compound of formula I, Ar is 2-naphthyl optionally substituted by halogen, hydroxyl, alkyl, haloalkyl, alkoxy, haloalkoxy, alkenyloxy, alkynyloxy, cyano, amino, alkylamino, dialkylamino, alkylthio, alkylsulfinyl, alkylsulfonyl, acyl, alkoxycarbonyl, aryl or heteroaryl, where aryl or heteroaryl may be further optionally substituted with one to three $R_2$. In other embodiments, Ar is 2-quinolinyl optionally substituted by halogen, hydroxyl, alkyl, haloalkyl, alkoxy, haloalkoxy, alkenyloxy, alkynyloxy, cyano, amino, alkylamino, dialkylamino, alkylthio, alkylsulfinyl, alkylsulfonyl, acyl, alkoxycarbonyl, aryl or heteroaryl, the last two of which may be further optionally substituted with one to three $R_2$. In still other embodiments, Ar is 2-, 5- or 6-indolyl optionally substituted by halogen, hydroxyl, alkyl, haloalkyl, alkoxy, haloalkoxy, alkenyloxy, alkynyloxy, cyano, amino, alkylamino, dialkylamino, alkylthio, alkylsulfinyl, alkylsulfonyl, acyl, alkoxycarbonyl, aryl or heteroaryl, the last two of which may be further optionally substituted with one to three $R_2$. In other embodiments, Ar is 7-isoquinolinyl optionally substituted by halogen, hydroxyl, alkyl, haloalkyl, alkoxy, haloalkoxy, alkenyloxy, alkynyloxy, cyano, amino, alkylamino, dialkylamino, alkylthio, alkylsulfinyl, alkylsulfonyl, acyl, alkoxycarbonyl, aryl or heteroaryl, where aryl or heteroaryl may be further optionally substituted with one to three $R_2$. In additional embodiments, Ar is 5-, or 6-(1H-1,2,3-benzotriazolyl) optionally substituted by halogen, hydroxyl, alkyl, haloalkyl, alkoxy, haloalkoxy, alkenyloxy, alkynyloxy, cyano, amino, alkylamino, dialkylamino, alkylthio, alkylsulfinyl, alkylsulfonyl, acyl, alkoxycarbonyl, aryl or heteroaryl, where aryl or heteroaryl may be further optionally substituted with one to three $R_2$. In other embodiments, Ar is 5-, 6-, or 7-(1H-indazolyl) optionally substituted by halogen, hydroxyl, alkyl, haloalkyl, alkoxy, haloalkoxy, alkenyloxy, alkynyloxy, cyano, amino, alkylamino, dialkylamino, alkylthio, alkylsulfinyl, alkylsulfonyl, acyl, alkoxycarbonyl, aryl or heteroaryl, where aryl or heteroaryl may be further optionally substituted with one to three $R_2$. In still other embodiments, Ar is 5-, or 6-(1H-indazolyl) optionally substituted by halogen, hydroxyl, alkyl, haloalkyl, alkoxy, haloalkoxy, alkenyloxy, alkynyloxy, cyano, amino, alkylamino, dialkylamino, alkylthio, alkylsulfinyl, alkylsulfonyl, acyl, alkoxycarbonyl, aryl or heteroaryl, where aryl or heteroaryl may be further optionally substituted with one to three $R_2$. In some other embodiments, Ar is 5- or 6-(1H-benzimidazolyl) optionally substituted by halogen, hydroxyl, alkyl, haloalkyl, alkoxy, haloalkoxy, alkenyloxy, alkynyloxy, cyano, amino, alkylamino, dialkylamino, alkylthio, alkylsulfinyl, alkylsulfonyl, acyl, alkoxycarbonyl, aryl or heteroaryl, where aryl or heteroaryl may be further optionally substituted with one to three $R_2$. In further embodiments, Ar is phenyl substituted by aryl optionally substituted with one to three $R_2$, or heteroaryl optionally substituted with one to three $R_2$. In yet further embodiments, Ar is phenyl substituted by heteroaryl optionally substituted with one to three $R_2$. In some embodiments of the compound of formula I, Ar is phenyl substituted by pyrazolyl, imidazolyl, oxadiazolyl, or pyrimidinyl, each optionally substituted with one to three $R_2$.

In some embodiments of the compound of formula I, $X_1$ is halogen, alkyl, alkoxy, haloalkoxy, cyano, $R_5R_6N-$, aminosulfonyl, carbamoylamino, acyl, acylamino, carboxy, alkoxycarbonyl, heteroaryl or heteroarylalkyl, where heteroaryl or heteroarylalkyl may be optionally substituted with one to three $R_4$. In other embodiments, $X_1$ and $X_2$ are independently halogen, alkyl, alkoxy, haloalkoxy, $R_5R_6N-$, or acetamido. In still other embodiments, $X_1$ and $X_2$ taken together on adjacent carbon atoms form a 4-membered bridge comprised of —CH=.

B. Methods of Making.

Compounds of formula I may be prepared by one of several methods understood by those of skill in the art. One synthetic approach is shown in Scheme 1. It involves the condensation of an N-substituted 4-piperidone III with either a 2-hydroxyarylcarboxamide (IIa, Z=O),

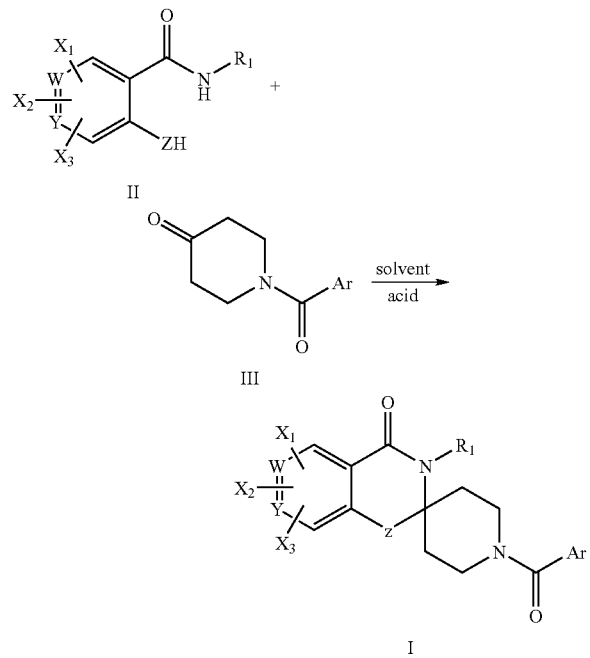

a 2-mercaptoarylcarboxamide (IIb, Z=S), or a 2-aminoarylcarboxamide (IIc, Z=$NR_3$) under acid catalysis (for example, p-toluenesulfonic acid) in an inert solvent such as toluene or chloroform with optional removal of water (azeotrope with toluene or chloroform at reflux temperature) to produce I. An alternative method especially useful for condensing an N-substituted 4-piperidone III with a 2-hydroxyarylcarboxamide (IIa, Z=O) involves the use of morpholine in an appropriate solvent (refluxing toluene/MeOH or MeOH only). In certain cases, especially with 2-aminoarylcarboxamide (IIc, Z=NR$_3$), a polar solvent such as ethanol or acetic acid with or without acid catalysis (e.g., concentrated sulfuric acid) may be used in the condensation with III.

Alternatively, compounds of formula I may be prepared as outlined in Scheme 2. Condensation of 1-tert-butyloxycarbonyl-4-piperidone IV with either a 2-hydroxyarylcarboxamide (IIa, Z=O), a 2-mercaptoarylcarboxamide (IIb, Z=S), or a 2-aminoarylcarboxamide (IIc, Z=NR$_3$) under acid catalysis in an inert solvent such as

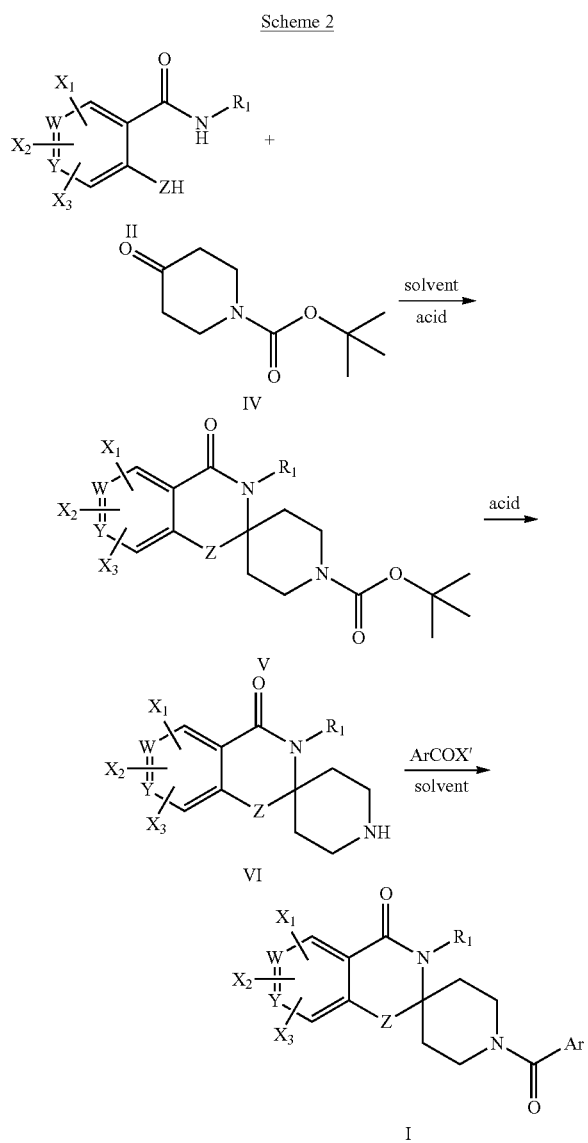

toluene or chloroform with optional removal of water (azeotrope with toluene or chloroform at reflux temperature) gives the N-Boc intermediate V. An alternative method especially useful for preparing V from 1-tert-butyloxycarbonyl-4-piperidone IV and a 2-hydroxyarylcarboxamide (IIa, Z=O) involves the use of morpholine in an appropriate solvent (refluxing toluene/MeOH or MeOH only). Acidic cleavage (preferably trifluoroacetic acid) of the N-Boc protecting group of V followed by acylation of the intermediate VI with ArCOX' (X' is a leaving group such as Cl or is OH) gives I. When X' is Cl, the acylation is typically carried out in the presence of a base in an inert solvent. When X' is OH, the reaction is typically effected by means of a coupling agent such as HATU [N,N,N',N'-tetramethyl-O-(7-azabenzotriazol-1-yl)uronium hexafluorophosphate] and an organic base in an inert solvent.

C. Exemplary Compounds.

Compounds of the invention that are especially useful as pharmaceuticals in the treatment of obesity, metabolic syndrome, atherosclerosis, cardiovascular disease, and insulin resistance, e.g., type II or adult-onset diabetes, diseases associated with reduced neuronal metabolism (e.g. Alzheimer's disease, Mild Cognitive Impairment, Parkinson's disease, Huntington's disease, epilepsy), and cancer, including, but not limited to, breast cancer, uterine cancer, ovarian cancer, colon cancer, prostate cancer, liver cancer, and endometrial cancer, as well as fungal pathogens of humans and animals and as crop protection agents to combat or prevent fungal infestations are those in which:

Ar is aryl or heteroaryl, each of which may be optionally substituted from one to three times by: halogen, hydroxyl, alkyl, haloalkyl, alkoxy, alkenyloxy, alkynyloxy, haloalkoxy, cyano, amino, alkylamino, dialkylamino, alkylthio, alkylsulfinyl, alkylsulfonyl, acyl, alkoxycarbonyl, aryl or heteroaryl, where aryl or heteroaryl may be further optionally substituted with one to three R$_2$;

and each R$_2$ is independently halogen, hydroxyl, alkyl, haloalkyl, alkoxy, haloalkoxy, cyano, alkylthio, alkylsulfinyl, alkylsulfonyl, acyl, alkoxycarbonyl;

Particular compounds are those wherein:

R$_1$ is hydrogen or lower alkyl;

Ar is aryl or heteroaryl, each of which may be optionally substituted from one to three times by: halogen, hydroxyl, alkyl, haloalkyl, alkoxy, alkenyloxy, alkynyloxy, haloalkoxy, cyano, amino, alkylamino, dialkylamino, alkylthio, alkylsulfinyl, alkylsulfonyl, acyl, alkoxycarbonyl, aryl or heteroaryl, where aryl or heteroaryl may be further optionally substituted with one to three R$_2$;

each R$_2$ is independently halogen, hydroxyl, alkyl, haloalkyl, alkoxy, haloalkoxy, cyano, alkylthio, alkylsulfinyl, alkylsulfonyl, acyl, alkoxycarbonyl;

W and Y each independently are N or CH;

Z is O or NR$_3$;

R$_3$ is hydrogen or lower alkyl;

X$_1$, X$_2$, and X$_3$ are each independently hydrogen, halogen, hydroxyl, alkyl, haloalkyl, alkoxy, haloalkoxy, alkenyl, haloalkenyl, alkenyloxy, haloalkenyloxy, alkynyl, haloalkynyl, alkynyloxy, haloalkynyloxy, cyano, R$_5$R$_6$N—, alkylthio, alkylsulfinyl, alkylsulfonyl, aminosulfonyl, carbamoylamino, acyl, acylamino, carboxy, alkoxycarbonyl, arylalkoxycarbonyl, alkylaminocarbonyl, dialkylaminocarbonyl, carboxyalkoxy, alkoxycarbonylalkoxy, alkylaminocarbonyloxy, dialkylaminocarbonyl, aryl, heteroaryl, arylalkyl, or heteroarylalkyl, where aryl, heteroaryl, arylalkyl, or heteroarylalkyl may be optionally substituted with one to three R$_4$;

or when W and Y are both CH, X$_1$ and X$_2$ taken together on adjacent carbon atoms form a 3- to 5-membered bridged ring comprised of elements from methylene, substituted methylene, —CH═, —C(R$_4$)═, C═O, —N═, NH, O, or S(O)$_n$;

each R$_4$ is independently halogen, hydroxyl, alkyl, haloalkyl, alkoxy, haloalkoxy, alkenyl, alkynyl, cyano, amino, alkylamino, dialkylamino, alkylthio, alkylsulfinyl, alkylsulfonyl, aminosulfonyl, carbamoylamino, acyl, acylamino, carboxy, alkoxycarbonyl, arylalkoxycarbonyl, alkylaminocarbonyl, dialkylaminocarbonyl, alkylaminocarbonyloxy, or dialkylaminocarbonyloxy;

each $R_5$ and $R_6$ are independently hydrogen, alkyl, arylalkyl, alkoxyalkyl, hydroxyalkyl; or taken together to form a 5- or 6-member heterocycle containing 2-5 C-atoms, 0-1 O-atom, 0-1 S-atom, and 1-3 N-atoms, which heterocycle may be optionally substituted on a C-atom or N-atom by alkyl, acyl, alkoxycarbonyl, or alkylsulfonyl; and n is 0, 1, or 2.

Other particular compounds are those wherein:

$R_1$ is hydrogen or lower alkyl;

Ar is naphthyl, quinolinyl, isoquinolinyl, indolyl, 1H-1,2,3-benzotriazolyl, 1-H-indazolyl, or 1-H-benzoimidazolyl, each of which may be optionally substituted from one to three times by: halogen, hydroxyl, alkyl, haloalkyl, alkoxy, alkenyloxy, alkynyloxy, haloalkoxy, cyano, amino, alkylamino, dialkylamino, alkylthio, alkylsulfinyl, alkylsulfonyl, acyl, alkoxycarbonyl, aryl or heteroaryl, where aryl or heteroaryl may be further optionally substituted with one to three $R_2$;

or Ar is phenyl substituted by heteroaryl, each optionally substituted with one to three $R_2$;

each $R_2$ is independently halogen, hydroxyl, alkyl, haloalkyl, alkoxy, haloalkoxy, cyano, alkylthio, alkylsulfinyl, alkylsulfonyl, acyl, or alkoxycarbonyl;

W is CH and Y is N or CH;

Z is O or $NR_3$;

$R_3$ is hydrogen or lower alkyl;

$X_1$, $X_2$, and $X_3$ are each independently hydrogen, halogen, hydroxyl, alkyl, haloalkyl, alkoxy, haloalkoxy, alkenyl, haloalkenyl, alkenyloxy, haloalkenyloxy, alkynyl, haloalkynyl, alkynyloxy, haloalkynyloxy, cyano, $R_5R_6N-$, alkylthio, alkylsulfinyl, alkylsulfonyl, aminosulfonyl, carbamoylamino, acyl, acylamino, carboxy, alkoxycarbonyl, arylalkoxycarbonyl, alkylaminocarbonyl, dialkylaminocarbonyl, carboxyalkoxy, alkoxycarbonylalkoxy, alkylaminocarbonyloxy, dialkylaminocarbonyl; aryl, heteroaryl, arylalkyl, or heteroarylalkyl, where aryl, heteroaryl, arylalkyl, or heteroarylalkyl may be each optionally substituted with one to three $R_4$;

or when W and Y are both CH, $X_1$ and $X_2$ taken together on adjacent carbon atoms form a 3- to 5-membered bridged ring comprised of elements from methylene, substituted methylene, —CH=, —C($R_4$)=, C=O, —N=, NH, O, or S(O)$_n$;

each $R_4$ is independently halogen, hydroxyl, alkyl, haloalkyl, alkoxy, haloalkoxy, alkenyl, alkynyl, cyano, amino, alkylamino, dialkylamino, alkylthio, alkylsulfinyl, alkylsulfonyl, aminosulfonyl, carbamoylamino, acyl, acylamino, carboxy, alkoxycarbonyl, arylalkoxycarbonyl, alkylaminocarbonyl, dialkylaminocarbonyl, alkylaminocarbonyloxy, or dialkylaminocarbonyloxy;

each $R_5$ and $R_6$ are independently hydrogen, alkyl, arylalkyl, alkoxyalkyl, hydroxyalkyl; or taken together to form a 5- or 6-member heterocycle containing 2-5 C-atoms, 0-1 O-atom, 0-1 S-atom, and 1-3 N-atoms, which heterocycle may be optionally substituted on a C-atom or N-atom by alkyl, acyl, alkoxycarbonyl, or alkylsulfonyl; and n is 0, 1, or 2.

Specific examples of the compounds of formula I include, but are not limited to, the following:

| Compound Number | Structure | Name |
|---|---|---|
| 1 | 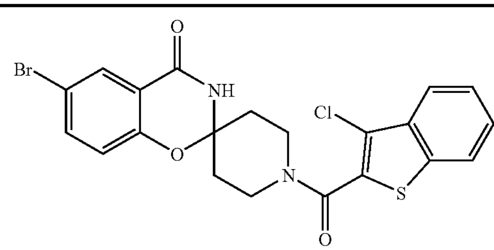 | 6-Bromo-1'-[(3-chlorobenzthien-2-yl)carbonyl]spiro[2H-1,3-benzoxazin-2,4'-piperidin]-4-(3H)-one; |
| 2 | 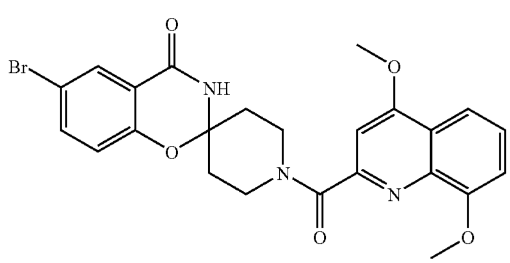 | 6-Bromo-1'-[4,8-dimethoxyquinolin-2-yl)carbonyl]spiro[2H-1,3-benzoxazin-2,4'-piperidin]-4-(3H)-one; |
| 3 | 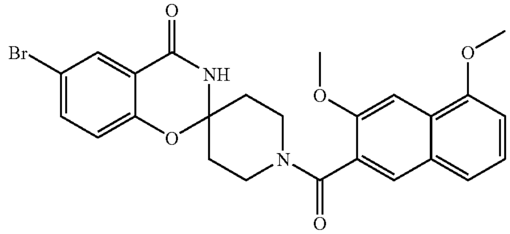 | 6-Bromo-1'-[3,5-dimethoxynaphth-2-yl)carbonyl]spiro[2H-1,3-benzoxazin-2,4'-piperidin]-4-(3H)-one; |

-continued

| Compound Number | Structure | Name |
|---|---|---|
| 4 | 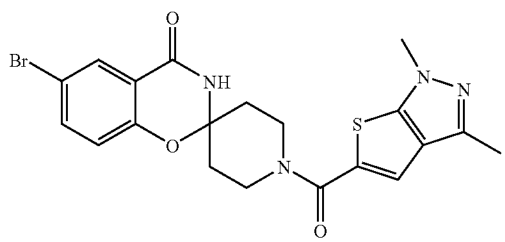 | 6-Bromo-1'-{(1,3-dimethyl-1H-thieno[2,3-c]pyrazol-5-yl)carbonyl}spiro[2H-1,3-benzoxazin-2,4'-piperidin]-4-(3H)-one; |
| 5 | 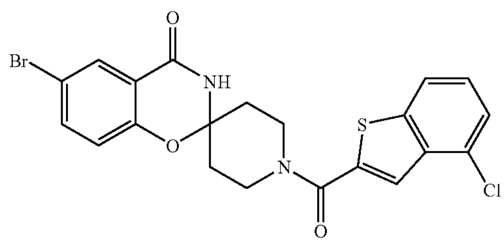 | 6-Bromo-1'-[(4-chlorobenzthien-2-yl)carbonyl]spiro[2H-1,3-benzoxazin-2,4'-piperidin]-4-(3H)-one; |
| 6 | 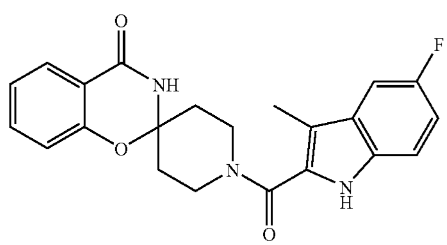 | 1'-[(5-Fluoro-3-methyl-1H-indol-2-yl)carbonyl]spiro[2H-1,3-benzoxazin-2,4'-piperidin]-4-(3H)-one; |
| 7 | 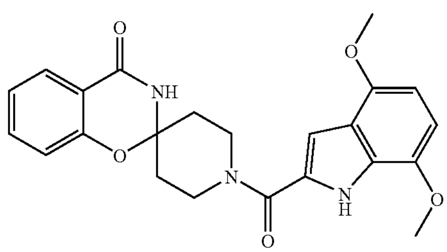 | 1'-[(4,7-Dimethoxy-1H-indol-2-yl)carbonyl]spiro[2H-1,3-benzoxazin-2,4'-piperidin]-4-(3H)-one; |
| 8 | 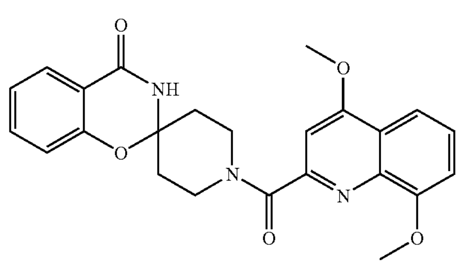 | 1'-[4,8-Dimethoxyquinolin-2-yl)carbonyl]spiro[2H-1,3-benzoxazin-2,4'-piperidin]-4-(3H)-one; |
| 9 | 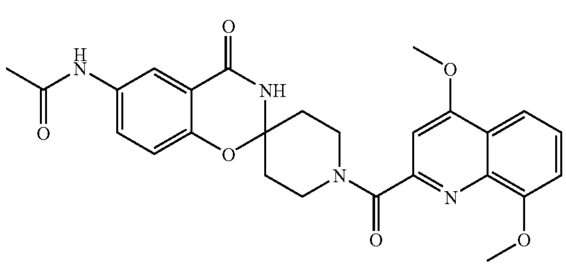 | 6-Acetamido-1'-[4,8-dimethoxyquinolin-2-yl)carbonyl]spiro[2H-1,3-benzoxazin-2,4'-piperidin]-4-(3H)-one; |

-continued

| Compound Number | Structure | Name |
|---|---|---|
| 10 | 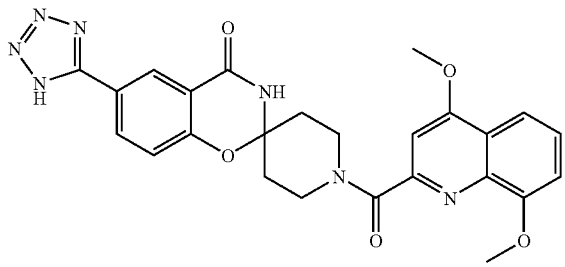 | 1'-[4,8-Dimethoxyquinolin-2-yl)carbonyl]-6-(1H-tetrazol-5-yl)spiro[2H-1,3-benzoxazin-2,4'-piperidin]-4-(3H)-one; |
| 11 | 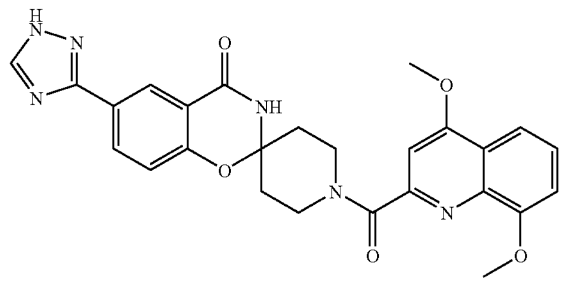 | 1'-[(4,8-Dimethoxyquinolin-2-yl)carbonyl]-6-(1H-1,2,4-triazol-3-yl)spiro[2H-1,3-benzoxazin-2,4'-piperidin]-4-(3H)-one; |
| 12 | 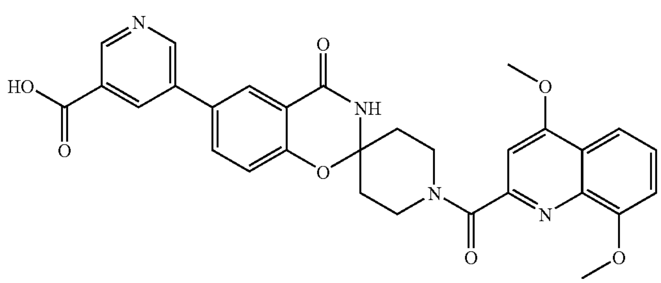 | 5-{1'-[4,8-Dimethoxyquinolin-2-yl)carbonyl]-4-oxo-spiro[2H-1,3-benzoxazin-2,4'-piperidin]-6-yl}nicotinic acid |
| 13 | 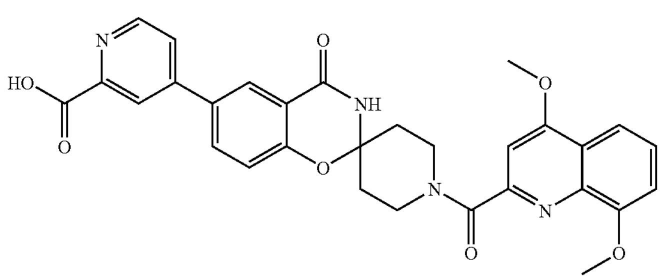 | 4-{1'-[4,8-Dimethoxyquinolin-2-yl)carbonyl]-4-oxo-spiro[2H-1,3-benzoxazin-2,4'-piperidin]-6-yl}pyridine-2-carboxylic acid; |
| 14 | 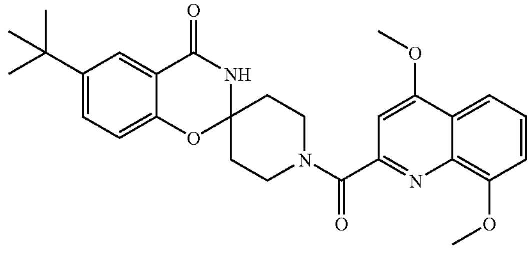 | 6-t-Butyl-1'-[4,8-dimethoxyquinolin-2-yl)carbonyl]spiro[2H-1,3-benzoxazin-2,4'-piperidin]-4-(3H)-one; |

-continued

| Compound Number | Structure | Name |
|---|---|---|
| 15 | 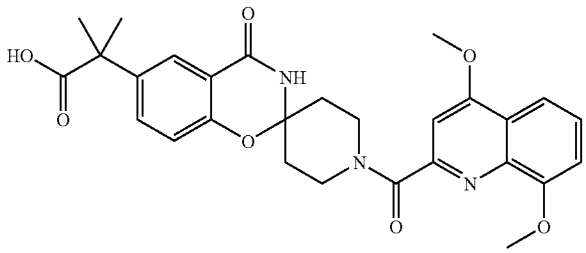 | 2-{-1'-[4,8-Dimethoxyquinolin-2-yl)carbonyl]-4-oxo-spiro[2H-1,3-benzoxazin-2,4'-piperidin]-6-yl}-2-methylpropanoic acid; |
| 16 | 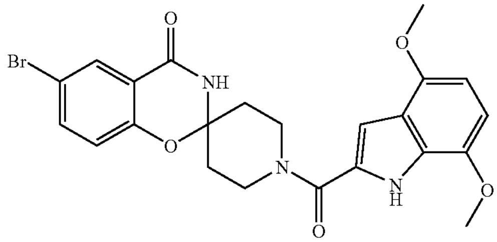 | 6-Bromo-1'-[4,7-dimethoxy-1H-indol-2-yl)carbonyl]spiro[2H-1,3-benzoxazin-2,4'-piperidin]-4-(3H)-one; |
| 17 | 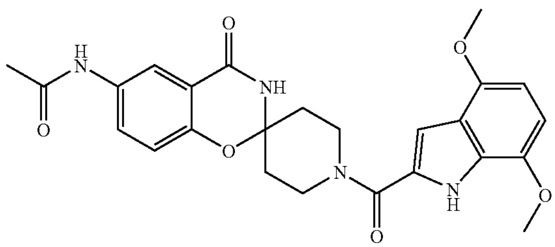 | 6-Acetamido-1'-[4,7-dimethoxy-1H-indol-2-yl)carbonyl]spiro[2H-1,3-benzoxazin-2,4'-piperidin]-4-(3H)-one; |
| 18 | 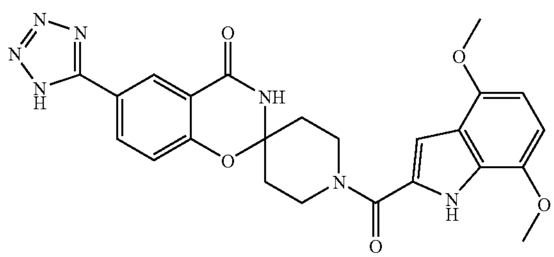 | 1'-[4,7-Dimethoxy-1H-indol-2-yl)carbonyl]-6-(1H-tetrazol-5-yl)spiro[2H-1,3-benzoxazin-2,4'-piperidin]-4-(3H)-one; |
| 19 | 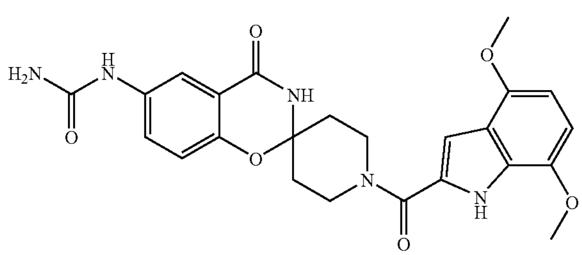 | N-{1'-[4,7-Dimethoxy-1H-indol-2-yl)carbonyl]-4-oxo-spiro[2H-1,3-benzoxazin-2,4'-piperidin]-6-yl}urea; |
| 20 | 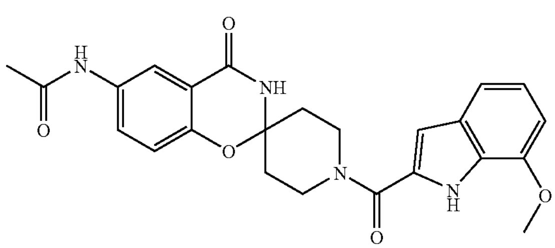 | 6-Acetamido-1'-[7-methoxy-1H-indol-2-yl)carbonyl]spiro[2H-1,3-benzoxazin-2,4'-piperidin]-4-(3H)-one; |

-continued

| Compound Number | Structure | Name |
|---|---|---|
| 21 | 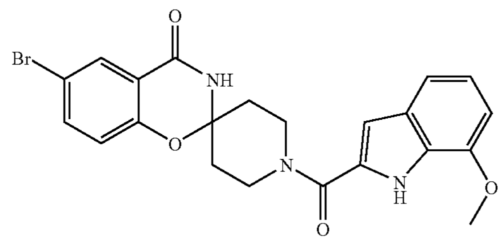 | 6-Bromo-1'-[7-methoxy-1H-indol-2-yl)carbonyl]spiro[2H-1,3-benzoxazin-2,4'-piperidin]-4-(3H)-one; |
| 22 | 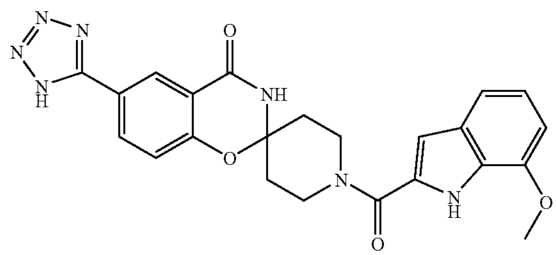 | 1'-[7-Methoxy-1H-indol-2-yl)carbonyl]-6-(1H-tetrazol-5-yl)spiro[2H-1,3-benzoxazin-2,4'-piperidin]-4-(3H)-one; |
| 23 | 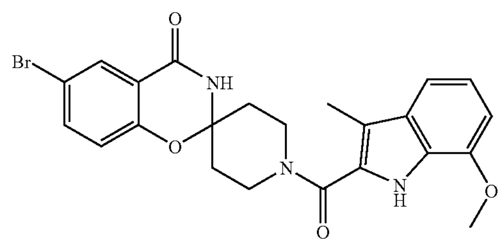 | 6-Bromo-1'-[7-methoxy-3-methyl-1H-indol-2-yl)carbonyl]spiro[2H-1,3-benzoxazin-2,4'-piperidin]-4-(3H)-one; |
| 24 | 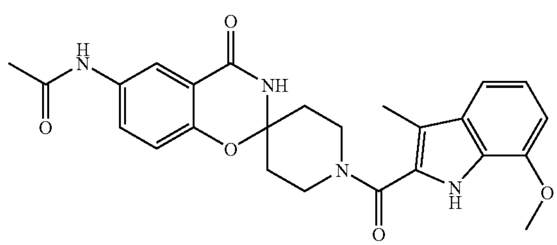 | 6-Acetamido-1'-[7-methoxy-3-methyl-1H-indol-2-yl)carbonyl]spiro[2H-1,3-benzoxazin-2,4'-piperidin]-4-(3H)-one; |
| 25 | 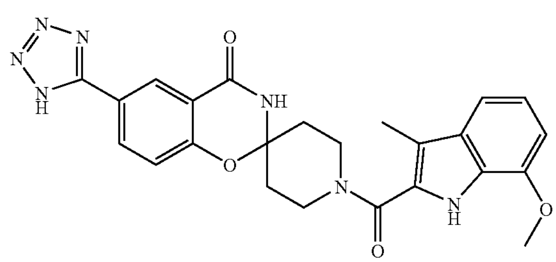 | 1'-[7-Methoxy-3-methyl-1H-indol-2-yl)carbonyl]-6-(1H-tetrazol-5-yl)spiro[2H-1,3-benzoxazin-2,4'-piperidin]-4-(3H)-one; |
| 26 | 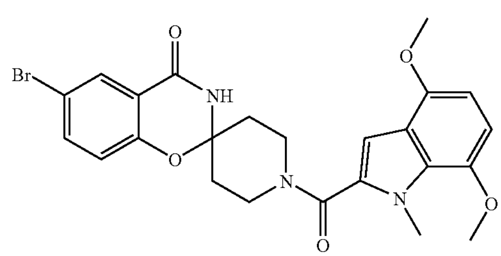 | 6-Bromo-1'-[4,7-dimethoxy-1-methyl-1H-indol-2-yl)carbonyl]spiro[2H-1,3-benzoxazin-2,4'-piperidin]-4-(3H)-one; |

-continued

| Compound Number | Structure | Name |
|---|---|---|
| 27 | 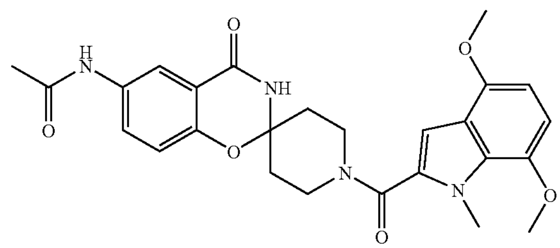 | 6-Acetamido-1'-[4,7-dimethoxy-1-methyl-1H-indol-2-yl)carbonyl]spiro[2H-1,3-benzoxazin-2,4'-piperidin]-4-(3H)-one; |
| 28 | 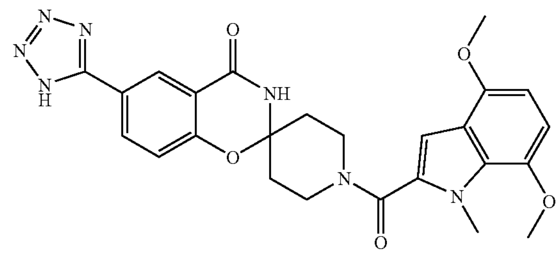 | 1'-[4,7-Dimethoxy-1-methylindol-2-yl)carbonyl]-6-(1H-tetrazol-5-yl)spiro[2H-1,3-benzoxazin-2,4'-piperidin]-4-(3H)-one; |
| 29 | 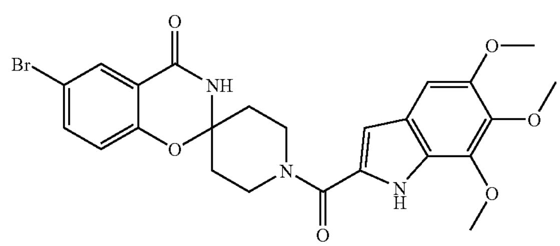 | 6-Bromo-1'-[5,6,7-trimethoxy-1H-indol-2-yl)carbonyl]spiro[2H-1,3-benzoxazin-2,4'-piperidin]-4-(3H)-one; |
| 30 | 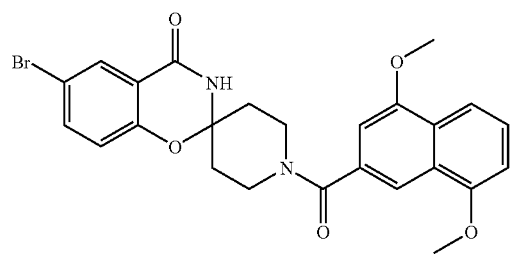 | 6-Bromo-1'-[4,8-dimethoxynaphth-2-yl)carbonyl]spiro[2H-1,3-benzoxazin-2,4'-piperidin]-4-(3H)-one; |
| 31 | 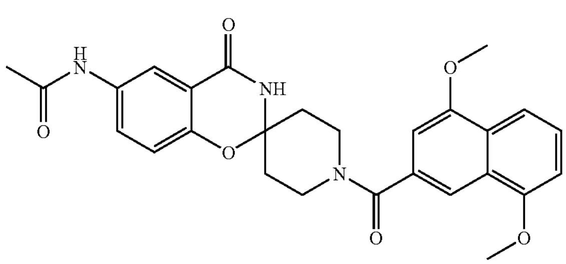 | 6-Acetamido-1'-[4,8-dimethoxynaphth-2-yl)carbonyl]spiro[2H-1,3-benzoxazin-2,4'-piperidin]-4-(3H)-one; |
| 32 | 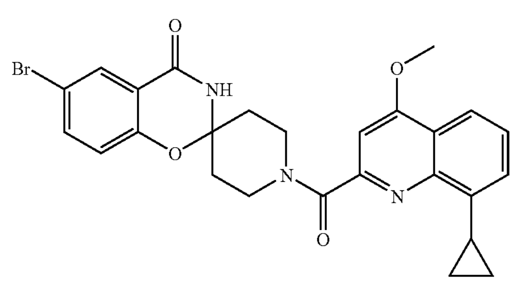 | 6-Bromo-1'-[8-cyclopropyl-4-methoxyquinolin-2-yl)carbonyl]spiro[2H-1,3-benzoxazin-2,4'-piperidin]-4-(3H)-one; |

-continued

| Compound Number | Structure | Name |
|---|---|---|
| 33 | 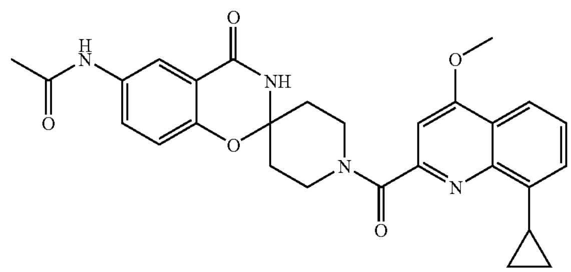 | 6-Acetamido-1'-[8-cyclopropyl-4-methoxyquinolin-2-yl)carbonyl]spiro[2H-1,3-benzoxazin-2,4'-piperidin]-4-(3H)-one; |
| 34 | 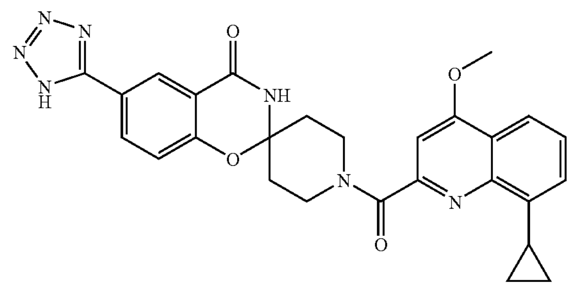 | 1'-[8-Cyclopropyl-4-methoxyquinolin-2-yl)carbonyl]-6-(1H-tetrazol-5-yl)spiro[2H-1,3-benzoxazin-2,4'-piperidin]-4-(3H)-one; |
| 35 | 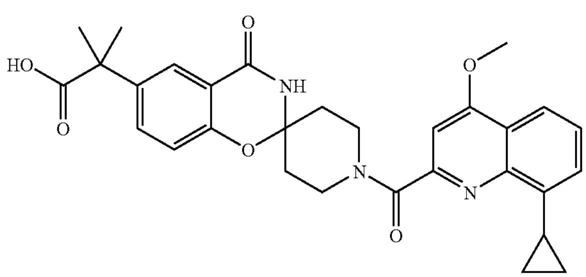 | 2-{-1'-[8-Cyclopropyl-4-methoxyquinolin-2-yl)carbonyl]-4-oxo-spiro[2H-1,3-benzoxazin-2,4'-piperidin]-6-yl}-2-methylpropanoic acid; |
| 36 | 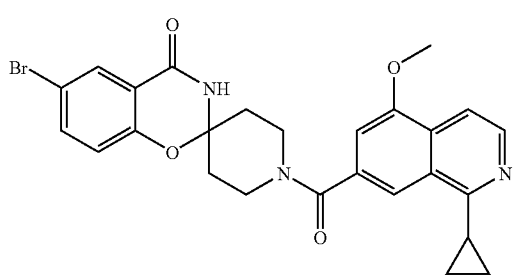 | 6-Bromo-1'-[1-cyclopropyl-5-methoxyisoquinolin-7-yl)carbonyl]spiro[2H-1,3-benzoxazin-2,4'-piperidin]-4-(3H)-one; |
| 37 | 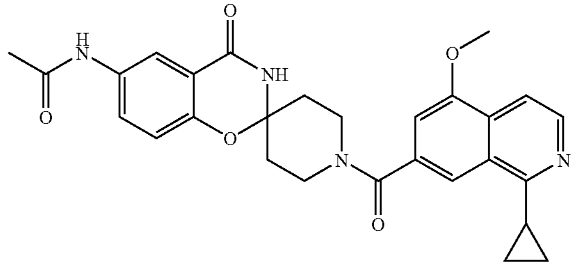 | 6-Acetamido-1'-[1-cyclopropyl-5-methoxyisoquinolin-7-yl)carbonyl]spiro[2H-1,3-benzoxazin-2,4'-piperidin]-4-(3H)-one; |

| Compound Number | Structure | Name |
|---|---|---|
| 38 | 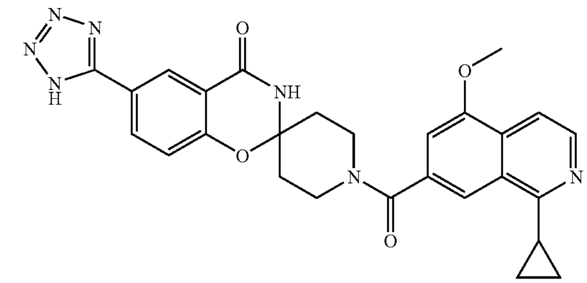 | 1'-[1-Cyclopropyl-5-methoxyisoquinolin-7-yl)carbonyl]-6-(1H-tetrazol-5-yl)spiro[2H-1,3-benzoxazin-2,4'-piperidin]-4-(3H)-one; |
| 39 | 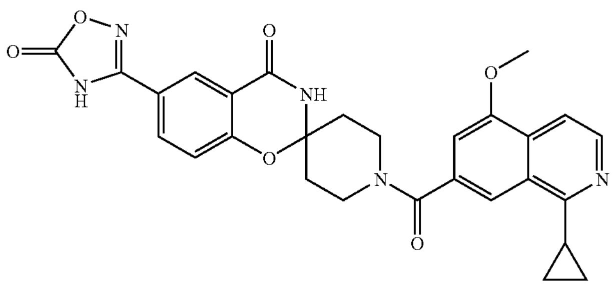 | 1'-[1-Cyclopropyl-5-methoxyisoquinolin-7-yl)carbonyl]-6-(5-oxo-4,5-dihydro-1,2,4-oxadiazol-3-yl)spiro[2H-1,3-benzoxazin-2,4'-piperidin]-4-(3H)-one; |
| 40 | 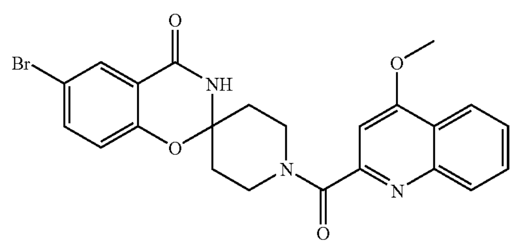 | 6-Bromo-1'-[4-methoxyquinolin-2-yl)carbonyl]spiro[2H-1,3-benzoxazin-2,4'-piperidin]-4-(3H)-one; |
| 41 | 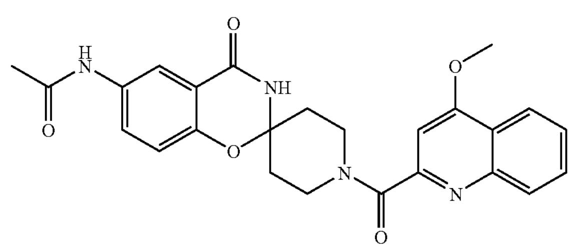 | 6-Acetamido-1'-[4-methoxyquinolin-2-yl)carbonyl]spiro[2H-1,3-benzoxazin-2,4'-piperidin]-4-(3H)-one; |
| 42 | 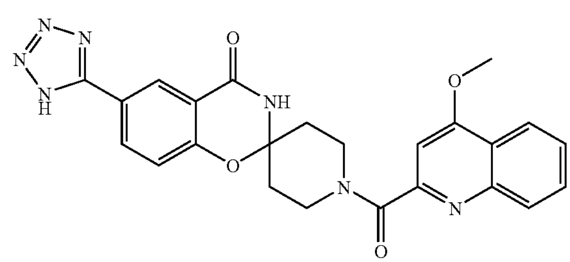 | 1'-4-Methoxyquinolin-2-yl)carbonyl]-6-(1H-tetrazol-5-yl)spiro[2H-1,3-benzoxazin-2,4'-piperidin]-4-(3H)-one; |
| 43 | 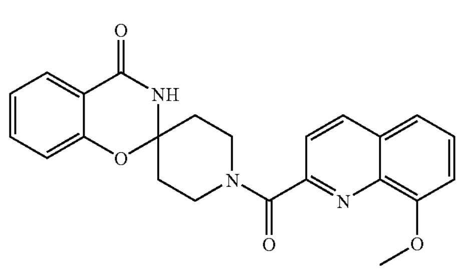 | 1'-[8-Methoxyquinolin-2-yl)carbonyl]-spiro[2H-1,3-benzoxazin-2,4'-piperidin]-4-(3H)-one; |

-continued

| Compound Number | Structure | Name |
|---|---|---|
| 44 | 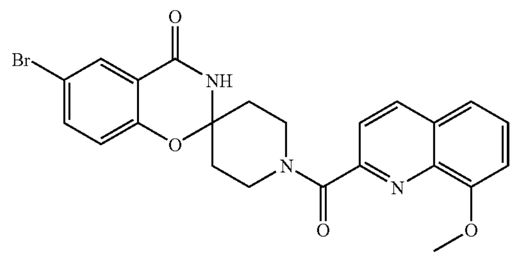 | 6-Bromo-1'-[8-methoxyquinolin-2-yl)carbonyl]spiro[2H-1,3-benzoxazin-2,4'-piperidin]-4-(3H)-one; |
| 45 | 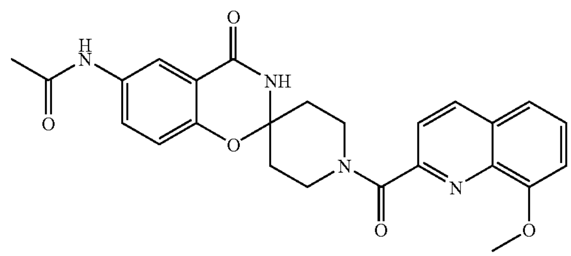 | 6-Acetamido-1'-[8-methoxyquinolin-2-yl)carbonyl]spiro[2H-1,3-benzoxazin-2,4'-piperidin]-4-(3H)-one; |
| 46 | 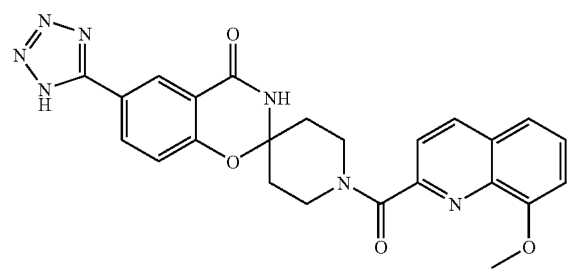 | 1'-[8-Methoxyquinolin-2-yl)carbonyl]-6-(1H-tetrazol-5-yl)spiro[2H-1,3-benzoxazin-2,4'-piperidin]-4-(3H)-one; |
| 47 | 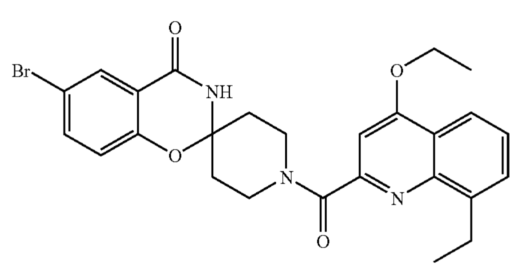 | 6-Bromo-1'-[4-ethoxy-8-ethylquinolin-2-yl)carbonyl]spiro[2H-1,3-benzoxazin-2,4'-piperidin]-4-(3H)-one; |
| 48 | 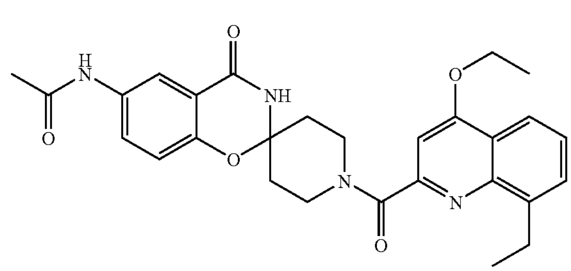 | 6-Acetamido-1'-[4-ethoxy-8-ethylquinolin-2-yl)carbonyl]spiro[2H-1,3-benzoxazin-2,4'-piperidin]-4-(3H)-one; |

-continued

| Compound Number | Structure | Name |
|---|---|---|
| 49 | 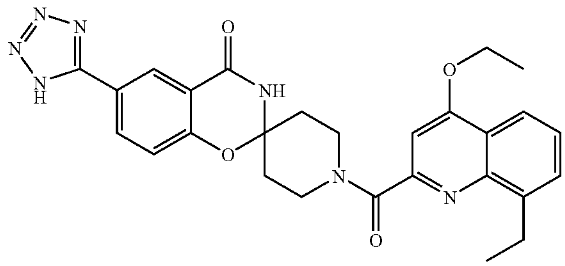 | 1'-[4-Ethoxy-8-ethylquinolin-2-yl)carbonyl]-6-(1H-tetrazol-5-yl)spiro[2H-1,3-benzoxazin-2,4'-piperidin]-4-(3H)-one; |
| 50 | 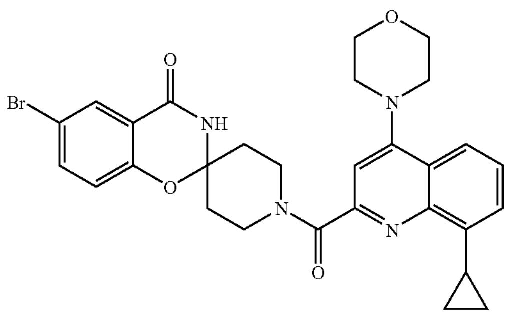 | 6-Bromo-1'-[8-cyclopropyl-4-(4-morpholinyl)quinolin-2-yl)carbonyl]spiro[2H-1,3-benzoxazin-2,4'-piperidin]-4-(3H)-one; |
| 51 | 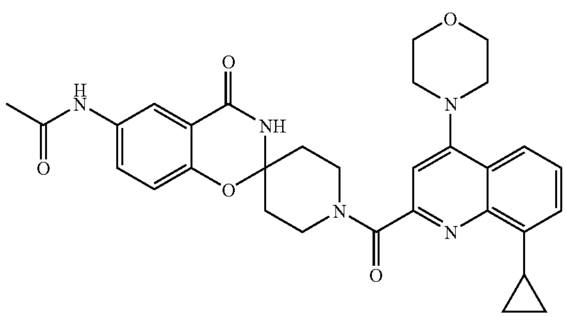 | 6-Acetamido-1'-[8-cyclopropyl-4-(4-morpholinyl)quinolin-2-yl)carbonyl]spiro[2H-1,3-benzoxazin-2,4'-piperidin]-4-(3H)-one; |
| 52 | 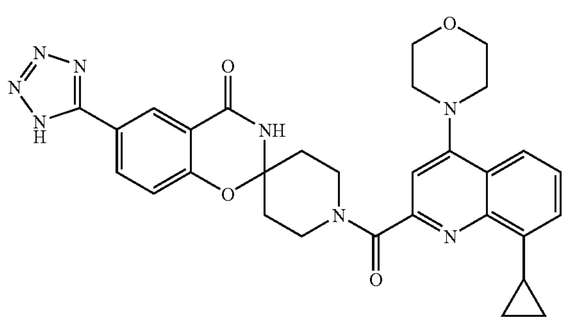 | 1'-[8-Cyclopropyl-4-(4-morpholinyl)quinolin-2-yl)carbonyl]-6-(1H-tetrazol-5-yl)spiro[2H-1,3-benzoxazin-2,4'-piperidin]-4-(3H)-one; |
| 53 | 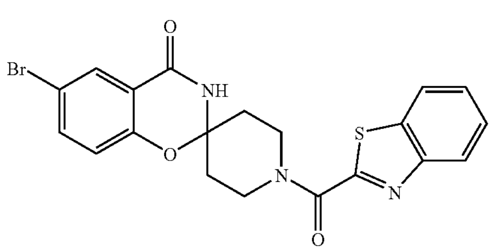 | 1'-[(Benzthiazol-2-yl)carbonyl]-6-bromospiro[2H-1,3-benzoxazin-2,4'-piperidin]-4-(3H)-one; |

-continued

| Compound Number | Structure | Name |
|---|---|---|
| 54 | 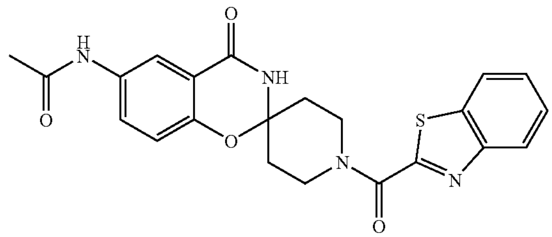 | 6-Acetamido-1'-[(benzthiazol-2-yl)carbonyl]spiro[2H-1,3-benzoxazin-2,4'-piperidin]-4-(3H)-one; |
| 55 | 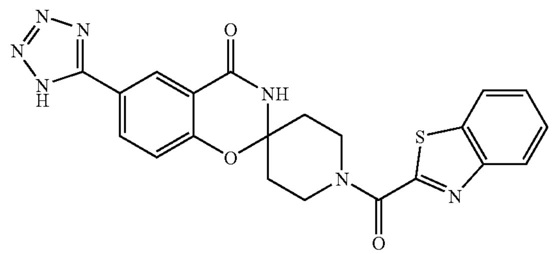 | 1'-[(Benzthiazol-2-yl)carbonyl]-6-(1H-tetrazol-5-yl)spiro[2H-1,3-benzoxazin-2,4'-piperidin]-4-(3H)-one; |
| 56 | 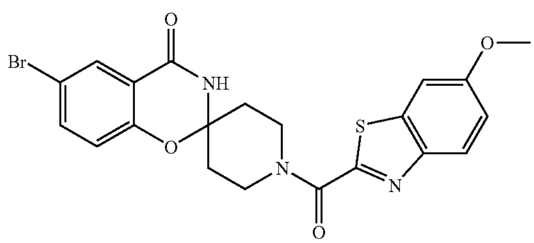 | 6-Bromo-1'-[(6-methoxybenzthiazol-2-yl)carbonyl]spiro[2H-1,3-benzoxazin-2,4'-piperidin]-4-(3H)-one; |
| 57 | 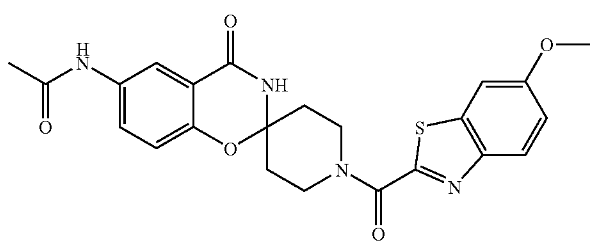 | 6-Acetamido-1'-[(6-methoxybenzthiazol-2-yl)carbonyl]spiro[2H-1,3-benzoxazin-2,4'-piperidin]-4-(3H)-one; |
| 58 | 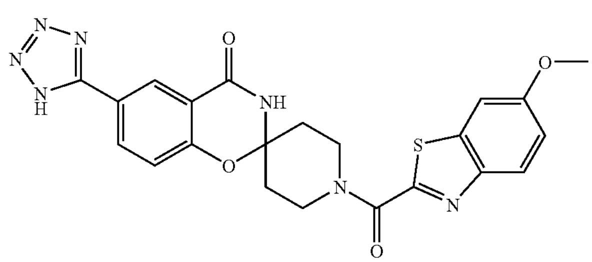 | 1'-[(6-Methoxybenzthiazol-2-yl)carbonyl]-6-(1H-tetrazol-5-yl)spiro[2H-1,3-benzoxazin-2,4'-piperidin]-4-(3H)-one; |
| 59 | 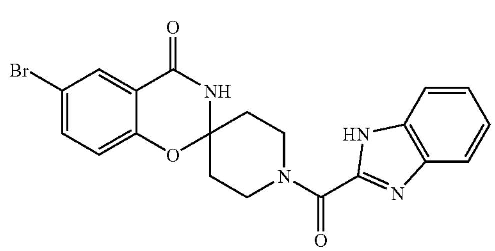 | 1'-[(1H-Benzimidazol-2-yl)carbonyl]-6-bromospiro[2H-1,3-benzoxazin-2,4'-piperidin]-4-(3H)-one |

-continued

| Compound Number | Structure | Name |
|---|---|---|
| 60 | 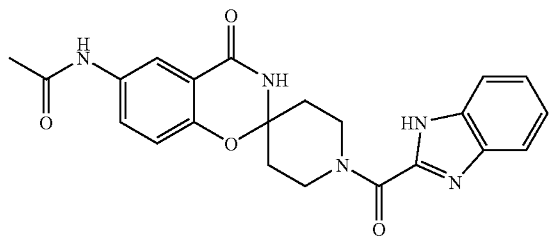 | 6-Acetamido-1'-[(1H-benzimidazol-2-yl)carbonyl]spiro[2H-1,3-benzoxazin-2,4'-piperidin]-4-(3H)-one; |
| 61 | 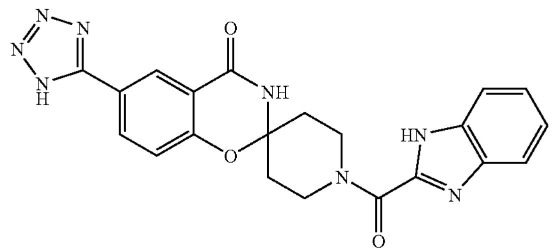 | 1'-[(1H-Benzimidazol-2-yl)carbonyl]-6-(1H-tetrazol-5-yl)spiro[2H-1,3-benzoxazin-2,4'-piperidin]-4-(3H)-one; |
| 62 | 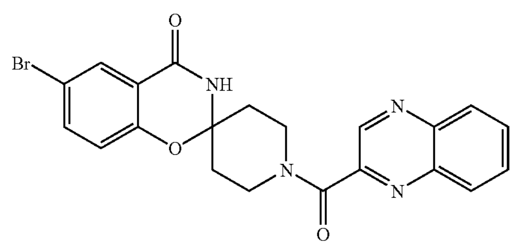 | 6-Bromo-1'-[(quinoxalin-2-yl)carbonyl]spiro[2H-1,3-benzoxazin-2,4'-piperidin]-4-(3H)-one; |
| 63 | 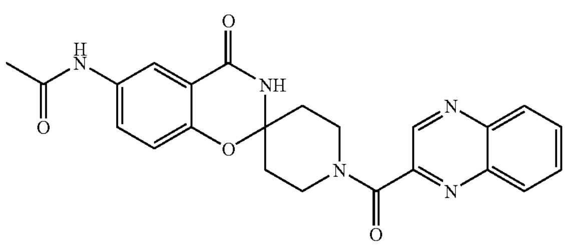 | 6-Acetamido-1'-[(quinoxalin-2-yl)carbonyl]spiro[1,3-benzoxazin-2,4'-piperidin]-4-(3H)-one; |
| 64 | 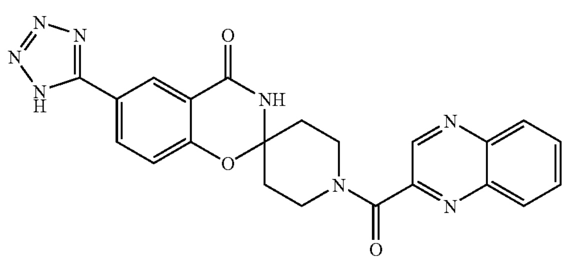 | 1'-[(Quinoxalin-2-yl)carbonyl]-6-(1H-tetrazol-5-yl)spiro[2H-1,3-benzoxazin-2,4'-piperidin]-4-(3H)-one; |
| 65 | 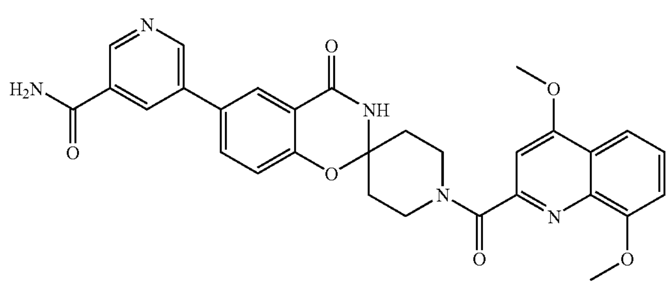 | 5-{1'-[4,8-Dimethoxyquinolin-2-yl)carbonyl]-4-oxo-spiro[2H1,3-benzoxazin-2,4'-piperidin]-6-yl}nicotinamide; |

-continued

| Compound Number | Structure | Name |
|---|---|---|
| 66 | 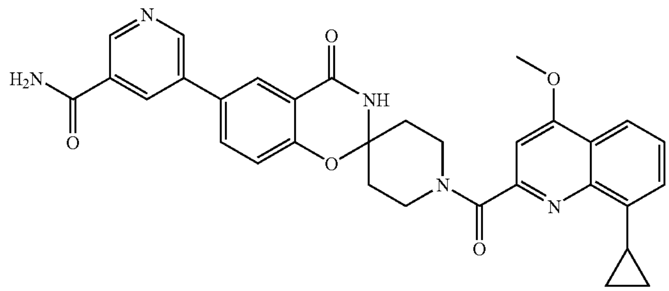 | 5-{1'-[(8-Cyclopropyl-4-methoxyquinolin-2-yl)carbonyl]-4-oxo-spiro[2H-1,3-benzoxazin-2,4'-piperidin]-6-yl}nicotinamide; |
| 67 | 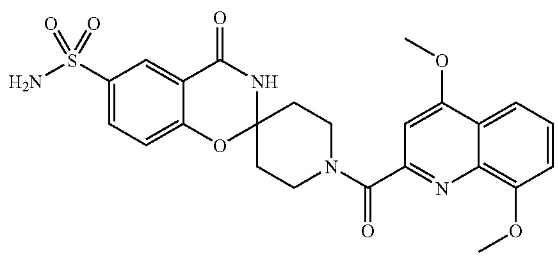 | 1'-[(4,8-Dimethoxyquinolin-2-yl)carbonyl]-4-oxo-spiro[2-H1,3-benzoxazin-2,4'-piperidin]-6-ylsulfonamide; |
| 68 | 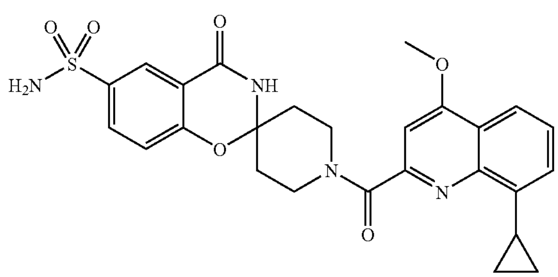 | 1'-[(8-Cyclopropyl-4-methoxyquinolin-2-yl)carbonyl]-4-oxo-spiro[2H-1,3-benzoxazin-2,4'-piperidin]-6-ylsulfonamide; |
| 69 | 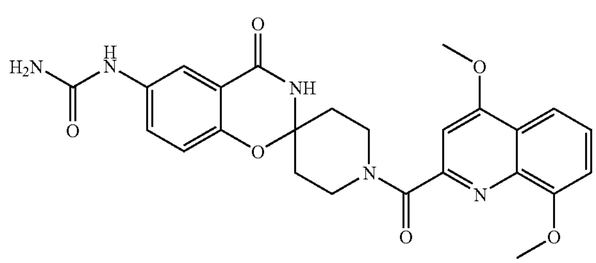 | N-{1'-[4,8-Dimethoxyquinolin-2-yl)carbonyl]-4-oxo-spiro[2H-1,3-benzoxazin-2,4'-piperidin]-6-yl}urea; |
| 70 | 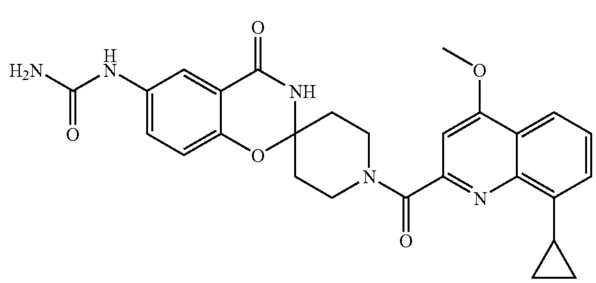 | N-{1'-[(8-Cyclopropyl-4-methoxyquinolin-2-yl)carbonyl]-4-oxo-spiro[2H-1,3-benzoxazin-2,4'-piperidin]-6-yl}urea; |

-continued

| Compound Number | Structure | Name |
|---|---|---|
| 71 | 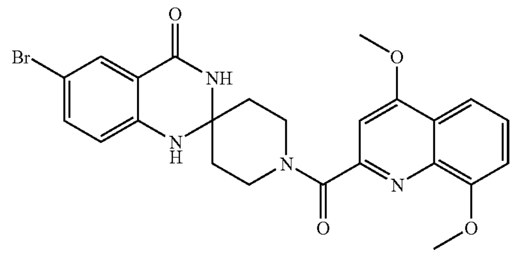 | 6'-Bromo-1-[(4,8-dimethoxyquinolin-2-yl)carbonyl]spiro[piperidine-4,2'(1'H)-quinazolin]-4'-(3'H)-one; |
| 72 | 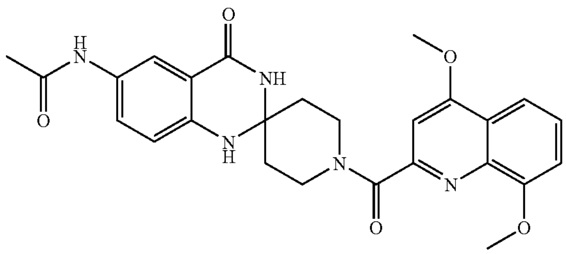 | 6'-Acetamdio-1-[4,8-dimethoxyquinolin-2-yl)carbonyl]spiro[piperidine-4,2'(1'H)-quinazolin]-4'-(3'H)-one; |
| 73 | 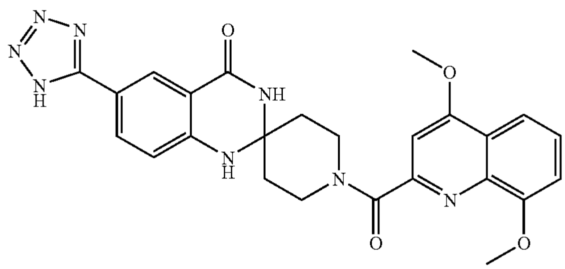 | 1-[(4,8-Dimethoxyquinolin-2-yl)carbonyl]-6'-(1H-tetrazol-5-yl)spiro[piperidine-4,2'(1'H)-quinazolin]-4'-(3'H)-one; |
| 74 | 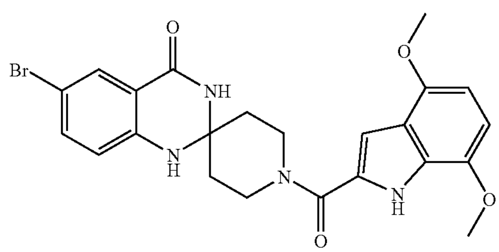 | 6'-Bromo-1-[4,7-dimethoxy-1H-indol-2-yl)carbonyl]spiro[piperidine-4,2'(1'H)-quinazolin]-4'-(3'H)-one; |
| 75 | 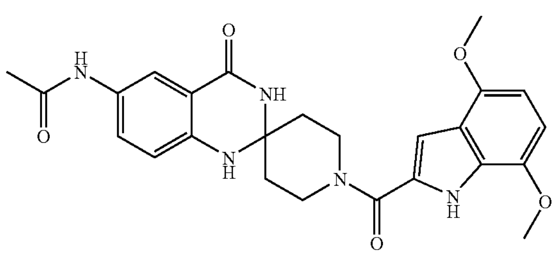 | 6'-Acetamido-1-[4,7-dimethoxy-1H-indol-2-yl)carbonyl]spiro[piperidine-4,2'(1'H)-quinazolin]-4'-(3'H)-one; |
| 76 | 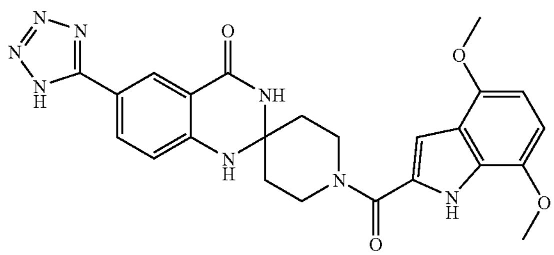 | 1-[4,7-Dimethoxy-1H-indol-2-yl)carbonyl]-6'-(1H-tetrazol-5-yl)spiro[piperidine-4,2'(1'H)-quinazolin]-4'-(3'H)-one; |

-continued

| Compound Number | Structure | Name |
|---|---|---|
| 77 | 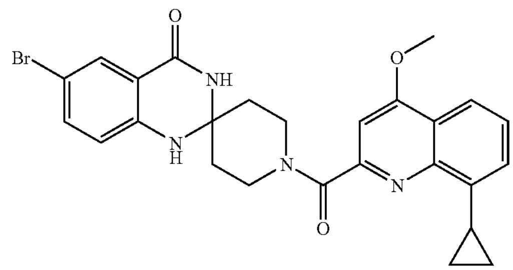 | 6'-Bromo-1-[8-cyclopropyl-4-methoxyquinolinyl)carbonyl]spiro[piperidine-4,2'(1'H)-quinazolin]-4'-(3'H)-one; |
| 78 | 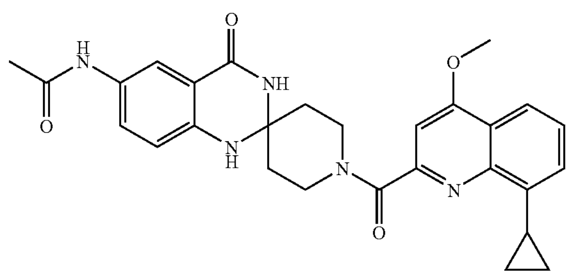 | 6'-Acetamido-1-[8-cyclopropyl-4-methoxyquinolinyl)carbonyl]spiro[piperidine-4,2'(1'H)-quinazolin]-4'-(3'H)-one; |
| 79 | 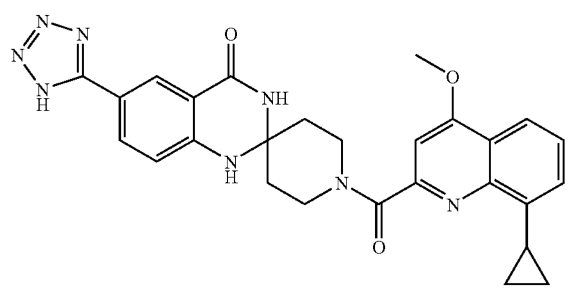 | 1-[8-Cyclopropyl-4-methoxyquinolin-2-yl)carbonyl]-6'-(1H-tetrazol-5-yl)spiro[piperidine-4,2'(1'H)-quinazolin]-4'-(3'H)-one; |
| 80 | 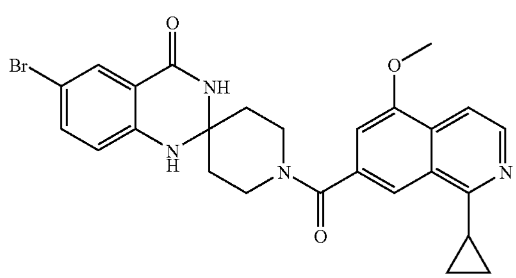 | 6'-Bromo-1-[1-cyclopropyl-5-methoxyisoquinolin-7-yl)carbonyl]spiro[piperidine-4,2'(1'H)-quinazolin]-4'-(3'H)-one; |
| 81 | 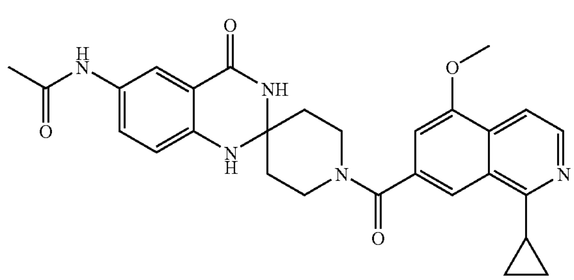 | 6'-Acetamido-1-[1-cyclopropyl-5-methoxyisoquinolin-7-yl)carbonyl]spiro[piperidine-4,2'(1'H)-quinazolin]-4'-(3'H)-one; |

-continued

| Compound Number | Structure | Name |
|---|---|---|
| 82 | 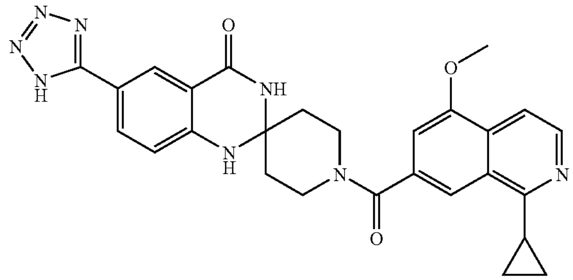 | 1-[1-Cyclopropyl-5-methoxyisoquinolin-7-yl)carbonyl]-6'-(1H-tetrazol-5-yl)spiro[piperidine-4,2'(1'H)-quinazolin]-4'-(3'H)-one; |
| 83 | 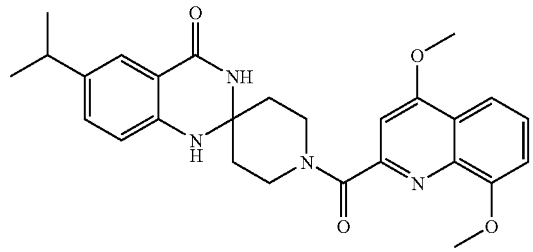 | 1-[(4,8-Dimethoxyquinolin-2-yl)carbonyl]-6'-isopropylspiro[piperidine-4,2'(1'H)-quinazolin]-4'-(3'H)-one; |
| 84 | 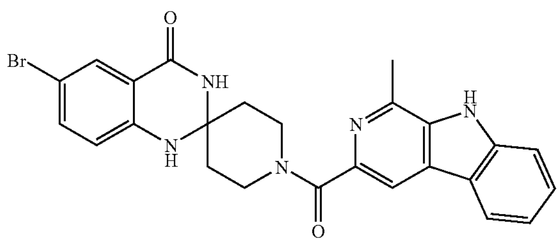 | 6'-Bromo-1-[(1-methyl-9H-pyrido[3,4-b]indol-3-yl)carbonyl]spiro[piperidine-4,2'(1'H)-quinazolin]-4'-(3'H)-one; |
| 85 | 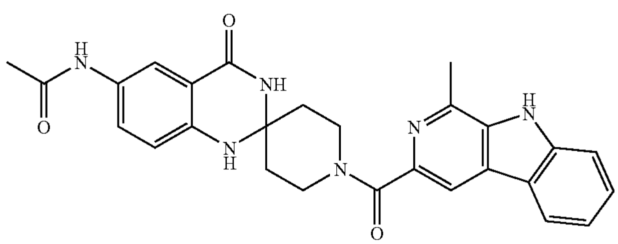 | 6'-Acetamido-1-[(1-methyl-9H-pyrido[3,4-b]indol-3-yl)carbonyl]spiro[piperidine-4,2'(1'H)-quinazolin]-4'-(3'H)-one; |
| 86 | 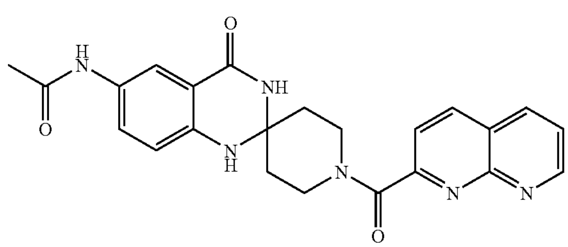 | 6'-Acetamido-1-[(pyrido[2,3-b]pyridin-2-yl)carbonyl]spiro[piperidine-4,2'(1'H)-quinazolin]-4'-(3'H)-one; |
| 87 | 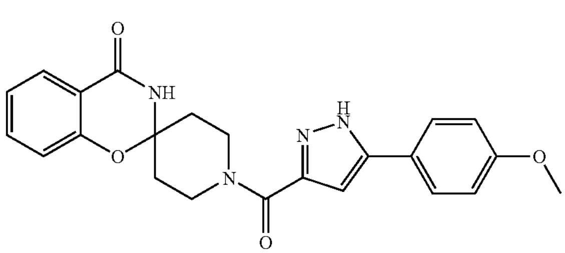 | 1'-[5-(4-Methoxyphenyl)-1(H)-pyrazol-3-ylcarbonyl]spiro[2H-1,3-benzoxazin-2,4'-piperidin]-4-(3H)-one; |

-continued

| Compound Number | Structure | Name |
|---|---|---|
| 88 | 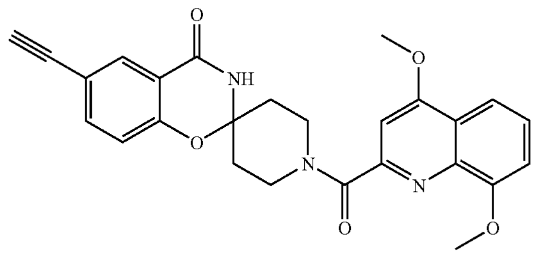 | 1'-[4,8-Dimethoxyquinolin-2-yl)carbonyl]-4-oxo-spiro[2H-1,3-benzoxazin-2,4'-piperidin]-6-ylacetylene; |
| 89 | 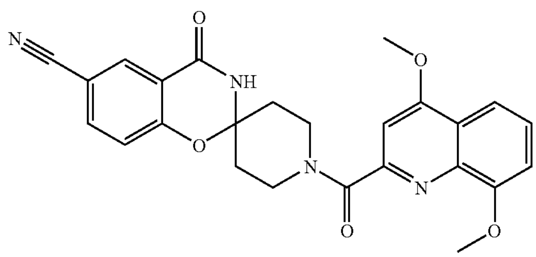 | 1'-[4,8-Dimethoxyquinolin-2-yl)carbonyl]-4-oxo-spiro[2H-1,3-benzoxazin-2,4'-piperidin]-6-ylcarbonitrile; |
| 90 | 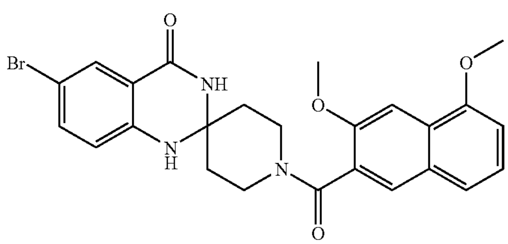 | 6'-Bromo-1-[3,5-dimethoxynaphth-2-yl)carbonyl]spiro[piperidine-4,2'(1'H)-quinazolin]-4'-(3'H)-one; |
| 91 | 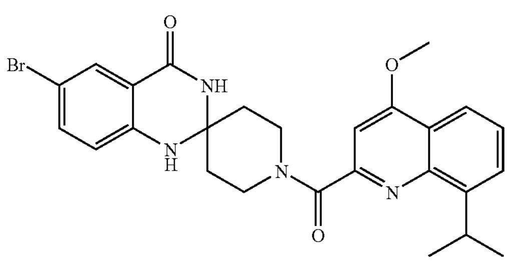 | 6'-Bromo-1-[8-isopropyl-4-methoxyquinolin-2-yl)carbonyl]spiro[piperidine-4,2'(1'H)-quinazolin]-4'-(3'H)-one; |
| 92 | 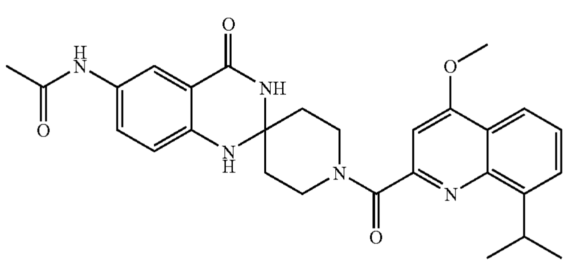 | 6'-Acetamido-1-[8-isopropyl-4-methoxyquinolin-2-yl)carbonyl]spiro[piperidine-4,2'(1'H)-quinazolin]-4'-(3'H)-one; |
| 93 | 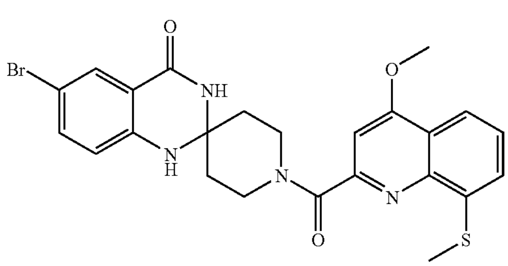 | 6'-Bromo-1-[4-methoxy-8-methylthioquinolin-2-yl)carbonyl]spiro[piperidine-4,2'(1'H)-quinazolin]-4'-(3'H)-one; |

| Compound Number | Structure | Name |
|---|---|---|
| 94 | 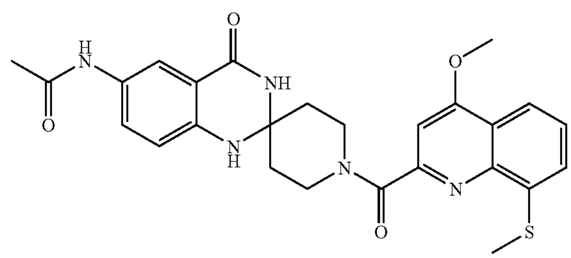 | 6'-Acetamido-1-[4-methoxy-8-methylthioquinolin-2-yl)carbonyl]spiro[piperidine-4,2'(1'H)-quinazolin]-4'-(3'H)-one; |
| 95 | 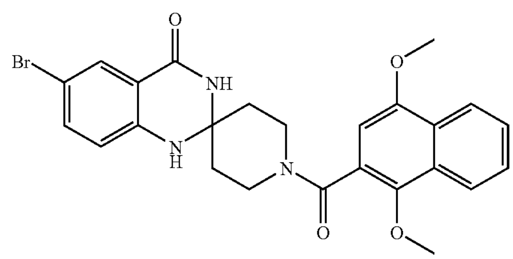 | 6'-Bromo-1-[1,4-dimethoxynaphth-2-yl)carbonyl]spiro[piperidine-4,2'(1'H)-quinazolin]-4'-(3'H)-one; |
| 96 | 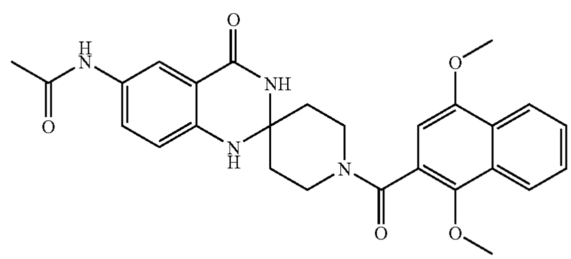 | 6'-Acetamido-1-[1,4-dimethoxynaphth-2-yl)carbonyl]spiro[piperidine-4,2'(1'H)-quinazolin]-4'-(3'H)-one; |
| 97 | 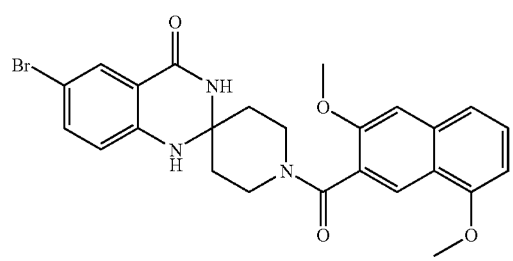 | 6'-Bromo-1-[3,8-dimethoxynaphth-2-yl)carbonyl]spiro[piperidine-4,2'(1'H)-quinazolin]-4'-(3'H)-one; |
| 98 | 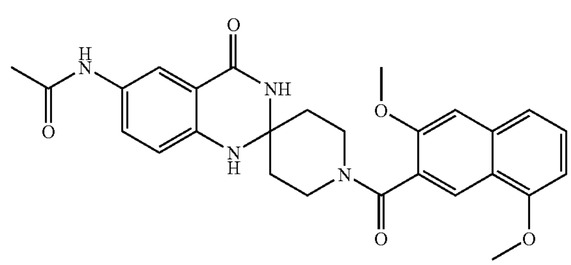 | 6'-Acetamido-1-[3,8-dimethoxynaphth-2-yl)carbonyl]spiro[piperidine-4,2'(1'H)-quinazolin]-4'-(3'H)-one; |
| 99 | 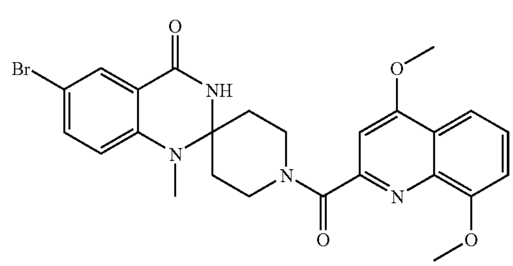 | 6'-Bromo-1-[4,8-dimethoxyquinolin-2-yl)carbonyl]-1'-methylspiro[piperidine-4,2'(1'H)-quinazolin]-4'-(3'H)-one; |

-continued

| Compound Number | Structure | Name |
|---|---|---|
| 100 | 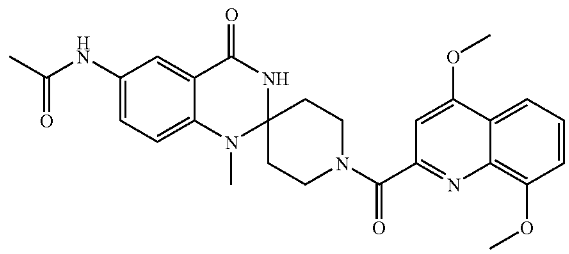 | 6'-Acetamido-1-[4,8-dimethoxyquinolin-2-yl)carbonyl]-1'-methylspiro[piperidine-4,2'(1'H)-quinazolin]-4'-(3'H)-one; |
| 101 | 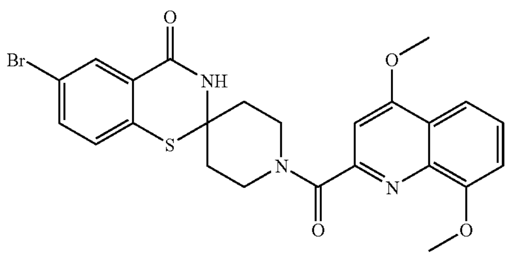 | 6-Bromo-1'-[4,8-dimethoxyquinolin-2-yl)carbonyl]spiro[2H-1,3-benzthiazin-2,4'-piperidin]-4-(3H)-one; |
| 102 | 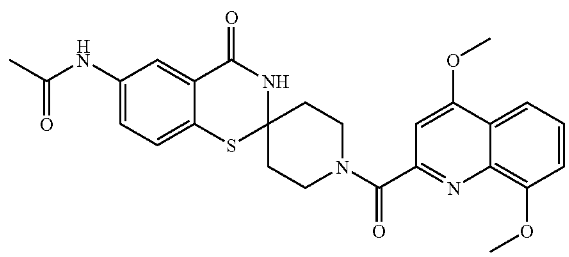 | 6-Acetamido-1'-[4,8-dimethoxyquinolin-2-yl)carbonyl]spiro[2H-1,3-benzthiazin-2,4'-piperidin]-4-(3H)-one; |
| 103 | 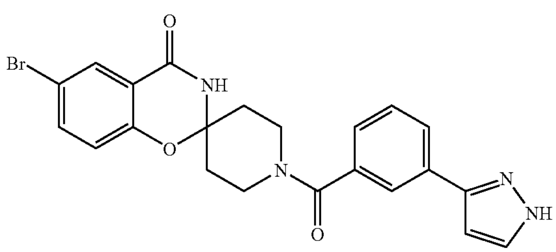 | 6-Bromo-1'-[3-(1H-pyrazol-3-yl)benzoyl]spiro[2H-1,3-benzoxazin-2,4'-piperidin]-4-(3H)-one; |
| 104 | 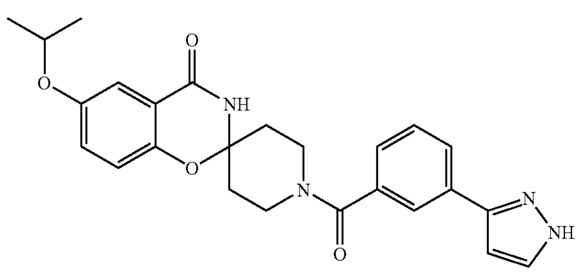 | 6-Isopropoxy-1'-[3-(1H-pyrazol-3-yl)benzoyl]spiro[2H-1,3-benzoxazin-2,4'-piperidin]-4-(3H)-one; |
| 105 | 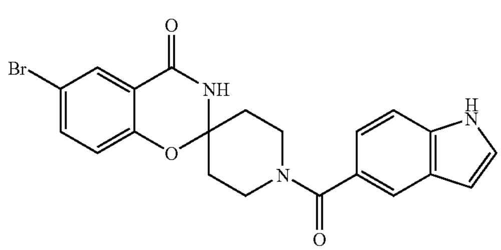 | 6-Bromo-1'-[(1H-indol-5-yl)carbonyl]spiro[2H-1,3-benzoxazin-2,4'-piperidin]-4-(3H)-one; |

| Compound Number | Structure | Name |
|---|---|---|
| 106 | 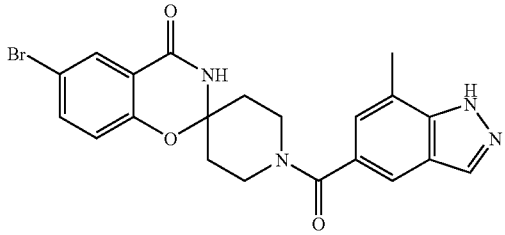 | 6-Bromo-1'-[(7-methyl-1H-indazol-5-yl)carbonyl]spiro[2H-1,3-benzoxazin-2,4'-piperidin]-4-(3H)-one; |
| 107 | 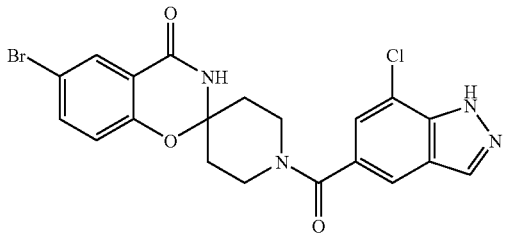 | 6-Bromo-1'-[(7-chloro-1H-indazol-5-yl)carbonyl]spiro[2H-1,3-benzoxazin-2,4'-piperidin]-4-(3H)-one; |
| 108 | 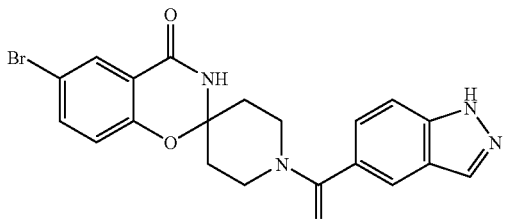 | 6-Bromo-1'-[(1H-indazol-5-yl)carbonyl]spiro[2H-1,3-benzoxazin-2,4'-piperidin]-4-(3H)-one; |
| 109 | 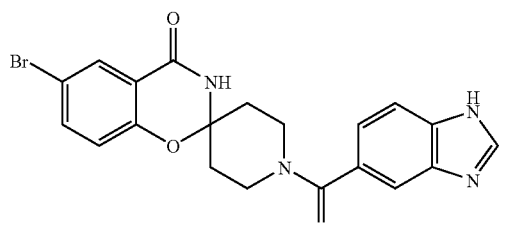 | 1'-[(1H-benzimidazol-5-yl)carbonyl]-6-bromospiro[2H-1,3-benzoxazin-2,4'-piperidin]-4-(3H)-one; |
| 110 | 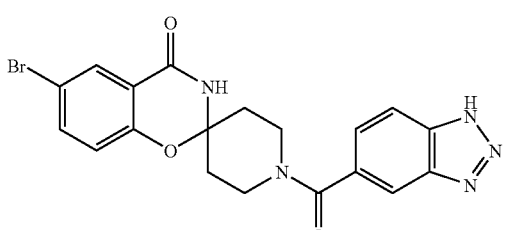 | 1'-[(1H-benzotriazol-5-yl)carbonyl]-6-bromospiro[2H-1,3-benzoxazin-2, 4'-piperidin]-4-(3H)-one; |
| 111 | 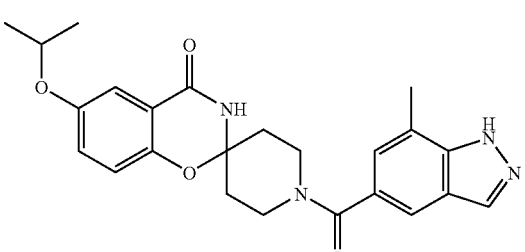 | 6-Isopropoxy-1'-[(7-methyl-1H-indazol-5-yl)carbonyl]spiro[2H-1,3-benzoxazin-2,4'-piperidin]-4-(3H)-one; |

-continued

| Compound Number | Structure | Name |
|---|---|---|
| 112 | 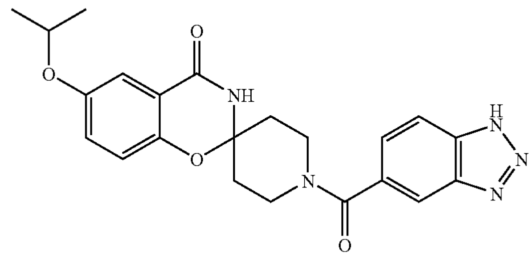 | 1'-[(1H-Benzotriazol-5-yl)carbonyl]-6-isopropoxyspiro[2H-1,3-benzoxazin-2,4'-piperidin]-4-(3H)-one; |
| 113 | 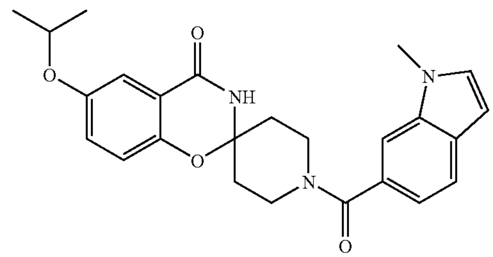 | 6-Isopropoxy-1'-[(1-methyl-1H-indol-6-yl)carbonyl]spiro[2H-1,3-benzoxazin-2,4'-piperidin]-4-(3H)-one; |
| 114 | 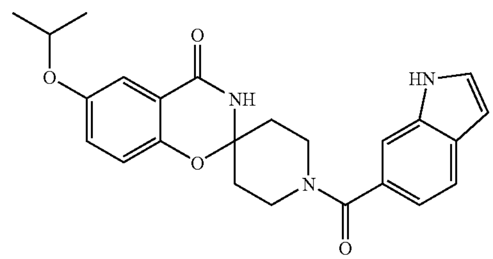 | 6-Isopropoxy-1'-[(1-methyl-1H-indol-6-yl)carbonyl]spiro[2H-1,3-benzoxazin-2,4'-piperidin]-4-(3H)-one; |
| 115 | 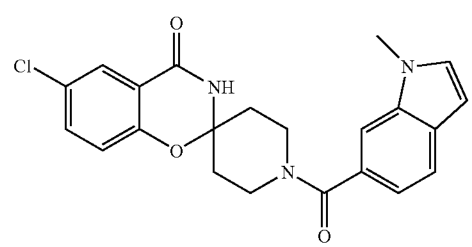 | 6-Chloro-1'-[(1-methyl-1H-indol-6-yl)carbonyl]spiro[2H-1,3-benzoxazin-2,4'-piperidin]-4-(3H)-one; |
| 116 | 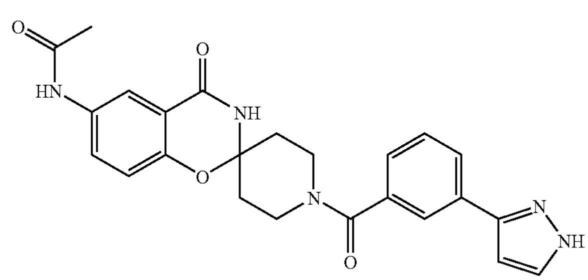 | 6-Acetamido-1'-[3-(1H-pyrazol-3-yl)benzoyl]spiro[2H-1,3-benzoxazin-2,4'-piperidin]-4-(3H)-one; |
| 117 | 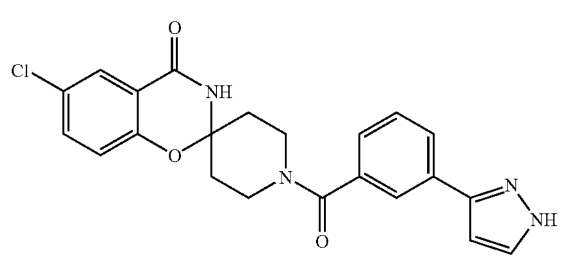 | 6-Chloro-1'-[3-(1H-pyrazol-3-yl)benzoyl]spiro[2H-1,3-benzoxazin-2,4'-piperidin]-4-(3H)-one; |

-continued

| Compound Number | Structure | Name |
|---|---|---|
| 118 | 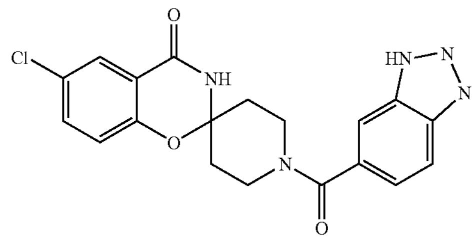 | 1'-[(1H-Benzotriazol-6-yl)carbonyl]-6-chlorospiro[2H-1,3-benzoxazin-2,4'-piperidin]-4-(3H)-one; |
| 119 | 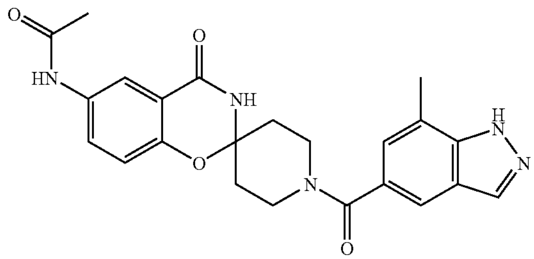 | 6-Acetamido-1'-[(7-methyl-1H-indazol-5-yl)carbonyl]spiro[2H-1,3-benzoxazin-2,4'-piperidin]-4-(3H)-one; |
| 120 | 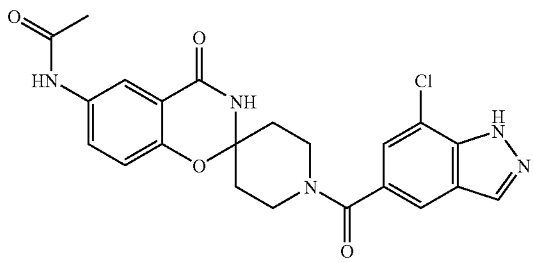 | 6-Acetamido-1'-[(7-chloro-1H-indazol-5-yl)carbonyl]spiro[2H-1,3-benzoxazin-2,4'-piperidin]-4-(3H)-one; |
| 121 | 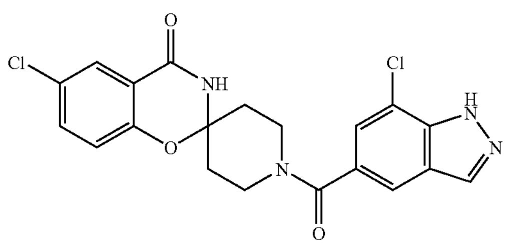 | 6-Chloro-1'-[(7-chloro-1H-indazol-5-yl)carbonyl]spiro[2H-1,3-benzoxazin-2,4'-piperidin]-4-(3H)-one; |
| 122 | 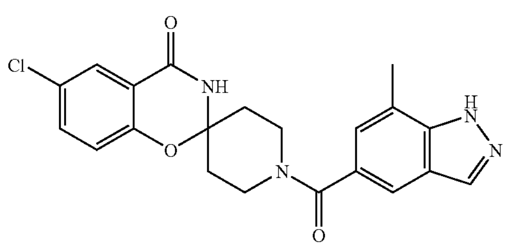 | 6-Chloro-1'-[(7-methyl-1H-indazol-5-yl)carbonyl]spiro[2H-1,3-benzoxazin-2,4'-piperidin]-4-(3H)-one; |
| 123 | 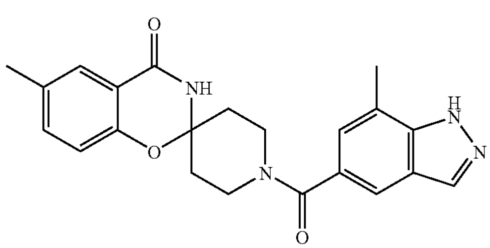 | 6-Methyl-1'-[(7-methyl-1H-indazol-5-yl)carbonyl]spiro[2H-1,3-benzoxazin-2,4'-piperidin]-4-(3H)-one; |

-continued

| Compound Number | Structure | Name |
|---|---|---|
| 124 | 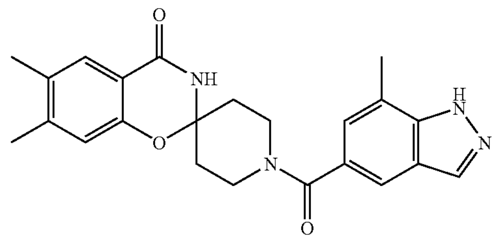 | 6,7-Dimethyl-1'-[(7-methyl-1H-indazol-5-yl)carbonyl]spiro[2H-1,3-benzoxazin-2,4'-piperidin]-4-(3H)-one; |
| 125 | 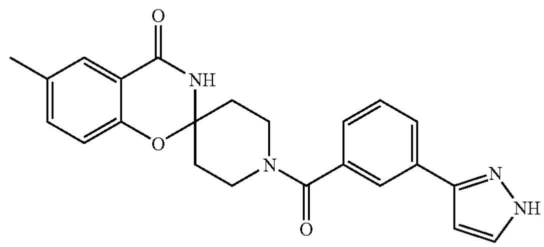 | 6-Methyl-1'-[3-(1H-pyrazol-3-yl)benzoyl]spiro[2H-1,3-benzoxazin-2,4'-piperidin]-4-(3H)-one; |
| 126 | 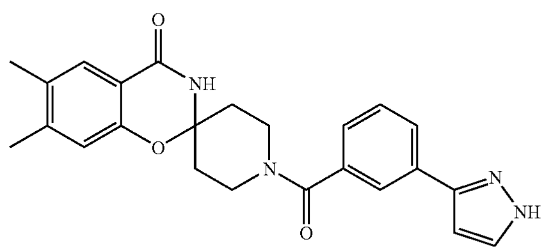 | 6,7-Dimethyl-1'-[3-(1H-pyrazol-3-yl)benzoyl]spiro[2H-1,3-benzoxazin-2,4'-piperidin]-4-(3H)-one; |
| 127 | 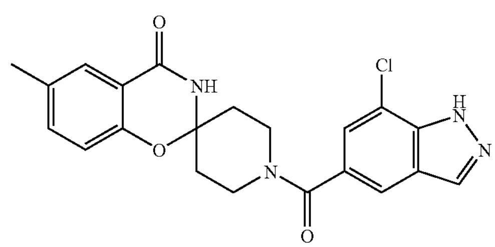 | 1'-[(7-Chloro-1H-indazol-5-yl)carbonyl]-6-methylspiro[2H-1,3-benzoxazin-2,4'-piperidin]-4-(3H)-one; |
| 128 | 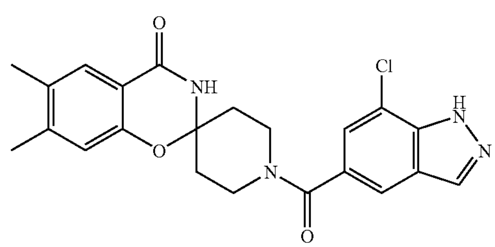 | 1'-[(7-Chloro-1H-indazol-5-yl)carbonyl]-6,7-dimethylspiro[2H-1,3-benzoxazin-2,4'-piperidin]-4-(3H)-one; |
| 129 | 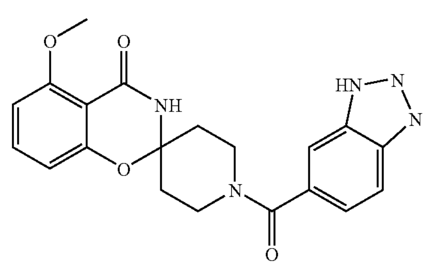 | 1'-[(1H-Benzotriazol-6-yl)carbonyl]-5-methoxyspiro[2H-1,3-benzoxazin-2,4'-piperidin]-4-(3H)-one; |

-continued

| Compound Number | Structure | Name |
|---|---|---|
| 130 | 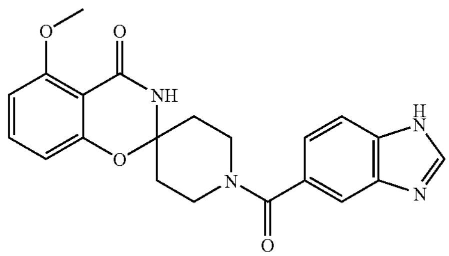 | 1'-[(1H-Benzimidazol-5-yl)carbonyl]-5-methoxyspiro[2H-1,3-benzoxazin-2,4'-piperidin]-4-(3H)-one; |
| 131 | 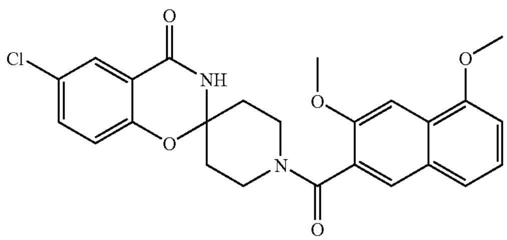 | 6-Chloro-1'-[(3,5-dimethoxynaphth-2-yl)carbonyl]spiro[2H-1,3-benzoxazin-2,4'-piperidin]-4-(3H)-one; |
| 132 | 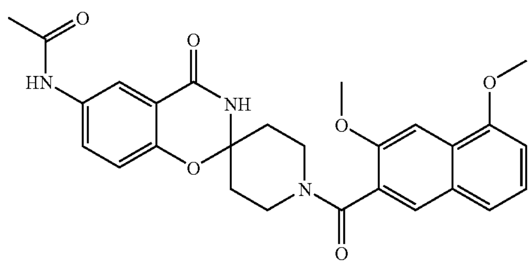 | 6-Acetamido-1'-[(3,5-dimethoxynaphth-2-yl)carbonyl]spiro[2H-1,3-benzoxazin-2,4'-piperidin]-4-(3H)-one; |
| 133 | 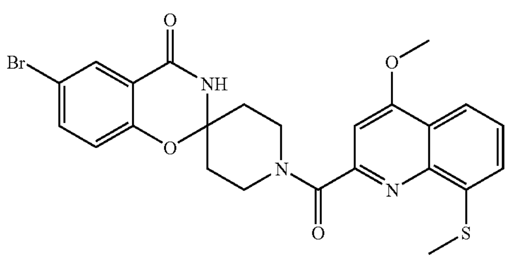 | 6-Bromo-1'-[4-methoxy-8methylthioquinolin-2-yl)carbonyl]spiro[2H-1,3-benzoxazin-2,4'-piperidin]-4-(3H)-one; |
| 134 | 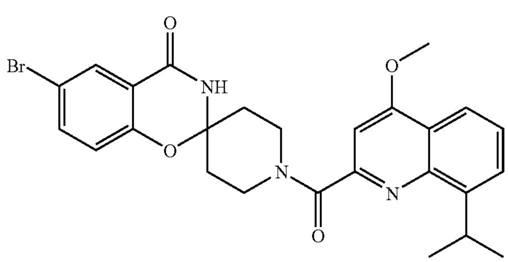 | 6-Bromo-1'-[8-isopropyl-4-methoxyquinolin-2-yl)carbonyl]spiro[2H-1,3-benzoxazin-2,4'-piperidin]-4-(3H)-one; |
| 135 | 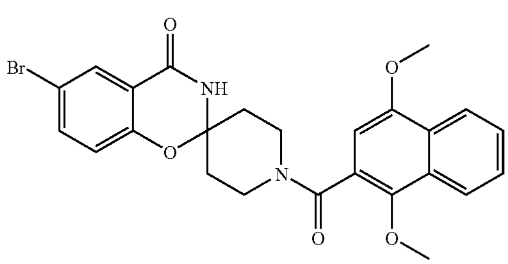 | 6-Bromo-1'-[1,4-dimethoxynaphth-2-yl)carbonyl]spiro[2H-1,3-benzoxazin-2,4'-piperidin]-4-(3H)-one; |

-continued

| Compound Number | Structure | Name |
|---|---|---|
| 136 | 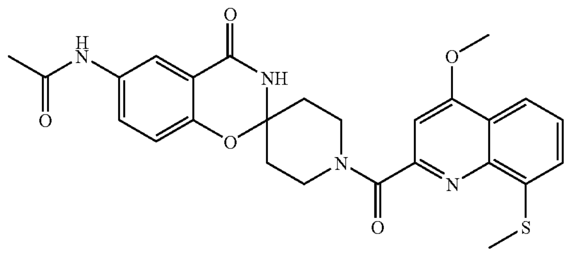 | 6-Acetamido-1'-[4-methoxy-8-methylthioquinolin-2-yl)carbonyl]spiro[2H-1,3-benzoxazin-2,4'-piperidin]-4-(3H)-one; |
| 137 | 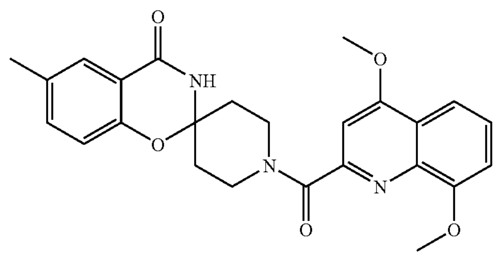 | 1'-[4,8-Dimethoxyquinolin-2-yl)carbonyl]-6-methylspiro[2H-1,3-benzoxazin-2,4'-piperidin]-4-(3H)-one; |
| 138 | 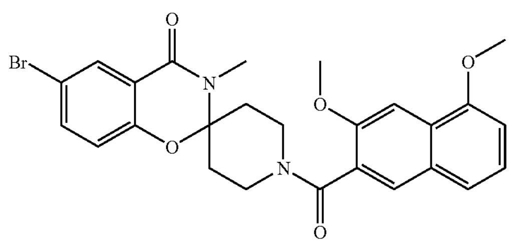 | 6-Bromo-1'-(3,5-dimethoxynaphth-2-yl)carbonyl]-3-methylspiro[2H-1,3-benzoxazin-2,4'-piperidin]-4-(3H)-one; |
| 139 | 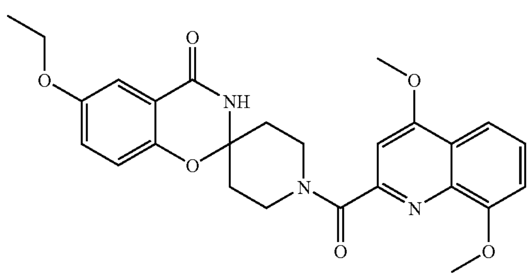 | 1'-[4,8-Dimethoxyquinolin-2-yl)carbonyl]-6-ethoxyspiro[2H-1,3-benzoxazin-2,4'-piperidin]-4-(3H)-one; |
| 140 | 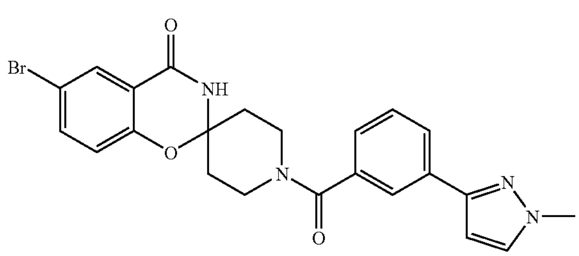 | 6-Bromo-1'-[3-(1-methyl-1H-pyrazol-3-yl)benzoyl]spiro[2H-1,3-benzoxazin-2,4'-piperidin]-4-(3H)-one; |
| 141 | 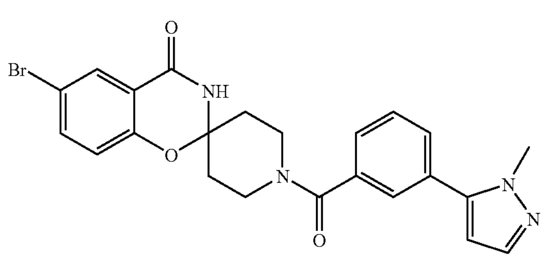 | 6-Bromo-1'-[3-(1-methyl-1H-pyrazol-3-yl)benzoyl]spiro[2H-1,3-benzoxazin-2,4'-piperidin]-4-(3H)-one; |

| Compound Number | Structure | Name |
|---|---|---|
| 142 | 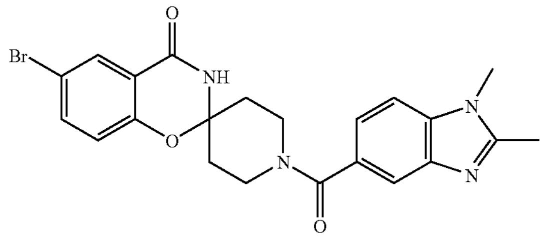 | 6-Bromo-1'-[(1,2-dimethyl-1H-benzimidazol-5-yl)carbonyl]spiro[2H-1,3-benzoxazin-2,4'-piperidin]-4-(3H)-one; |
| 143 | 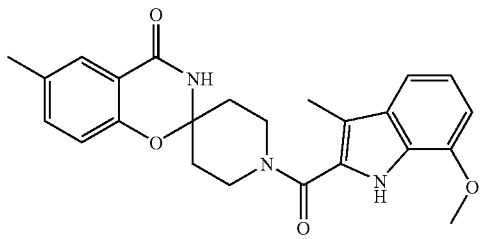 | 1'-[7-Methoxy-3-methyl-1H-indol-2-yl)carbonyl]-6-methylspiro[2H-1,3-benzoxazin-2,4'-piperidin]-4-(3H)-one |
| 144 | 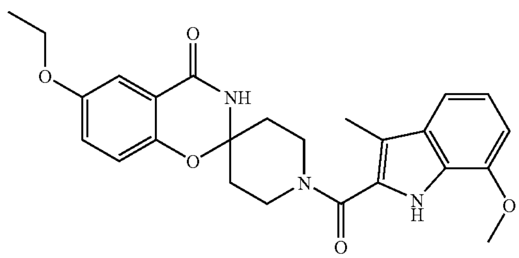 | 6-Ethoxy-1'-[7-methoxy-3-methyl-1H-indol-2-yl)carbonyl]spiro[2H-1,3-benzoxazin-2,4'-piperidin]-4-(3H)-one; |
| 145 | 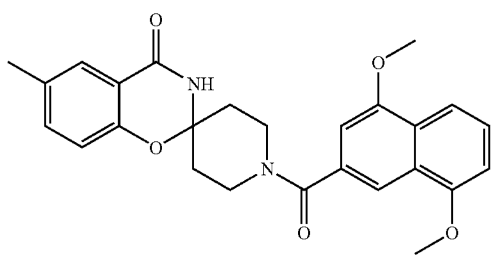 | 1'-[(4,8-Dimethoxynaphth-2-yl)carbonyl]-6-methylspiro[2H-1,3-benzoxazin-2,4'-piperidin]-4-(3H)-one; |
| 146 | 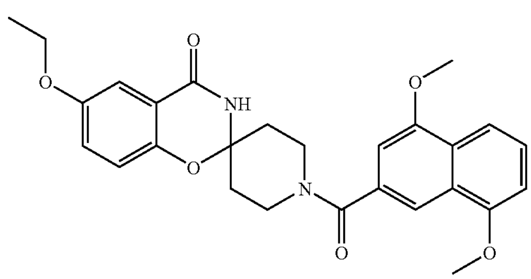 | 1'-[(4,8-Dimethoxynaphth-2-yl)carbonyl]-6-ethoxyspiro[2H-1,3-benzoxazin-2,4'-piperidin]-4-(3H)-one; |
| 147 | 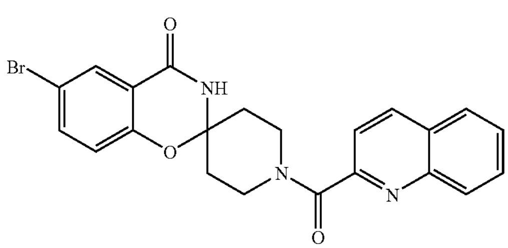 | 6-Bromo-1'-[(quinolin-2-yl)carbonyl]spiro[2H-1,3-benzoxazin-2,4'-piperidin]-4-(3H)-one; |

-continued

| Compound Number | Structure | Name |
|---|---|---|
| 148 | 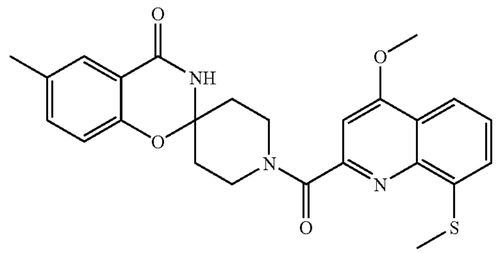 | 1'-[4-Methoxy-8-methylthioquinolin-2-yl)carbonyl]-6-methylspiro[2H-1,3-benzoxazin-2,4'-piperidin]-4-(3H)-one; |
| 149 | 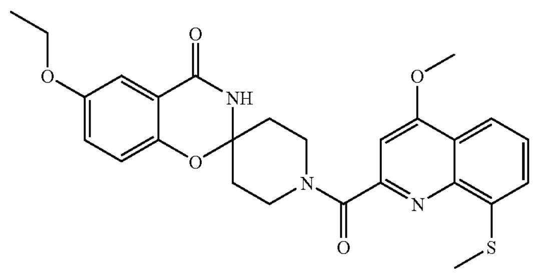 | 6-Ethoxy-1'-[4-methoxy-8-methylthioquinolin-2-yl)carbonyl]spiro[2H-1,3-benzoxazin-2,4'-piperidin]-4-(3H)-one; |
| 150 | 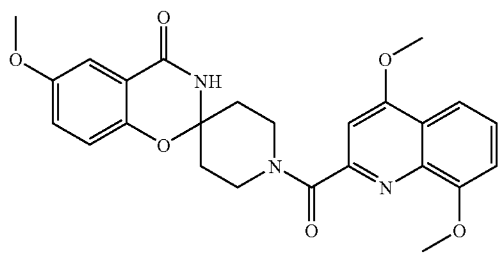 | 1'-[4,8-Dimethoxyquinolin-2-yl)carbonyl]-6-methoxyspiro[2H-1,3-benzoxazin-2,4'-piperidin]-4-(3H)-one; |
| 151 | 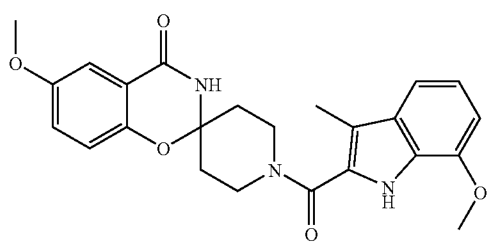 | 6-Methoxy-1'-[7-methoxy-3-methyl-1H-indol-2-yl)carbonyl]spiro[2H-1,3-benzoxazin-2,4'-piperidin]-4-(3H)-one; |
| 152 | 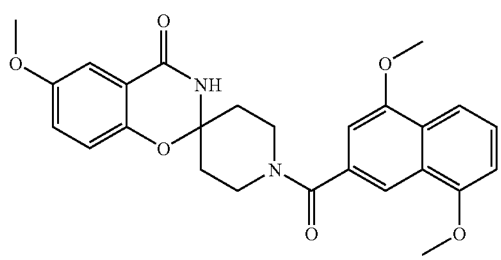 | 1'-[(4,8-Dimethoxynaphth-2-yl)carbonyl]-6-methoxyspiro[2H-1,3-benzoxazin-2,4'-piperidin]-4-(3H)-one; |
| 153 | 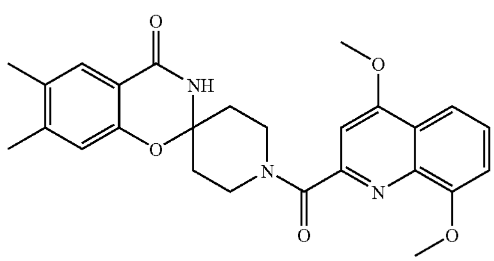 | 1'-[(4,8-Dimethoxyquinolin-2-yl)carbonyl]6,7-dimethylspiro[2H-1,3-benzoxazin-2,4'-piperidin]-4-(3H)-one; |

| Compound Number | Structure | Name |
|---|---|---|
| 154 | 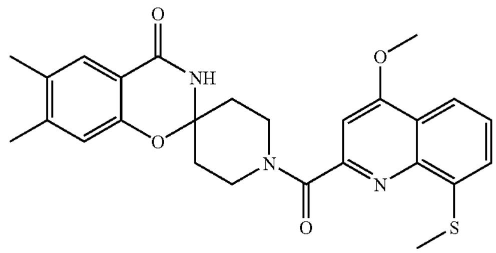 | 6,7-Dimethyl-1'-[4-methoxy-8-methylthioquinolin-2-yl)carbonyl]spiro[2H-1,3-benzoxazin-2,4'-piperidin]-4-(3H)-one; |
| 155 | 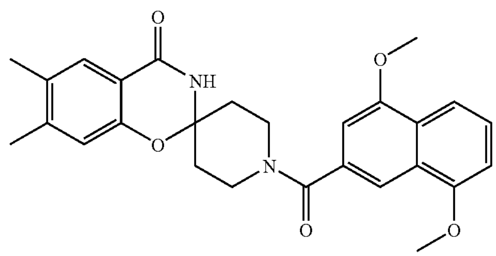 | 1'-[(4,8-Dimethoxynapth-2-yl)carbonyl]6,7-dimethylspiro[2H-1,3-benzoxazin-2,4'-piperidin]-4-(3H)-one; |
| 156 | 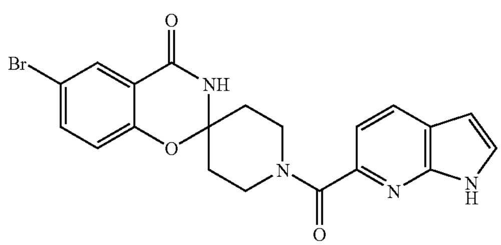 | 6-Bromo-1'-[(7H-pyrrolo[2,3-b]pyridin-2-yl)carbonyl]spiro[2H-1,3-benzoxazin-2,4'-piperidin]-4-(3H)-one; |
| 157 | 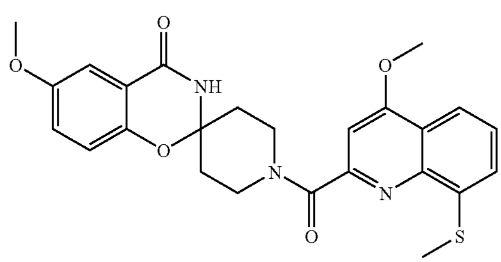 | 6-Methoxy-1'-[4-methoxy-8-methylthioquinolin-2-yl)carbonyl]spiro[2H-1,3-benzoxazin-2,4-piperidin]-4-(3H)-one; |
| 158 | 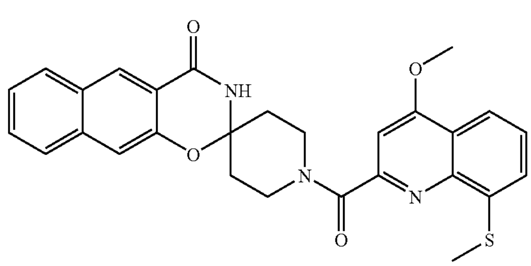 | 1'-[4-methoxy-8-methylthioquinolin-2-yl)carbonyl]spiro[2H-naphtho[2,3-e]-1,3-oxazin-2,4'-piperidin]-4-(3H)-one; |
| 159 | 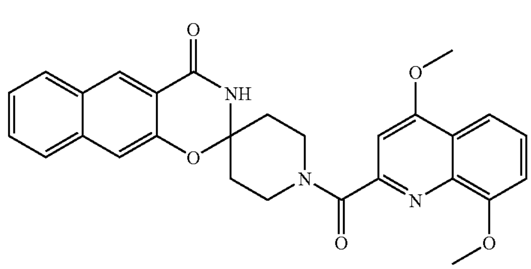 | 1'-[4,8-Dimethoxyquinolin-2-yl)carbonyl]spiro[2H-naphtho[2,3-e]-1,3-oxazin-2,4'-piperidin]-4-(3H)-one; |

| Compound Number | Structure | Name |
|---|---|---|
| 160 | 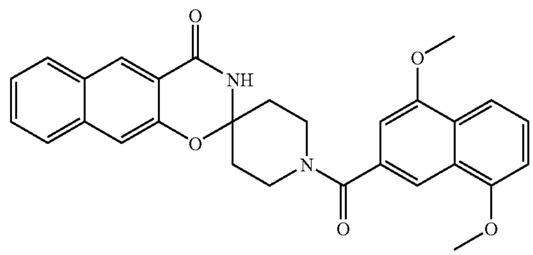 | 1'-[4,8-Dimethoxynaphth-2-yl)carbonyl]spiro[2H-naphtho[2,3-e]-1,3-oxazin-2,4'-piperidin]-4-(3H)-one; |
| 161 | 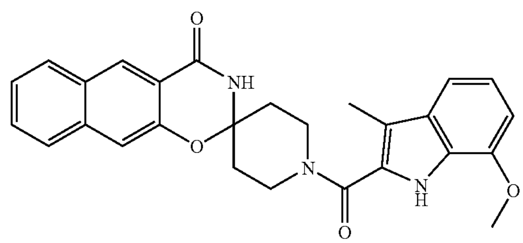 | 1'-[[7-Methoxy-3-methyl-1H-indol-2-yl)carbonyl]spiro[2H-naphtho[2,3-e]-1,3-oxazin-2,4'-piperidin]-4-(3H)-one; |
| 162 | 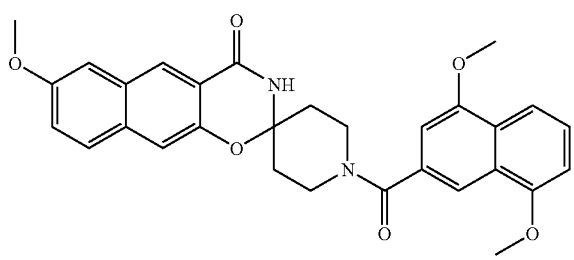 | 1'-[4,8-Dimethoxynaphth-2-yl)carbonyl]-7-methoxyspiro[2H-naphtho[2,3-e]-1,3-oxazin-2,4'-piperidin]-4-(3H)-one; |
| 163 | 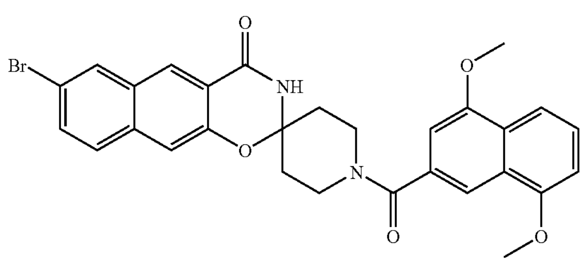 | 7-Bromo-1'-[4,8-Dimethoxynaphth-2-yl)carbonyl]spiro[2H-naphtho[2,3-e]-1,3-oxazin-2,4'-piperidin]-4-(3H)-one; |
| 164 | 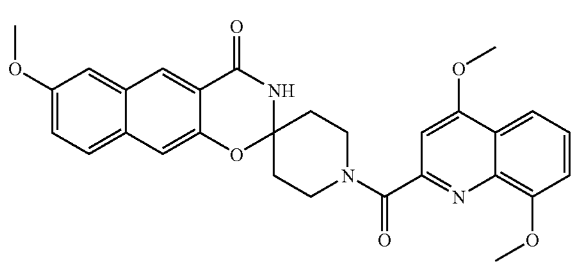 | 1'-[4,8-Dimethoxyquinolin-2-yl)carbonyl]-7-methoxyspiro[2H-naphtho[2,3-e]-1,3-oxazin-2,4'-piperidin]-4-(3H)-one; |
| 165 | 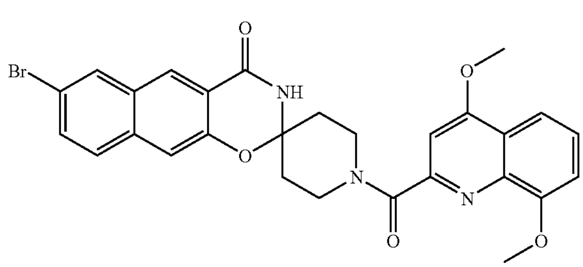 | 7-Bromo-1'-[4,8-Dimethoxyquinolin-2-yl)carbonyl]spiro[2H-naphtho[2,3-e]-1,3-oxazin-2,4'-piperidin]-4-(3H)-one |

-continued

| Compound Number | Structure | Name |
|---|---|---|
| 166 | 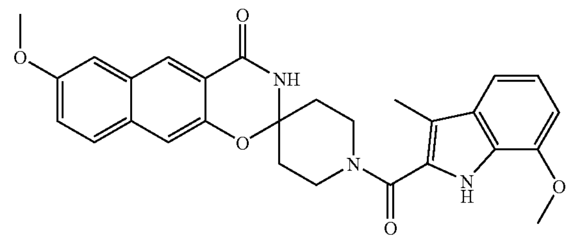 | 7-Methoxy-1'-[[7-methoxy-3-methyl-1H-indol-2-yl)carbonyl]spiro[2H-naphtho[2,3-e]-1,3-oxazin-2,4'-piperidin]-4-(3H)-one |
| 167 | 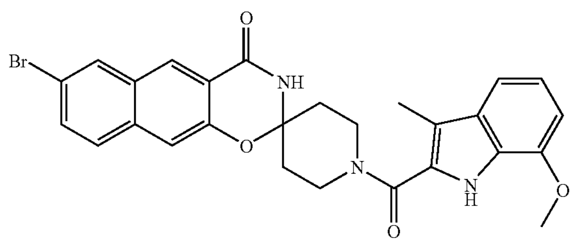 | 7-Bromo-1'-[[7-methoxy-3-methyl-1H-indol-2-yl)carbonyl]spiro[2H-naphtho[2,3-e]-1,3-oxazin-2,4'-piperidin]-4-(3H)-one |
| 168 | 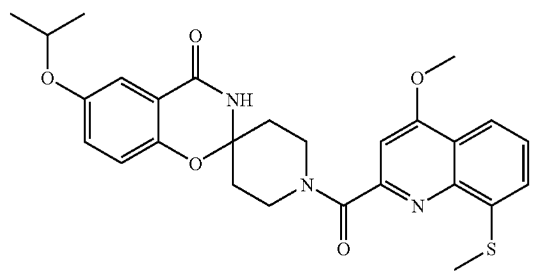 | 6-Isopropoxy-1'-[4-methoxy-8-methylthioquinolin-2-yl)carbonyl]spiro[2H-1,3-benzoxazin-2,4'-piperidin]-4-(3H)-one; |
| 169 | 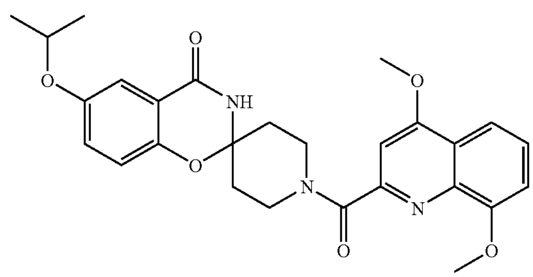 | 1'-[4,8-Dimethoxyquinolin-2-yl)carbonyl]-6-isopropoxyspiro[1,3-benzoxazin-2,4'-piperidin]-4-(3H)-one; |
| 170 | 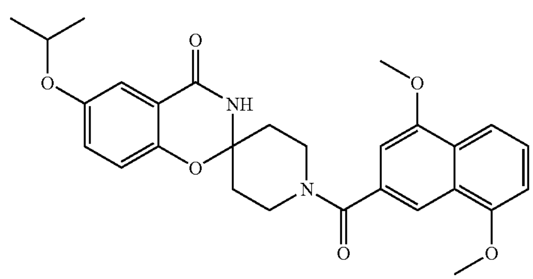 | 1'-[4,8-Dimethoxynapth-2-yl)carbonyl]-6-isopropoxyspiro[1,3-benzoxazin-2,4'-piperidin]-4-(3H)-one; |
| 171 | 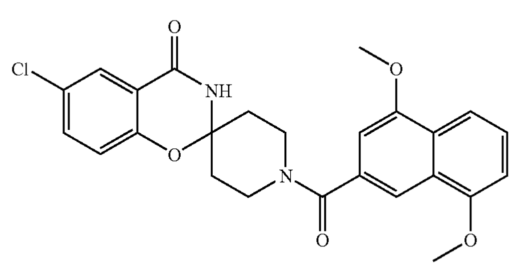 | 6-Chloro-1'-[4,8-dimethoxynaphth-2-yl)carbonyl]spiro[1,3-benzoxazin-2,4'-piperidin]-4-(3H)-one; |

-continued

| Compound Number | Structure | Name |
|---|---|---|
| 172 | 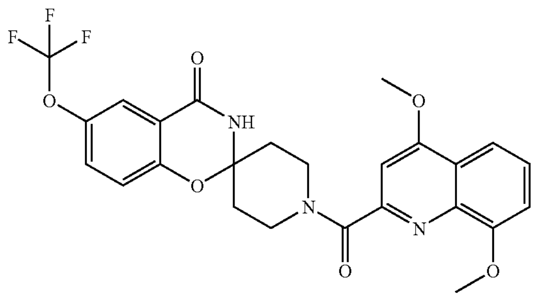 | 1'-[4,8-Dimethoxyquinolin-2-yl)carbonyl]-6-trifluoromethoxyspiro[1,3-benzoxazin-2,4'-piperidin]-4-(3H)-one; |
| 173 | 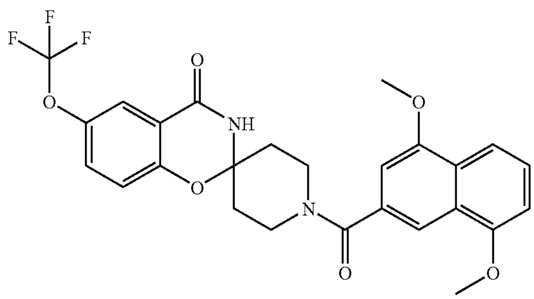 | 1'-[4,8-Dimethoxynaphth-2-yl)carbonyl]-6-trifluoromethoxyspiro[1,3-benzoxazin-2,4'-piperidin]-4-(3H)-one; |
| 174 | 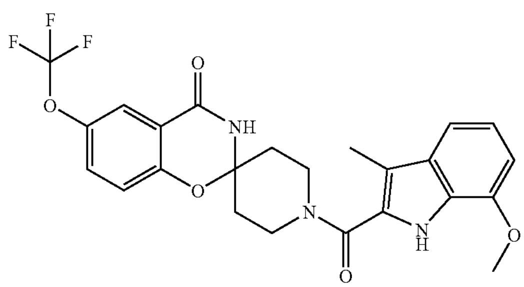 | 1'-[7-Methoxy-3-methyl-1H-indol-2-yl)carbonyl]-6-trifluoromethoxyspiro[1,3-benzoxazin-2,4'-piperidin]-4-(3H)-one; |
| 175 | 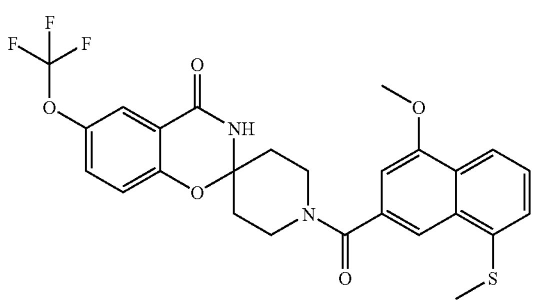 | 1'-[4-Methoxy-8-methylthionaphth-2-yl)carbonyl]-6-trifluoromethoxyspiro[1,3-benzoxazin-2,4'-piperidin]-4-(3H)-one; |
| 176 | 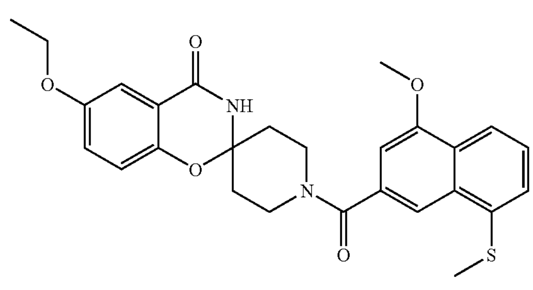 | 6-Ethoxy-1'-[4-methoxy-8-methylthionaphth-2-yl)carbonyl]spiro[1,3-benzoxazin-2,4'-piperidin]-4-(3H)-one; |

| Compound Number | Structure | Name |
|---|---|---|
| 177 | 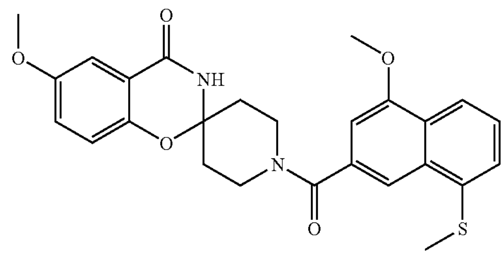 | 6-Methoxy-1'-[4-methoxy-8-methylthionaphth-2-yl)carbonyl]spiro[1,3-benzoxazin-2,4'-piperidin]-4-(3H)-one; |
| 178 | 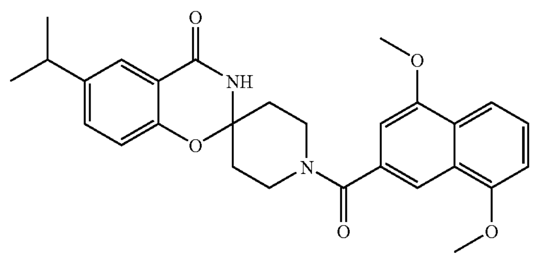 | 1'-[4,8-Dimethoxynaphth-2-yl)carbonyl]-6-isopropylspiro[1,3-benzoxazin-2,4'-piperidin]-4-(3H)-one; |
| 179 | 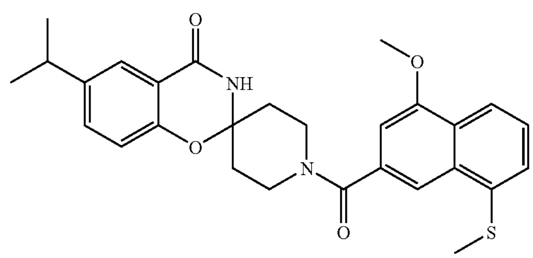 | 6-Isopropyl-1'-[4-methoxy-8-methylthionaphth-2-yl)carbonyl]spiro[1,3-benzoxazin-2,4'-piperidin]-4-(3H)-one; |
| 180 | 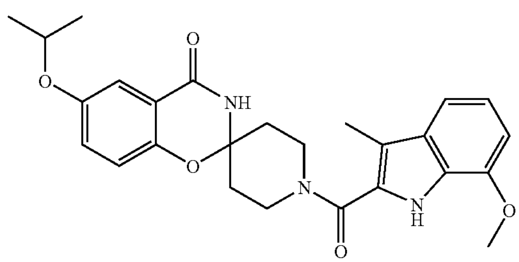 | 6-Isopropoxy-1'-[7-methoxy-3-methyl-1H-indol-2-yl)carbonyl]spiro[1,3-benzoxazin-2,4'-piperidin]-4-(3H)-one; |
| 181 | 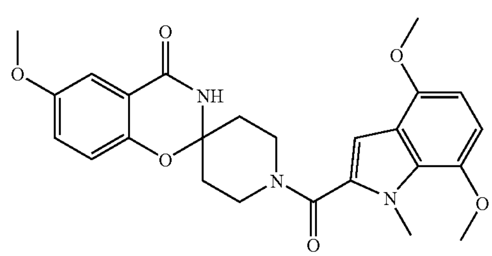 | 1'-[4,7-Dimethoxy-1-methyl-1H-indol-2-yl)carbonyl]-6-methoxy-spiro[1,3-benzoxazin-2,4'-piperidin]-4-(3H)-one; |
| 182 | 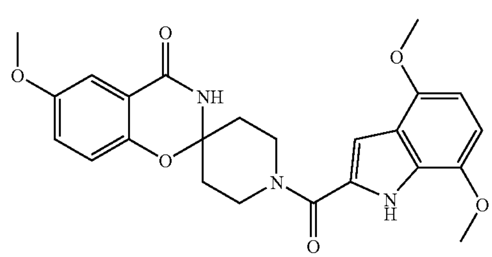 | 1'-[4,7-Dimethoxy-1H-indol-2-yl)carbonyl]-6-methoxy-spiro[1,3-benzoxazin-2,4'-piperidin]-4-(3H)-one; |

-continued

| Compound Number | Structure | Name |
|---|---|---|
| 183 | 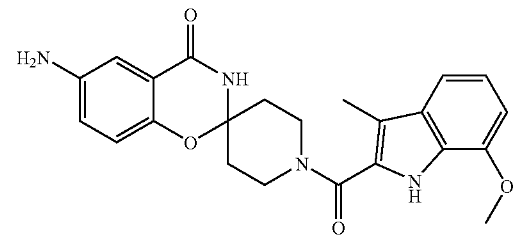 | 6-Amino-1'-[7-methoxy-3-methyl-1H-indol-2-yl)carbonyl]spiro[1,3-benzoxazin-2,4'-piperidin]-4-(3H)-one; |
| 184 | 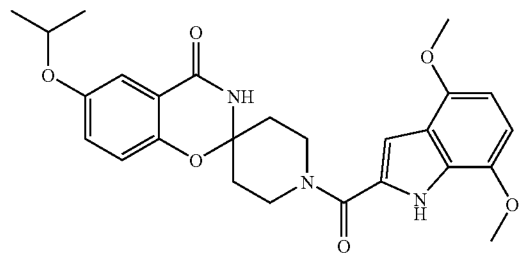 | 1'-[4,7-Dimethoxy-1H-indol-2-yl)carbonyl]-6-isopropoxy-spiro[1,3-benzoxazin-2,4'-piperidin]-4-(3H)-one; |
| 185 | 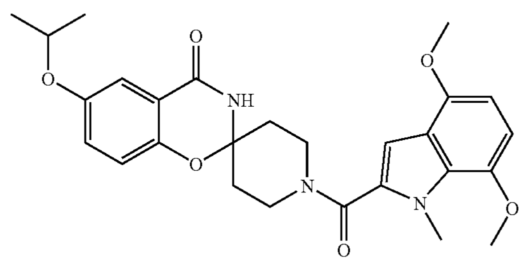 | 1'-[4,7-Dimethoxy-1-methyl-1H-indol-2-yl)carbonyl]-6-isopropoxy-spiro[1,3-benzoxazin-2,4'-piperidin]-4-(3H)-one; |
| 186 | 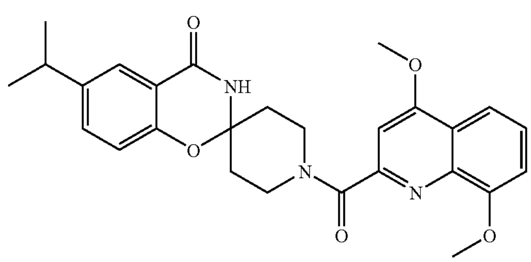 | 1'-[4,8-Dimethoxyquinolin-2-yl)carbonyl]-6-isopropylspiro[1,3-benzoxazin-2,4'-piperidin]-4-(3H)-one; |
| 187 | 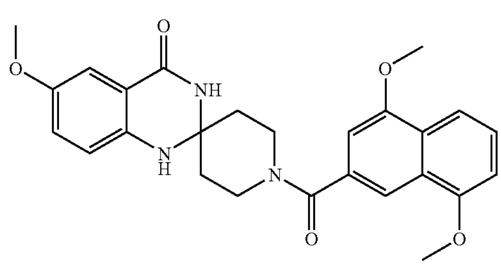 | 1-[4,8-Dimethoxynaphth-2-yl)carbonyl]-6'-methoxyspiro[piperidine-4,2'(1'H)-quinazolin]-4'-(3'H)-one; |
| 188 | 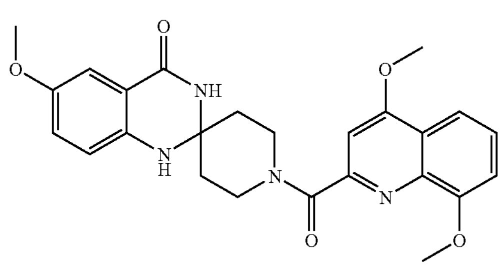 | 1-[4,8-Dimethoxyquinolin-2-yl)carbonyl]-6'-methoxyspiro[piperidine-4,2'(1'H)-quinazolin]-4'-(3'H)-one; |

-continued

| Compound Number | Structure | Name |
|---|---|---|
| 189 | 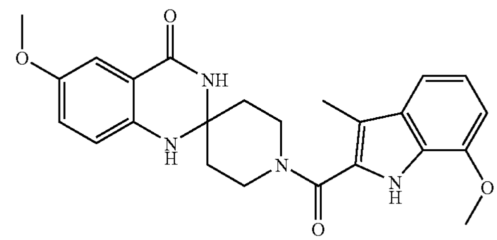 | 6'-Methoxy-1-[[7-methoxy-3-methyl-1H-indol-2-yl)carbonyl]spiro[piperidine-4,2'(1'H)-quinazolin]-4'-(3'H)-one; |
| 190 | 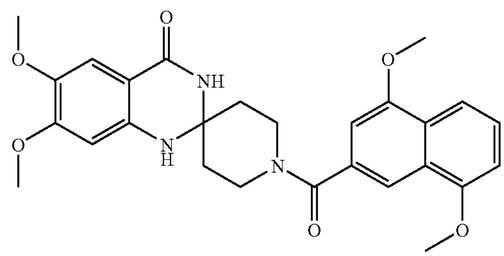 | 6',7'-Dimethoxy-1-[4,8-dimethoxynaphth-2-yl)carbonyl]spiro[piperidine-4,2'(1'H)-quinazolin]-4'-(3'H)-one; |
| 191 | 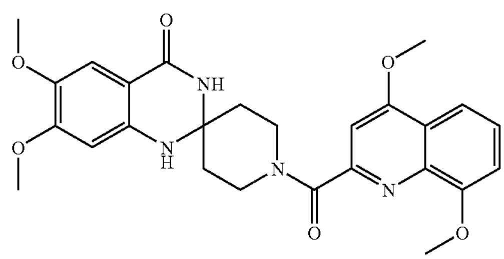 | 6',7'-Dimethoxy-1-[4,8-dimethoxyquinolin-2-yl)carbonyl]spiro[piperidine-4,2'(1'H)-quinazolin]-4'-(3'H)-one; |
| 192 | 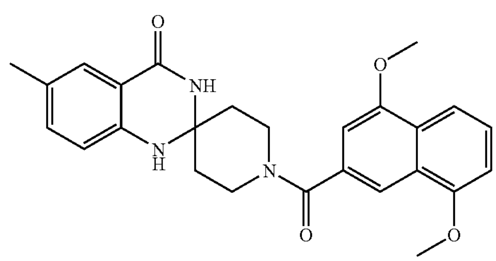 | 1-[4,8-Dimethoxynaphth-2-yl)carbonyl]-6'-methylspiro[piperidine-4,2'(1'H)-quinazolin]-4'-(3'H)-one; |
| 193 | 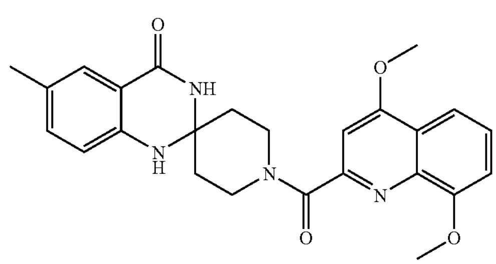 | 1-[4,8-dimethoxyquinolin-2-yl)carbonyl]-6'-methylspiro[piperidine-4,2'(1'H)-quinazolin]-4'-(3'H)-one; |
| 194 | 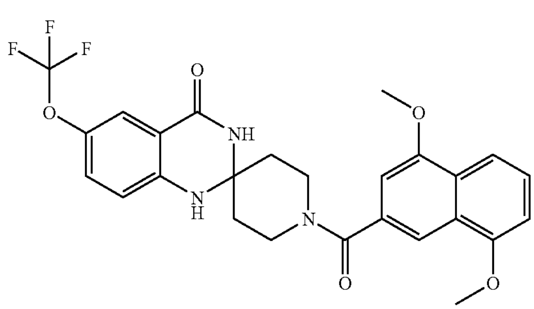 | 1-[4,8-Dimethoxynaphth-2-yl)carbonyl]-6'-trifluoromethoxyspiro[piperidine-4,2'(1'H)-quinazolin]-4'-(3'H)-one; |

| Compound Number | Structure | Name |
|---|---|---|
| 195 | 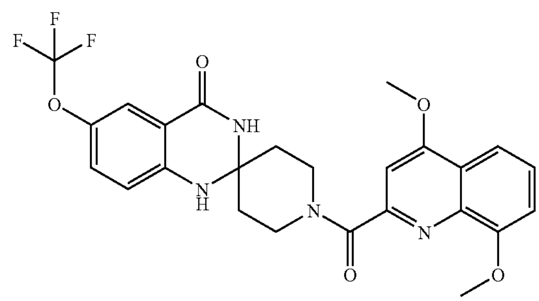 | 1-[4,8-Dimethoxyquinolin-2-yl)carbonyl]-6'-trifluoromethoxyspiro[piperidine-4,2'(1'H)-quinazolin]-4'-(3'H)-one; |
| 196 | 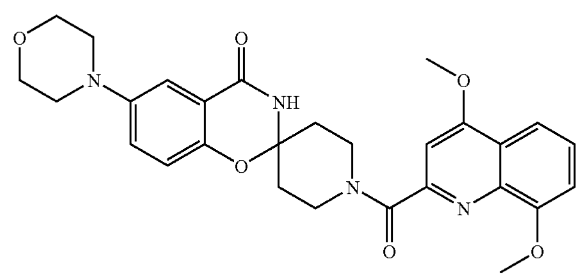 | 1'-[4,8-Dimethoxyquinolin-2-yl)carbonyl]-6-(morpholin-4-yl)spiro[1,3-benzoxazin-2,4'-piperidin]-4-(3H)-one |
| 197 | 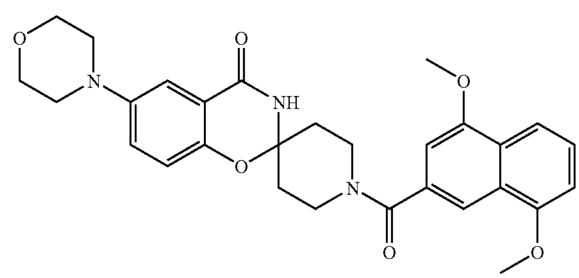 | 1'-[4,8-Dimethoxynaphth-2-yl)carbonyl]-6-(morpholin-4-yl)spiro[1,3-benzoxazin-2,4'-piperidin]-4-(3H)-one |
| 198 | 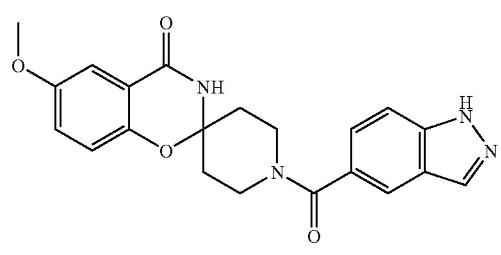 | 1'-[1H-Indazol-5-yl)carbonyl]-6-methoxy-spiro[1,3-benzoxazin-2,4'-piperidin]-4-(3H)-one; |
| 199 | 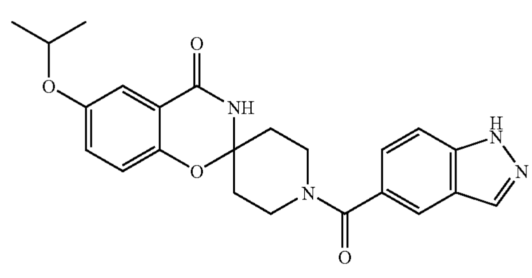 | 1'-[1H-Indazol-5-yl)carbonyl]-6-isopropoxy-spiro[1,3-benzoxazin-2,4'-piperidin]-4-(3H)-one; |

-continued

| Compound Number | Structure | Name |
|---|---|---|
| 200 | 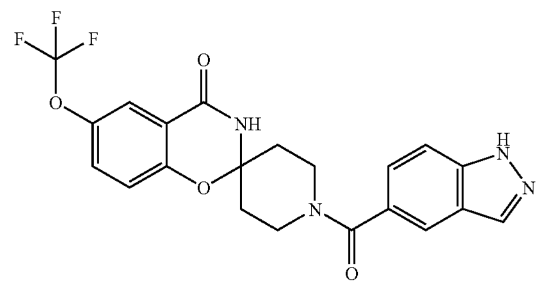 | 1'-[1H-Indazol-5-yl)carbonyl]-6-trifluoromethoxy-spiro[1,3-benzoxazin-2,4'-piperidin]-4-(3H)-one; |
| 201 | 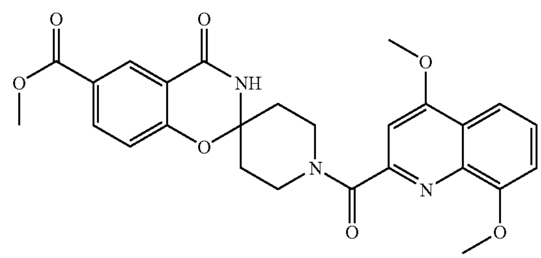 | 1'-[4,8-Dimethoxyquinolin-2-yl)carbonyl]-6-(methoxycarbonyl)spiro[2H-1,3-benzoxazin-2,4'-piperidin]-4-(3H)-one |
| 202 | 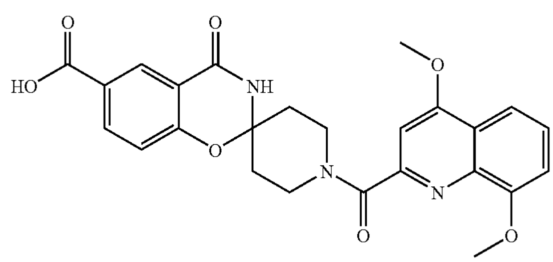 | 6-Carboxy-1'-[4,8-dimethoxyquinolin-2-yl)carbonyl]spiro[2H-1,3-benzoxazin-2,4'-piperidin]-4-(3H)-one; |
| 203 | 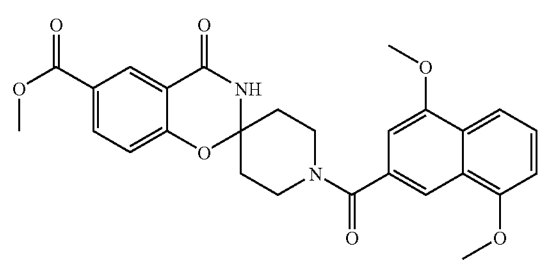 | 1'-[4,8-Dimethoxynaphth-2-yl)carbonyl]-6-(methoxycarbonyl)spiro[2H-1,3-benzoxazin-2,4'-piperidin]-4-(3H)-one; |
| 204 | 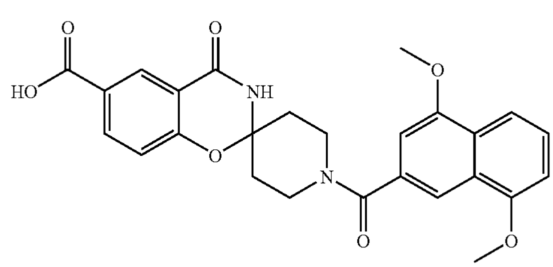 | 6-Carboxy-1'-[4,8-dimethoxynaphth-2-yl)carbonyl]spiro[2H-1,3-benzoxazin-2,4'-piperidin]-4-(3H)-one; |

| Compound Number | Structure | Name |
|---|---|---|
| 205 | 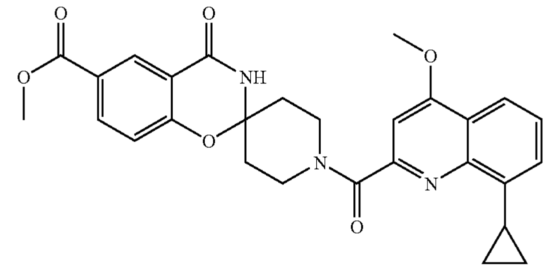 | 1'-[8-Cyclopropyl-4-methoxyquinolin-2-yl)carbonyl]-6-(methoxycarbonyl)spiro[2H-1,3-benzoxazin-2,4'-piperidin]-4-(3H)-one; |
| 206 | 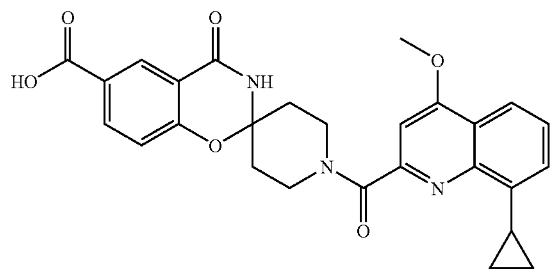 | 6-Carboxy-1'-[8-cyclopropyl-4-methoxyquinolin-2-yl)carbonyl]spiro[2H-1,3-benzoxazin-2,4'-piperidin]-4-(3H)-one |
| 207 | 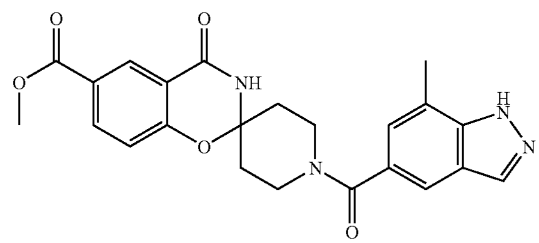 | 6-Methoxycarbonyl-1'-[7-methyl-1H-indazol-5-yl)carbonyl]spiro[1,3-benzoxazin-2,4'-piperidin]-4-(3H)-one; |
| 208 | 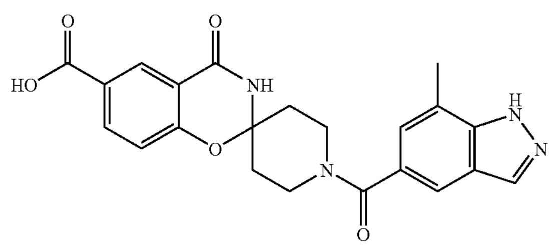 | 6-Carboxy-1'-[7-methyl-1H-indazol-5-yl)carbonyl]spiro[1,3-benzoxazin-2,4'-piperidin]-4-(3H)-one; |
| 209 | 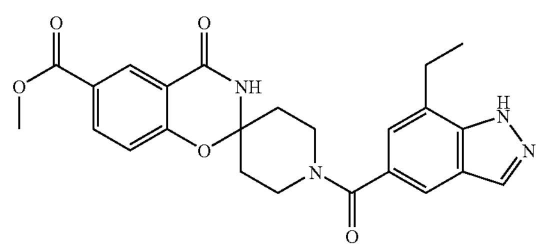 | 1'-[7-Ethyl-1H-indazol-5-yl)carbonyl]-6-(methoxycarbonyl)spiro[1,3-benzoxazin-2,4'-piperidin]-4-(3H)-one; |
| 210 | 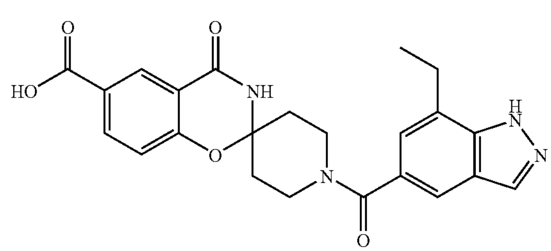 | 6-Carboxy-1'-[7-ethyl-1H-indazol-5-yl)carbonyl]spiro[1,3-benzoxazin-2,4'-piperidin]-4-(3H)-one; |

-continued

| Compound Number | Structure | Name |
|---|---|---|
| 211 | 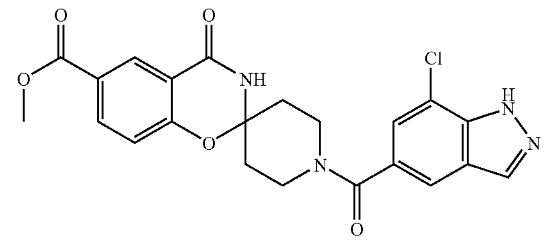 | 1'-[7-Chloro-1H-indazol-5-yl)carbonyl]-6-(methoxycarbonyl)spiro[1,3-benzoxazin-2,4'-piperidin]-4-(3H)-one; |
| 212 | 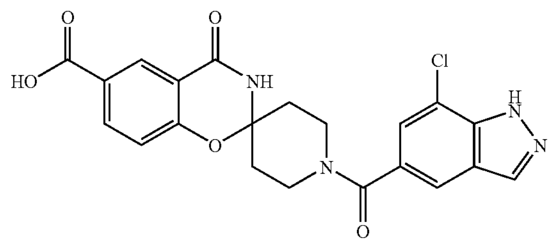 | 6-Carboxy-1'-[7-chloro-1H-indazol-5-yl)carbonyl]spiro[1,3-benzoxazin-2,4'-piperidin]-4-(3H)-one; |
| 213 | 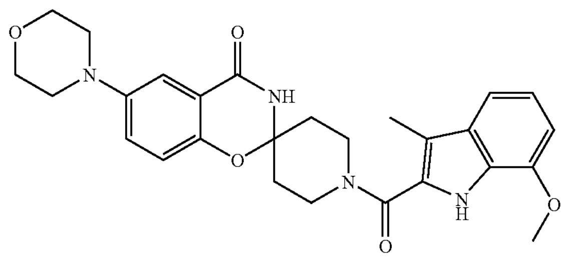 | 1'-[7-Methoxy-3-methyl-1H-indol-2-yl)carbonyl]-6-(morpholin-4-yl)spiro[1,3-benzoxazin-2,4'-piperidin]-4-(3H)-one; |
| 214 | 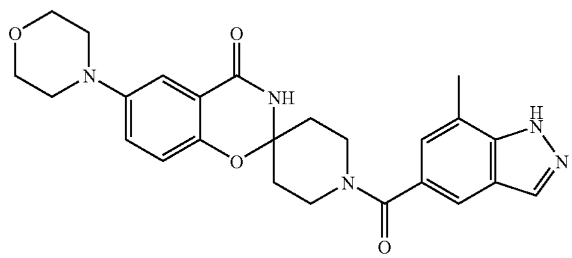 | 1'-[7-Methyl-1H-indazol-5-yl)carbonyl]-6-(morpholin-4-yl)spiro[1,3-benzoxazin-2,4'-piperidin]-4-(3H)-one; |
| 215 | 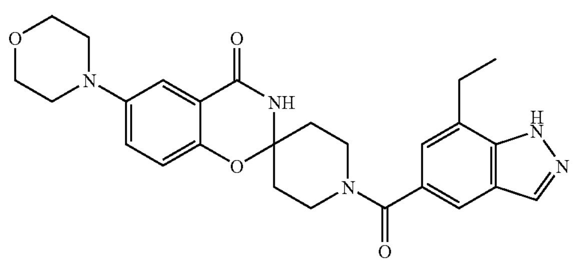 | 1'-[7-Ethyl-1H-indazol-5-yl)carbonyl]-6-(morpholin-4-yl)spiro[1,3-benzoxazin-2,4'-piperidin]-4-(3H)-one; |
| 216 | 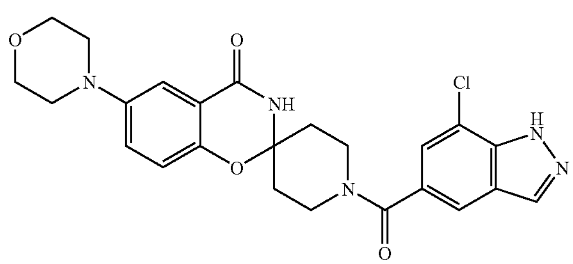 | 1'-[7-Chloro-1H-indazol-5-yl)carbonyl]-6-(morpholin-4-yl)spiro[1,3-benzoxazin-2,4'-piperidin]-4-(3H)-one; |

| Compound Number | Structure | Name |
|---|---|---|
| 217 | 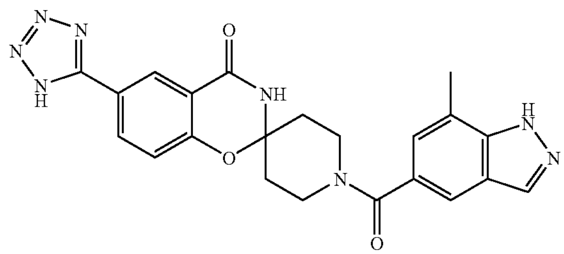 | 1'-[7-Methyl-1H-indazol-5-yl)carbonyl]-6-(1H-tetrazol-5-yl)spiro[2H-1,3-benzoxazin-2,4'-piperidin]-4-(3H)-one; |
| 218 | 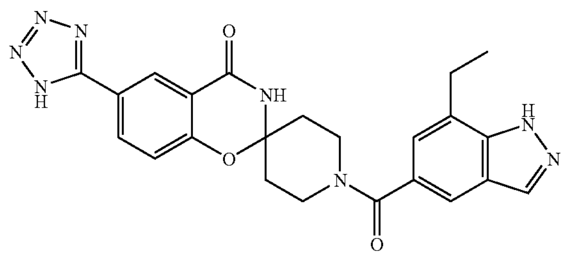 | 1'-[7-Ethyl-1H-indazol-5-yl)carbonyl]-6-(1H-tetrazol-5-yl)spiro[2H-1,3-benzoxazin-2,4'-piperidin]-4-(3H)-one; |
| 219 | 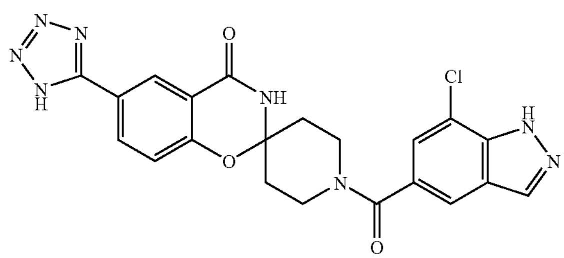 | 1'-[7-Chloro-1H-indazol-5-yl)carbOnyl]-6-(1H-tetrazol-5-yl)spiro[2H-1,3-benzoxazin-2,4'-piperidin]-4-(3H)-one; |
| 220 | 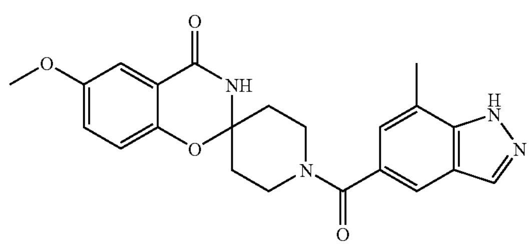 | 6-Methoxy-1'-[(7-methyl-1H-indazol-5-yl)carbonyl]spiro[2H-1,3-benzoxazin-2 4'-piperidin]-4-(3H)-one; |
| 221 | 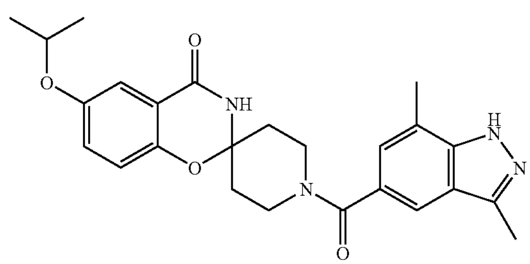 | 1'-[(3,7-Dimethyl-1H-indazol-5-yl)carbonyl]6-isopropoxyspiro[2H-1,3-benzoxazin-2,4'-piperidin]-4-(3H)-one; |
| 222 | 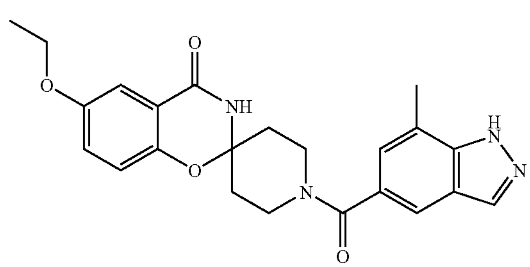 | 6-Ethoxy-1'-[(7-methyl-1H-indazol-5-yl)carbonyl]spiro[2H-1,3-benzoxazin-2,4'-piperidin]-4-(3H)-one; |

-continued

| Compound Number | Structure | Name |
|---|---|---|
| 223 | 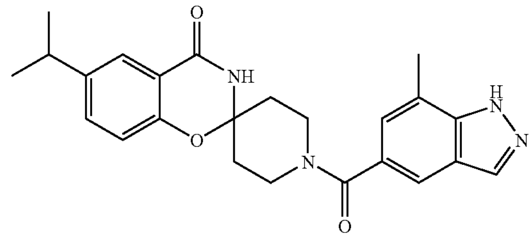 | 6-Isopropyl-1'-[(7-methyl-1H-indazol-5-yl)carbonyl]spiro[2H-1,3-benzoxazin-2,4'-piperidin]-4-(3H)-one; |
| 224 | 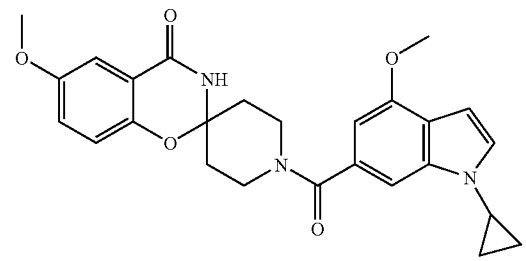 | 1'-[(1-Cyclopropyl-4-methoxy-1H-indol-6-yl)carbonyl]-6-methoxyspiro[2H-1,3-benzoxazin-2,4'-piperidin]-4-(3H)-one; |
| 225 | 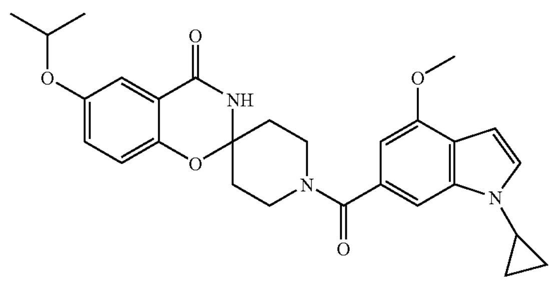 | 1'-[(1-Cyclopropyl-4-methoxy-1H-indol-6-yl)carbonyl]-6-isopropoxyspiro[2H-1,3-benzoxazin-2,4'-piperidin]-4-(3H)-one; |
| 226 | 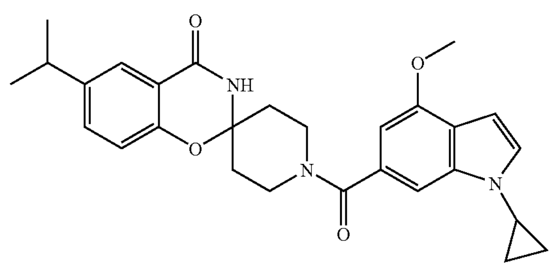 | 1'-[(1-Cyclopropyl-4-methoxy-1H-indol-6-yl)carbonyl]-6-isopropylspiro[2H-1,3-benzoxazin-2,4'-piperidin]-4-(3H)-one; |
| 227 | 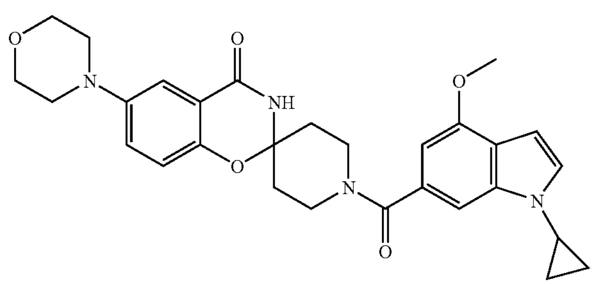 | 1'-[(1-Cyclopropyl-4-methoxy-1H-indol-6-yl)carbonyl]-6-(morpholin-4-yl)spiro[2H-1,3-benzoxazin-2,4'-piperidin]-4-(3H)-one; |

| Compound Number | Structure | Name |
|---|---|---|
| 228 | 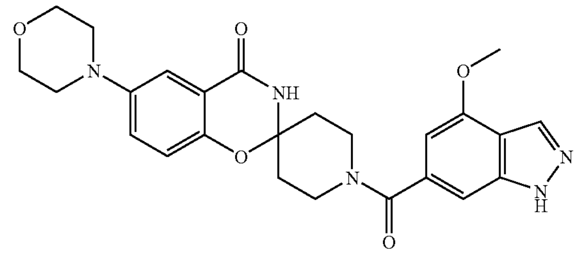 | 1'-[4-Methoxy-1H-indazol-6-yl)carbonyl]-6-(morpholin-4-yl)spiro[1,3-benzoxazin-2,4'-piperidin]-4-(3H)-one; |
| 229 | 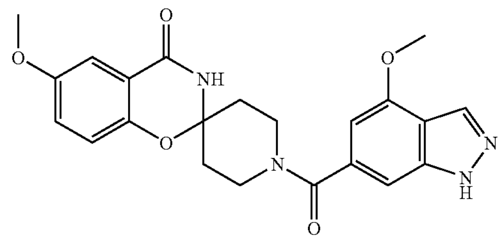 | 6-Methoxy-1'-[4-methoxy-1H-indazol-6-yl)carbonyl]spiro[1,3-benzoxazin-2,4'-piperidin]-4-(3H)-one; |
| 230 | 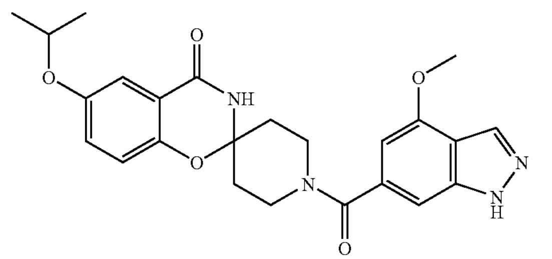 | 6-Isopropoxy-1'-[4-methoxy-1H-indazol-6-yl)carbonyl]spiro[1,3-benzoxazin-2,4'-piperidin]-4-(3H)-one; |
| 231 | 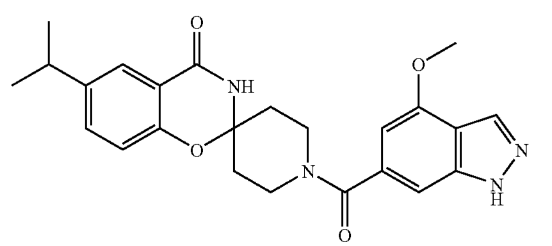 | 6-Isopropyl-1'-[4-methoxy-1H-indazol-6-yl)carbonyl]spiro[1,3-benzoxazin-2,4'-piperidin]-4-(3H)-one; |
| 232 | 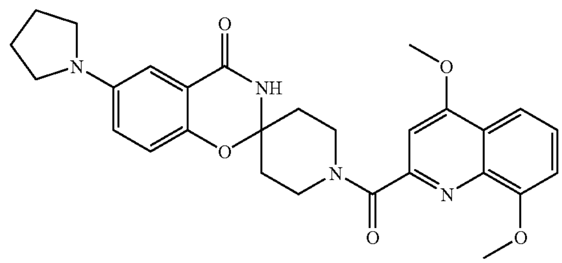 | 1'-[4,8-Dimethoxyquinolin-2-yl)carbonyl]-6-(pyrrolidin-1-yl)spiro[1,3-benzoxazin-2,4'-piperidin]-4-(3H)-one; |
| 233 | 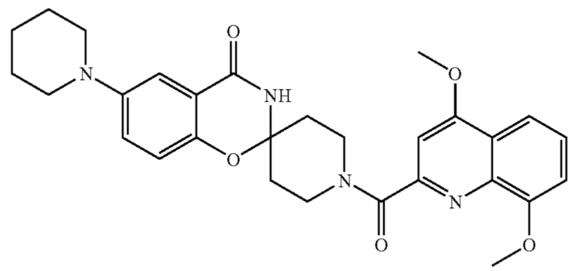 | 1'-[4,8-Dimethoxyquinolin-2-yl)carbonyl]-6-(piperidin-1-yl)spiro[1,3-benzoxazin-2,4'-piperidin]-4-(3H)-one; |

-continued

| Compound Number | Structure | Name |
|---|---|---|
| 234 | 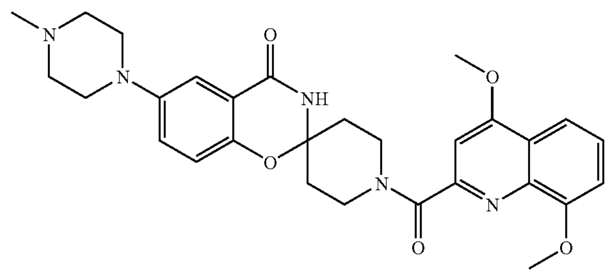 | 1'-[4,8-Dimethoxyquinolin-2-yl)carbonyl]-6-(4-methylpiperazin-1-yl)spiro[1,3-benzoxazin-2,4'-piperidin]-4-(3H)-one; |
| 235 | 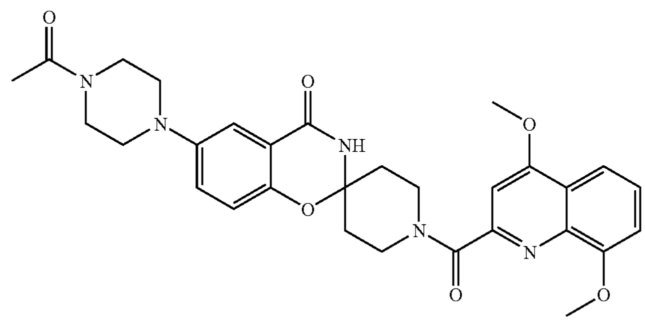 | 1'-[4,8-Dimethoxyquinolin-2-yl)carbonyl]-6-(4-acetylpiperazin-1-yl)spiro[1,3-benzoxazin-2,4'-piperidin]-4-(3H)-one; |
| 236 | 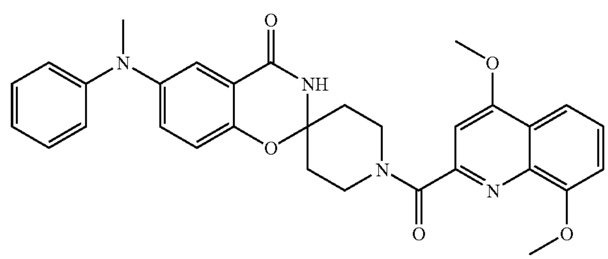 | 1'-[4,8-Dimethoxyquinolin-2-yl)carbonyl]-6-(N-methylanilino)spiro[1,3-benzoxazin-2,4'-piperidin]-4-(3H)-one; |
| 237 | 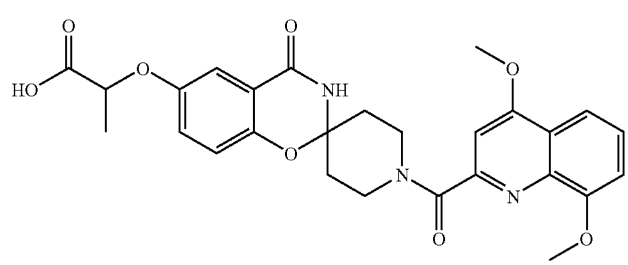 | 2-{-1'-[4,8-Dimethoxyquinolin-2-yl)carbonyl]-4-oxo-spiro[2H-1,3-benzoxazin-2,4'-piperidin]-6-yl}-2-propanoic acid; |
| 238 | 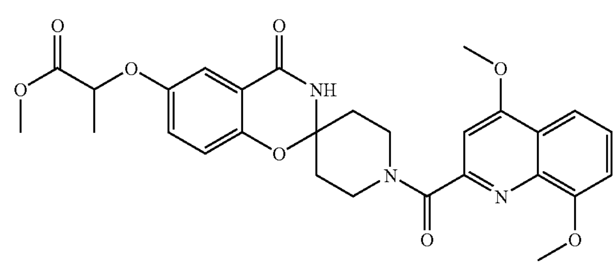 | Methyl 2-{-1'-14, 8-dimethoxyquinolin-2-yl)carbonyl]-4-oxo-spiro[2H-1,3-benzoxazin-2,4'-piperidin]-6-yl}-2-propanoate; |

-continued

| Compound Number | Structure | Name |
|---|---|---|
| 239 | 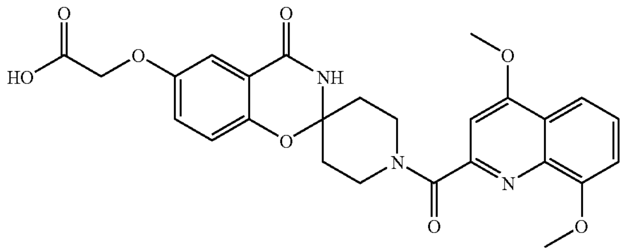 | 2-{-1'-[4,8-Dimethoxyquinolin-2-yl)carbonyl]-4-oxo-spiro[2H-1,3-benzoxazin-2,4'-piperidin]-6-yl}-2-acetic acid; |
| 240 | 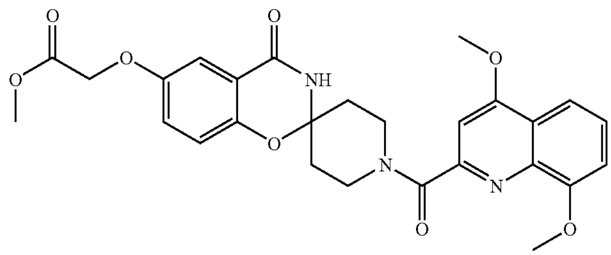 | Methyl 2-{-1'-[4,8-dimethoxyquinolin-2-yl)carbonyl]-4-oxo-spiro[2H-1,3-benzoxazin-2,4'-piperidin]-6-yl}-2-acetate; |
| 241 | 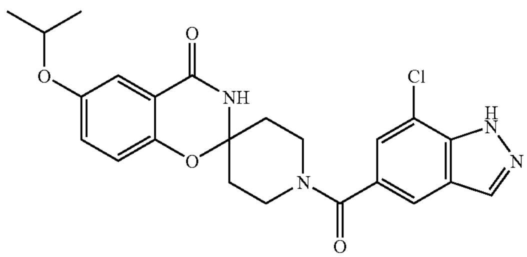 | 1'-[(7-Chloro-1H-indazol-5-yl)carbonyl]-6-isopropoxyspiro[2H-1,3-benzoxazin-2,4'-piperidin]-4-(3H)-one |
| 242 | 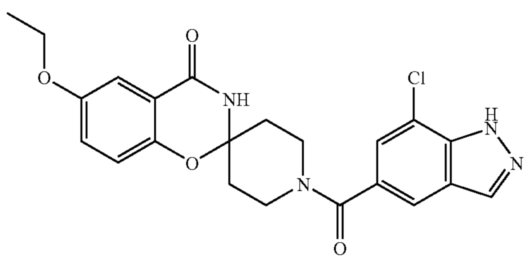 | 1'-[(7-Chloro-1H-indazol-5-yl)carbonyl]-6-ethoxyspiro[2H-1,3-benzoxazin-2,4'-piperidin]-4-(3H)-one; |
| 243 | 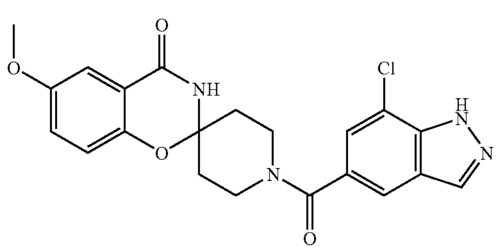 | 1'-[(7-Chloro-1H-indazol-5-yl)carbonyl]-6-methoxyspiro[2H-1,3-benzoxazin-2,4'-piperidin]-4-(3H)-one; |
| 244 | 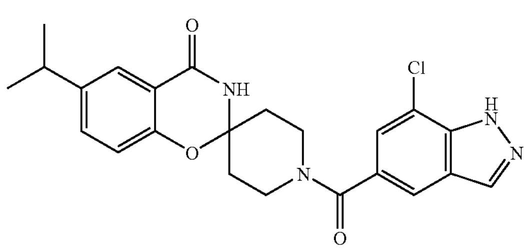 | 1'-[(7-Chloro-1H-indazol-5-yl)carbonyl]-6-isopropylspiro[2H-1,3-benzoxazin-2,4'-piperidin]-4-(3H)-one; |

-continued

| Compound Number | Structure | Name |
|---|---|---|
| 245 | 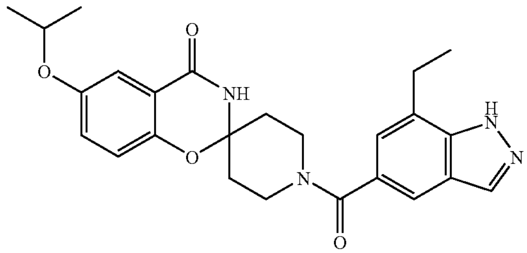 | 1'-[7-Ethyl-1H-indazol-5-yl)carbonyl]-6-isopropoxyspiro[1,3-benzoxazin-2,4'-piperidin]-4-(3H)-one; |
| 246 | 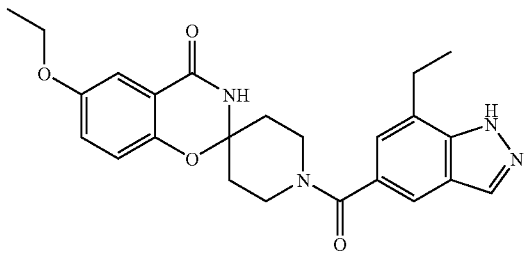 | 6-Ethoxy-1'-[7-ethyl-1H-indazol-5-yl)carbonyl]spiro[1,3-benzoxazin-2,4'-piperidin]-4-(3H)-one; |
| 247 | 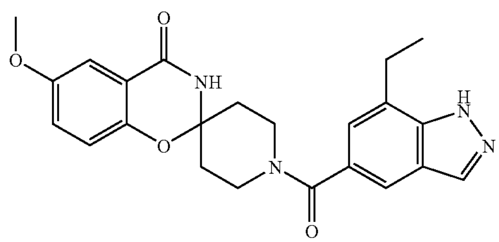 | 1'-[7-Ethyl-1H-indazol-5-yl)carbonyl]-6-methoxyspiro[1,3-benzoxazin-2,4'-piperidin]-4-(3H)-one; |
| 248 | 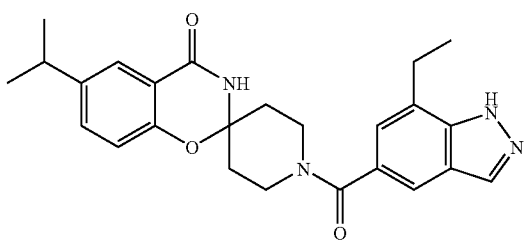 | 1'-[7-Ethyl-1H-indazol-5-yl)carbonyl]-6-isopropylspiro[1,3-benzoxazin-2,4'-piperidin]-4-(3H)-one; |
| 249 | 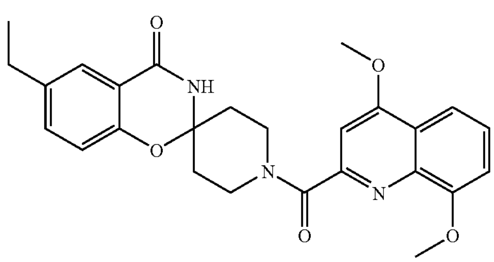 | 1'-[4,8-Dimethoxyquinolin-2-yl)carbonyl]-6-ethylspiro[2H-1,3-benzoxazin-2,4'-piperidin]-4-(3H)-one; |
| 250 | 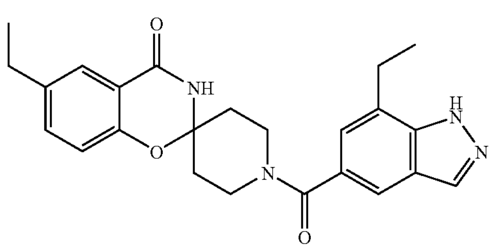 | 6-Ethyl-1'-[7-ethyl-1H-indazol-5-yl)carbonyl]spiro[1,3-benzoxazin-2,4'-piperidin]-4-(3H)-one; and/or |

| Compound Number | Structure | Name |
|---|---|---|
| 251 | 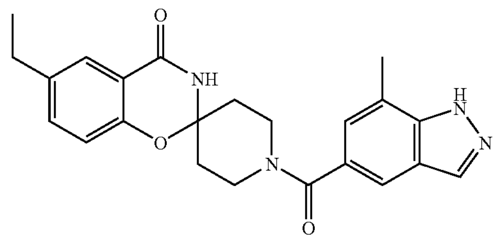 | 6-Ethyl-1'-[7-methyl-1H-indazol-5-yl)carbonyl]spiro[1,3-benzoxazin-2,4'-piperidin]-4-(3H)-one. |

In some embodiments, the compound of formula I is 1'-[4,8-dimethoxyquinoline-2-yl)carbonyl]-6-methoxyspiro[2H-1,3-benzoxazin-2,4'-piperidin]-4-(3H)-one (compound 150). In other embodiments, the compound is 1'-[4,8-dimethoxyquinoline-2-yl)carbonyl]-6-isopropoxyspiro[1,3-benzoxazin-2,4'-piperidin]-4-(3H)-one (compound 169). In yet other embodiments, the compound is 1'-[4,8-dimethoxyquinoline-2-yl)carbonyl]-6-isopropylspiro[1,3-benzoxazin-2,4'-piperidin]-4-(3H)-one (compound 186). In still other embodiments, the compound is 1'-[4,8-dimethoxyquinoline-2-yl)carbonyl]-6-(morpholin-4-yl)spiro[1,3-benzoxazin-2,4'-piperidin]-4-(3H)-one (compound 196). In some embodiments, the compound is 1'-[(4,8-dimethoxynaphth-2-yl)carbonyl]-6-methoxyspiro[2H-1,3-benzoxazin-2,4'-piperidin]-4-(3H)-one (compound 152). In other embodiments, the compound is 6-isopropoxy-1'-[7-methoxy-3-methyl-1H-indol-2-yl)carbonyl]spiro[1,3-benzoxazin-2,4'-piperidin]-4-(3H)-one (compound 180). In still other embodiments, the compound is 1-[4,8-dimethoxynaphth-2-yl)carbonyl]-6'-methoxyspiro[piperidine-4,2'(1'H)-quinazolin]-4'-(3'H)-one (compound 187).

3. Pharmaceutical uses. Active compounds of the present invention can be used in the treatment of fungal infections of human and animal subjects (including but not limited to horses, cattle, sheep, dogs, cats, etc.) for medical and veterinary purposes. Examples of such infections include, but are not limited to, ailments such as onychomycosis, sporotichosis, hoof rot, jungle rot, *Pseudallescheria boydii*, scopulariopsis or athletes foot, sometimes generally referred to as "white-line" disease, as well as fungal infections in immunocomprised patients such as AIDS patients and transplant patients. Thus, fungal infections may be of skin or of keratinaceous material such as hair, hooves, or nails, as well as systemic infections such as those caused by *Candida* spp., *Cryptococcus neoformans*, and *Aspergillus* spp., such as as in pulmonary aspergillosis and *Pneumocystis carinii* pneumonia. Active compounds as described herein may be combined with a pharmaceutically acceptable carrier and administered or applied to such subjects or infections (e.g., topically, parenterally) in an amount effective to treat the infection in accordance with known techniques, as (for example) described in U.S. Pat. Nos. 6,680,073; 6,673,842; 6,664,292; 6,613,738; 6,423,519; 6,413,444; 6,403,063; and 6,042,845; the disclosures of which are incorporated by reference herein in their entirety.

Accordingly, some embodiments of the present invention provide compositions for treating a fungal infection in a subject in need thereof, comprising, in combination, a compound of formula I or a pharmaceutically acceptable salt thereof together with a pharmaceutically acceptable carrier. In further embodiments, the present invention provides a method of treating a fungal infection in a subject in need thereof, comprising: administering a compound of formula I or a pharmaceutically acceptable salt thereof to said subject in an amount effective to treat said fungal infection In addition to the foregoing, the compounds may be used for the treatment of obesity, an overweight condition, hypertriglyceridemia, hyperlipidemia, hypoalphalipoproteinemia, metabolic syndrome, atherosclerosis, cardiovascular disease, cerebrovascular disease or congestive heart failure, diabetes mellitus, hyperinsulinemia, impaired glucose tolerance, insulin resistance, e.g., type II or adult-onset diabetes, diabetic complications, diseases associated with reduced neuronal metabolism (e.g. Alzheimer's disease, Mild Cognitive Impairment, Parkinson's disease, Huntington's disease, epilepsy), atherosclerosis, hypertension, coronary heart disease, hypercholesterolemia, stroke, polycystic ovary disease, and cancer, including, but not limited to, breast cancer, uterine cancer, ovarian cancer, colon cancer, prostate cancer, and endometrial cancer, in human or animal subjects.

Thus, in some embodiments of the present invention, a method is provided for treating obesity, an overweight condition, hypertriglyceridemia, hyperlipidemia, hypoalphalipoproteinemia, Metabolic Syndrome, diabetes mellitus, hyperinsulinemia, impaired glucose tolerance, insulin resistance, diabetic complications, atherosclerosis, hypertension, coronary heart disease, hypercholesterolemia, stroke, polycystic ovary disease, cancer, cerebrovascular disease or congestive heart failure, in a subject by administering to said subject in need of such treatment a therapeutically effective amount of a compound of formula I, a prodrug thereof, or a pharmaceutically acceptable salt of said compound or of said prodrug. In some embodiments, the subject is afflicted with diabetes. In other embodiments, the subject is afflicted with obesity. In still other embodiments of the present invention, the cancer is breast cancer, uterine cancer, ovarian cancer, colon cancer, prostate cancer, endometrial cancer, liver cancer, or a combination thereof.

The compounds of the present invention can further be utilized for the preparation of a medicament for the treatment of a range of medical conditions involving gastrointestinal motility disorders.

A "subject" of this invention includes any subject that is susceptible to the various diseases and disorders described herein. Nonlimiting examples of a subject of this invention include mammals, such as humans, nonhuman primates, domesticated mammals (e.g., dogs, cats, rabbits, guinea pigs, rats), livestock and agricultural mammals (e.g., horses, bovine, pigs, goats). In other embodiments, the subject may be animals such as birds or reptiles. Thus, in some embodiments, a subject can be any domestic, commercially or clinically valuable animal. Subjects may be male or female and may be any age including neonate, infant, juvenile, adolescent, adult, and geriatric subjects. In particular embodiments, the subject is a human. A human subject of this invention can be of any age, gender, race or ethnic group (e.g., Caucasian (white), Asian, African, black, African American, African European, Hispanic, Mideastern, etc.).

The compounds of this invention may also be used in conjunction with other pharmaceutical agents for the treatment of the diseases/conditions described herein, as described hereinabove and below. In combination therapy treatment, both the compounds of this invention and the other drug therapies are administered to subjects by conventional methods. Representative examples of second compounds in the combination aspect of this invention include, but are not limited to, any antiatherosclerosis agent, cholesterol absorption inhibitor, HMG-CoA reductase inhibitor, MTP/Apo B secretion (microsomal triglyceride transfer protein and/or apolipoprotein B secretion) inhibitor, or HMG-CoA synthase inhibitor. Examples of other second compounds are described in U.S. Patent Application Publication No. 2003/0187254A1.

Accordingly, in some embodiments, the present invention provides a pharmaceutical composition which comprises in combination a compound of formula I, a prodrug thereof, or a pharmaceutically acceptable salt of said compound or of said prodrug and a pharmaceutically acceptable carrier, vehicle or diluent. In further embodiments, the present invention provides a pharmaceutical combination composition comprising in combination: a therapeutically effective amount of a composition comprising a first compound, said first compound is a compound of formula I, a prodrug thereof, or a pharmaceutically acceptable salt of said compound or of said prodrug; a second compound, said second compound being an anti-atherosclerosis agent, an anti-diabetic agent, an anti-obesity agent or a cardiovascular agent and/or optionally a pharmaceutically acceptable vehicle, diluent or carrier.

In some embodiments, the compounds of the present invention can further be utilized for the preparation of a medicament for the treatment of a range of medical conditions including fungal infection, obesity, metabolic syndrome, atherosclerosis, cardiovascular disease, insulin resistance, e.g., type II or adult-onset diabetes, diseases associated with reduced neuronal metabolism (e.g., Alzheimer's disease, Mild Cognitive Impairment, Parkinson's disease, Huntington's disease, epilepsy), cancer, including breast cancer, uterine cancer, ovarian cancer, colon cancer, prostate cancer, liver cancer, and endometrial cancer.

"Pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically-acceptable carrier" as used herein means a pharmaceutically-acceptable material, composition or vehicle, such as a liquid or solid filler, diluent, excipient, solvent or encapsulating material, involved in carrying or transporting the subject peptidomimetic agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, and the particular mode of administration. The amount of active ingredient which can be combined with a carrier material to produce a single dosage form will generally be that amount of the active ingredient which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

The ointments, pastes, creams and gels may contain, in addition to the active ingredient, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a freeflowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Pharmaceutical compositions of this invention suitable for parenteral administration comprise one or more active compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. These compositions may also contain adjuvants such as preservatives, wetting agents, emulsifying agents and dispersing agents. Prevention of the action of microorganisms may be ensured by the inclusion of various antibacterial and other antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The preparations of the present invention may be given by any suitable means of administration including orally, parenterally, topically, transdermally, rectally, etc. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Topical or parenteral administration is preferred.

"Parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

Actual dosage levels of the active ingredients in the pharmaceutical compositions of this invention may be varied so as to obtain an amount of the active ingredient which is effective to achieve the desired therapeutic response, e.g., antimycotic activity, for a particular patient, composition, and mode of administration, without being toxic to the patient. The selected dosage level will depend upon a variety of factors including the activity of the particular active compound employed, the route of administration, the time of administration, the rate of excretion of the particular active compound being employed, the duration of the treatment, other drugs, compounds and/or materials used in combination with the particular inhibitor employed, the age, sex, weight, condition, general health and prior medical history of the patient being treated, and like factors well known in the medical arts. A health care professional such as a physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. As a general proposition, a dosage from about 0.01 or 0.1 to about 50, 100 or 200 mg/kg will have therapeutic efficacy, with all weights being calculated based upon the weight of the active compound, including the cases where a salt is employed.

4. Agrochemical compositions and use. In addition to the foregoing, active compounds of the present invention can be used to prepare agrochemical compositions and used to control fungi in like manner as other antifungal compounds. See, e.g., U.S. Pat. No. 6,617,330; see also U.S. Pat. Nos. 6,616, 952; 6,569,875; 6,541,500, and 6,506,794.

Active compounds described herein can be used for protecting plants against diseases that are caused by fungi. For the purposes herein, oomycetes shall be considered fungi. The active compounds can be used in the agricultural sector and related fields as active ingredients for controlling plant pests. The active compounds can be used to inhibit or destroy the pests that occur on plants or parts of plants (fruit, blossoms, leaves, stems, tubers, roots) of different crops of useful plants, optionally while at the same time protecting also those parts of the plants that grow later e.g. from phytopathogenic micro-organisms.

Accordingly, in some embodiments of the invention a composition for controlling and preventing plant pathogenic microorganisms is provided comprising, in combination, a compound of formula I together with a suitable carrier. In other embodiments of the invention, a composition for controlling and preventing infection by plant pathogenic microorganisms is provided, further comprising at least one additional fungicide or systemically acquired resistance inducer. Thus, in particular embodiments, a method is provided of controlling or preventing infestation of cultivated plants by plant pathogenic fungi, comprising applying a compound of formula I to said plants, parts thereof or the locus thereof in an amount effective to control said plant pathogenic fungi. In other embodiments, a method is provided of controlling or preventing infestation of cultivated plants by plant pathogenic fungi, comprising applying in combination, a compound of formula I together with a suitable carrier, to said plants, parts thereof or the locus thereof in an amount effective to control said plant pathogenic fungi. In other embodiments of the invention, a composition for controlling and preventing infection by plant pathogenic fungi is provided, further comprising at least one additional fungicide or systemically acquired resistance inducer.

Active compounds may be used as dressing agents for the treatment of plant propagation material, in particular of seeds (fruit, tubers, grains) and plant cuttings (e.g. rice), for the protection against fungal infections as well as against phytopathogenic fungi occurring in the soil.

The active compounds may be used, for example, against the phytopathogenic fungi of the following classes: Fungi imperfecti (e.g. *Botrytis, Pyricularia, Heiminthosporium,*

*Fusarium, Septoria, Cercospora* and *Alternaria*) and Basidiomycetes (e.g. *Rhizoctonia, Hemileia, Puccinia*). Additionally, they may also be used against the Ascomycetes classes (e.g. *Venturia* and *Erysiphe, Podosphaera, Monilinia, Uncinula*) and of the Oomycetes classes (e.g. *Phytophthora, Pythium, Plasmopara*). Specific examples of fungi that may be treated include, but are not limited to, *Septoria tritici, Stagonospora nodorum, Phytophthora infestans, Botrytis cinerea, Sclerotinia homoeocarpa* and *Puccinia* recondite.

Target crops to be protected with active compounds and compositions of the invention typically comprise the following types of plants: cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucumbers, melons); fiber plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, cinnamon, camphor) or plants such as tobacco, nuts, coffee, eggplants, sugar cane, tea, pepper, vines including grape-bearing vines, hops, bananas, turf and natural rubber plants, as well as ornamentals (flowers, shrubs, broad-leafed trees and evergreens, such as conifers). This list does not represent any limitation.

The active compounds can be used in the form of compositions and can be applied to the crop area or plant to be treated, simultaneously or in succession with further compounds. These further compounds can be e.g. fertilizers or micronutrient donors or other preparations which influence the growth of plants. They can also be selective herbicides as well as insecticides, fungicides, bactericides, nematicides, molluscicides, plant growth regulators, plant activators or mixtures of several of these preparations, if desired together with further carriers, surfactants or application promoting adjuvants customarily employed in the art of formulation.

Thus, in some embodiments, the present invention provides a method of controlling or preventing infestation of cultivated plants by pathogenic microorganisms, comprising: applying a compound according to formula I to said plants, parts thereof or the locus thereof in an amount effective to control said microorganisms. In some embodiments, the microorganism is a fungal organism. In further embodiments, a method is provided for controlling or preventing infestation of plant propagation material by pathogenic microorganisms, the method comprising: applying a compound according to formula I to said plant propagation material in an amount effective to control said microorganisms. In still further embodiments, the plant propagation material comprises seeds. In some embodiments, the microorganism is a fungal organism.

The active compounds can be mixed with other fungicides, resulting in some cases in unexpected synergistic activities.

Mixing components which are particularly preferred are azoles such as azaconazole, bitertanol, propiconazole, difenoconazole, diniconazole, cyproconazole, epoxiconazole, fluquinconazole, flusilazole, flutriafol, hexaconazole, imazalil, imibenconazole, ipconazole, tebuconazole, tetraconazole, fenbuconazole, metconazole, myclobutanil, pefurazoate, penconazole, bromuconazole, pyrifenox, prochloraz, triadimefon, triadimenol, triflumizole or triticonazole; pyrimidinyl carbinoles such as ancymidol, fenarimol or nuarimol; 2-amino-pyrimidine such as bupirimate, dimethirimol or ethirimol; morpholines such as dodemorph, fenpropidin, fenpropimorph, spiroxamin or tridemorph; anilinopyrimidines such as cyprodinil, pyrimethanil or mepanipyrim; pyrroles such as fenpiclonil or fludioxonil; phenylamides such as benalaxyl, furalaxyl, metalaxyl, R-metalaxyl, ofurace or oxadixyl; benzimidazoles such as benomyl, carbendazim, debacarb, fuberidazole or thiabendazole; dicarboximides such as chlozolinate, dichlozoline, iprodione, myclozolin, procymidone or vinclozolin; carboxamides such as carboxin, fenfuram, flutolanil, mepronil, oxycarboxin or thifluzamide; guanidines such as guazatine, dodine or iminoctadine; strobilurines such as azoxystrobin, kresoxim-methyl, metominostrobin, pyraclostrobin, picoxystrobin, SSF-129, methyl 2-[(2-trifluoromethyl)-pyrid-6-yloxymethyl]-3-methoxy-acrylate or methyl (alphaE)-alpha-(methoxyimino)-2-[[[(E)-[1-[3-(trifluoromethyl)phenyl] ethylidene]amino]oxy]-methyl]benzeneacetate (trifloxystrobin); dithiocarbamates such as ferbam, mancozeb, maneb, metiram, propineb, thiram, zineb or ziram; N-halomethylthio-dicarboximides such as captafol, captan, dichlofluanid, fluoromide, folpet or tolyfluanid; copper compounds such as Bordeaux mixture, copper hydroxide, copper oxychloride, copper sulfate, cuprous oxide, mancopper or oxine-copper; nitrophenol derivatives such as dinocap or nitrothal-isopropyl; organo phosphorous derivatives such as edifenphos, iprobenphos, isoprothiolane, phosdiphen, pyrazophos or tolclofos-methyl; and other compounds of diverse structures such as acibenzolar-S-methyl, harpin, anilazine, blasticidin-S, chinomethionat, chloroneb, chlorothalonil, cymoxanil, dichlone, diclomezine, dicloran, diethofencarb, dimethomorph, dithianon, etridiazole, famoxadone, fenamidone, fentin, ferimzone, fluazinam, flusulfamide, fenhexamid, fosetyl-aluminium, hymexazol, kasugamycin, methasulfocarb, pencycuron, phthalide, polyoxins, probenazole, propamocarb, pyroquilon, quinoxyfen, quintozene, sulfur, triazoxide, tricyclazole, triforine, validamycin, (S)-5-methyl-2-methylthio-5-phenyl-3-phenylamino-3,5-di-hydroimidazol-4-one (RPA 407213), 3,5-dichloro-N-(3-chloro-1-ethyl-1-methyl-2-oxopropyl)-4-methylbenzamide (RH-7281), N-allyl-4,5-dimethyl-2-trimethylsilylthiophene-3-carboxamide (MON 65500), 4-chloro-4-cyano-N,N-dimethyl-5-p-tolylimidazole-1-sulfon-amide (IKF-916), N-(1-cyano-1,2-dimethylpropyl)-2-(2,4-dichlorophenoxy)-propionamide (AC 382042) or iprovalicarb (SZX 722).

The active compounds can be mixed with one or more systemically acquired resistance inducer ("SAR" inducer), alone or in combination with a fungicide as above. SAR inducers are known and described in, for example, U.S. Pat. No. 6,919,298. In general, a SAR inducer is any compound which has the ability to turn on resistance in a plant to a disease-causing agent, including, but not limited to, a virus, a bacterium, a fungus, or combinations of these agents. In addition, an SAR inducer may induce resistance to insect feeding in a plant, as defined by Enyedi et al. (1992; *Cell* 70: 879-886). Exemplary SAR inducers cover many structural families of compounds, but are united by their ability to induce a resistance to plant diseases and/or pest feeding. One class of SAR inducers is the salicylates. The commercial SAR inducers acibenzolar-s-methyl (available as Actigard® from Syngenta), harpin protein (available as Messenger™ from Eden Biosciences), yeast extract hydrolysate from *Saccharomyces cerevisiae* (available as Keyplex®, 350-DP® from Morse Enterprises Limited, Inc. of Miami, Fla.), and Oryzemate® are useful in the present invention. Elicitors, including the Goemar products are another class of SAR inducers that can also be used. In addition, ethylene, its biosynthetic precursors, or ethylene releasing compounds such as Ethrel are considered SAR inducers of utility in this context. See also U.S. Pat. No. 6,919,298.

Suitable carriers and adjuvants can be solid or liquid and are substances useful in formulation technology, e.g. natural or regenerated mineral substances, solvents, dispersants, wetting agents, tackifiers, thickeners, binders or fertilizers.

A particular method of applying an active compound of the invention, or an agrochemical composition which contains at least one of said compounds, is foliar application. The frequency of application and the rate of application will depend on the risk of infestation by the corresponding pathogen. However, the active compounds can also penetrate the plant through the roots via the soil (systemic action) by drenching the locus of the plant with a liquid formulation, or by applying the compounds in solid form to the soil, e.g. in granular form (soil application). For crops grown in water such as rice, such granulates can be applied to the flooded rice field. The active compounds may also be applied to seeds (coating) by impregnating the seeds or tubers either with a liquid formulation of the fungicide or coating them with a solid formulation.

The term "locus" as used herein is intended to embrace the fields on which the treated crop plants are growing, or where the seeds of cultivated plants are sown, or the place where the seed will be placed into the soil. The term seed is intended to embrace plant propagating material such as cuttings, seedlings, seeds, and germinated or soaked seeds.

The active compounds are used in unmodified form or, preferably, together with the adjuvants conventionally employed in the art of formulation. To this end they are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomizing, dusting, scattering, coating or pouring, are chosen in accordance with the intended objectives and the prevailing circumstances.

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient dosages are from 10 mg to 1 g of active substance per kg of seeds.

The formulation, i.e. the compositions containing the compound of formula I and, if desired, a solid or liquid adjuvant, are prepared in known manner, typically by intimately mixing and/or grinding the compound with extenders, e.g. solvents, solid carriers and, optionally, surface active compounds (surfactants).

Suitable carriers and adjuvants may be solid or liquid and correspond to the substances ordinarily employed in formulation technology, such as, e.g. natural or regenerated mineral substances, solvents, dispersants, wetting agents, tackifiers, thickeners binding agents or fertilizers. Such carriers are for example described in WO 97/33890.

Further surfactants customarily employed in the art of formulation are known to the expert or can be found in the relevant literature.

The agrochemical formulations will usually contain from 0.1 to 99% by weight, preferably from 0.1 to 95% by weight, of the compound of formula I, 99.9 to 1% by weight, preferably 99.8 to 5% by weight, of a solid or liquid adjuvant, and from 0 to 25% by weight, preferably from 0.1 to 25% by weight, of a surfactant.

Whereas it is preferred to formulate commercial products as concentrates, the end user will normally use dilute formulations.

The compositions may also contain further adjuvants such as stabilizers, antifoams, viscosity regulators, binders or tackifiers as well as fertilizers, micronutrient donors or other formulations for obtaining special effects.

5. Technical materials. The compounds and combinations of the present invention may also be used in the area of controlling fungal infestation (particularly by mold and mildew) of technical materials, including protecting technical material against attack of fungi and reducing or eradicating fungal infestation of technical materials after such infestation has occurred. Technical materials include, but are not limited to, organic and inorganic materials, wood, paper, leather, natural and synthetic fibers, composites thereof such as particle board, plywood, wall-board and the like, woven and non-woven fabrics, construction surfaces and materials, cooling and heating system surfaces and materials, ventilation and air conditioning system surfaces and materials, and the like. The compounds and combinations according to the present invention can be applied to such materials or surfaces in an amount effective to inhibit or prevent disadvantageous effects such as decay, discoloration or mold in like manner as described above. Structures and dwellings constructed using or incorporating technical materials in which such compounds or combinations have been applied are likewise protected against attack by fungi.

Accordingly, the present invention provides a method of controlling or preventing infestation of a technical material by pathogenic microorganisms, comprising: applying a compound according to formula I to said technical material in an amount effective to control said microorganisms.

Embodiments of the present invention provide kits including one or more containers having pharmaceutical or agricultural dosage units including an effective amount of the compositions described herein, wherein the container is packaged with optional instructions for the use thereof. In some embodiments of the invention, the instructions include directions for the administration of active ingredients (a) and (b) in a manner to achieve a desired therapeutic effect.

The present invention is explained in greater detail in the following non-limiting Examples.

EXAMPLE 1

6-Bromo-1'-[(4,8-dimethoxyquinoline-2-yl)carbonyl]spiro[2H-1,3-benzoxazine-2,4'-piperidine]-4(3H)-one (Compound 2)

To a solution of 27 mg (0.12 mmol) of 4,8-dimethoxyquinoline-2-carboxylic acid (see US2007/0021453A1), 43.5 mg (0.12 mmol) of HATU, and 0.04 mL (0.23 mmol) of diisopropylethylamine in 1.2 mL of DMF is added 45 mg (0.11 mmol) of the trifluoroacetic acid (TFA) salt of 6-bromospiro[1,3-benzoxazine-2,4'-piperidine]-4(3H)-one (from 6-bromo-1'-(tert-butyloxycarbonyl)spiro[1,3-benzoxazine-2,4'-piperidine]-4(3H)-one; available from Apollo Scientific, by treatment with TFA in dichloromethane). The mixture is stirred at room temperature for 3 hr., and then diluted with ethyl acetate. The ethyl acetate solution is washed with aqueous sodium bicarbonate, then brine, and is finally dried over $Na_2SO_4$. After solvent removal by rotoevaporation, the crude product is purified by preparative TLC to give 40 mg (0.078 mmol, 71% yield) 6-bromo-1'-[(4,8-dimethoxyquinoline-2-yl)carbonyl]spiro-[2H-1,3-benzoxazine-2,4'-piperidine]-4(3H)-one (Compound 2): $^1$H NMR ($CDCl_3$): δ 1.90 (m, 2H), 2.05 (m, 1H), 2.19 (m, 1H), 3.36 (m, 2H), 3.75 (m, 1H), 3.95 (s, 3H), 4.06 (s, 3H), 4.31 (m, 1H), 7.1 (d, 1H, J=8.8 Hz), 7.19 (s, 1H), 7.24 (dd, 1H, J=8 Hz, J=1.2 Hz), 7.52 (dd, 1, J=8.0

Hz, J=8.0 Hz), 7.68 (dd, 1H, J=8.4 Hz, J=1.2 Hz), 7.71 (dd, 1H, J=8.8 Hz, J=2.4 Hz), 7.83 (d, 1H, J=2.4 Hz), and 9.03 ppm (s, 1H). MS m/z: 513.3 (M+H)$^+$, 535 (M+Na)$^+$.

EXAMPLE 2

6-Bromo-1'-[(3,5-dimethoxynaphth-2-yl)carbonyl] spiro[2H-1,3-benzoxazine-2,4'-piperidine]-4(3H)-one (Compound 3)

This compound is prepared as described in Example 1 except that 3,5-dimethoxynaphthalene-2-carboxylic acid is used instead of 4,8-dimethoxyquinoline-2-carboxylic acid to give 6-bromo-1'-[(3,5-dimethoxynaphth-2-yl)carbonyl]spiro [2H-1,3-benzoxazine-2,4'-piperidine]-4(3H)-one (Compound 3): $^1$H NMR (CDCl$_3$): δ 1.65-2.00 (m, 3H), 2.15 (m, 1H), 3.25 (m, 3H), 3.91 and 3.93 (two s, 3H), 3.98 (s, 3H), 4.34 (m, 1H), 7.00 (d, 1H, J=8.0 Hz), 7.06 and 7.12 (two d, 1H, J=8.4 Hz), 7.32 (m, 1H), 7.45 (m, 1H), 7.50 (s, 1H), 7.69 (m, 1H), 7.73 and 7.76 (two s, 1H), 8.81 (m, 1H), and 8.93 and 9.04 ppm (two s, 1H). MS m/z: 512.1 (M+H)$^+$, 534.0 (M+Na)$^+$.

EXAMPLE 3

6-Bromo-1'-[(3-chlorobenzothien-2-yl)carbonyl] spiro[2H-1,3-benzoxazine-2,4'-piperidine]-4(3H)-one (Compound 1)

To a solution of 45 mg (0.11 mmol) of the trifluoroacetic acid salt of 6-bromospiro[1,3-benzoxazine-2,4'-piperidine]-4(3H)-one and 0.076 mL (0.44 mmol) of diisopropylethylamine in 1.5 mL of dichloromethane is added 27 mg (0.12 mmol) of 3-chlorobenzothienyl-2-carbonyl chloride. The reaction mixture is stirred overnight at room temperature, and then diluted with ethyl acetate. The ethyl acetate solution is washed with aqueous sodium bicarbonate, then brine and is finally dried over Na$_2$SO$_4$. After solvent removal by rotoevaporation, the crude product is purified by preparative TLC to give 25 mg (0.051 mmol. 46% yield) 6-bromo-1'-[(3-chlorobenzothien-2-yl)carbonyl]spiro[2H-1,3-benzoxazine-2,4'-piperidine]-4(3H)-one (Compound 1): $^1$H NMR (DMSO-d$_6$): δ 1.87 (m, 2H), 2.14 (m, 2H), 3.47 (m, 1H), 3.60 (m, 1H), 4.30 (m, 1H), 7.11 (d, 1H, J=8.8 Hz), 7.59 (m, 2H), 7.71 (dd, 1H, J=8.8 Hz, J=2.8 Hz), 7.82 (d, 11, J=2.4 Hz), 7.86 (m, 1H), 8.12 (m, 1H), and 8.97 ppm (s, 1H). MS m/z: 492.5 (M+H)$^+$.

EXAMPLES 4-36

1'-Arylcarbonyl derivatives of 6-bromospiro[2H-1,3-benzoxazine-2,4'-piperidine]-4(3H)-one (Compounds 4, 5, 16, 21, 23, 26, 29, 30, 32, 36, 40, 44, 47, 50, 53, 56, 59, 62, 103, 105-110, 133-135, 140-142, 147, and 156)

These compounds are prepared as described in Examples 1, 2, and 3 except that the corresponding requisite aryl carboxylic acids are used to give the following 1'-arylcarbonyl derivatives of 6-bromospiro[2H-1,3-benzoxazine-2,4'-piperidine]-4(3H)-one:
  4. 6-Bromo-1'-{(1,3-dimethyl-1H-thieno[2,3-c]pyrazol-5-yl)carbonyl} spiro[2H-1,3-benzoxazin-2,4'-piperidin]-4-(3H)-one (Compound 4): MS m/z: 476.0 (M+H)$^+$;
  5. 6-Bromo-1'-[(4-chlorobenzthien-2-yl)carbonyl]spiro [2H-1,3-benzoxazin-2,4'-piperidin]-4-(3H)-one (Compound 5);
  6. 6-Bromo-1'-[4,7-dimethoxy-1H-indol-2-yl)carbonyl] spiro[2H-1,3-benzoxazin-2,4'-piperidin]-4-(3H)-one (Compound 16): $^1$H NMR (DMSO-d$_6$): δ 3.81 (s, 3H), 3.84 (s, 3H), 6.38 (d, 1H), 6.59 (d, 1H), 6.64 (d, 1H), 7.09 (d, 1H), 7.72 (d of d, 1H), 7.83 (d, 1H), 9.01 (s, 1H), and 11.55 ppm (d, 1H). MS m/z: 523.0 (M+Na)$^+$;
  7. 6-Bromo-1'-[7-methoxy-1H-indol-2-yl)carbonyl]spiro [2H-1,3-benzoxazin-2,4'-piperidin]-4-(3H)-one (Compound 21);
  8. 6-Bromo-1'-[7-methoxy-3-methyl-1H-indol-2-yl)carbonyl]spiro[2H-1,3-benzoxazin-2,4'-piperidin]-4-(3H)-one (Compound 23): MS m/z: 485.0 (M+H)$^+$, 507.0 (M+Na)$^+$;
  9. 6-Bromo-1'-[4,7-dimethoxy-1-methyl-1H-indol-2-yl) carbonyl]spiro[2H-1,3-benzoxazin-2,4'-piperidin]-4-(3H)-one (Compound 26): $^1$H NMR (DMSO-d$_6$): δ 3.80 (s, 3H), 3.84 (s, 3H), 3.94 (s, 3H), 6.40 (d, 1H), 6.54 (s, 1H), 6.62 (d, 1H), 7.08 (d, 1H), 7.71 (d of d, 1H), 7.82 (d, 1H), and 8.91 ppm (s, 1H). MS m/z: 515.1 (M)$^+$, 537.0 (M+Na)$^+$;
  10. 6-Bromo-1'-[5,6,7-trimethoxy-1H-indol-2-yl)carbonyl]spiro[2H-1,3-benzoxazin-2,4'-piperidin]-4-(3H)-one (Compound 29);
  11. 6-Bromo-1'-[(4,8-dimethoxynaphth-2-yl)carbonyl] spiro[2H-1,3-benzoxazin-2,4'-piperidin]-4-(3H)-one (Compound 30): $^1$H NMR (DMSO-d$_6$): δ 3.97 (s, 3H), 3.99 (s, 3H), 6.96 (d, 1H), 7.06 (d, 1H), 7.09 (d, 1H), 7.48 (m, 1H), 7.71 (m, 1H), 7.82 (d, 1H), and 8.95 ppm (s, 1H). MS n1/z: 512.0 (M+H)$^+$, 534.0 (M+Na)$^+$;
  12. 6-Bromo-1'-[8-cyclopropyl-4-methoxyquinolin-2-yl) carbonyl]spiro[2H-1,3-benzoxazin-2,4'-piperidin]-4-(3H)-one (Compound 32): $^1$H NMR (DMSO-d$_6$): δ 0.81 (m, 2H), 1.09 (m, 2H), 4.08 (s, 3H), 7.10 (d, 1H), 7.21 (s, 1H), 7.27 (d of d, 1H), 7.50 (d of d, 1H), 7.71 (d of d, 1H), 7.83 (d, 1H), 7.95 (d of d, 1H) and 9.04 ppm (s, 1H). MS m/z: 523.0 (M+H)$^+$, 545.0 (M+Na)$^+$;
  13. 6-Bromo-1'-[1-cyclopropyl-5-methoxyisoquinolin-7-yl)carbonyl]spiro[2H-1,3-benzoxazin-2,4'-piperidin]-4-(3H)-one (Compound 36);
  14. 6-Bromo-1'-[4-methoxyquinolin-2-yl)carbonyl]spiro [2H-1,3-benzoxazin-2,4'-piperidin]-4-(3H)-one (Compound 40) $^1$H NMR (DMSO-d$_6$): δ 4.09 (s, 3H), 7.10 (d, 1H), 7.17 (s, 1H), 7.63 (m, 1H), 7.71 (d of d, 1H), 7.80 (m, 1H), 7.83 (d, 1H), 7.95 (d, 1H), 8.16 (d of d, 1H), and 8.99 ppm (s, 1H). MS m/z: 483.0 (M+H)$^+$, 505.0 (M+Na)$^+$;
  15. 6-Bromo-1'-[8-methoxyquinolin-2-yl)carbonyl]spiro [2H-1,3-benzoxazin-2,4'-piperidin]-4-(3H)-one (Compound 44): $^1$H NMR (DMSO-d$_6$): δ 3.97 (s, 3H), 7.10 (d, 1H), 7.25 (d of d, 1H), 7.58 (m, 2H), 7.71 (m, 2H), 7.82 (m, 1H), 8.44 (d, 1H), and 9.01 ppm (s, 1H). MS m/z: 483.0 (M+H)$^+$, 505.0 (M+Na)$^+$;
  16. 6-Bromo-1'-[4-ethoxy-8-ethylquinolin-2-yl)carbonyl] spiro[2H-1,3-benzoxazin-2,4'-piperidin]-4-(3H)-one (Compound 47);
  17. 6-Bromo-1'-[8-cyclopropyl-4-(4-morpholinyl)quinolin-2-yl)carbonyl]spiro[2H-1,3-benzoxazin-2,4'-piperidin]-4-(3H)-one (Compound 50);
  18. 1'-[(Benzothiazol-2-yl)carbonyl]-6-bromospiro[2H-1,3-benzoxazin-2,4'-piperidin]-4-(3H)-one (Compound 53): MS m/z: 459.0 (M+H)$^+$, 481.0 (M+Na)$^+$;
  19. 6-Bromo-1'-[(6-methoxybenzothiazol-2-yl)carbonyl] spiro[2H-1,3-benzoxazin-2,4'-piperidin]-4-(3H)-one (Compound 56);
  20. 1'-[(1H-Benzimidazol-2-yl)carbonyl]-6-bromospiro [2H-1,3-benzoxazin-2,4'-piperidin]-4-(3H)-one (Compound 59): MS m/z: 442.0 (M+H)$^+$, 464.0 (M+Na)$^+$.

21. 6-Bromo-1'-[(quinoxalin-2-yl)carbonyl]spiro[2H-1,3-benzoxazin-2,4'-piperidin]-4(3H)-one (Compound 62): MS m/z: 454.0 (M+H)$^+$, 476.0 (M+Na)$^+$;

22. 6-Bromo-1'-[3-(1H-pyrazol-3-yl)benzoyl]spiro[2H-1,3-benzoxazin-2,4'-piperidin]-4-(3H)-one (Compound 103): $^1$H NMR (DMSO-d$_6$): δ 6.78 (d, 1H), 7.08 (d, 1H), 7.31 (d, 1H), 7.48 (m, 1H), 7.71 (d of d, 1H), 7.82 (d, 2H), 7.88 (d, 1H) and 8.96 ppm (s, 1H). MS m/z: 468.0 (M+H)$^+$, 490.0 (M+Na)$^+$;

23. 6-Bromo-1'-[(1H-indol-5-yl)carbonyl]spiro[2H-1,3-benzoxazin-2,4'-piperidin]-4-(3H)-one (Compound 105);

24. 6-Bromo-1'-[(7-methyl-1H-indazol-5-yl)carbonyl]spiro[2H-1,3-benzoxazin-2,4'-piperidin]-4-(3H)-one (Compound 106);

25. 6-Bromo-1'-[(7-chloro-1H-indazol-5-yl)carbonyl]spiro[2H-1,3-benzoxazin-2,4'-piperidin]-4-(3H)-one (Compound 107);

26. 6-Bromo-1'-[(1H-indazol-5-yl)carbonyl]spiro[2H-1,3-benzoxazin-2,4'-piperidin]-4-(3H)-one (Compound 108);

27. 1'-[(1H-benzimidazol-5-yl)carbonyl]-6-bromospiro[2H-1,3-benzoxazin-2,4'-piperidin]-4-(3H)-one (Compound 109): $^1$H NMR (DMSO-d$_6$): δ 7.09 (d, 1H), 7.24 (d of d, 1H), 7.57 (m, 1H), 7.68 (m, 1H), 7.70 (d of d, 1H), 7.81 (d, 1H), 8.31 (s, 1H), 8.94 (s, 1H), and 12.63 ppm (s, 1H). MS m/z: 442.0 (M+H)$^+$, 464.0 (M+Na)$^+$;

28. 1'-[(1H-benzotriazol-5-yl)carbonyl]-6-bromospiro[2H-1,3-benzoxazin-2,4'-piperidin]-4-(3H)-one (Compound 110): $^1$H NMR (DMSO-d$_6$): δ 7.07 (d, 1H), 4.45 (d of d, 1H), 7.70 (d of d, 1H), 7.82 (d, 1H), 7.96 (m, 2H) and 8.97 ppm (s, 1H);

29. 6-Bromo-1'-[4-methoxy-8-methylthioquinolin-2-yl)carbonyl]spiro[2H-1,3-benzoxazin-2,4'-piperidin]-4-(3H)-one (Compound 133): $^1$H NMR (DMSO-d$_6$): δ 2.50 (s, 3H), 3.32 (s, 3H), 4.08 (s, 3H), 7.11 (d, 1H), 7.27 (s, 1H), 7.50 (d of d, 1H), 7.57 (m, 1H), 7.71 (d of d, 1H), 7.83 (d, 1H), 7.87 (d of d, 1H) and 9.05 ppm (s, 1H). MS m/z: 529.0 (M+H)$^+$, 551.0 (M+Na)$^+$;

30. 6-Bromo-1'-[8-isopropyl-4-methoxyquinolin-2-yl)carbonyl]spiro[2H-1,3-benzoxazin-2,4'-piperidin]-4-(3H)-one (Compound 134): $^1$H NMR (DMSO-d$_6$): δ 1.29 (d of d, 6H), 4.07 (s, 3H), 4.19 (m, 1H), 7.11 (d, 1H), 7.19 (s, 1H), 7.58 (m, 1H), 7.70 (m, 2H), 8.01 (d of d, 1H), and 9.06 ppm (s, 1H).). MS m/z: 525.0 (M+H)$^+$, 547.0 (M+Na)$^+$;

31. 6-Bromo-1'-[(1,4-dimethoxynaphth-2-yl)carbonyl]spiro[2H-1,3-benzoxazin-2,4'-piperidin]-4-(3H)-one (Compound 135): $^1$H NMR (DMSO-d$_6$): δ 3.83 and 3.86 (two s, 3H), 3.95 and 3.97 (two s, 3H), 6.75 (d, 1H), 7.06 and 7.12 (two d, 1H), 7.62 (m, 2H), 7.70 (d of d, 1H), 7.82 (m, 1H), 8.06 (m, 1H), 8.16 (d, 1H), and 8.95 and 9.00 ppm (two s, 1H). MS m/z: 512.0 (M+H)$^+$, 534.0 (M+Na)$^+$;

32. 6-Bromo-1'-[3-(1-methyl-1H-pyrazol-3-yl)benzoyl]spiro[2H-1,3-benzoxazin-2,4'-piperidin]-4-(3H)-one (Compound 140): $^1$H NMR (DMSO-d$_6$): δ 3.87 (s, 3H), 6.46 (d, 1H), 7.07 (d, 1H), 7.46 (d of t, 1H), 7.48 (d, 1H), 7.53 (m, 1H), 7.57 (d of d, 1H), 7.62 (d of t, 1H), 7.71 (d of d, 1H), 7.82 (d, 1H), and 8.95 ppm (s, 1H). MS m/z: 482.0 (M+H)$^+$, 504.0 (M+Na)$^+$.

33. 6-Bromo-1'-[3-(1-methyl-1H-pyrazol-5-yl)benzoyl]spiro[2H-1,3-benzoxazin-2,4'-piperidin]-4-(3H)-one (Compound 141): $^1$H NMR (DMSO-d$_6$): δ 3.88 (s, 3H), 6.75 (d, 1H), 7.08 (d, 1H), 7.29 (d of t, 1H), 7.46 (d of d, 1H), 7.71 (d of d, 1H), 7.75 (d, 1H), 7.78 (m, 1H), 7.81 (d, 1H), 7.85 (d of t, 1H), and 8.95 ppm (s, 1H). MS m/z: 482.0 (M+H)$^+$, 504.0 (M+Na)$^+$;

34. 6-Bromo-1'-[(1,2-dimethyl-1H-benzimidazol-5-yl)carbonyl]spiro[2H-1,3-benzoxazin-2,4'-piperidin]-4-(3H)-one (Compound 142): $^1$H NMR (DMSO-d$_6$): δ 2.53 (s, 3H), 3.74 (s, 3H), 7.08 (d, 1H), 7.23 (d of d, 1H), 7.53 (d, 1H), 7.54 (s, 1H), 7.70 (d of d, 1H), 7.81 (d, 1H), and 8.93 ppm (s, 1H). MS m/z: 470.1 (M+H)$^+$.

35. 6-Bromo-1'-[(quinolin-2-yl)carbonyl]spiro[2H-1,3-benzoxazin-2,4'-piperidin]-4-(3H)-one (Compound 147): MS m/z: 453.0 (M+H)$^+$, 475.0 (M+Na)$^+$;

36. 6-Bromo-1'-[(7H-pyrrolo[2,3-b]pyridin-2-yl)carbonyl]spiro[2H-1,3-benzoxazin-2,4'-piperidin]-4-(3H)-one (Compound 156): $^1$H NMR (DMSO-d$_6$): δ 6.51 (d of d, 1H), 7.09 (d, 1H), 7.28 (d, 1H), 7.59 (d of d, 1H), 7.70 (d of d, 1H), 7.82 (d, 1H), 8.05 (d, 1H), 8.98 (s, 1H), and 11.78 ppm (s, 1H). MS m/z: 442.0 (M+H)$^+$, 464.0 (M+Na)$^+$.

EXAMPLE 37

6-Chloro-1'-[(3,5-dimethoxynaphth-2-yl)carbonyl]spiro[2H-1,3-benzoxazin-2,4'-piperidin]-4-(3H)-one (Compound 131)

To a solution of 131 mg (0.56 mmol) of 3,5-dimethoxynaphthyl-2-carboxylic acid, 213 mg (0.56 mmol) of HATU, and 0.22 mL (1.23 mmol) of diisopropylethylamine in 1.0 mL of DMF is added 119 mg (0.56 mmol) of the trifluoroacetic acid (TFA) salt of 4-piperidone (prepared by TFA cleavage of 1-Boc-4-piperidone in dichloromethane). After stirring overnight at room temperature, the reaction mixture is poured into aqueous sodium bicarbonate and extracted with ethyl acetate twice. The combined ethyl acetate extracts are washed with brine and dried over Na$_2$SO$_4$. After solvent removal by rotoevaporation, 175 mg (0.56 mmol) of hygroscopic N-[3,5-dimethoxynaphth-2-yl)carbonyl]-4-piperidone is isolated and used without purification.

A mixture of 25 mg (0.080 mmol) of N-[3,5-dimethoxynaphth-2-yl)carbonyl]-4-piperidone, 13.7 mg (0.080 mmol) of 5-chloro-2-hydroxybenzamide, and 0.010 mL of conc. sulfuric acid in 0.4 mL of acetic acid is stirred overnight at room temperature. The reaction mixture is diluted with ethyl acetate, and washed with water, brine, and dried over Na$_2$SO$_4$. After solvent removal by rotoevaporation, the crude product is purified by preparative TLC to give 11 mg (0.024 mmol, 30% yield) of 6-chloro-1'-[3,5-dimethoxynaphth-2-yl)carbonyl]spiro[2H-1,3-benzoxazin-2,4'-piperidin]-4-(3H)-one (Compound 131): MS m/z: 467.1 (M+H)$^+$, 489.0 (M+Na)$^+$.

EXAMPLES 38-43

1'-Arylcarbonyl derivatives of 6-chlorospiro[2H-1,3-benzoxazine-2,4'-piperidine]-4(3H)-one (Compounds 115, 117, 118, 121, 122, and 171)

These compounds are prepared as described in Example 37 except that the corresponding requisite aryl carboxylic acids are used to give the following 1'-arylcarbonyl derivatives of 6-chlorospiro[2H-1,3-benzoxazine-2,4'-piperidine]-4 (3H)— one:

38. 6-Chloro-1'-[(1-methyl-1H-indol-6-yl)carbonyl]spiro[2H-1,3-benzoxazin-2,4'-piperidin]-4-(3H)-one (Compound 115);

39. 6-Chloro-1'-[3-(1H-pyrazol-3-yl)benzoyl]spiro[2H-1,3-benzoxazin-2,4'-piperidin]-4-(3H)-one (Compound 117);

40. 1'-[(1H-Benzotriazol-6-yl)carbonyl]-6-chlorospiro[2H-1,3-benzoxazin-2,4'-piperidin]-4-(3H)-one (Compound 118);

41. 6-Chloro-1'-[(7-chloro-1H-indazol-5-yl)carbonyl]spiro[2H-1,3-benzoxazin-2,4'-piperidin]-4-(3H)-one (Compound 121);

42. 6-Chloro-1'-[(7-methyl-1H-indazol-5-yl)carbonyl]spiro[2H-1,3-benzoxazin-2,4'-piperidin]-4-(3H)-one (Compound 122);

43. 6-Chloro-1'-[4,8-dimethoxynaphth-2-yl)carbonyl]spiro[1,3-benzoxazin-2,4'-piperidin]-4-(3H)-one (Compound 171); condensation of 5-chloro-2-hydroxybenzamide and N-[4,8-dimethoxynaphth-2-yl)carbonyl]-4-piperidone achieved with morpholine in toluene/MeOH, 1:3 at reflux for 20 hr.): $^1$H NMR (DMSO-d$_6$): δ 3.98 (s, 3H), 3.99 (s, 3H), 6.97 (d, 1H), 7.07 (d, 1H), 7.15 (d, 1H), 7.49 (d of d, 1H), 7.60 (d of d, 1H), 7.71 (m, 3H), and 8.93 ppm (s, 1H). MS m/z: 467.0 (M+H)$^+$, 489.0 (M+Na)$^+$.

EXAMPLE 44

6-Acetamido-1'-[4,8-dimethoxyquinoline-2-yl)carbonyl]spiro[2H-1,3-benzoxazin-2,4'-piperidin]-4-(3H)-one (Compound 9)

To a solution of 83 mg (0.36 mmol) of 4,8-dimethoxyquinoline-2-carboxylic acid, 135 mg (0.36 mmol) of HATU, and 0.14 mL (0.78 mmol) of diisopropylethylamine in 1.0 mL of DMF is added 72 mg (0.34 mmol) of the trifluoroacetic acid (TFA) salt of 4-piperidone (prepared by TFA cleavage of 1-Boc-4-piperidone in dichloromethane). After 4 hr., the reaction mixture is poured into aqueous sodium bicarbonate and extracted with ethyl acetate twice. The combined ethyl acetate extracts are washed with brine and dried over Na$_2$SO$_4$. After solvent removal by rotoevaporation, the crude product is purified by preparative TLC to give 105 mg (0.33 mmol) of hygroscopic N-[4,8-dimethoxyquinoline-2-yl)carbonyl]-4-piperidone.

A mixture of 24 mg (0.077 mmol) of N-[4,8-dimethoxyquinoline-2-yl)carbonyl]-4-piperidone, 15 mg (0.077 mmol) of 5-acetamido-2-hydroxybenzamide, and 0.020 mL of morpholine in 3 mL of methanol is refluxed for 48 hr. The reaction mixture is diluted with ethyl acetate, and washed with water, brine, and dried over Na$_2$SO$_4$. After solvent removal by rotoevaporation, the crude product is purified by preparative TLC to give 11 mg (0.022 mmol, 30% yield) of 6-acetamido-1'-[4,8-dimethoxyquinoline-2-yl)carbonyl]spiro[2H-1,3-benzoxazin-2,4'-piperidin]-4-(3H)-one (Compound 9): $^1$H NMR (DMSO-d$_6$): δ 2.02 (s, 3H), 3.95 (s, 3H), 4.06 (s, 3H), 7.03 (d, 1H), 8.19 (s, 1H), 7.24 (d of d, 1H), 7.52 (d of d, 1H), 7.67 (m, 2H), 8.02 (d, 1H), 8.82, (s, 1H) and 9.98 ppm (s, 1H). MS m/z: 491.1 (M+H)$^+$, 513.2 (M+Na)$^+$.

EXAMPLES 44a-64

1'-Arylcarbonyl derivatives of 6-acetamidospiro[2H-1,3-benzoxazine-2,4'-piperidine]-4(3H)-one (Compounds 17, 20, 24, 27, 31, 33, 37, 41, 45, 48, 51, 54, 57, 60, 63, 116, 119, 120, and 136)

These compounds are prepared as described in Example 44 except that the corresponding requisite aryl carboxylic acids are used to give the following 1'-arylcarbonyl derivatives of 6-acetamidospiro[2H-1,3-benzoxazine-2,4'-piperidine]-4(3H)-one:

44a. Acetamido-1'-[4,7-dimethoxy-1H-indol-2-yl)carbonyl]spiro[2H-1,3-benzoxazin-2,4'-piperidin]-4-(3H)-one (Compound 17): $^1$H NMR (DMSO-d$_6$): 2.03 (s, 3H), 3.81 (s, 3H), 3.84 (s, 3H), 6.38 (d, 1H), 6.59 (d, 1H), 6.64 (d, 1H), 7.02 (d, 1H), 7.68 (d of d, 1H). 8.02 (d, 1H), 8.78 (s, 1H), 9.98 (s, 1H), and 11.54 ppm (s, 1H). MS m/z: 479.1 (M+H)$^+$, 501.1 (M+Na)$^+$;

45. 6-Acetamido-1'-[7-methoxy-1H-indol-2-yl)carbonyl]spiro[2H-1,3-benzoxazin-2,4'-piperidin]-4-(3H)-one (Compound 20);

46. 6-Acetamido-1'-[7-methoxy-3-methyl-1H-indol-2-yl)carbonyl]spiro[2H-1,3-benzoxazin-2,4'-piperidin]-4-(3H)-one (Compound 24): $^1$H NMR (DMSO-d$_6$): 2.02 (s, 3H), 2.22 (s, 3H), 3.89 (s, 3H), 6.70 (d, 1H), 6.95 (d of d, 1H), 7.02 (d, 1H), 7.10 (d, 1H), 7.67 (d of d, 1H), 8.00 (d, 1H), 8.81 (s, 1H), 9.98 (s, 1H), and 11.22 ppm (s, 1H). MS m/z: 463.2 (M+H)$^+$, 485.0 (M+Na)$^+$;

47. 6-Acetamido-1'-[4,7-dimethoxy-1-methyl-1H-indol-2-yl)carbonyl]spiro[2H-1,3'-benzoxazin-2,4'-piperidin]-4-(3H)-one (Compound 27);

48. 6-Acetamido-1'-[(4,8-dimethoxynaphth-2-yl)carbonyl]spiro[2H-1,3-benzoxazin-2,4'-piperidin]-4-(3H)-one (Compound 31): $^1$H NMR (DMSO-d$_6$): 2.02 (s, 3H), 3.97 (s, 3H), 3.99 (s, 3H), 6.96 (s, 1H), 7.02 (d, 1H), 7.06 (d, 1H), 7.48 (d of d, 1H), 7.68 (d of d, 1H), 7.72 (m, 2H), 8.01 (d, 1H), 8.70 (s, 1H), and 9.96 ppm (s, 1H). MS m/z: 490.2 (M+H)$^+$, 512.2 (M+Na)$^+$;

49. 6-Acetamido-1'-[8-cyclopropyl-4-methoxyquinolin-2-yl)carbonyl]spiro[2H-1,3-benzoxazin-2,4'-piperidin]-4-(3H)-one (Compound 33): MS m/z: 501.2 (M+H)$^+$, 523.2 (M+Na)$^+$;

50. 6-Acetamido-1'-[1-cyclopropyl-5-methoxyisoquinolin-7-yl)carbonyl]spiro-[2H-1,3-benzoxazin-2,4'-piperidin]-4-(3H)-one (Compound 37);

51. 6-Acetamido-1'-[4-methoxyquinolin-2-yl)carbonyl]spiro[2H-1,3-benzoxazin-2,4'-piperidin]-4-(3H)-one (Compound 41);

52. 6-Acetamido-1'-[8-methoxyquinolin-2-yl)carbonyl]spiro[2H-1,3-benzoxazin-2,4'-piperidin]-4-(3H)-one (Compound 45);

53. 6-Acetamido-1'-[4-ethoxy-8-ethylquinolin-2-yl)carbonyl]spiro[2H-1,3-benzoxazin-2,4'-piperidin]-4-(3H)-one (Compound 48);

54. 6-Acetamido-1'-[8-cyclopropyl-4-(4-morpholinyl)quinolin-2-yl)carbonyl]spiro[2H-1,3-benzoxazin-2,4'-piperidin]-4-(3H)-one (Compound 51);

55. 6-Acetamido-1'-[(benzthiazol-2-yl)carbonyl]spiro[2H-1,3-benzoxazin-2,4'-piperidin]-4-(3H)-one (Compound 54);

56. 6-Acetamido-1'-[(6-methoxybenzothiazol-2-yl)carbonyl]spiro[2H-1,3-benzoxazin-2,4'-piperidin]-4-(3H)-one (Compound 57);

57. 6-Acetamido-1'-[(1H-benzimidazol-2-yl)carbonyl]spiro[2H-1,3-benzoxazin-2,4'-piperidin]-4-(3H)-one (Compound 60);

58. 6-Acetamido-1'-[(quinoxalin-2-yl)carbonyl]spiro[1,3-benzoxazin-2,4'-piperidin]-4(3H)-one (Compound 63);

59. 6-Acetamido-1'-[3-(1H-pyrazol-3-yl)benzoyl]spiro[2H-1,3-benzoxazin-2,4'-piperidin]-4-(3H)-one (Compound 116);

60. 6-Acetamido-1'-[(7-methyl-1H-indazol-5-yl)carbonyl]spiro[2H-1,3-benzoxazin-2,4'-piperidin]-4-(3H)-one (Compound 119);

61. 6-Acetamido-1'-[(7-chloro-1H-indazol-5-yl)carbonyl]spiro[2H-1,3-benzoxazin-2,4'-piperidin]-4-(3H)-one (Compound 120);

62. 6-Acetamido-1'-[(3,5-dimethoxynaphth-2-yl)carbonyl]spiro[2H-1,3-benzoxazin-2,4'-piperidin]-4-(3H)-one (Compound 132): $^1$H NMR (DMSO-$d_6$): 2.02 (s, 3H), 3.91 and 3.93 (two s, 3H), 3.97 (s, 3H), 7.01 (m, 2H), 7.32 (m, 1H), 7.45 (d of d, 1H), 7.50 (s, 1H), 7.66 (m, 1H), 7.74 (d, 1H), 8.00 (d of d, 1H), 8.71 and 8.83 (two s, 1H), and 9.97 ppm (s, 1H). MS m/z: 490.1 (M+H)$^+$, 512.2 (M+Na)$^+$.

63. 6-Acetamido-1'-[4-methoxy-8-methylthioquinolin-2-yl)carbonyl]spiro[2H-1,3-benzoxazin-2,4'-piperidin]-4-(3H)-one (Compound 136): $^1$H NMR (DMSO-$d_6$): 2.02 (s, 3H), 2.48 (s, 3H), 4.04 (s, 3H), 7.03 (d, 1H), 7.27 (s, 1H), 7.49 (d of d, 1H), 7.57 (d of d, 1H), 7.67 (d of d, 1H), 7.86 (d of d, 1H), 8.02 (d, 1H), 8.84 (s, 1H) and 9.98 ppm (s, 1H). MS m/z: 507.0 (M+H)$^+$, 529.0 (M+Na)$^+$.

EXAMPLE 64

1'-[4,8-Dimethoxyquinoline-2-yl)carbonyl]-6-methoxyspiro[2H-1,3-benzoxazin-2,4'-piperidin]-4-(3H)-one (Compound 150)

Method A: A mixture of 26 mg (0.083 mmol) of N-[4,8-dimethoxyquinoline-2-yl)carbonyl]-4-piperidone (prepared as described in Example 44), 14 mg (0.083 mmol) of 2-hydroxy-5-methoxybenzamide, and 0.020 mL of morpholine in a mixture of 0.2 mL of toluene and 0.6 mL of methanol is refluxed for 20 hr. The reaction mixture is diluted with ethyl acetate, and washed with water, brine, and dried over Na$_2$SO$_4$. After solvent removal by rotoevaporation, the crude product is purified by preparative TLC to give 17 mg (0.037 mmol, 45% yield) of 1'-[4,8-dimethoxyquinoline-2-yl)carbonyl]-6-methoxyspiro-[2H-1,3-benzoxazin-2,4'-piperidin]-4-(3H)-one (Compound 150): $^1$H NMR (DMSO-$d_6$): δ 3.76 (s, 3H), 3.95 (s, 3H), 4.07 (s, 3H), 7.04 (d, 1H), 7.12 (d of d, 1H), 7.19 (s, 1H), 7.24 (m, 2H), 7.52 (d of d, 1H), 7.68 (d, 1H), and 8.85 ppm (s, 1H). MS m/z: 464.1 (M+H)$^+$, 486.2 (M+Na)$^+$.

Method B: Alternatively, to a solution of 43 mg (0.18 mmol) of 4,8-dimethoxyquinoline-2-carboxylic acid (see US2007/0021453A1), 70 mg (0.18 mmol) of HATU, and 0.067 mL (0.39 mmol) of diisopropylethylamine in 1.0 mL of DMF is added 50 mg (0.18 mmol) 6-methoxyspiro-[2H-1,3-benzoxazin-2,4'-piperidin]-4-(3H)-one hydrochloride (prepared by Apollo Scientific from 2-hydroxy-5-methoxybenzamide and 1-Boc-4-piperidone followed by hydrochloric acid cleavage of the Boc protecting group). The mixture is stirred at room temperature for 3 hr., and then diluted with ethyl acetate. The ethyl acetate solution is washed with aqueous sodium bicarbonate, then brine, and is finally dried over Na$_2$SO$_4$. After solvent removal by rotoevaporation, the crude product is crystallized from ether to give 53 mg (0.11 mmol, 64% yield) 1'-[(4,8-dimethoxyquinoline-2-yl)carbonyl]-6-methoxyspiro-[2H-1,3-benzoxazine-2,4'-piperidine]-4(3H)-one (Compound 150).

EXAMPLES 65-102

Alkoxy substituted 1'-[arylcarbonyl]spiro[2H-1,3-benzoxazin-2,4'-piperidin]-4-(3H)-ones (Compounds 104, 111, 112, 113, 114, 129, 130, 139, 144, 146, 149, 151, 152, 157, 168, 169, 170, 172, 173, 174, 175, 176, 180, 181, 182, 184, 185, 198, 199, 200, 220, 221, 222, 224, 225, 229, 230 and 247)

The following alkoxy substituted spiro[2H-1,3-benzoxazin-2,4'-piperidin]-4-(3H)-ones are prepared similarly to Example 64 but incorporating the appropriate building blocks according to the Method indicated:

Methoxy Substituted Compounds:

65. 1'-[(1H-Benzotriazol-6-yl)carbonyl]-5-methoxyspiro[2H-1,3-benzoxazin-2,4'-piperidin]-4-(3H)-one (Compound 129; Method A);

66. 1'-[(1H-Benzimidazol-5-yl)carbonyl]-5-methoxyspiro[2H-1,3-benzoxazin-2,4'-piperidin]-4-(3H)-one (Compound 130; Method A);

67. 6-Methoxy-1'-[7-methoxy-3-methyl-1H-indol-2-yl)carbonyl]spiro[2H-1,3-benzoxazin-2,4'-piperidin]-4-(3H)-one (Compound 151; Method A, B): $^1$H NMR (CDCl$_3$): δ 2.22 (s, 3H), 3.75 (s, 3H), 3.89 (s, 3H), 6.71 (d, 1H), 6.95 (d of d, 1H), 7.03 (d, 1H), 7.11 (m, 2H), 7.23 (d, 1H), 8.84 (s, 1H) and 11.23 ppm (s, 1H). MS m/z: 458.0 (M+Na)$^+$;

68. 1'-[(4,8-Dimethoxynaphth-2-yl)carbonyl]-6-methoxyspiro[2H-1-1,3-benzoxazin-2,4'-piperidin]-4-(3H)-one (Compound 152; Method A, B): $^1$H NMR (CDCl$_3$): δ 3.75 (s, 3H), 3.97 (s, 3H), 3.99 (s, 3H), 6.96 (s, 1H), 7.04 (m, 2H), 7.12 (d of d, 1H), 7.23 (d, 1H), 7.48 (d of d, 1H), 7.71 (m, 1H), and 8.76 ppm (s, 1H). MS m/z: 463.1 (M+H)$^+$, 485.1 (M+Na)$^+$;

69. 6-Methoxy-1'-[4-methoxy-8-methylthioquinolin-2-yl)carbonyl]spiro[2H-1,3-benzoxazin-2,4'-piperidin]-4-(3H)-one (Compound 157; Method A): $^1$H NMR (CDCl$_3$): δ 2.48 (s, 3H), 3.76 (s, 3H), 4.10 (s, 3H), 7.04 (d, 1H), 7.13 (d of d, 1H), 7.25 (d, 1H), 7.27 (s, 1H), 7.50 (d of d, 1H), 7.58 (d of d, 1H), 7.87 (d of d, 1H), and 8.84 ppm (s, 1H). MS m/z: 480.1 (M+H)$^+$, 502.1 (M+Na)$^+$;

70. 6-Methoxy-1'-[(7-methyl-1H-indazol-5-yl)carbonyl]spiro[2H-1,3-benzoxazin-2,4'-piperidin]-4-(3H)-one (Compound 220; Method B);

71. 1'-[4,7-Dimethoxy-1-methyl-1H-indol-2-yl)carbonyl]-6-methoxy-spiro[1,3-benzoxazin-2,4'-piperidin]-4-(3H)-one (Compound 181; Method B): $^1$H NMR (CDCl$_3$): δ 3.75 (s, 3H), 3.80 (s, 3H), 3.84 (s, 3H), 3.94 (s, 3H), 6.40 (d, 1H), 6.53 (s, 1H), 6.62 (d, 1H), 7.02 (d, 1H), 7.12 (d, 1H), 7.24 (s, 1H) and 8.74 pp (s, 1H). MS m/z: 466.0 (M+H)$^+$, 488.1 (M+Na)$^+$;

72. 1'-[4,7-Dimethoxy-1H-indol-2-yl)carbonyl]-6-methoxy-spiro[1,3-benzoxazin-2,4'-piperidin]-4-(3H)-one (Compound 182; Method B): $^1$H NMR (CDCl$_3$): δ 3.76 (s, 3H), 3.81 (s, 3H), 3.84 (s, 3H), 6.38 (d, 1H), 6.59 (d, 1H), 6.64 (d, 1H), 7.03 (d, 1H), 7.12 (d of d, 1H), 7.24 (d, 1H), and 8.83 ppm (s, 1H);

73. 1'-[1H-Indazol-5-yl)carbonyl]-6-methoxy-spiro[1,3-benzoxazin-2,4'-piperidin]-4-(3H)-one (Compound 198; Method B): $^1$H NMR (CDCl$_3$): δ 3.75 (s, 3H), 7.02 (d, 1H), 7.12 (d of d, 1H), 7.23 (d, 1H), 7.39 (d of d, 1H), 7.59 (d, 1H), 7.86 (s, 1H), 8.15 (s, 1H), 8.77 (s, 1H), and 13.25 ppm (s, 1H). MS m/z: 392.9 (M+H)$^+$, 414.7 (M+Na)$^+$;

74. 1'-[(1-Cyclopropyl-4-methoxy-1H-indol-6-yl)carbonyl]-6-methoxyspiro[2H-1,3-benzoxazin-2,4'-piperidin]-4-(3H)-one (Compound 224; Method B);

75. 6-Methoxy-1'-[4-methoxy-1H-indazol-6-yl)carbonyl]spiro[1,3-benzoxazin-2,4'-piperidin]-4-(3H)-one (Compound 229; Method B): $^1$H NMR (CDCl$_3$): δ 3.75 (s, 3H), 3.94 (s, 3H), 6.52 (s, 1H), 7.01 (d, 1H), 7.10 (m, 1.5H), 7.13 (d, 0.5H), 7.23 (d, 1H), 8.07 (d of d, 1H), 8.77 (s, 1H), and 13.23 ppm (d, 1H). MS m/z: 423.2 (M+H)$^+$, 445.1 (M+Na)$^+$;

76. 1'-[7-Ethyl-1H-indazol-5-yl)carbonyl]-6-methoxyspiro[1,3-benzoxazin-2,4'-piperidin]-4-(3H)-one (Compound 247, Method B).

Ethoxy Substituted Compounds:

77. 1'-[4,8-Dimethoxyquinoline-2-yl)carbonyl]-6-ethoxyspiro[2H-1,3-benzoxazin-2,4'-piperidin]-4-(3H)-one (Compound 139; Method A): $^1$H NMR (CDCl$_3$): δ 1.31 (t, 3H), 3.95 (s, 3H), 4.01 (q, 2H), 4.06 (s, 1H), 7.02 (d, 1H), 7.10 (d of d, 1H), 7.19 (s, 1H), 7.21 (d, 1H), 7.23 (d of d, 1H) 7.52 (d of d, 1H), 7.68 (d of d, 1H), and 8.83 ppm (s, 1H). MS m/z: 478.1 (M+H)$^+$, 500.0 (M+Na)$^+$;

78. 6-Ethoxy-1'-[7-methoxy-3-methyl-1H-indol-2-yl)carbonyl]spiro[2H-1,3-benzoxazin-2,4'-piperidin]-4-(3H)-one (Compound 144; Method A): $^1$H NMR (CDCl$_3$): δ 1.31 (t, 3H), 3.89 (s, 3H), 4.01 (q, 2H), 6.71 (d, 1H), 6.95 (d of d, 1H), 7.01 (d, 1H), 7.10 (m, 2H), 7.21 (d, 1H), 8.83 (s, 1H), and 11.23 ppm (s, 1H). MS m/z: 450.1 (M+H)$^+$, 472.0 (M+Na)$^+$;

79. 1'-[(4,8-Dimethoxynaphth-2-yl)carbonyl]-6-ethoxyspiro[2H-1,3-benzoxazin-2,4'-piperidin]-4-(3H)-one (Compound 146; Method A): $^1$H NMR (CDCl$_3$): δ 1.31 (t, 3H), 3.97 (s, 3H), 3.99 (s, 3H), 4.01 (q, 2H), 6.96 (d, 1H), 7.01 (d, 1H), 7.06 (d, 1H), 7.10 (d of d, 1H), 7.21 (d, 1H), 7.48 (d of d, 1H), 7.71 (m, 2H), 8.74 ppm (s, 1H). MS m/z: δ 477.0 (M+H)$^+$, 499.1 (M+Na)$^+$;

80. 6-Ethoxy-1'-[4-methoxy-8-methylthioquinolin-2-yl)carbonyl]spiro[2H-1,3'-benzoxazin-2,4'-piperidin]-4-(3H)-one (Compound 149: Method A): $^1$H NMR (CDCl$_3$): δ 1.31 (t, 3H), 3.32 (s, 3H), 4.01 (q, 2H), 4.08 (s, 3H), 7.03 (d, 1H), 7.11 (d of d, 1H), 7.22 (d, 1H), 7.27 (s, 1H), 7.49 (d, 1H) 7.57 (d of d, 1H), 7.87 (d of d, 1H), and 8.86 ppm (s, 1H). MS m/z: 494.1 (M+H)$^+$, 516.2 (M+Na)$^+$;

81. 6-Ethoxy-1'-[4-methoxy-8-methylthionaphth-2-yl)carbonyl]spiro[1,3-benzoxazin-2,4'-piperidin]-4-(3H)-one (Compound 176; Method A): $^1$H NMR (CDCl$_3$): δ 1.31 (t, 3H), 2.59 (s, 3H), 4.00 (s, 3H), 7.01 (m, 2H), 7.10 (d, 1H), 7.20 (s, 1H), 7.51 (m, 2H), 7.68 (s, 1H), 7.99 (d, 1H), and 8.77 ppm (s, 1H). MS m/z: δ 493.0 (M+H)$^+$, 515.1 (M+Na)$^+$;

82. 6-Ethoxy-1'-[(7-methyl-1H-indazol-5-yl)carbonyl]spiro[2H-1,3-benzoxazin-2,4'-piperidin]-4-(3H)-one (Compound 222; Method B).

Isopropoxy Substituted Compounds:

83. 6-Isopropoxy-1'-[3-(1H-pyrazol-3-yl)benzoyl]spiro[2H-1,3-benzoxazin-2,4'-piperidin]-4-(3H)-one (Compound 104; Method B);

84. 6-Isopropoxy-1'-[(7-methyl-1H-indazol-5-yl)carbonyl]spiro[2H-1,3-benzoxazin-2,4'-piperidin]-4-(3H)-one (Compound III; Method B);

85. 1'-[(1H-Benzotriazol-5-yl)carbonyl]-6-isopropoxyspiro[2H-1,3-benzoxazin-2,4'-piperidin]-4-(3H)-one (Compound 112; Method B);

86. 6-Isopropoxy-1'-[(1-methyl-1H-indol-6-yl)carbonyl]spiro[2H-1,3-benzoxazin-2,4'-piperidin]-4-(3H)-one (Compound 113; Method B);

87. 6-Isopropoxy-1'-[(1-methyl-1H-indol-6-yl)carbonyl]spiro[2H-1,3-benzoxazin-2,4'-piperidin]-4-(3H)-one (Compound 114; Method B);

88. 6-Isopropoxy-1'-[4-methoxy-8-methylthioquinolin-2-yl)carbonyl]spiro[2H-1,3-benzoxazin-2,4'-piperidin]-4-(3H)-one (Compound 168; Method B);

89. 1'-[4,8-Dimethoxyquinoline-2-yl)carbonyl]-6-isopropoxyspiro[1,3-benzoxazin-2,4'-piperidin]-4-(3H)-one (Compound 169; Method B): $^1$H NMR (CDCl$_3$): δ 1.24 (d, 6H), 3.95 (s, 3H), 4.06 (s, 3H), 4.54 (septet, 1H), 7.01 (d, 1H), 7.09 (d of d, 1H), 7.22 (m, 3H), 7.52 (d of d, 1H), 7.68 (d, 1H), and 8.84 ppm (s, 1H). MS m/z: 492.0 (M+H), 514.0 (M+Na)$^+$;

90. 1'-[4,8-Dimethoxynaphth-2-yl)carbonyl]-6-isopropoxyspiro[1,3-benzoxazin-2,4'-piperidin]-4-(3H)-one (Compound 170; Method B); $^1$H NMR (CDCl$_3$): δ 1.24 (d, 6H), 3.97 (s, 3H), 3.98 (s, 3H), 4.53 (septet, 1H), 6.96 (s, 1H), 7.00 (d, 1H), 7.08 (m, 2H), 7.20 (d, 1H), 7.48 (d of d, 1H), 7.71 (m, 2H), and 8.75 ppm (s, 1H). MS m/z: δ 491.0 (M+H)$^+$, 513.0 (M+Na)$^+$;

91. 6-Isopropoxy-1'-[7-methoxy-3-methyl-1H-indol-2-yl)carbonyl]spiro[1,3-benzoxazin-2,4'-piperidin]-4-(3H)-one (Compound 180; Method B): $^1$H NMR (CDCl$_3$): δ 1.24 (d, 6H), 2.22 (s, 3H), 3.89 (s, 3H), 4.53 (septet, 1H), 6.70 (d, 1H), 6.95 (d of d, 1H), 6.98 (d, 1H), 7.01 (s, 1H), 7.08 (d of d, 1H), 7.11 (d, 1H), 7.20 (d, 1H), 8.84 (s, 1H) and 11.24 ppm (s, 1H). MS m/z: 464.0 (M+H)$^+$, 486.0 (M+Na)$^+$;

92. 1'-[4,7-Dimethoxy-1H-indol-2-yl)carbonyl]-6-isopropoxy-spiro[1,3-benzoxazin-2,4'-piperidin]-4-(3H)-one (Compound 184; Method B): $^1$H NMR (CDCl$_3$): δ 1.25 (d, 6H), 3.81 (s, 3H), 3.84 (s, 3H), 4.54 (septet, 1H), 6.38 (d, 1H), 6.59 (d, 1H), 6.64 (d, 1H), 7.00 (d, 1H), 7.09 (d of d, 1H), 7.21 (d, 1H), 8.81 (s, 1H), and 11.55 ppm (d, 1H). MS m/z: 480.0 (M+H)$^+$, 502.1 (M+Na)$^+$;

93. 1'-[4,7-Dimethoxy-1-methyl-1H-indol-2-yl)carbonyl]-6-isopropoxy-spiro[1,3-benzoxazin-2,4'-piperidin]-4-(3H)-one (Compound 185; Method B): $^1$H NMR (CDCl$_3$): δ 1.24 (d, 6H), 3.80 (, 3H), 3.84 (s, 3H) 3.94 (s, 3H), 4.54 (septet, 1H), 6.40 (d, 1H), 6.53 (s, 1H), 6.62 (d, 1H), 7.00 (d, 1H), 7.09 (d of d, 1H), and 8.73 ppm (1H). MS m/z: 494.1 (M+H)$^+$, 516.1 (M+Na)$^+$;

94. 1'-[1H-Indazol-5-yl)carbonyl]-6-isopropoxy-spiro[1,3-benzoxazin-2,4'-piperidin]-4-(3H)-one (Compound 199; Method B): $^1$H NMR (CDCl$_3$): δ 1.24 (d, 6H), 4.53 (septet, 1H), 6.99 (d, 1H), 7.08 (d of d, 1H), 7.20 (d, 1H), 7.39 (d, 1H), 7.58 (d, 1H), 7.86 (s, 1H), 8.14 (s, 1H) 8.76 (s, 1H), and 13.25 ppm (s, 1H). MS m/z: 421.0 (M+H)$^+$, 442.9 (M+Na)$^+$;

95. 6-Isopropoxy-1'-[(7-methyl-1H-indazol-5-yl)carbonyl]spiro[2H-1,3-benzoxazin-2,4'-piperidin]-4-(3H)-one (Compound 221; Method B);

96. 1'-[(1-Cyclopropyl-4-methoxy-1H-indol-6-yl)carbonyl]-6-isopropoxyspiro[2H-1,3-benzoxazin-2,4'-piperidin]-4-(3H)-one (Compound 225; Method B);

97. 6-Isopropoxy-1'-[4-methoxy-1H-indazol-6-yl)carbonyl]spiro[1,3-benzoxazin-2,4'-piperidin]-4-(3H)-one (Compound 230; Method B): $^1$H NMR (CDCl$_3$): δ 1.24 (d, 6H), 3.94 (s, 3H), 4.53 (septet, 1H), 6.52 (s, 1H), 6.98 (d, 1H), 7.08 (d, 0.5H), 7.10 (m, 1.5H), 7.20 (d, 1H), 8.07 (s, 1H), 8.76 (s, 1H), and 13.22 (d, 1H). MS m/z: 451.1 (M+H)$^+$, 473.1 (M+Na)$^+$;

Trifluoromethoxy Substituted Compounds:

98. 1'-[4,8-Dimethoxyquinoline-2-yl)carbonyl]-6-trifluoromethoxyspiro[1,3-benzoxazin-2,4'-piperidin]-4-(3H)-one (Compound 172; Method A): $^1$H NMR (CDCl$_3$): δ 3.95 (s, 3H), 4.07 (s, 3H), 7.20 (s, 1H), 7.24 (d of d, 1H), 7.25 (d, 1H), 7.52 (d of d, 1H), 7.58 (d of d, 1H), 7.64 (d, 1H) 7.68 (d of d, 1H), and 9.12 ppm (s, 1H). MS m/z: 518.0 (M+H)$^+$;

99. 1'-[4,8-Dimethoxynaphth-2-yl)carbonyl]-6-trifluoromethoxyspiro[1,3-benzoxazin-2,4'-piperidin]-4-(3H)-one (Compound 173; Method A): $^1$H NMR (CDCl$_3$): δ 3.97 (S, 3H), 3.98 (s, 3H), 6.96 (d, 1H), 7.06 (d, 1H), 7.23 (d, 1H), 7.48 (d of d, 1H), 7.58 (d of d, 1H), 7.63 (d, 1H), 7.71 (d, 1H), 7.71 (s, 1H), and 9.03 ppm (s, 1H). MS m/z: 517.0 (M+H)$^+$, 539.0 (M+Na)$^+$;

100. 1'-[7-Methoxy-3-methyl-1H-indol-2-yl)carbonyl]-6-trifluoromethoxyspiro-[1,3-benzoxazin-2,4'-piperidin]-4-(3H)-one (Compound 174; Method B): $^1$H NMR (CDCl$_3$): δ 2.22 (s, 3H), 3.89 (s, 3H), 6.71 (d, 1H), 6.95 (d of d, 1H), 7.11 (d, 1H), 7.24 (d, 1H), 7.57 (d of d, 1H), 7.64 (d, 1H), 9.11 (s, 1H) and 11.24 ppm (S, 1H). MS m/z: 489.9 (M+H)$^+$, 512.0 (M+Na)$^+$;

101. 1'-[4-Methoxy-8-methylthionaphth-2-yl)carbonyl]-6-trifluoromethoxyspiro-[1,3-benzoxazin-2,4'-piperidin]-4-(3H)-one (Compound 175; Method A): $^1$H NMR (CDCl$_3$): δ 2.59 (s, 3H), 4.00 (s, 3H), 6.99 (d, 1H), 7.01 (d, 1H) 7.24 (d, 1H), 7.44 (m, 1H), 7.49 (d of d, 1H), 7.55 (d of d, 1H), 7.58 (m, 1H), 7.64 (d of d, 1H), 7.68 (s, 1H), and 9.05 ppm (s, 1H). MS m/z: 555.0 (M+Na)$^+$;

102. 1'-[1H-Indazol-5-yl)carbonyl]-6-trifluoromethoxyspiro[1,3-benzoxazin-2,4'-piperidin]-4-(3H)-one (Compound 200; Method B): $^1$H NMR (CDCl$_3$): δ 7.23 (d, 1H), 7.39 (d of d, 1H), 7.58 (d of d, 1H), 7.58 (s, 1H), 7.64 (d, 1H), 7.86 (s, 1H), 8.15 (s, 1H), 9.05 (s, 1H), and 13.25 ppm (s, 1H). MS m/z: 447.0 (M+H)$^+$, 469.0 (M+Na).

EXAMPLE 103

1'-[4,8-Dimethoxyquinoline-2-yl)carbonyl]-6-methylspiro[2H-1,3-benzoxazin-2,4'-piperidin]-4-(3H)-one (Compound 137)

To a solution of 500 mg (3.01 mmol) of methyl 2-hydroxy-5-methylbenzoate in 2 mL of dioxane is added 2 mL of aqueous 28% ammonium hydroxide. The solution is heated at 80° C. for 20 hr., then concentrated to dryness. The light brown solid is triturated with diethyl ether to remove unrelated ester. The remaining solid (480 mg, 2.89 mmol) is pure 2-hydroxy-5-methylbenzamide (96% yield).

A mixture of 26 mg (0.083 mmol) of N-[4,8-dimethoxyquinoline-2-yl)carbonyl]-4-piperidone (prepared as described in Example 44), 12.5 mg (0.083 mmol) of 2-hydroxy-5-methylbenzamide, and 0.020 mL of morpholine in 2 mL of methanol is refluxed for 20 hr. The reaction mixture is diluted with ethyl acetate, and washed with water, brine, and dried over Na$_2$SO$_4$. After solvent removal by rotoevaporation, the crude product is purified by preparative TLC to give 20 mg (0.045 mmol, 54% yield) of 1'-[4,8-dimethoxyquinoline-2-yl)carbonyl]-6-methylspiro-[2H-1,3-benzoxazin-2,4'-piperidin]-4-(3H)-one (Compound 137): $^1$H NMR (DMSO-d$_6$): δ 2.28 (s, 3H), 3.95 (s, 3H), 4.06 (s, 3H), 6.98 (d, 1H), 7.19 (s, 1H), 7.23 (d of d, 1H), 7.33 (d of d, 1H), 7.52 (d of d, 1H), 7.56 (d, 1H), 7.68 (d of d, 1H), and 8.77 ppm (s, 1H). MS m/z: 448.1 (M+H)$^+$, 470.0 (M+Na)$^+$.

EXAMPLE 104

6-Methyl-1'-[(7-methyl-1H-indazol-5-yl)carbonyl]spiro[2H-1,3-benzoxazin-2,4'-piperidin]-4-(3H)-one (Compound 123)

To a solution of 32 mg (0.18 mmol) of 7-methyl-1H-indazole-5-carboxylic acid (see WO2008/065508), 70 mg (0.18 mmol) of HATU, and 0.067 mL (0.39 mmol) of diisopropylethylamine in 1.0 mL of DMF is added 62 mg (0.18 mmol) of the trifluoroacetic acid salt of 6-methylspiro-[2H-1,3-benzoxazin-2,4'-piperidin]-4-(3H)-one (from TFA cleavage of 6-methyl-1'-(tert-butyloxycarbonyl)spiro[1,3-benzoxazine-2,4'-piperidine]-4(3H)-one, purchased from Apollo Scientific). The mixture is stirred at room temperature for 3 hr., and then diluted with ethyl acetate. The ethyl acetate solution is washed with aqueous sodium bicarbonate, then brine, and is finally dried over Na$_2$SO$_4$. After solvent removal by rotoevaporation, the crude product is purified by preparative TLC to give to give 38 mg (0.10 mmol. 56% yield) 6-methyl-1'-[(7-methyl-1H-indazol-5-yl)carbonyl]spiro[2H-1,3-benzoxazin-2,4'-piperidin]-4-(3H)-one (Compound 123): MS m/z: 391.0 (M+H)$^+$, 413.0 (M+Na)$^+$.

EXAMPLES 105-122

Alkyl substituted 1'-[arylcarbonyl]spiro[2H-1,3-benzoxazin-2,4'-piperidin]-4-(3H)-ones (Compounds 14, 124, 125, 126, 127, 128, 143, 145, 148, 153, 154, 155, 178, 179, 186, 223, 226, and 231)

The following alkyl substituted spiro[2H-1,3-benzoxazin-2,4'-piperidin]-4-(3H)-ones are prepared by methodology used in Examples 103 or 104 as indicated, but incorporating the appropriate building blocks:

Methyl and Dimethyl Substituted Compounds:

105. 6-Methyl-1'-[3-(1H-pyrazol-3-yl)benzoyl]spiro[2H-1,3-benzoxazin-2,4'-piperidin]-4-(3H)-one (Compound 125; Method of Example 104);

106. 1'-[(7-Chloro-1H-indazol-5-yl)carbonyl]-6-methylspiro[2H-1,3-benzoxazin-2,4'-piperidin]-4-(3H)-one (Compound 127; Method of Example 104);

107. 1'-[7-Methoxy-3-methyl-1H-indol-2-yl)carbonyl]-6-methylspiro[2H-1,3-benzoxazin-2,4'-piperidin]-4-(3H)-one (Compound 143; Method of Example 103): $^1$H NMR (DMSO-d$_6$): δ 2.28 (s, 1H), 3.89 (s, 3H), 6.71 (d, 1H), 6.96 (m, 2H), 7.11 (d, 1H), 7.33 (d of d, 1H), 7.55 (d, 1H), 8.77 (s, 1H), and 11.23 ppm (s, 1H). MS m/z: 420.2 (M+H)$^+$, 442.1 (M+Na)$^+$;

108. 1'-[(4,8-Dimethoxynaphth-2-yl)carbonyl]-6-methylspiro[2H-1,3-benzoxazin-2,4'-piperidin]-4-(3H)-one (Compound 145; Method of Example 103): $^1$H NMR (DMSO-d$_6$): δ 2.28 (s, 3H), 3.97 (s, 3H), 3.99 (s, 3H), 6.96 (s, 1H), 3.97 (d, 1H), 7.06 (d, 1H), 7.33 (d of d, 1H), 7.55 (d, 1H), 7.71 (m, 2H), and 8.68 ppm (s, 1H). MS m/z: 447.1 (M+H)$^+$, 469.0 (M+Na)$^+$;

109. 1'-[4-Methoxy-8-methylthioquinolin-2-yl)carbonyl]-6-methylspiro[2H-1,3-benzoxazin-2,4'-piperidin]-4-(3H)-one (Compound 148; Method of Example 103): $^1$H NMR (DMSO-d$_6$): δ 2.29 (3H), 2.48 (s, 3H), 4.08 (s, 3H), 6.99 (d, 1H), 7.27 (s, 1H), 7.34 (d of d, 1H), 7.49 (d of d, 1H), 7.56 (d, 1H), 7.58 (d of d, 1H), 7.87 (d of d, 1H), and 8.80 ppm (s, 1H). MS m/z: 464.1 (M+H)$^+$, 486.0 (M+Na)$^+$;

110. 6,7-Dimethyl-1'-[(7-methyl-1H-indazol-5-yl)carbonyl]spiro[2H-1,3-benzoxazin-2,4'-piperidin]-4-(3H)-one (Compound 124; Method of Example 104);

111. 6,7-Dimethyl-1'-[3-(1H-pyrazol-3-yl)benzoyl]spiro[2H-1,3-benzoxazin-2,4'-piperidin]-4-(3H)-one (Compound 126; Method of Example 104);

112. 1'-[(7-Chloro-1H-indazol-5-yl)carbonyl]-6,7-dimethylspiro[2H-1,3-benzoxazin-2,4'-piperidin]-4-(3H)-one (Compound 128; Method of Example 104);

113. 1'-[4,8-Dimethoxyquinoline-2-yl)carbonyl]-6,7-dimethylspiro[2H-1,3-benzoxazin-2,4'-piperidin]-4-(3H)-one (Compound 153; Method of Example 103): $^1$H NMR (DMSO-d$_6$): δ 2.19 (s, 3H), 2.24 (s, 3H), 3.96 (s, 3H), 4.07 (s, 3H), 6.89 (s, 1H), 7.19 (s, 1H), 7.25 (m, 1H), 7.53 (m, 2H), 7.68 (d, 1H), 8.63 (s 0.8H), and 8.73 ppm (s, 0.2H). MS m/z: 462.0 (M+H)$^+$, 484.1 (M+Na)$^+$;

114. 6,7-Dimethyl-1'-[4-methoxy-8-methylthioquinolin-2-yl)carbonyl]spiro[2H-1,3-benzoxazin-2,4'-piperidin]-4-(3H)-one (Compound 154; Method of Example 103): ¹H NMR (DMSO-d₆): δ 2.19 (s, 3H), 2.24 (s, 3H), 2.48 (s, 3H), 4.09 (s, 3H), 6.83 (d, 0.3H), 6.90 (s, 0.7H), 7.27 (d, 0.3H), 7.27 (S, 1H), 7.49 (d, 0.7H), 7.50 (s, 1H), 7.57 (d of d, 1H), 7.87 (d, 1H), 8.65 (s, 0.7H) and 8.74 ppm (s, 0.3H). MS m/z: 478.1 (M+H)$^+$, 500.1 (M+Na)$^+$;

115. 1'-[(4,8-Dimethoxynaphth-2-yl)carbonyl]-6,7-dimethylspiro[2H-1,3-benzoxazin-2,4'-piperidin]-4-(3H)-one (Compound 155; Method of Example 103): ¹H NMR (DMSO-d₆): δ 2.19 (s, 3H), 2.24 (s, 3H), 3.98 (s, 3H), 3.99 (s, 3H), 6.82 (d, 0.3H), 6.88 (s, 0.7H), 6.96 (s, 1H), 7.06 (d, 1H), 7.27 (d, 0.3H), 7.48 (m, 1.7H), 7.72 (m, 2H), 8.54 (s, 0.7H), and 8.65 ppm (s, 0.3H). MS m/z: 461.1 (M+H)$^+$, 483.2 (M+Na)$^+$.

Isopropyl and Tert-Butyl Substituted Compounds:

116. 6-tert-Butyl-1'-[4,8-dimethoxyquinoline-2-yl)carbonyl]spiro[2H-1,3-benzoxazin-2,4'-piperidin]-4-(3H)-one (Compound 14: Method of Example 103);

117. 1'-[4,8-Dimethoxynaphth-2-yl)carbonyl]-6-isopropylspiro[1,3-benzoxazin-2,4'-piperidin]-4-(3H)-one (Compound 178; Method of Example 103): ¹H NMR (DMSO-d₆): δ 1.18 (d, 6H), 2.89 (septet, 1H), 3.97 (s, 3H), 3.98 (s, 3H), 6.96 (d, 1H), 7.00 (d, 1H), 7.06 (d, 1H), 7.42 (d of d, 1H), 7.48 (d of d, 1H), 7.60 (d, 1H), 7.71 (d, 1H), 7.71 (s, 1H), and 8.71 ppm (s, 1H). MS m/z: 475.0 (M+H)$^+$, 497.1 (M+Na)$^+$;

118. 6-Isopropyl-1'-[4-methoxy-8-methylthionaphth-2-yl)carbonyl]spiro[1,3-benzoxazin-2,4'-piperidin]-4-(3H)-one (Compound 179; Method of Example 103): ¹H NMR (DMSO-d₆): δ 1.18 (d, 6H), 2.59 (s, 3H), 4.00 (s, 3H), 7.00 (s, 2H), 7.42 (d, 1H), 7.51 (m, 2H), 7.60 (s, 1H), 7.68 (s, 1H), 7.99 (d, 1H), and 8.73 ppm (s, 1H). MS m/z: 491.0 (M+H)$^+$, 513.0 (M+Na)$^+$;

119. 1'-[4,8-Dimethoxyquinoline-2-yl)carbonyl]-6-isopropylspiro[1,3-benzoxazin-2,4'-piperidin]-4-(3H)-one (Compound 186; Method of Example 103): ¹H NMR (DMSO-d₆): δ 1.18 (d, 6H), 2.89 (septet, 1H), 3.95 (s, 3H), 4.06 (s, 3H), 7.01 (d, 1H), 7.19 (s, 1H), 7.23 (d, 1H), 7.42 (d of d, 1H), 7.52 (d of d, 1H), 7.61 (d, 1H), 7.68 (d, 1H), and 8.81 ppm (s, 1H). MS m/z: 476.0 (M+H)$^+$, 498.1 (M+Na)$^+$;

120. 6-Isopropyl-1'-[(7-methyl-1H-indazol-5-yl)carbonyl]spiro[2H-1,3-benzoxazin-2,4'-piperidin]-4-(3H)-one (Compound 223; Method of Example 104);

121. 1'-[(1-Cyclopropyl-4-methoxy-1H-indol-6-yl)carbonyl]-6-isopropylspiro-[2H-1,3-benzoxazin-2,4'-piperidin]-4-(3H)-one (Compound 226; Method of Example 104);

122. 6-Isopropyl-1'-[4-methoxy-1H-indazol-6-yl)carbonyl]spiro[1,3-benzoxazin-2,4'-piperidin]-4-(3H)-one (Compound 231; method of Example 104): ¹H NMR (DMSO-d₆): δ 1.18 (d, 6H), 2.89 (septet, 1H), 3.93 (s, 3H), 6.50 (s, 1H), 6.97 (d, 1H), 7.08 (d, 1H), 7.40 (d of d, 1H), 7.58 (d, 1H), 8.05 (s, 1H), 8.69 (s, 1H), and 13.22 ppm (s, 1H). MS m/z: 435.0 (M+H)$^+$, 457.0 (M+Na)$^+$.

EXAMPLE 123

1'-[4,8-Dimethoxyquinoline-2-yl)carbonyl]spiro[2H-naphtho[2,3-e]-1,3-oxazin-2,4'-piperidin]-4-(3H)-one (Compound 159)

A mixture of 26 mg (0.083 mmol) of N-[4,8-dimethoxyquinoline-2-yl)carbonyl]-4-piperidone (prepared as described in Example 44), 15.5 mg (0.083 mmol) of 3-hydroxy-2-naphthalenecarboxamide, and 0.020 mL of morpholine in a mixture of 0.2 mL of toluene and 0.6 mL of methanol is refluxed for 20 hr. The reaction mixture is diluted with ethyl acetate, and washed with water, brine, and dried over Na₂SO₄. After solvent removal by rotoevaporation, the crude product is purified by preparative TLC to give 11 mg (0.023 mmol, 27% yield) of 1'-[4,8-dimethoxyquinoline-2-yl)carbonyl]spiro[2H-naphtho[2,3-e]-1,3-oxazin-2,4'-piperidin]-4-(3H)-one (Compound 159): ¹H NMR (DMSO-d₆): δ 3.95 (s, 3H), 4.07 (s, 3H), 7.20 (s, 1H), 7.23 (d, 1H), 7.44 (d of d, 1H), 7.55 (m, 3H), 7.67 (d, 1H), 8.04 (d, 1H), 8.46 (s, 1H), and 9.09 ppm (s, 1H). MS m/z: 484.0 (M+H)$^+$, 506.0 (M+Na)$^+$.

EXAMPLES 124-132

1'-Arylcarbonyl derivatives of spiro[2H-naphtho[2,3-e]-1,3-oxazin-2,4'-piperidin]-4-(3H)-ones (Compounds 158, 160, 161, 162, 163, 164, 165, 166, and 167)

The following 1'-arylcarbonyl derivatives of unsubstituted and substituted spiro[2H-naphtho[2,3-e]-1,3-oxazin-2,4'-piperidin]-4-(3H)-ones are prepared by methodology used in Example 123, but incorporating the appropriate building blocks 124. 1'-[4-methoxy-8-methylthioquinolin-2-yl)carbonyl]spiro[2H-naphtho[2,3-e]-1,3-oxazin-2,4'-piperidin]-4-(3H)-one (Compound 158): ¹H NMR (DMSO-d₆): δ 2.48 (s, 3H), 4.09 (s, 3H), 7.28 (s, 1H), 7.44 (d of d, 1H), 7.49 (d, 1H), 7.57 (m, 3H), 7.86 (d of d, 2H), 8.05 (d, 1H), 8.46 (s, 1H), and 9.08 ppm (s, 1H). MS m/z: 500.1 (M+H)$^+$, 522.2 (M+Na)$^+$;

125. 1'-[4,8-Dimethoxynaphth-2-yl)carbonyl]spiro[2H-naphtho[2,3-e]-1,3-oxazin-2,4'-piperidin]-4-(3H)-one (Compound 160): ¹H NMR (DMSO-d₆): δ 3.98 (s, 3H), 4.00 (s, 3H), 6.98 (s, 1H), 7.07 (d, 1H), 7.45 (d of d, 1H), 7.48 (d of d, 1H), 7.54 (s, 1H), 7.58 (d of d, 1H), 7.72 (d, 1H), 7.74 (s, 1H), 7.86 (d, 1H), 8.05 (d, 1H), 8.46 (s, 1H), and 8.97 ppm (s, 1H). MS m/z: 483.2 (M+H)$^+$, 505.0 (M+Na)$^+$;

126. 1'-[[7-Methoxy-3-methyl-1H-indol-2-yl)carbonyl]spiro[2H-naphtho[2,3-e]-1,3-oxazin-2,4'-piperidin]-4-(3H)-one (Compound 161): ¹H NMR (DMSO-d₆): δ 2.23 (s, 3H), 3.87 (s, 3H), 6.70 (d, 1H), 6.95 (d of d, 1H), 7.11 (d, 1H), 7.44 (d of d, 1H), 7.55 (s, 1H), 7.56 (d of d, 1H), 7.86 (d, 1H), 8.04 (d, 1H), 8.45 (s, 1H), 9.09 (s, 1H), and 11.26 ppm (s, 1H). MS m/z: 456.0 (M+H)$^+$, 478.0 (M+Na)$^+$;

127. 1'-[4,8-Dimethoxynaphth-2-yl)carbonyl]-7-methoxyspiro[2H-naphtho[2,3-e]-1,3-oxazin-2,4'-piperidin]-4-(3H)-one (Compound 162): ¹H NMR (DMSO-d₆): δ 3.85 (s, 3H), 3.97 (s, 3H), 3.99 (s, 3H), 6.97 (br s, 1H), 7.06 (d, 1H), 7.24 (d of d, 1H), 7.47 (d of d, 1H), 7.48 (s, 1H), 7.71 (d, 1H), 7.72 (s, 1H), 7.78 (d, 1H), 8.33 (s, 1H), and 8.92 ppm (s, 1H). MS m/z: 513.0 (M+H)$^+$, 535.0 (M+Na)$^+$;

128. 7-Methoxy-1'-[[7-methoxy-3-methyl-1H-indol-2-yl)carbonyl]spiro[2H-naphtho[2,3-e]-1,3-oxazin-2,4'-piperidin]-4-(3H)-one (Compound 166): ¹H NMR (DMSO-d₆): δ 2.23 (s, 3H), 3.85 (s, 3H), 3.88 (s, 3H), 6.70 (d, 1H), 6.95 (d of d, 1H), 7.11 (d, 1H), 7.24 (d of d, 1H), 7.48 (m, 2H), 7.78 (s, 1H), 9.02 (s, 1H), and 11.25 ppm (s, 1H). MS m/z: 486.0 (M+H)$^+$, 508.0 (M+Na)$^+$;

129. 7-Bromo-1'-[4,8-Dimethoxynaphth-2-yl)carbonyl]spiro[2H-naphtho[2,3-e]-1,3-oxazin-2,4'-piperidin]-4-(3H)-one (Compound 163);

130. 1'-[4,8-Dimethoxyquinoline-2-yl)carbonyl]-7-methoxyspiro[2H-naphtho[2,3-e]-1,3-oxazin-2,4'-piperidin]-4-(3H)-one (Compound 164): ¹H NMR (DMSO-d₆): δ 3.85 (s, 1H), 3.95 (s, 2H), 4.07 (s, 1H), 7.20 (s, 1H), 7.24 (m, 2H), 7.50 (m, 3H), 7.68 (d of d, 1H), 7.78 (d, 1H), 8.34 (s, 1H), and 9.02 ppm (s, 1H). MS m/z: 514.0 (M+H)$^+$, 536.0 (M+Na)$^+$;

131. 7-Bromo-1'-[4,8-Dimethoxyquinoline-2-yl)carbonyl]spiro[2H-naphtho[2,3-e]-1,3-oxazin-2,4'-piperidin]-4-(3H)-one (Compound 165);
132. 7-Bromo-1'-[[7-methoxy-3-methyl-1H-indol-2-yl)carbonyl]spiro[2H-naphtho[2,3-e]-1,3-oxazin-2,4'-piperidin]-4-(3H)-one (Compound 167).

EXAMPLES 133-137

1'-Arylcarbonyl derivatives of spiro[2H-1,3-benzoxazin-2,4'-piperidin]-4-(3H)-one (Compounds 6, 7, 8, 43, and 87)

The following 1'-arylcarbonyl derivatives of spiro[2H-1,3-benzoxazin-2,4'-piperidin]-4-(3H)-one are prepared by methodology used in Example 123, but incorporating the appropriate building blocks:
133. 1'-[(5-Fluoro-3-methyl-1H-indol-2-yl)carbonyl]spiro[2H-1,3-benzoxazin-2,4'-piperidin]-4-(3H)-one (Compound 6);
134. 1'-[(4,7-Dimethoxy-1H-indol-2-yl)carbonyl]spiro[2H-1,3-benzoxazin-2,4'-piperidin]-4-(3H)-one (Compound 7);
135. 1'-[4,8-Dimethoxyquinoline-2-yl)carbonyl]spiro[2H-1,3-benzoxazin-2,4'-piperidin]-4-(3H)-one (Compound 8);
136. 1'-[8-Methoxyquinolin-2-yl)carbonyl]spiro[2H-1,3-benzoxazin-2,4'-piperidin]-4-(3H)-one (Compound 43);
137. 1'-[5-(4-Methoxyphenyl)-1(H)-pyrazol-3-ylcarbonyl]spiro[2H-1,3-benzoxazin-2,4'-piperidin]-4-(3H)-one (Compound 87).

EXAMPLE 138

1'-[4,8-Dimethoxyquinoline-2-yl)carbonyl]-6-(methoxycarbonyl)spiro[2'-1,3-benzoxazin-2,4'-piperidin]-4-(3H)-one (Compound 201)

To a solution of 1.4 gm (5.2 mmol) of methyl 4-benzyloxy-3-formylbenzoate (prepared by benzylation of methyl 3-formyl-4-hydroxybenzoate) in 25 mL of acetonitrile is added an aqueous solution of $NaH_2PO_4.2H_2O$ (268 mg, 1.68 mmol in 3 mL of water) and 2.8 mL (5 equiv) of 30% hydrogen peroxide. To this mixture is added dropwise an aqueous solution of 79% sodium chlorite (830 mg, 7.25 mmol of $NaClO_2$ in 7 mL of water). After 2 hr at room temperature at room temperature, the reaction mixture is concentrated to remove most of the acetonitrile. The residue is taken up in water and acidified with aqueous HCl. The aqueous acidic solution is extracted with ethyl acetate several times. The combined extracts are washed with brine and dried over $Na_2SO_4$. Rotoevaporation of solvent gives 1.5 gm (5.2 mmol) of methyl 4-benzyloxy-3-carboxybenzoate.

To a solution of 1.5 gm (5.2 mmol) of methyl 4-benzyloxy-3-carboxybenzoate in 8 mL of DMF is added 0.85 gm (6.2 mmol) of HOBT and 1.2 gm (6.2 mmol) of 1-ethyl-3-(3-dimethylaminopropyl)carbodiimide (EDC). After 1 hr, 0.86 mL of 30% ammonium hydroxide is added, and the solution stirred for an additional 2 hr. The reaction mixture is concentrated to remove most of the DMF, and the residue is taken up in ethyl acetate. The ethyl acetate solution is washed with brine and dried over $Na_2SO_4$. Removal of solvent by rotoevaporation gives 1.37 gm (4.8 mmol) of methyl 4-benzyloxy-3-carbamoylbenzoate.

Hydrogenolysis is effected by dissolving 1.2 gm (4.2 mmol) of methyl 4-benzyloxy-3-carbamoylbenzoate in 60 mL of methanol (warmed to effect solution), adding 1 gm of 10% Pd/C (50% water) catalyst, and stirring under 48 psi of hydrogen overnight at room temperature. The reaction mixture is filtered, and the catalyst is repeatedly washed with 10% MeOH/DCM. The combined filtrates are evaporated to dryness to give 0.79 gm (4.05 mmol, 96% yield) of methyl 3-carbamoyl-4-hydroxybenzoate.

A mixture of 125 mg (0.64 mmol) of methyl 3-carbamoyl-4-hydroxybenzoate, 192 mg (0.96 mmol) of 1-Boc-4-piperidone, and 120 μL of morpholine in 10 mL of MeOH is refluxed for 72 hr. The MeOH is removed by rotoevapoation, and DCM is added to the residue. Insoluble material is filtered off, and the filtrate is concentrated by rotoevaporation. The residue is purified by preparative TLC to give 93 mg (0.25 mmol, 39% yield) of 1'-(tert-butyloxycarbonyl)-6-methoxycarbonylspiro[1,3-benzoxazine-2,4'-piperidine]-4(3H)-one which on treatment with 40% TFA in dichloromethane gives the TFA salt of 6-methoxycarbonylspiro[1,3-benzoxazine-2,4'-piperidine]-4(3H)-one in quantitative yield.

To a solution of 72 mg (0.31 mmol) of 4,8-dimethoxyquinoline-2-carboxylic acid, 117 mg (0.31 mmol) of HATU, and 0.22 mL (1.24 mmol) of diisopropylethylamine in 1.5 mL of DMF is added 93 mg (0.25 mmol) of the trifluoroacetic acid (TFA) salt of 6-methoxycarbonylspiro[1,3-benzoxazine-2,4'-piperidine]-4(3H)-one. The mixture is stirred at room temperature for 5 hr., and then diluted with ethyl acetate. The ethyl acetate solution is washed with aqueous sodium bicarbonate, then brine, and is finally dried over $Na_2SO_4$. After solvent removal by rotoevaporation, the crude product is crystallized from ethyl acetate to give 96 mg (0.20 mmol, 80% yield) 1'-[(4,8-dimethoxyquinoline-2-yl)carbonyl]-6-methoxycarbonylspiro-[2H-1,3-benzoxazine-2,4'-piperidine]-4(3H)-one (Compound 201): $^1$H NMR (CDCl$_3$): δ MS m/z: 491.9 (M+H)$^+$, 514.0 (M+Na)$^+$.

EXAMPLE 139

6-Carboxy-1'-[4,8-dimethoxyquinoline-2-yl)carbonyl]spiro[2H-1,3-benzoxazin-2,4'-piperidin]-4-(3H)-one (Compound 202)

To 21 mg (0.043 mmol) of 1'-[(4,8-dimethoxyquinoline-2-yl)carbonyl]-6-methoxycarbonylspiro-[2H-1,3-benzoxazine-2,4'-piperidine]-4(3H)-one in 3 mL of THF/H$_2$O (2:1) is added 3.6 mg (0.086 mmol, 2 equiv) of lithium hydroxide monohydrate. After the reaction is stirred overnight at room temperature, the solvents are removed by rotoevaporation to give 20 mg of 6-carboxy-1'-[4,8-dimethoxyquinoline-2-yl)carbonyl]spiro[2H-1,3-benzoxazin-2,4'-piperidin]-4-(3H)-one as its lithium salt. 6 MS m/z: 476.0 (acid M−H)$^+$, 477.0 (acid M)$^+$.

EXAMPLE 140

1'-[4,8-Dimethoxyquinoline-2-yl)carbonyl]-6-(1H-tetrazol-5-yl)spiro[2H-1,3-benzoxazin-2,4'-piperidin]-4-(3H)-one (Compound 10)

A mixture of 695 mg (1.76 mmol) of benzyl 2-benzyloxy-5-bromobenzoate, 175 mg (0.41 mmol) of potassium hexacyanoferrate(II) trihydrate, 41 mg (0.8 mmol) of palladium(II) acetate, and 189 mg (1.75 mmol) of sodium carbonate in 3 mL of dimethylacetamide is heated at 120° C. for 24 hrs. The reaction mixture is diluted with water and extracted several times with ethyl acetate. Combined extracts are washed with brine and dried over $Na_2SO_4$. After solvent removal by rotoevaporation, the crude product is purified by preparative TLC to give 436 mg (1.27 mmol, 72% yield) of benzyl 2-benzyloxy-5-cyanobenzoate.

A solution of 436 mg (1.27 mmol) of benzyl 2-benzyloxy-5-cyanobenzoate, 91 mg (1.40 mmol) of sodium azide, and 68 mg (1.27 mmol) of ammonium chloride in 5 mL of DMF is heated at 120° C. for 24 hrs. The DMF was removed by rotoevaporation, the residue is taken up in water, and acidified. The white precipitate is collected by filtration and dried to give 500 mg of unpurified benzyl 2-benzyloxy-5-(1H-tetrazol-5-yl)benzoate, which is treated with 28% aqueous ammonium hydroxide in 5 mL of MeOH at 85° C. for 72 hrs. The reaction mixture was concentrated, taken up in water, and then acidified. Filtration of the precipitate gives 400 mg (1.04 mmol, 82% yield) of 2-benzyloxy-5-(1H-tetrazol-5-yl)benzamide.

A suspension of 400 mg (1.04 mmol) of 2-benzyloxy-5-(1H-tetrazol-5-yl)benzamide and 500 mg of 10% Pd/C (50% water) in 2 mL of methanol containing 1 mL of 28% aqueous ammonium hydroxide is stirred under hydrogen at 48 psi for 24 hr. The reaction mixture is filtered and the filtrate concentrated to give 210 mg (1.02 mmol, 98% yield) of 2-hydroxy-5-(1H-tetrazol-5-yl)benzamide.

A mixture of 75 mg (0.37 mmol) of 2-hydroxy-5-(1H-tetrazol-5-yl)benzamide, 110 mg (0.55 mmol) of 1-Boc-4-piperidone, and 71 µL of morpholine in 8 mL of MeOH is refluxed for 72 hr. The MeOH is removed by rotoevapoation and the residue is purified by preparative TLC to give 29 mg (0.08 mmol, 15% yield) of 1'-(tert-butyloxycarbonyl)-6-(1H-tetrazol-5-yl)spiro[1,3-benzoxazine-2,4'-piperidine]-4(3H)-one which on treatment with 40% TFA in dichloromethane at room temperature for 3 hr. gives the TFA salt of 6-(1H-tetrazol-5-yl)spiro[1,3-benzoxazine-2,4'-piperidine]-4(3H)-one in quantitative yield.

To a solution of 19.5 mg (0.084 mmol) of 4,8-dimethoxyquinoline-2-carboxylic acid, 32 mg (0.084 mmol) of HATU, and 39 µL (0.22 mmol) of diisopropylethylamine in 1.0 mL of DMF is added 32 mg (0.08 mmol) of the trifluoroacetic acid (TFA) salt of 6-(1H-tetrazol-5-yl)spiro[1,3-benzoxazine-2,4'-piperidine]-4(3H)-one. The mixture is stirred at room temperature for 3 hr., and then diluted with ethyl acetate. The ethyl acetate solution is washed with brine and dried over $Na_2SO_4$. After solvent removal by rotoevaporation, the crude product is purified by preparative TLC to give 21 mg (0.04 mmol, 50% yield) 1'-[(4,8-dimethoxyquinoline-2-yl)carbonyl]-6-(1H-tetrazol-5-yl)spiro-[2H-1,3-benzoxazine-2,4'-piperidine]-4(3H)-one (Compound 10): $^1$H NMR (CDCl$_3$): δ MS m/z: (M+H)$^+$, (M+Na)$^+$.

EXAMPLES 141-157

1'-Arylcarbonyl derivatives of 6-(1H-tetrazol-5-yl)spiro[1,3-benzoxazine-2,4'-piperidine]-4(3H)-one (Compounds 18, 22, 25, 28, 34, 38, 42, 46, 49, 52, 55, 58, 61, 64, 217, 218, and 219)

The following 1'-arylcarbonyl 6-(1H-tetrazol-5-yl)spiro[2H-1,3-benzoxazin-2,4'-piperidin]-4(3H)-ones are prepared similarly to Example 140 from the TFA salt of 6-(1H-tetrazol-5-yl)spiro[1,3-benzoxazine-2,4'-piperidine]-4(3H)-one and the requisite arylcarboxylic acid:

141. 1'-[4,7-Dimethoxy-1H-indol-2-yl)carbonyl]-6-(1H-tetrazol-5-yl)spiro[2H-1,3-benzoxazin-2,4'-piperidin]-4-(3H)-one (Compound 18);
142. 1'-[7-Methoxy-1H-indol-2-yl)carbonyl]-6-(1H-tetrazol-5-yl)spiro[2H-1,3-benzoxazin-2,4'-piperidin]-4-(3H)-one (Compound 22);
143. 1'-[7-Methoxy-3-methyl-1H-indol-2-yl)carbonyl]-6-(1H-tetrazol-5-yl)spiro[2H-1,3-benzoxazin-2,4'-piperidin]-4-(3H)-one (Compound 25);
144. 1'-[4,7-Dimethoxy-1-methylindol-2-yl)carbonyl]-6-(1H-tetrazol-5-yl)spiro[2H-1,3-benzoxazin-2,4'-piperidin]-4-(3H)-one (Compound 28);
145. 1'-[8-Cyclopropyl-4-methoxyquinolin-2-yl)carbonyl]-6-(1H-tetrazol-5-yl)spiro[2H-1,3-benzoxazin-2,4'-piperidin]-4-(3H)-one (Compound 34);
146. 1'-[1-Cyclopropyl-5-methoxyisoquinolin-7-yl)carbonyl]-6-(1H-tetrazol-5-yl)spiro[2H-1,3-benzoxazin-2,4'-piperidin]-4-(3H)-one (Compound 38);
147. 1'-[4-Methoxyquinolin-2-yl)carbonyl]-6-(1H-tetrazol-5-yl)spiro[2H-1,3-benzoxazin-2,4'-piperidin]-4-(3H)-one Compound 42);
148. 1'-[8-Methoxyquinolin-2-yl)carbonyl]-6-(1H-tetrazol-5-yl)spiro[2H-1,3-benzoxazin-2,4'-piperidin]-4-(3H)-one (Compound 46);
149. 1'-[4-Ethoxy-8-ethylquinolin-2-yl)carbonyl]-6-(1H-tetrazol-5-yl)spiro[2H-1,3-benzoxazin-2,4'-piperidin]-4-(3H)-one (Compound 49);
150. 1'-[8-Cyclopropyl-4-(4-morpholinyl)quinolin-2-yl)carbonyl]-6-(1H-tetrazol-5-yl)spiro[2H-1,3-benzoxazin-2,4'-piperidin]-4-(3H)-one (Compound 52);
151. 1'-[(Benzthiazol-2-yl)carbonyl]-6-(1H-tetrazol-5-yl)spiro[2H-1,3-benzoxazin-2,4'-piperidin]-4-(3H)-one (Compound 55);
152. 1'-[(6-Methoxybenzothiazol-2-yl)carbonyl]-6-(1H-tetrazol-5-yl)spiro[2H-1,3-benzoxazin-2,4'-piperidin]-4-(3H)-one (Compound 58);
153. 1'-[(1H-Benzimidazol-2-yl)carbonyl]-6-(1H-tetrazol-5-yl)spiro[2H-1,3-benzoxazin-2,4'-piperidin]-4-(3H)-one (Compound 61);
154. 1'-[(Quinoxalin-2-yl)carbonyl]-6-(1H-tetrazol-5-yl)spiro[2H-1,3-benzoxazin-2,4'-piperidin]-4-(3H)-one (Compound 64);
155. 1'-[7-Methyl-1H-indazol-5-yl)carbonyl]-6-(1H-tetrazol-5-yl)spiro[2H-1,3-benzoxazin-2,4'-piperidin]-4-(3H)-one (Compound 217);
156. 1'-[7-Ethyl-1H-indazol-5-yl)carbonyl]-6-(1H-tetrazol-5-yl)spiro[2H-1,3-benzoxazin-2,4'-piperidin]-4-(3H)-one (Compound 218);
157. 1'-[7-Chloro-1H-indazol-5-yl)carbonyl]-6-(1H-tetrazol-5-yl)spiro[2H-1,3-benzoxazin-2,4'-piperidin]-4-(3H)-one (Compound 219).

EXAMPLE 158

1'-[4,8-Dimethoxyquinoline-2-yl)carboyl]-6-(morpholin-4-yl)spiro[1,3-benzoxazin-2,4'-piperidin]-4-(3H)-one (Compound 196)

A solution of 500 mg (1.26 mmol) of benzyl 2-benzyloxy-5-bromobenzoate, 132 µL (132 mg, 1.5 mmol) of morpholine, 6 mg of palladium(II) acetate, 8.5 mg of (2-biphenyl)di-tert-butylphosphine, and 170 mg, 1.76 mmol) of sodium tert-butoxide in 3 mL of toluene is heated at 85° C. for 2 hrs. The reaction mixture is then diluted with ethyl acetate, washed with brine and dried over $Na_2SO_4$. After removal of solvent by rotoevaporation, the crude product is chromatographed to give 121 mg (0.30 mmol) of benzyl 2-benzyloxy-5-(morpholin-4-yl)benzoate and 72 mg (0.20 mmol) of tert-butyl 2-benzyloxy-5-(morpholin-4-yl)benzoate.

In a manner identical to Example 140, 121 mg (0.30 mmol) of benzyl 2-benzyloxy-5-(morpholin-4-yl)benzoate is converted to 2-benzyloxy-5-(morpholin-4-yl)benzamide which on hydrogenolysis gives 56 mg (0.25 mmol, 83% yield) of 2-hydroxy-5-(morpholin-4-yl)benzamide.

A mixture of 50 mg (0.23 mmol) of 2-hydroxy-5-(morpholin-4-yl)benzamide, 59 mg (0.30 mmol) of 1-Boc-4-piperidone, and 40 µL of morpholine in 3 mL of MeOH is refluxed for 6 days. Removal of solvent by rotoevaporation and purification by preparative TLC gives 53 mg (0.13 mmol, 57% yield) of 1'-(tert-butyloxycarbonyl)-6-(morpholin-4-yl)spiro[1,3-benzoxazine-2,4'-piperidine]-4(3H)-one which on treatment with 40% TFA in dichloromethane at room temperature for 2 hr. gives the bis-TFA salt of 6-(morpholin-4-yl)spiro[1,3-benzoxazine-2,4'-piperidine]-4(3H)-one in quantitative yield.

To a solution of 37 mg (0.16 mmol) of 4,8-dimethoxyquinoline-2-carboxylic acid, 32 mg (0.13 mmol) of the bis-trifluoroacetic acid (TFA) salt of 6-(morpholin-4-yl)spiro[1,3-benzoxazine-2,4'-piperidine]-4(3H)-one, and 109 µL (0.63 mmol) of diisopropylethylamine in 1.0 mL of DMF is added 60 mg (0.16 mmol) of HATU. The mixture is stirred at room temperature overnight, and then diluted with ethyl acetate. The ethyl acetate solution is washed with aqueous sodium bicarbonate, brine, and dried over Na$_2$SO$_4$. After solvent removal by rotoevaporation, the crude product is purified by preparative TLC to give 50 mg (0.08 mmol, 62% yield) 1'-[(4,8-dimethoxyquinoline-2-yl)carbonyl]-6-(morpholin-4-yl)spiro-[2H-1,3-benzoxazine-2,4'-piperidine]-4(3H)-one (Compound 196): $^1$H NMR (CDCl$_3$): δ 3.04 (m, 4H), 3.73 (m, 4H), 3.95 (s, 3H), 4.06 (s, 3H), 6.99 (d, 1H), 7.19-7.23 (4H), 7.52 (d of d, 1H), 7.68 (d of d, 1H), and 8.77 ppm (s, 1H). MS m/z: 519.2 (M+H)$^+$, 541.3 (M+Na)$^+$.

EXAMPLES 159-165

1'-Arylcarbonyl derivatives of 6-(morpholin-4-yl) spiro[1,3-benzoxazin-2,4'-piperidin]-4-(3H)-one (Compounds 197, 213, 214, 215, 216, 227, and 228)

The following 1'-arylcarbonyl 6-(morpholin-4-yl)spiro[2H-1,3-benzoxazin-2,4'-piperidin]-4-(3H)-ones are prepared similarly to Example 158 from the TFA salt of 6-(morpholin-4-yl)spiro[1,3-benzoxazine-2,4'-piperidine]-4(3H)-one and the requisite arylcarboxylic acid:

159. 1'-[4,8-Dimethoxynaphth-2-yl)carbonyl]-6-(morpholin-4-yl)spiro[1,3-benzoxazin-2,4'-piperidin]-4-(3H)-one (Compound 197): $^1$H NMR (CDCl$_3$): δ 3.04 (m, 4H), 3.73 (m, 4H), 3.97 (s, 3H), 3.99 (s, 3H), 6.96 (s, 1H), 6.99 (d, 1H), 7.06 (d, 1H), 7.20 (d of d, 1H), 7.23 (7.23 (m, 1H), 7.48 (d of d, 1H), 7.71 (m, 2H), and 8.68 ppm (s, 1H). MS m/z: 518.0 (M+H)$^+$, 540.1 (M+Na)$^+$;

160. 1'-[7-Methoxy-3-methyl-1H-indol-2-yl)carbonyl]-6-(morpholin-4-yl)spiro[1,3-benzoxazin-2,4'-piperidin]-4-(3H)-one (Compound 213);

161. 1'-[7-Methyl-1H-indazol-5-yl)carbonyl]-6-(morpholin-4-yl)spiro[1,3-benzoxazin-2,4'-piperidin]-4-(3H)-one (Compound 214);

162. 1'-[7-Ethyl-1H-indazol-5-yl)carbonyl]-6-(morpholin-4-yl)spiro[1,3-benzoxazin-2,4'-piperidin]-4-(3H)-one (Compound 215);

163. 1'-[7-Chloro-1H-indazol-5-yl)carbonyl]-6-(morpholin-4-yl)spiro[1,3-benzoxazin-2,4'-piperidin]-4-(3H)-one (Compound 216);

164. 1'-[(1-Cyclopropyl-4-methoxy-1H-indol-6-yl)carbonyl]-6-(morpholin-4-yl)spiro[2H-1,3-benzoxazin-2,4'-piperidin]-4-(3H)-one (Compound 227);

165. 1'-[4-Methoxy-1H-indazol-6-yl)carbonyl]-6-(morpholin-4-yl)spiro[1,3-benzoxazin-2,4'-piperidin]-4-(3H)-one (Compound 228).

EXAMPLE 166

6-Bromo-1'-[(3,5-dimethoxynaphth-2-yl)carbonyl]-3-methylspiro[2H-1,3-benzoxazin-2,4'-piperidin]-4-(3H)-one (Compound 138)

To 48 mg (0.094 mmol) of 6-bromo-1'-[(3,5-dimethoxynaphth-2-yl)carbonyl]-3-methylspiro[2H-1,3-benzoxazin-2,4'-piperidin]-4-(3H)-one (Compound 3, Example 2) in 3 mL of THF is added 7.5 mg (0.19 mmol of NaH) of 60% NaH in oil dispersion. The resultant suspension is heated at 60° C. for 1 hr., then 7.5 µL (17.1 mg, 0.12 mmol) of methyl iodide is added, and the reaction mixture is heated at 60° C. for another 2 hrs. The reaction mixture is poured into ethyl acetate, washed with brine, and dried over Na$_2$SO$_4$. Removal of solvent by rotoevaporation and purification of the residue by preparative TLC gives 15 mg (0.029 mmol, 31% yield) of 6-bromo-1'-[(3,5-dimethoxynaphth-2-yl)carbonyl]-3-methylspiro[2H-1,3'-benzoxazin-2,4'-piperidin]-4-(3H)-one (Compound 138): $^1$H NMR (CDCl$_3$): δ 3.03 and 3.04 (two s, 3H); 3.90, 3.94, and 3.98 (three s, 6H); 7.00 (d, 1H), 7.13 and 7.19 (two d, 1H), 7.33 (m, 1H), 7.44 (d, 1H), 7.51 (d, 1H), 7.72 (d of d, 1H), 7.72 (s, 0.5H), 7.83 (d of d, 1H), and 7.88 ppm (s, 0.5H). MS m/z: 526.0 (M+H)$^+$, 548.0 (M+Na)$^+$.

EXAMPLE 167

6'-Bromo-1-[3,5-dimethoxynaphth-2-yl)carbonyl] spiro[piperidine-4,2'(1'H)-quinazolin]-4'-(3'H)-one (Compound 90)

A solution of 1.0 gm (5.03 mmol) of 1-Boc-4-piperidone in 5 mL of 40% trifluoroacetic acid (TFA) in dichloromethane is stirred for 3 hr at room temperature. The solution is concentrated to dryness, and the solid is dried under high vacuum to give the hygroscopic TFA salt of 4-piperidone in quantitative yield.

To a solution of 131 mg (0.56 mmol) of 3,5-dimethoxy-2-naphthoic acid, 213 mg (0.56 mmol) of HATU, and 0.215 mL (1.23 mmol) of diisopropylethylamine in 0.8 mL of DMF is added a solution of 119 mg (0.56 mmol) of the TFA salt of 4-piperidone in 0.5 mL of DMF. The resulting mixture is stirred at room temperature overnight, and then diluted with ethyl acetate. The ethyl acetate solution is washed with aqueous sodium bicarbonate, then brine, and is finally dried over Na$_2$SO$_4$. Solvent removal by rotoevaporation gives 200 mg of the hygroscopic product, 1-(3,5-dimethoxy-2-naphthoyl)-4-piperidone, which is used directly without purification.

To a solution of 42 mg (0.13 mmol) of 1-(3,5-dimethoxy-2-naphthoyl)-4-piperidone and 26 mg (0.12 mmol) of 2-amino-5-bromobenzamide in 0.6 mL of acetic acid is added 0.010 mL of concentrated sulfuric acid. The reaction mixture is stirred overnight at room temperature, and then is poured into saturated aqueous sodium bicarbonate and ethyl acetate. A crystalline white solid precipitates and is collected by filtration. The solid is washed with water and ethyl acetate to give 35 mg (0.069 mmol) of the desired 6'-bromo-1-[3,5-dimethoxynaphth-2-yl)carbonyl]spiro[piperidine-4,2'(1'H)-quinazolin]-4'-(3'H)-one (Compound 90): $^1$H NMR (CDCl$_3$): δ 1.87 (m, 4H), 3.60 (m, 4H), 3.93 (s, 3H), 4.05 (s, 3H), 6.78

(d, 1H), 7.17 (m, 2H), 7.21 (m, 1H), 7.39 (m, 1H), 7.50 (m, 1H), 7.66 (m, 2H), and 8.38 ppm (s, 1H). MS m/z: 510.1 (M+H)$^+$, 533.2 (M+Na)$^+$.

EXAMPLE 168

6'-Bromo-1-[(4,8-dimethoxyquinoline-2-yl)carbonyl]spiro[piperidine-4,2'(1'H)-quinazolin]-4'-(3'H)-one (Compound 71)

A mixture of 33 mg (0.15 mmol) of 2-amino-5-bromobenzamide and 30 mg (0.15 mmol) of 1-Boc-4-piperidone in 400 μL of acetic acid containing 10 μL of sulfuric acid is stirred overnight at room temperature. The reaction mixture is diluted with diethyl ether. The yellow precipitate is collected by filtration, washed with excess ether, and dried under vacuum to give 55 mg (0.15 mmol) of the acetic acid salt of 6'-bromospiro-[piperidine-4,2'(1'H)-quinazolin]-4'-(3'H)-one. MS m/z: 297.0 (M+H)$^+$, 319.0 (M+Na)$^+$.

To a solution of 17 mg (0.07 mmol) of 4,8-dimethoxyquinoline-2-carboxylic acid, 27 mg (0.07 mmol) of HATU, and 25 μL (0.14 mmol) of diisopropylethylamine in 0.8 mL of DMF is added 24 mg (0.067 mmol) of the acetic acid salt of 6'-bromospiro-[piperidine-4,2'(1'H)-quinazolin]-4'-(3'H)-one. The reaction mixture is stirred at room temperature for 16 hrs. and then diluted with ethyl acetate and saturated sodium bicarbonate. The insoluble solid is filtered and washed with water and then ethyl acetate to give 22 mg (0.043 mmol, 61% yield) of 6'-bromo-1-[(4,8-dimethoxyquinoline-2-yl)carbonyl]spiro-[piperidine-4,2'(1'H)-quinazolin]-4'-(3'H)-one (Compound 71): $^1$H NMR (CDCl$_3$): δ 1.83-1.92 (m, 4H), 3.54-3.70 (m, 3H), 3.95-4.02 (m, 1H), 3.95 (s, 3H), 4.06 (s, 3H), 6.79 (d, 1H), 7.14 (s, 1H), 7.16 (br s, 1H), 7.24 (d of d, 1H), 7.40 (d of d, 1H), 7.52 (d of d, 1H), 7.65 (d, 1H), 7.68 (d of d, 1H), and 8.39 ppm (s, 1H). MS m/z: 512.0 (M+H)$^+$, 534.0 (M+Na)$^+$.

EXAMPLES 169-202

1-Arylcarbonyl derivatives of 6'-substituted spiro [piperidine-4,2'(1'H)-quinazolin]-4'-(3'H)-one (Compounds 72-86, 91-100, 187-195)

The following 1-arylcarbonyl 6'-substituted spiro[piperidine-4,2'(1'H)-quinazolin]-4'-(3'H)-ones are prepared similarly to either Example 167 (Method C: acylation of the TFA salt of 4-piperidone with the requisite arylcarboxylic acid, and then condensation of the product with the requisite 2-aminobenzamide) or to Example 168 (Method D: condensation of the requisite 2-aminobenzamide with 1-Boc-4-piperidone with concomitant cleavage of the Boc-protecting group, and acylation with the requisite arylcarboxylic acid:

169. 6'-Acetamido-1-[(4,8-dimethoxyquinoline-2-yl)carbonyl]spiro[piperidine-4,2'(1'H)-quinazolin]-4'-(3'H)-one (Compound 72, Method C);
170. 1-[(4,8-Dimethoxyquinoline-2-yl)carbonyl]-6'-(1H-tetrazol-5-yl)spiro[piperidine-4,2'(1'H)-quinazolin]-4'-(3'H)-one (Compound 73, Method C);
171. 6'-Bromo-1-[4,7-dimethoxy-1H-indol-2-yl)carbonyl]spiro[piperidine-4,2'(1'H)-quinazolin]-4'-(3'H)-one (Compound 74, Method D);
172. 6'-Acetamido-1-[4,7-dimethoxy-1H-indol-2-yl)carbonyl]spiro[piperidine-4,2'(1'H)-quinazolin]-4'-(3'H)-one (Compound 75, Method C);
173. 1-[4,7-Dimethoxy-1H-indol-2-yl)carbonyl]-6'-(1H-tetrazol-5-yl)spiro[piperidine-4,2'(1'H)-quinazolin]-4'-(3'H)-one (Compound 76, Method C);
174. 6'-Bromo-1-[8-cyclopropyl-4-methoxyquinolinyl) carbonyl]spiro-[piperidine-4,2'(1'H)-quinazolin]-4'-(3'H)-one (Compound 77, Method D);
175. 6'-Acetamido-1-[8-cyclopropyl-4-methoxyquinolinyl)carbonyl]spiro-[piperidine-4,2'(1'H)-quinazolin]-4'-(3'H)-one (Compound 78, Method C);
176. 1-[8-Cyclopropyl-4-methoxyquinolin-2-yl)carbonyl]-6'-(1H-tetrazol-5-yl)spiro[piperidine-4,2'(1'H)-quinazolin]-4'-(3'H)-one (Compound 79, Method C);
177. 6'-Bromo-1-[1-cyclopropyl-5-methoxyisoquinolin-7-yl)carbonyl]spiro-[piperidine-4,2'(1'H)-quinazolin]-4'-(3'H)-one (Compound 80, Method D);
178. 6'-Acetamido-1-[1-cyclopropyl-5-methoxyisoquinolin-7-yl)carbonyl]-spiro[piperidine-4,2'(1'H)-quinazolin]-4'-(3' H)-one (Compound 81, Method C);
179. 1-[1-Cyclopropyl-5-methoxyisoquinolin-7-yl)carbonyl]-6'-(1H-tetrazol-5-yl)spiro[piperidine-4,2'(1'H)-quinazolin]-4'-(3'H)-one (Compound 82, Method C);
180. 1-[(4,8-Dimethoxyquinoline-2-yl)carbonyl]-6'-isopropylspiro[piperidine-4,2'(1'H)-quinazolin]-4'-(3'H)-one (Compound 83, Method D);
181. 6'-Bromo-1-[(1-methyl-9H-pyrido[3,4-b]indol-3-yl) carbonyl]spiro-[piperidine-4,2'(1'H)-quinazolin]-4'-(3'H)-one (Compound 84, Method C);
182. 6'-Acetamido-1-[(1-methyl-9H-pyrido[3,4-b]indol-3-yl)carbonyl]spiro-[piperidine-4,2'(1'H)-quinazolin]-4'-(3'H)-one (Compound 85, Method C);
183. 6'-Acetamido-1-[(pyrido[2,3-b]pyridin-2-yl)carbonyl]spiro[piperidine-4,2'(1'H)-quinazolin]-4'-(3'H)-one (Compound 86, Method C);
184. 6'-Bromo-1-[8-isopropyl-4-methoxyquinolin-2-yl) carbonyl]spiro[piperidine-4,2'(1'H)-quinazolin]-4'-(3'H)-one (Compound 91, Method D): $^1$H NMR (CDCl$_3$): δ 1.29 (d of d, 6H), 1.89-1.94 (m, 4H), 3.62-3.67 (m, 2H), 3.76 (m, 1H), 4.03 (m, 1H), 4.07 (s, 3H), 6.80 (d, 1H), 7.16 (s, 1H), 7.18 (br s, 1H), 7.41 (d of d, 1H), 7.58 (d of d, 1H), 7.65 (d, 1H), 7.69 (d of d, 1H), 8.01 (d of d, 1H), and 8.41 ppm (s, 1H). MS m/z: 524.2 (M+H)$^+$, 546.1 (M+Na)$^+$;
185. 6'-Acetamido-1-[8-isopropyl-4-methoxyquinolin-2-yl)carbonyl]spiro[piperidine-4,2'(1'H)-quinazolin]-4'-(3'H)-one (Compound 92, Method C);
186. 6'-Bromo-1-[4-methoxy-8-methylthioquinolin-2-yl) carbonyl]spiro[piperidine-4,2'(1'H)-quinazolin]-4'-(3'H)-one (Compound 93, Method D): $^1$H NMR (CDCl$_3$): δ 1.93 (m, 4H), 3.70 (m, 2H), 3.85 (m, 1H), 4.01 (m, 1H), 4.08 (s, 3H), 6.80 (d, 1H), 7.19 (s, 1H), 7.24 (s, 1H), 7.419 d of d, 1H), 7.49 (d of d, 1H), 7.57 (d of d, 1H), 7.65 (d, 1H), 7.87 (d of d, 1H), and 8.41 ppm (s, 1H);
187. 6'-Acetamido-1-[4-methoxy-8-methylthioquinolin-2-yl)carbonyl]spiro-[piperidine-4,2'(1'H)-quinazolin]-4'-(3'H)-one (Compound 94, Method C);
188. 6'-Bromo-1-[1,4-dimethoxynaphth-2-yl)carbonyl] spiro[piperidine-4,2'(1'H)-quinazolin]-4'-(3'H)-one (Compound 95, method D): $^1$H NMR (CDCl$_3$): δ 1.90 (m, 4H), 3.85 and 3.86 (two s, 3H), 3.95 and 3.96 (two s, 3H), 6.69 (d, 1H), 6.78 (d of d, 1H), 7.09 and 7.18 (br s, 1H), 7.40 (d of d, 1H), 7.56-7.65 (m, 3H), 8.065 (d of d, 1H), 8.16 (d, 1H), 8.30 and 8.41 ppm (two s, 1H). MS m/z: 511.0 (M+H)$^+$, 533.0 (M+Na)$^+$;
189. 6'-Acetamido-1-[1,4-dimethoxynaphth-2-yl)carbonyl]spiro[piperidine-4,2'(1'H)-quinazolin]-4'-(3'H)-one (Compound 96, Method C);
190. 6'-Bromo-1-[3,8-dimethoxynaphth-2-yl)carbonyl] spiro[piperidine-4,2'(1'H)-quinazolin]-4'-(3'H)-one (Compound 97, Method D);

191. 6'-Acetamido-1-[3,8-dimethoxynaphth-2-yl)carbonyl]spiro[piperidine-4,2'(1'H)-quinazolin]-4'-(3'H)-one (Compound 98, Method C);
192. 6'-Bromo-1-[4,8-dimethoxyquinoline-2-yl)carbonyl]-1'-methylspiro-[piperidine-4,2'(1'H)-quinazolin]-4'-(3'H)-one (Compound 99, Method D);
193. 6'-Acetamido-1-[4,8-dimethoxyquinoline-2-yl)carbonyl]-1'-methylspiro-[piperidine-4,2'(1'H)-quinazolin]-4'-(3'H)-one (Compound 100, Method C);
194. 1-[4,8-Dimethoxynaphth-2-yl)carbonyl]-6'-methoxyspiro[piperidine-4,2'(1'H)-quinazolin]-4'-(3'H)-one (Compound 187, Method C): $^1$H NMR (CDCl$_3$): δ 3.68 (s, 3H), 3.97 (s, 3H), 3.99 (s, 3H), 6.77 (d, 1H), 6.91 (d, 1H), 6.94 (d of d, 1H), 7.06 (d, 1H), 7.13 (d, 1H), 7.20 (d of d, 0.6H), 7.35 (d, 0.4H), 7.48 (d of d, 1H), 7.69 (s, 1H), 7.71 (d, 1H), and 8.20 ppm (s, 1H). MS m/z: 462.0 (M+H)$^+$, 484.0 (M+Na)$^+$;
195. 1-[4,8-Dimethoxyquinoline-2-yl)carbonyl]-6'-methoxyspiro[piperidine-4,2'(1'H)-quinazolin]-4'-(3'H)-one (Compound 188, Method D): $^1$H NMR (CDCl$_3$): δ 3.68 (s, 3H), 3.95 (s, 3H), 4.06 (s, 3H), 6.57 (s, 1H), 6.78 (d, 1H), 6.94 (d of d, 1H), 7.13 (s, 2H), 7.24 (d, 1H), 7.52 (d of d, 1H), 7.68 (d of d, 1H), and 8.25 ppm (s, 1H). MS m/z: 463.0 (M+H)$^+$, 485.0 (M+Na)$^+$;
196. 6'-Methoxy-1-[[7-methoxy-3-methyl-1H-indol-2-yl)carbonyl]spiro-[piperidine-4,2'(1'H)-quinazolin]-4'-(3'H)-one (Compound 189, Method C): $^1$H NMR (CDCl$_3$): δ 2.22 (s, 3H), 3.68 (s, 3H), 3.89 (s, 3H), 6.70 (d, 1H), 6.78 (d, 1H), 6.94 (m, 2H), 7.11 (d, 1H), 7.13 (d, 1H), 8.24 (s, 1H), and 11.25 ppm (s, 1H). MS m/z: 435.0 (M+H)$^+$, 457.0 (M+Na)$^+$;
197. 6',7'-Dimethoxy-1-[4,8-dimethoxynaphth-2-yl)carbonyl]spiro[piperidine-4,2'(1'H)-quinazolin]-4'-(3'H)-one (Compound 190, Method C): $^1$H NMR (CDCl$_3$): δ 3.66 (s, 3H), 3.75 (s, 3H), 3.97 (s, 3H), 3.99 (s, 3H), 6.39 (s, 1H), 6.91 (s, 1H), 7.07 (d, 1H), 7.08 (s, 1H), 7.48 (d of d, 1H), 7.69 (s, 1H), 7.72 (d, 1H), 7.92 ppm (s, 1H). MS m/z: 492.0 (M+H)$^+$;
198. 6',7'-Dimethoxy-1-[4,8-dimethoxyquinoline-2-yl) carbonyl]spiro[piperidine-4,2'(1'H)-quinazolin]-4'-(3'H)-one (Compound 191, Method C): $^1$H NMR (CDCl$_3$): δ 3.67 (s, 3H), 3.76 (s, 3H), 3.95 (s, 3H), 4.07 (s, 3H), 6.41 (s, 1H), 6.67 (s, 1H), 7.09 (s, 1H), 7.13 (s, 1H), 7.24 (d, 1H), 7.52 (d of d, 1H), 7.68 (d, 1H), and 7.97 (s, 1H). MS m/z: 493.0 (M+H)$^+$, 515.0 (M+Na)$^+$;
199. 1-[4,8-Dimethoxynaphth-2-yl)carbonyl]-6'-methylspiro[piperidine-4,2'(1'H)-quinazolin]-4'-(3'H)-one (Compound 192, Method C): $^1$H NMR (CDCl$_3$): δ 2.18 (s, 3H), 3.97 (s, 3H), 3.99 (s, 3H), 6.68 (s, 1H), 6.71 (d, 1H), 6.91 (d, 1H), 7.07 (d, 1H), 7.09 (d of d, 1H), 7.70 (d, 1H), 7.48 (d of d, 1H), 7.69 (s, 1H), 7.72 (d, 1H), and 8.11 ppm (s, 1H). MS m/z: 446.0 (M+H)$^+$, 467.9 (M+Na)$^+$;
200. 1-[4,8-dimethoxyquinoline-2-yl)carbonyl]-6'-methylspiro[piperidine-4,2'(1'H)-quinazolin]-4'-(3'H)-one (Compound 193, Method C): $^1$H NMR (CDCl$_3$): δ 2.18 (s, 3H), 3.95 (s, 3H), 4.06 (s, 3H), 6.72 (d, 1H), 6.73 (s, 1H), 7.09 (d of d, 1H), 7.13 (S, 1 h), 7.24 (d of d, 1H), 7.40 (d, 1H), 7.52 (d of d, 1H), 7.68 (d of d, 1H), and 8.16 ppm (s, 1H). MS m/z: 446.9 (M+H)$^+$, 469.0 (M+Na)$^+$;
201. 1-[4,8-Dimethoxynaphth-2-yl)carbonyl]-6'-trifluoromethoxyspiro-[piperidine-4,2'(1'H)-quinazolin]-4'-(3'H)-one (Compound 194, Method D): $^1$H NMR (CDCl$_3$): δ 3.97 (s, 3H), 3.99 (s, 3H), 6.88 (d, 1H), 6.91 (d, 1H), 7.07 (d, 1H), 7.21 (s, 1H), 7.29 (d of d, 1H), 7.46 (s, 1H), 7.49 (d of d, 1H), 7.69 (s, 1H), 7.72 (d, 1H), and 8.43 ppm (s, 1H). MS m/z: 516.0 (M+H)$^+$, 538.0 (M+Na)$^+$;
202. 1-[4,8-Dimethoxyquinoline-2-yl)carbonyl]-6'-trifluoromethoxyspiro-[piperidine-4,2'(1'H)-quinazolin]-4'-(3'H)-one (Compound 195, Method D): $^1$H NMR (CDCl$_3$): δ 3.95 (s, 3H), 4.07 (s, 3H), 6.90 (d, 1H), 7.14 (s, 1H), 7.23-7.31 (m, 3H), 7.46 (d, 1H), 7.53 (d of d, 1H), 7.68 9 d of d, 1H), and 8.48 ppm (s, 1H). MS m/z: 517.0 (M+H)$^+$, 539.0 (M+Na)$^+$.

EXAMPLE 203

In Vivo and In Vitro Assays

In vitro IC$_{50}$ values of human ACC were determined using recombinant enzyme produced by standard procedures. For example, full-length cDNAs for both the human isoforms (hACC1 and hACC2) were each cloned and expressed as a recombinant protein using a baculovirus system. Double stranded cDNA from human fetal liver (Quick-Clone cDNA, cat. #7171-1) was purchased from BD/Clontech (Mt. View, Calif.). PCR primers were designed for full-length hACC1 and hACC2 using GenBank submissions AY237919 and AJ575592, respectively. The Advantage GC 2 PCR kit (BD/Clontech) was used for amplification. The PCR products (about 7 Kb) were TOPO-cloned into the pCR4Blunt vector (Invitrogen, Carlsbad, Calif.), and 6 clones of each gene were isolated. All clones had high error rates and the ACC2 clones showed evidence of alternately spliced mRNAs whose physiological significance is unknown. Full length versions of the two cDNAs corresponding to their respective Genbank sequences were assembled in pBluescript SK+ (Stratagene, La Jolla, Calif.) by combining error-free fragments from the PCR clones. The resulting hACC1 clone, designated pCS35, has six silent nucleotide differences compared to Genbank accession AY237919. The final hACC2 clone, designated pCS36, has ten silent nucleotide differences compared to Genbank accession AJ575592. Primers were designed to PCR amplify the cDNAs along with the in-frame 3'-his tag sequences from the pET vector and TOPO-cloned the resulting products into the Gateway® entry vector pENTR/D-TOPO. The ACC2 primers were designed to delete amino acids 1-148 and add Met-Gly in front of Lys149 in the final product. The resulting entry clones were transferred to BaculoDirect™ linear DNA (Invitrogen corp.) using the Gateway® LR recombination reaction. The recombinant baculovirus DNA was transfected into insect cells and viral amplification was performed according to the manufacturer's protocols. For protein expression sf9 cells were infected with a P3 viral stock in the presence of 50 uM biotin. The cells were harvested after 48-72 hr, lysed by sonication, and the resulting extract was clarified by centrifugation. ACC in the crude extract was concentrated by ammonium sulfate precipitation (40% w/v) and purified by Ni$^{2+}$-NTA chromatography (Novagen) followed by anion exchange chromatography on a UNO-Q column (BioRad).

Overall ACC activity in the hACC preparations is measured by following incorporation of [$^{14}$C]bicarbonate into acetyl-CoA essentially as described (Thumpy and Wakil, J Biol Chem 260, 6318-6323 (1985). Briefly, the reaction mixture (50 µL) contains: 50 mM Hepes (pH7.4), 20 mM K-Citrate, 20 mM Mg-Acetate 1.5 mM MgSO$_4$, 2 mM DTT, 2 mM acetyl-CoA, 12 mM NaHCO$_3$, 0.2 mM NaH$^{14}$CO$_3$ (~50 mCi/mmol), 0.01% (v/v) Triton X-100, 0.75 mg/mL BSA, 1% (v/v) DMSO (with or without inhibitor), and 0.3 µg (hACC1) or 0.15 µg (hACC2) enzyme. Reactions are initiated by the addition of ATP to a final concentration 2 mM. After 10 minutes at 37° C., the reaction is stopped by the addition of 2N HCl (50 μL). The samples are evaporated in a hood overnight, resuspended in $H_2O$ (200 μL), and incorporated label is quantified by scintillation counting in scintillation cocktail (3 mL). Inhibition data are fit to dose-response curves and $IC_{50}$ values are reported (i.e. the concentration of inhibitor that gives 50% inhibition). Data from representative compounds is shown in Table 2.

TABLE 2

In vitro inhibition of ACC enzymes. hACC1 and hACC2 are human isoforms of ACC and uACC is *Ustilago maydis* ACC. hACC1, hACC2, and uACC IC50 values were determined using a [$^{14}$C]bicarbonate incorporation assay, which measures overall ACC activity. The hACC-CT IC50 values were determined using an isotope exchange assay that specifically measures the CT half-reaction.

| | $IC_{50}$ (μM) | | | |
|---|---|---|---|---|
| Compound | hACC1 | hACC2 | hACC1-CT | uACC |
| 1 | 6.0 | 5.4 | | 160 |
| 2 | 0.088 | 0.051 | 0.1 | 11 |
| 3 | 0.86 | 0.29 | | 90 |
| 4 | 2.8 | 2.9 | | 50 |
| 5 | 4.5 | 2.1 | | >135 |
| 6 | 2.3 | 2 | | 40 |
| 7 | 1.1 | 0.85 | 1.2 | 20 |
| 9 | 0.092 | 0.056 | | |
| 10 | 0.016 | 0.011 | | |
| 17 | 0.26 | 0.31 | | |
| 16 | 0.26 | 0.20 | | |
| 23 | 0.14 | 0.18 | | |
| 24 | 0.10 | 0.077 | | |
| 26 | 0.83 | 0.59 | | |
| 30 | 0.016 | 0.017 | | 20 |
| 31 | 0.0062 | 0.003 | | |
| 32 | 0.18 | 0.11 | | |
| 33 | 0.073 | 0.051 | | 19.3 |
| 40 | | 0.90 | | |
| 44 | 0.74 | 0.49 | | |
| 71 | 1.0 | 0.49 | | |
| 87 | 9.7 | 12 | | 220 |
| 90 | 2.2 | 1.1 | | |
| 91 | 2.0 | 3.7 | | |
| 93 | 0.43 | 1.1 | | |
| 103 | 1.3 | 0.70 | | |
| 109 | 0.60 | 2.9 | | |
| 110 | 6.7 | 4.6 | | |
| 131 | 1.9 | 0.45 | | |
| 132 | 0.80 | 0.30 | | |
| 133 | 0.14 | 0.11 | | |
| 134 | 4.7 | | | |
| 135 | 2.2 | | | |
| 136 | 0.075 | 0.055 | | |
| 137 | 0.067 | 0.029 | | |
| 138 | 1.2 | 0.88 | | |
| 139 | 0.05 | 0.033 | | 20 |
| 141 | | 1.3 | | |
| 143 | 0.13 | 0.19 | | |
| 144 | 0.061 | 0.088 | | 14 |
| 145 | 0.011 | 0.007 | | 5.2 |
| 146 | 0.005 | 0.004 | | 3.0 |
| 148 | 0.088 | 0.066 | | |
| 149 | 0.035 | 0.025 | | |
| 150 | 0.026 | 0.023 | | |
| 151 | 0.082 | 0.096 | | |
| 152 | 0.004 | 0.003 | | |
| 153 | 0.035 | 0.016 | | |
| 154 | 0.030 | 0.027 | | |
| 155 | 0.005 | 0.004 | | |
| 157 | 0.033 | 0.048 | | |
| 158 | | 0.008 | | |
| 159 | 0.004 | 0.005 | | |
| 160 | 0.004 | 0.003 | | |
| 161 | 0.008 | | | |
| 162 | 0.005 | | | |

TABLE 2-continued

In vitro inhibition of ACC enzymes. hACC1 and hACC2 are human isoforms of ACC and uACC is *Ustilago maydis* ACC. hACC1, hACC2, and uACC IC50 values were determined using a [$^{14}$C]bicarbonate incorporation assay, which measures overall ACC activity. The hACC-CT IC50 values were determined using an isotope exchange assay that specifically measures the CT half-reaction.

| | $IC_{50}$ (μM) | | | |
|---|---|---|---|---|
| Compound | hACC1 | hACC2 | hACC1-CT | uACC |
| 164 | 0.004 | 0.004 | | |
| 166 | 0.036 | 0.031 | | |
| 169 | 0.0075 | 0.0074 | | |
| 170 | 0.006 | | | |
| 171 | 0.028 | 0.014 | | |
| 172 | 0.007 | | | |
| 173 | 0.006 | | | |
| 175 | 0.021 | | | |
| 176 | 0.005 | | | |
| 177 | 0.005 | | | |
| 178 | 0.014 | | | |
| 179 | 0.038 | | | |
| 180 | 0.036 | 0.042 | | |
| 181 | 0.42 | | | |
| 182 | 0.16 | | | |
| 183 | 0.43 | | | |
| 184 | 0.48 | 0.40 | | |
| 185 | 0.09 | 0.083 | | |
| 186 | 0.002 | 0.002 | | |
| 187 | 0.087 | | | |
| 188 | 0.26 | | | |
| 189 | 0.50 | | | |
| 190 | 0.062 | | | |
| 191 | 0.19 | | | |
| 192 | 0.16 | | | |
| 194 | 0.07 | | | |
| 195 | 0.50 | | | |
| 196 | 0.20 | 0.021 | | |
| 197 | 0.004 | | | |
| 201 | 0.02 | 0.018 | | |
| 230 | 0.11 | 0.085 | | |
| 231 | 0.047 | 0.033 | | |

Overall ACC activity is comprised of two half-reactions, the BC reaction (the ATP-dependent carboxylation of biotin) and the CT reaction (the transfer of the carboxyl group from biotin to acetyl-CoA to form malonyl-CoA). Thus, it is of interest to localize the site of action of ACC inhibitors. To this end, representative compounds are tested in an acetyl-CoA/malonyl-CoA isotope exchange reaction which specifically measures the CT-half reaction. This assay is performed with slight modifications of published procedures (Gregolin et al., *J Biol Chem*, 1968, 243:4227-4235; Rendina et al., *J Agric Food Chem*, 1990, 38:1282-1287). Briefly, the reaction mixture (50 μL) contained 50 mM Hepes (pH 7.4), 20 mM K-citrate, 1.5 mM $MgSO_4$, 4 mM malonyl-CoA, 1.67 mM acetyl-CoA, 0.34 mM [$^{14}$C]acetyl-CoA (about 60 mCi/mmol), 0.75 mg/mL BSA, and 1% (v/v) DMSO with or without inhibitor. Reactions are initiated by the addition of hACC1 (0.3 μg) or hACC2 (0.15 μg) enzyme and incubated at 37° C. for 10 min. Reactions are stopped by addition of a 0.2M sodium arsenate solution containing 1U of phosphotransacetylase (13.5 μL) and incubation at room temperature for 30 min. Then 3N HCl (25 μL) is added and the reactions are microcentrifuged for 5 minutes, transferred to new tubes, and evaporated to dryness in a speedvac. The samples are then resuspended with water (5 μL) and cyclohexane (62.5 μL) and evaporated to dryness at 90° C. in a hood. The samples are then resuspended in water (200 μL), added to scintillation cocktail (3 mL), and counted in a scintillation counter to quantify radiolabel incorporated into malonyl-CoA. Data are fit to dose-response curves and $IC_{50}$ values are reported for representative compounds in Table 2. Note that the test compounds exhibit $IC_{50}$ values in this assay that are similar to their respective $IC_{50}$ values in the overall ACC activity assay demonstrating that these compounds are acting on the CT domain.

The in vivo ACC inhibitory activity of compounds in this invention can be confirmed in cultured cells using standard procedures that are well known to those skilled in the art. For example, since ACC catalyzes the first committed step in fatty acid biosynthesis, the in vivo activity of compounds can be confirmed by measuring their ability to prevent the formation of radiolabeled fatty acids from radiolabeled acetate in cultured human hepatoma cells (HepG2). In addition, since the malonyl-CoA produced by ACC inhibits fatty acid oxidation, the in vivo ACC inhibitory activity of compounds can be further confirmed by measuring the stimulation of fatty acid oxidation in cultured mouse myoblast cells (C2C12).

Fatty acid synthesis assays are performed with slight modifications to published procedures (Beckers et al., *Cancer Res*, 2007, 67: 8180-8187; Wang, *J Lipid Res.*, 2006, 47:2028-41). Briefly, HepG2 cells are grown in Dulbecco's modified eagles medium containing 10% fetal calf serum in 6-well culture plates. Cells are treated for 24 h with test compounds added as DMSO stock solutions to a final DMSO concentration of 0.5% (v/v). After test compound incubation, $^{14}C$—[2]-acetate is added (3 µCi/6 well plate) and cells are further incubated for 4 hrs. Cells are then harvested in 40% methanol and assayed for total protein. Total lipids are extracted with chloroform:methanol (2:1) and $^{14}C$-radioactivity is quantified in the aqueous and organic phases. Total lipids in the organic phase are separated by thin-layer chromatography (TLC, silica gel 60A) using hexane:ether:acetic acid (90:30:1) as the mobile phase. Radioactivity distribution of lipid classes on TLC plates is quantified by phosphorimaging (Molecular Dynamics Storm 820). Compound 6 inhibited radiolabel incorporation into phospholipids 32% and 14% at 10 µM and 1 µM, respectively, while Compound 2 inhibited radiolabel incorporation into phospholipids 93% and 42% at 10 µM and 1 µM, respectively. These results confirm that both compounds inhibit ACC activity in vivo in cultured HepG2 cells.

Fatty acid oxidation assays are performed essentially as described (Beckers et al., *Cancer Res*, 2007, 67: 8180-8187). Briefly, C2C12 cells are plated at 600,000 cells/T25 flask. The next day, media is changed and the DMSO with or without test compound is added to a final concentration of 0.5% (v/v). After 1 h at 37° C. in atmosphere of 5% $CO_2$, freshly made 2 uCi of FA-free bovine serum albumin-[1-$^{14}C$] palmitate complex is added to each flask. The flasks are then sealed with a stopper and incubated 6 h at 37° C. after which evolved $CO_2$ is liberated by injection of perchloric acid to final concentration of 5% and captured by incubating the flasks overnight in the presence of filter paper soaked with 5% KOH. The filters are then air-dried and incubated with scintillation cocktail overnight for equilibrium. Radioactivity is quantified by scintillation counting. Compound 6 was found to stimulate fatty acid oxidation 299% and 260% at 2 µM and 0.2 µM, respectively, while Compound 2 was found to stimulate fatty acid oxidation 320% and 170% at 1 µM and 0.1 µM, respectively, compared to untreated controls. These results confirm that both compounds inhibit ACC activity in vivo in cultured C2C12 cells.

Antiproliferation effects of ACC inhibitors. Effects of ACC inhibitors on cancer cell proliferation and cytotoxicity can be assayed using standard procedures. For example, after treatment with ACC inhibitors, cells are collected and cell number and viability can be determined using a trypan blue dye exclusion assay (Brusselmans et al., *Int J Cancer* 106:856-862 (2003)). Cell proliferation can also be quantified using the bromodeoxyuridine (BrdUrd) labeling and detection kit III (Roche Diagnostics) 72 hr after treatment of cells with ACC inhibitors.

The anti-proliferative activity of test compounds against human tumor cell lines is evaluated in vitro using the ATCC's MTT Cell Proliferation Assay (Catalog No. 30-100K). Cell lines are grown using media, serum, and culture conditions recommended by the ATCC. Stock cultures are allowed to grow to 70-80% confluence. Cells are seeded into 96-well culture plates at a predetermined density on day 0 in complete medium (0.1 mL). Plates are placed in a humidified incubator at 37° C. with 5% $CO_2$ and 95% HEPA filtered room air for 24 hours. At this point compound (0.1 mL of 2× stock (in media)) is added to the indicated wells and the plates are returned to the incubator for 72 hours. Cell proliferation is measured by addition of MTT reagent to each well and incubated for an additional 4 hours, followed by addition of cell lysis/MTT soluble reagent and incubating overnight. Absorbance (570 nm) of the plate wells is measured and quantitated relative to wells that did not contain compound. Results are expressed as percent of control cells versus compound concentration.

Compounds of the present invention, and salts thereof, were evaluated for anti-proliferative activity as described above. As shown in Table 3, below, these compounds demonstrate anti-proliferative activity (reduced absorbance at 570 nm) in human ovary cancer (A2780), human colon cancer (HCT-116), human breast cancer (MDA-MB-231), and human prostate cancer (PC3) cell lines.

TABLE 3

Anti-proliferation activity against human tumor cell lines.

| Compound | Concentration (uM) | Percent of Control | | | |
|---|---|---|---|---|---|
| | | A2780 | HCT-116 | MDA-MB-231 | PC-3 |
| 196 | 10.0 | 56.4 | 58.5 | 56.1 | 39.0 |
| | 3.3 | 81.6 | 63.6 | 73.7 | 50.7 |
| 139 | 10.0 | 60.1 | 49.9 | 46.4 | 54.7 |
| | 3.3 | 85.9 | 68.4 | 70.3 | 57.0 |
| 144 | 10.0 | 25.1 | 39.1 | 34.5 | 67.2 |
| | 3.3 | 65.0 | 64.9 | 88.9 | 76.5 |
| 150 | 10.0 | 57.6 | 59.4 | 50.2 | 47.7 |
| | 3.3 | 86.5 | 70.2 | 76.1 | 60.7 |
| 169 | 10.0 | 56.5 | 45.0 | 47.8 | 52.1 |
| | 3.3 | 80.5 | 57.2 | 81.4 | 54.7 |
| 186 | 10.0 | 52.1 | 41.8 | 39.2 | 33.2 |
| | 3.3 | 59.5 | 53.6 | 74.2 | 48.9 |
| 201 | 10.0 | 46.4 | 46.8 | 61.5 | 37.1 |
| | 3.3 | 83.2 | 59.8 | 82.5 | 52.7 |
| 188 | 10.0 | 51.4 | 68.2 | 28.7 | 19.0 |
| | 3.3 | 94.8 | 90.3 | 70.3 | 62.6 |
| 152 | 10.0 | 56.9 | 42.0 | 25.7 | — |
| | 3.3 | 84.1 | 53.3 | 57.0 | 88.0 |
| 187 | 10.0 | 64.9 | 56.1 | 45.6 | 52.2 |
| | 3.3 | 102.4 | 71.0 | 80.8 | 69.9 |
| 151 | 10.0 | 64.0 | 61.8 | 50.1 | 68.5 |
| | 3.3 | 92.7 | 78.6 | 82.9 | 86.1 |
| 180 | 10.0 | 21.2 | 29.8 | 9.3 | 56.8 |
| | 3.3 | 79.4 | 52.6 | 68.7 | 79.5 |
| 184 | 10.0 | 44.7 | 40.4 | 46.1 | 64.6 |
| | 3.3 | 90.0 | 65.5 | 75.8 | 81.3 |
| 172 | 10.0 | 65.5 | 41.6 | 29.5 | 55.7 |
| | 3.3 | 97.4 | 61.4 | 54.1 | 63.0 |
| 164 | 10.0 | 46.0 | 43.5 | 13.9 | — |
| | 3.3 | 73.1 | 54.0 | 47.6 | 68.0 |

Apoptosis in cancer cells. Detection of apoptosis in cancer cells resulting from ACC inhibition can be performed according to standard procedures that are well known to those skilled in the art. For example, cells are plated in 6-cm dishes and treated with ACC inhibitors. After 96 hr, Hoechst 33342

(Sigma) is added to the culture medium of living cells and fragmentation of the nucleus into oligonucleosomes and chromatin condensation is detected by fluorescence microscopy using a 365 nm filter. Apoptosis can also be determined with an Annexin V-FITC/Propidium Iodide Apoptosis detection kit (Clonetech Laboratories) according to the manufacturer's procedures. Cells are washed and subsequently incubated with Annexin V-FITC for 15 min at room temperature and counterstained with propidium iodide (final concentration 1 ug/ml). Apoptosis is then analyzed by fluorescence microscopy using a dual filter set for FITC and propidium iodide.

Inhibition of cancer cell growth in mice. The ability of ACC inhibitors to inhibit growth of NT5 cancer cell allografts in mice can be demonstrated using FVB/N mice. In such an experiment, animals receive packed cultured NT5 cells (0.1 mL) in the flank. When measurable tumors appear, animals are treated with ACC inhibitors or vehicle control (e.g. by intraperitoneal injection) every 6 days (or some other interval) and tumor volumes are measured over this time. (See, e.g., WO 2004/041189).

The ability of ACC inhibitors to inhibit cancer development can be demonstrated using the HER-2/neu breast cancer transgenic mouse model. In a typical study thirty HER-2/neu breast cancer transgenic mice are used. Fifteen (15) mice receive weekly doses of ACC inhibitor for three months beginning at 5 weeks of age. 15 mice receive vehicle only. Mice are then observed daily for appearance of breast tumors. (See, e.g., WO 2004/041189).

In vivo evaluation of ACC inhibition. Confirmation of the ability of compounds of this invention, and the salts of such compounds, to inhibit ACC in vivo can be accomplished by evaluating their ability to inhibit hepatic fatty acid synthesis and to stimulate whole body fatty acid oxidation using methods based on standard procedures. For example, since ACC catalyzes the first committed step in fatty acid biosynthesis, the in vivo activity of these compounds can be confirmed by measuring the ability of the compounds of this invention, and the salts of such compounds, to prevent the formation of newly synthesized, radiolabeled fatty acids from radiolabeled acetate in the livers of treated animals.

Direct assessment of radiolabeled malonyl-CoA production from radiolabeled acetate in tissues that synthesize (e.g. adipose tissue and liver) or do not synthesize (e.g. skeletal muscle) can also be used to determine ACC inhibition in those tissues. Because reduced malonyl-CoA levels as a consequence of ACC inhibition, relieve the malonyl-CoA mediated feedback inhibition of carnitine-palmitoyl transferase 1, the enzyme that catalyzes the rate limiting reaction in mitochondrial fatty acid oxidation, the in vivo activity of the compounds of this invention, and the salts thereof, can be confirmed by measuring their ability to increase the utilization of fatty acids as a source of energy, as assessed by a reduction in respiratory quotient in treated mammals.

In vivo measurement of fatty acid synthesis inhibition in mammals. Incorporation of $[2-^{14}C]$acetate into saponifiable lipids in the livers of mammals (e.g. Sprague Dawley rats, Charles River Laboratories, Boston, Mass. or Harlan Laboratories, Indianapolis, Ind.) can be measured as described previously (Harwood Jr. H. J. et al., *J Biol Chem*, 39: 37099-37111 (2003)). For example, animals given food and water ad libitum are treated orally at volume of 1.0 ml/200 g of body weight with either an aqueous solution containing 0.5% methyl cellulose (vehicle) or an aqueous solution containing 0.5% methyl cellulose containing test compound. One hour after compound administration, animals receive an intraperitoneal injection of $[2-^{14}C]$acetate (0.02 mL, 1 mCi/mL; 50 mCi/mmol. One hour after radiolabel administration, animals are sacrificed by $CO_2$ asphyxiation, and two liver pieces (about 0.75 g each) are removed and saponified at 70° C. for 120 min in 2.5 M NaOH (1.5 mL). After saponification, absolute EtOH (2.5 mL) is added to each sample and the solutions are mixed and allowed to stand overnight. Petroleum ether (4.8 mL) is then added to each sample, and after vigorous shaking (2 min) the mixtures are centrifuged at 1000×g (5 min). The petroleum ether layer containing the nonsaponifiable lipids is removed and discarded. The remaining aqueous layer is acidified (pH<2) by addition of 12 M HCl (0.6 mL) and extracted two times with petroleum ether (4.8 mL). The pooled organic fractions are transferred to liquid scintillation vials, dried under nitrogen, dissolved in Aquasol scintillation fluid (7 ml), and radioactivity is quantified by liquid scintillation counting. Inhibition of fatty acid synthesis by the test compound is expressed as a relative percent inhibition of measured incorporation of $[2-^{14}C]$acetate into saponifiable lipids during the interval between $[2-^{14}C]$acetate injection and $CO_2$ asphyxiation in animals receiving test compound, compared to control animals receiving only the vehicle.

Compounds of the present invention, and salts thereof, were evaluated for inhibition of fatty acid synthesis as described above. As shown in Table 4 these compounds demonstrate inhibition of in vivo fatty acid synthesis.

TABLE 4

In vivo inhibition of rat hepatic fatty acid synthesis ((—) not tested).

| Compound | Percent Inhibition at 10 mg/Kg | Percent Inhibition at 30 mg/Kg |
|---|---|---|
| 150 | 20 | 54 |
| 169 | 30 | 60 |
| 172 | 5 | — |
| 186 | 55 | 78 |
| 196 | 67 | — |
| 144 | — | 9 |

In vivo ACC inhibition can also be demonstrated by assessing malonyl-CoA production in tissues through its stoichiometric conversion to radiolabeled palmitate in the presence of purified fatty acid synthetase and radiolabeled acetyl-CoA. Malonyl-CoA concentrations can be determined in both tissues that synthesize fatty acids (e.g. liver and adipose tissue) and tissues that do not synthesize fatty acids (e.g. skeletal muscle) by previously reported methods (Harwood Jr. H. J. et al., *J Biol Chem* 39: 37099-37111 (2003); McGarry J. D. et al., *J Biol Chem* 253: 8291-8293 (1978)). Animals can be treated with vehicle with or without test compound as described above in the section entitled "In vivo measurement of fatty acid synthesis inhibition in mammals." Tissue samples are removed from animals that are anesthetized, immediately freeze-clamped, placed in a cryotube, and immersed in liquid nitrogen. Frozen tissues are pulverized under liquid nitrogen, and the resulting powdered tissues (1.0 g) are extracted with 10% (w/v) $HClO_4$ (4 mL), neutralized to pH 6.0 with 5 M KOH, and centrifuged to remove particulate residue. Briefly, malonyl-CoA concentrations are determined with a reaction mixture containing: 250 mM potassium phosphate buffer (pH 7.0), 2.5 mM dithiothreitol, 2.0 mM EDTA, 0.2 mM NADPH, 1 mg/ml fatty acid-free bovine serum albumin, 0.66 μM [$^3$H]acetyl-CoA (150000 dpm/nmol), 0.2 μM malonyl-CoA and the appropriate tissue extract. Reactions are initiated by the addition of purified fatty acid synthetase (25 milliunits). After a 45 minute incubation at 37° C., reactions are terminated by addition of 70% (w/v) $HClO_4$ (25 μL). Extraction of palmitate is accomplished by the addition of EtOH (1 mL) and petroleum ether (5 mL), followed by vigorous mixing and centrifugation. The separated petroleum ether phase is transferred to a second-glass tube containing water (2 mL), shaken, re-centrifuged, and 2.0 mL of the petroleum ether phase is transferred to a liquid scintillation vial, dried, and after the addition of liquid scintillation fluid, the radioactivity was quantified by liquid scintillation counting. Control reactions containing no malonyl-CoA or tissue extract are included with each series of reactions and are subtracted from all values. Tissue malonyl-CoA concentrations are typically expressed as (nmol of malonyl-CoA per gram of tissue).

Subchronic assessment of anti-diabetic efficacy in rats. The antidiabetic potential of compounds of this invention, and salts thereof, can be demonstrated by evaluating their anti-hyperinsulinemia potential and insulin sensitizing potential using methods based on standard procedures. For example, the anti-hyperinsulinemia potential and insulin sensitizing potential of these compounds can be demonstrated in Sprague Dawley rats (Charles River Laboratories, Boston, Mass. or Harlan Laboratories, Indianapolis, Ind.) that are fed either a standard rodent diet or a high carbohydrate diet (AIN76A) ad libitum for 3-4 weeks prior to and during test compound administration. Animals are treated for 1-4 weeks with test compound administered by oral gavage in water or methylcellulose (0.25-0.5%) in water using a single dose (S.D.), twice a day (B.I.D.), or three times a day (T.I.D) dosing regimen or via in feed administration using a powdered version of the diets described above. Control animals are treated with the appropriate vehicle.

In studies to evaluate the anti-hyperinsulinemia potential of compounds of this invention, and the salts of such compounds, blood is collected using either the tail-slice method or in sacrificed animals, the vena cava. The freshly collected samples are centrifuged (10000×g, 2 minutes) and the serum supernatant is stored at −80° C. until analysis. Serum insulin concentration is determined using standard kits, for example Equate® RIA INSULIN (Binax, South Portland, Me.). Serum insulin lowering activity of test compounds is determined by statistical analysis of the mean serum insulin concentration between the test compound group and the appropriate vehicle-treated group.

The insulin-sensitizing potential (glucose tolerance test) of compounds of this invention, and the salts of such compounds, is evaluated using standard methods. For example during the previously described study, fasted animals are administered (oral or intraperitoneal) a bolus of glucose (e.g., 1.0 g/Kg body weight), and blood is collected, processed and stored as described above at various time points after glucose administration. Serum insulin is determined using standard kits as described above. Serum glucose concentration is determined using standard procedures, for example using the Abbott VPT™ (Abbott Laboratories, Diagnostics Division, Irving, Tex.) and VP Super System® Autoanalyzer (Abbott Laboratories, Irving, Tex.). The insulin-sensitizing activity of the test compounds are determined by statistical analysis of the mean difference in peak insulin and glucose concentrations and the rate of insulin and glucose disappearance from the plasma after their respective peak levels between the test compound group and the vehicle-treated control group.

The lipid-lowering potential of compounds of this invention, and the salts of such compounds, is evaluated using standard methods. For example, at various times during the study described above section entitled *Subchronic assessment of anti-diabetic efficacy in rats*, blood is collected, processed and stored as described previously. Serum total triglycerides and total cholesterol levels are determined by standard methods, for example with an Abbott VP™ (Abbott Laboratories, Irving, Tex.) and VP Super System® Autoanalyzer (Abbott Laboratories, Irving, Tex.) and the A-Gent™ Triglycerides Test reagent system (Abbott Laboratories, Diagnostics Division, Irving, Tex.) and A-Gent™ Cholesterol Test reagent system, respectively. Serum free fatty acid concentrations are determined with a kit from Amano International Enzyme Co., Inc., as adapted for use with the Abbott VP™ (Abbott Laboratories, Irving, Tex.) and VP Super System® Autoanalyzer (Abbott Laboratories, Irving, Tex.). The serum triglyceride, cholesterol and free fatty acid lowering activity of the compounds of this invention, and the salts of such compounds, are determined by statistical analysis of the mean serum triglyceride, cholesterol, and free fatty acid concentrations between the cohorts of rats receiving test compound and the vehicle-treated control cohort of rats.

Subchronic assessment of anti-obesity efficacy in rats. The anti-obesity potential of compounds of this invention, and the salts of such compounds, can be demonstrated by evaluating their ability to produce a reduction in body weight, a reduction in percentage body fat, and a reduction in plasma leptin levels.

For example, as described previously for evaluating the anti-hyperinsulinemia potential and insulin sensitizing potential of these compounds, the body weight reduction, percentage body fat reduction, and plasma leptin reduction potential of compounds of this invention, and the salts of such compounds can be demonstrated in Sprague Dawley rats (Charles River Laboratories, Boston, Mass. or Harlan Laboratories, Indianapolis, Ind.) fed either a standard rodent diet or a high carbohydrate diet (AIN76A) ad libitum for 3-4 weeks prior to and during test compound administration. Animals are treated for 1-4 weeks with test compound administered by oral gavage in water or methylcellulose (0.25-0.5%) in water using a S.D., B.I.D., or T.I.D. dosing regimen or via in feed administration using a powdered version of the diets described above. Control animals are treated with the appropriate vehicle.

Whole body weight loss can be assessed simply by comparison of total body weight before and after treatment with test compound. Assessment of weight loss and changes in body composition between groups of animals receiving test compound and control groups of animals receiving vehicle only is determined by whole-body scanning using either a dual-energy x-ray absorptiometry (e.g. DEXA, QDR-1000/W Hologic Inc., Waltham, Mass.) or a QNMR system (e.g. Echo Magnetic Resonance Imaging, Echo Medical System, Houston Tex.). The activity of the test compounds in lowering whole body weight, percentage body fat, and the ratio of fat mass to lean body mass is determined by statistical analysis of the mean whole body weight, percentage body fat, and ratio of fat mass to lean body mass between the test compound group and the vehicle-treated control group.

Changes in plasma leptin levels closely parallel changes in percentage body fat and are therefore a useful marker for assessing anti-obesity potential. For assessment of changes in plasma leptin levels in response to treatment with test compounds, blood is collected at various times during the study described above and processed and stored as described previously. Serum leptin concentration is determined using a standard kit as described by the manufacturer. An example of such a kit is the rat leptin RIA kit (Cat # RL-83K, Millipore, St. Charles, Mo.) or a rat leptin ELISA kit (Cat # EZRL-83K, Millipore, St. Charles, Mo.). The serum leptin lowering ability of the test compounds is determined by statistical analysis of the mean serum leptin concentration between the cohorts of rats receiving test compound and the vehicle-treated control cohort of rats.

Determination of blood levels of ketone bodies after oral dosing of ACC inhibitors. Compounds of this invention, and salts thereof, can be evaluated for their potential as treatments for diseases caused by reduced neuronal metabolism by assessing their effects on plasma levels of beta-hydroxybutyrate. Inhibition of ACC leads to increased rates of fatty acid oxidation and therefore production of beta-hydroxybutyrate.

Rats (Sprague Rats (Sprague Dawley, Charles River Laboratories, Boston, Mass.) are acclimated for at least 4 days prior to dosing. For example, animals given food and water ad libitum are treated at volume of 1.0 mL/200 g of body weight with either an aqueous solution containing 0.5% methyl cellulose (vehicle) or an aqueous solution containing 0.5% methyl cellulose containing test compound. At various times after compound administration whole blood is collected from a jugular vein catheter into lithium heparin coated tubes, mixed gently, kept on ice and centrifuged (2500×g, 15 minutes at 4° C.) within 1 hour of collection. The isolated plasma is kept frozen at −20° C. until further processing. Plasma levels of beta-hydroxybutyrate are determined using a beta-hydroxybutyrate detection kit following the manufacturer's directions (StanBio Laboratory, Boerne, Tex.).

Compounds of the present invention, and salts thereof, were assessed for their ability to increase serum beta-hydroxybutyrate levels as described above. In Table 5, are representative data for two compounds demonstrating a temporal elevation in serum beta-hydroxybutyrate levels in rats, which is indicative of inhibition of ACC.

TABLE 5

In vivo elevation of rat serum beta-hydroxybutyrate levels.

| Time (min) | Average beta-Hydroxybutyrate Concentration (mM) | |
|---|---|---|
| | Compound 150 | Compound 169 |
| 15 | 0.160 | 0.149 |
| 30 | 0.214 | 0.201 |
| 60 | 0.147 | 0.135 |
| 120 | 0.140 | 0.126 |
| 240 | 0.102 | 0.118 |

Beta-hydroxybutyrate levels were determined in samples taken at the designated times after the compounds were administered (orally at 30 mg/Kg).

The foregoing is illustrative of the present invention, and is not to be construed as limiting thereof. The invention is defined by the following claims, with equivalents of the claims to be included therein.

All publications, patent applications, patents, patent publications, and other references cited herein are incorporated by reference in their entireties for the teachings relevant to the sentence and/or paragraph in which the reference is presented.

That which is claimed is:

1. A compound of formula I:

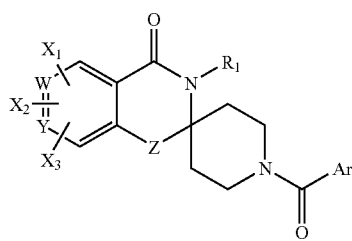

I wherein:
$R_1$ is hydrogen or alkyl, wherein the alkyl may be optionally substituted with halogen, hydroxyl, alkoxy, haloalkoxy, cyano, amino, alkylamino, dialkylamino, alkylthio, alkylsulfinyl, alkylsulfonyl, acyl, alkoxycarbonyl, aryl or heteroaryl,
where aryl or heteroaryl may be further optionally substituted with one to three $R_2$;
Ar is aryl or heteroaryl, each of which may be optionally substituted from one to three times by:
halogen, hydroxyl, alkyl, haloalkyl, alkoxy, alkenyloxy, alkynyloxy, haloalkoxy, cyano, amino, alkylamino, dialkylamino, alkylthio, alkylsulfinyl, alkylsulfonyl, acyl, alkoxycarbonyl, aryl or heteroaryl,
where aryl or heteroaryl may be further optionally substituted with one to three $R_2$;
W and Y each independently are N or CH;
Z is O;
each $R_2$ is independently halogen, hydroxyl, alkyl, haloalkyl, alkoxy, haloalkoxy, cyano, alkylthio, alkylsulfinyl, alkylsulfonyl, acyl or alkoxycarbonyl;
$X_1$, $X_2$, and $X_3$ are each independently hydrogen, halogen, hydroxyl, alkyl, haloalkyl, alkoxy, haloalkoxy, alkenyl, haloalkenyl, alkenyloxy, haloalkenyloxy, alkynyl, haloalkynyl, alkynyloxy, haloalkynyloxy, cyano, $R_5R_6N-$, alkylthio, alkylsulfinyl, alkylsulfonyl, aminosulfonyl, carbamoylamino, acyl, acylamino, carboxy, alkoxycarbonyl, arylalkoxycarbonyl, alkylaminocarbonyl, dialkylaminocarbonyl, carboxyalkoxy, alkoxycarbonylalkoxy, alkylaminocarbonyloxy, dialkylaminocarbonyl, aryl, heteroaryl, arylalkyl, or heteroarylalkyl,
where aryl, heteroaryl, arylalkyl, or heteroarylalkyl may be optionally substituted with one to three $R_4$;
or when W and Y are both CH, $X_1$ and $X_2$ taken together on adjacent carbon atoms form a 3- to 5-membered bridged ring consisting of elements from methylene, substituted methylene, —CH=, —C($R_4$)=, C=O, —N=, NH, O, or $S(O)_n$;
each $R_4$ is independently halogen, hydroxyl, alkyl, haloalkyl, alkoxy, haloalkoxy, alkenyl, alkynyl, cyano, amino, alkylamino, dialkylamino, alkylthio, alkylsulfinyl, alkylsulfonyl, aminosulfonyl, carbamoylamino, acyl, acylamino, carboxy, alkoxycarbonyl, arylalkoxycarbonyl, alkylaminocarbonyl, dialkylaminocarbonyl, alkylaminocarbonyloxy, or dialkylaminocarbonyloxy;
each $R_5$ and $R_6$ are independently hydrogen, alkyl, arylalkyl, alkoxyalkyl, hydroxyalkyl; or taken together to form a 5- or 6-member heterocycle containing 2-5 C-atoms, 0-1 O-atom, 0-1 S-atom, and 1-3 N-atoms, which heterocycle may be optionally substituted on a C-atom or N-atom by alkyl, acyl, alkoxycarbonyl, or alkylsulfonyl;
n is 0, 1, or 2;
or a pharmaceutically or agriculturally acceptable salt thereof;
subject to the proviso that
when $R_1$ is H, Z is O, W and Y are CH, $X_1$ is H, and Ar is phenyl, then $X_2$ and $X_3$ cannot be taken together at the 7,8-positions of the benzoxazinone to form a fused phenyl ring;
when $R_1$ is H, Z is O, W and Y are CH, $X_1$ and $X_2$ and $X_3$ are all H, then Ar cannot be 2-fluorophenyl, 4-aminocarbonyl-2-fluorophenyl, 4-amino-5-chloro-methoxyphenyl, 4-(3-thietanyloxy)phenyl, 3-pyridyl, 2-pyrazinyl, 2,3-dihydro-1-methylsulfonyl-1H-indol-5-yl, 2,3-dihydro-1-(2-methoxyethyl)-2-oxo-1H-benzimidazol-5-yl, 2,3-dihydro-1,3-dimethyl-2-oxo-1H-benzimidazol-5-yl, 3,4-dihydro-3-oxo-2H-1,4-benzoxazin-6-yl, 2,3-dihydro-2-(2-methylpropyl)-3-oxo-1H-isoindol-4-yl, or 4-(3,5-dimethylpyrazol-1-yl)phenyl; or
when $R_1$ is H, Z is O, W and Y are CH, and $X_1$ and $X_2$ and $X_3$ are all H, or $X_1$ is 6-bromo and $X_2$ and $X_3$ are H, then Ar cannot be 2-amino-1-benzothiophen-3-yl or 2-(3-ethylureido)-1-benzothiophen-3-yl.

2. The compound of claim 1, wherein, $R_1$ is selected from the group consisting of hydrogen and alkyl.

3. The compound of claim 1, wherein $R_1$ is selected from the group consisting of hydrogen, methyl, and ethyl.

4. The compound of claim 1, wherein Ar is aryl optionally substituted by halogen, hydroxyl, alkyl, haloalkyl, alkoxy, haloalkoxy, alkenyloxy, alkynyloxy, cyano, amino, alkylamino, dialkylamino, alkylthio, alkylsulfinyl, alkylsulfonyl, acyl, alkoxycarbonyl, aryl or heteroaryl,
where aryl or heteroaryl may be further optionally substituted with one to three $R_2$.

5. The compound of claim 1, wherein Ar is heteroaryl optionally substituted by halogen, hydroxyl, alkyl, haloalkyl, alkoxy, haloalkoxy, alkenyloxy, alkynyloxy, cyano, amino, alkylamino, dialkylamino, alkylthio, alkylsulfinyl, alkylsulfonyl, acyl, alkoxycarbonyl, aryl or heteroaryl,
where aryl or heteroaryl may be further optionally substituted with one to three $R_2$.

6. The compound of claim 1, wherein W and Y are CH.

7. The compound of claim 1, wherein W is N and Y is CH.

8. The compound of claim 1, wherein W is CH and Y is N.

9. The compound of claim 1, wherein Z is O.

10. The compound of claim 1, wherein Ar is 2-naphthyl optionally substituted by halogen, hydroxyl, alkyl, haloalkyl, alkoxy, haloalkoxy, alkenyloxy, alkynyloxy, cyano, amino, alkylamino, dialkylamino, alkylthio, alkylsulfinyl, alkylsulfonyl, acyl, alkoxycarbonyl, aryl or heteroaryl,
where aryl or heteroaryl may be further optionally substituted with one to three $R_2$.

11. The compound of claim 1, wherein Ar is 2-quinolinyl optionally substituted by halogen, hydroxyl, alkyl, haloalkyl, alkoxy, haloalkoxy, alkenyloxy, alkynyloxy, cyano, amino, alkylamino, dialkylamino, alkylthio, alkylsulfinyl, alkylsulfonyl, acyl, alkoxycarbonyl, aryl or heteroaryl,
where aryl or heteroaryl may be further optionally substituted with one to three $R_2$.

12. The compound of claim 1, wherein Ar is 2-, 5- or 6-indolyl optionally substituted by halogen, hydroxyl, alkyl, haloalkyl, alkoxy, haloalkoxy, alkenyloxy, alkynyloxy, cyano, amino, alkylamino, dialkylamino, alkylthio, alkylsulfinyl, alkylsulfonyl, acyl, alkoxycarbonyl, aryl or heteroaryl,
where aryl or heteroaryl may be further optionally substituted with one to three $R_2$.

13. The compound of claim 1, wherein Ar is 7-isoquinolinyl optionally substituted by halogen, hydroxyl, alkyl, haloalkyl, alkoxy, haloalkoxy, alkenyloxy, alkynyloxy, cyano, amino, alkylamino, dialkylamino, alkylthio, alkylsulfinyl, alkylsulfonyl, acyl, alkoxycarbonyl, aryl or heteroaryl,
where aryl or heteroaryl may be further optionally substituted with one to three $R_2$.

14. The compound of claim 1, wherein Ar is 5- or 6-(1H-1,2,3-benzotriazolyl) optionally substituted by halogen, hydroxyl, alkyl, haloalkyl, alkoxy, haloalkoxy, alkenyloxy, alkynyloxy, cyano, amino, alkylamino, dialkylamino, alkylthio, alkylsulfinyl, alkylsulfonyl, acyl, alkoxycarbonyl, aryl or heteroaryl,
where aryl or heteroaryl may be further optionally substituted with one to three $R_2$.

15. The compound of claim 1, wherein Ar is 5-, 6-, or 7-(1H-indazolyl) optionally substituted by halogen, hydroxyl, alkyl, haloalkyl, alkoxy, haloalkoxy, alkenyloxy, alkynyloxy, cyano, amino, alkylamino, dialkylamino, alkylthio, alkylsulfinyl, alkylsulfonyl, acyl, alkoxycarbonyl, aryl or heteroaryl,
where aryl or heteroaryl may be further optionally substituted with one to three $R_2$.

16. The compound of claim 1, wherein Ar is 5- or 6-(1H-benzimidazolyl) optionally substituted by halogen, hydroxyl, alkyl, haloalkyl, alkoxy, haloalkoxy, alkenyloxy, alkynyloxy, cyano, amino, alkylamino, dialkylamino, alkylthio, alkylsulfinyl, alkylsulfonyl, acyl, alkoxycarbonyl, aryl or heteroaryl,
where aryl or heteroaryl may be further optionally substituted with one to three $R_2$.

17. The compound of claim 1, wherein Ar is phenyl substituted by aryl optionally substituted with one to three $R_2$, or heteroaryl optionally substituted with one to three $R_2$.

18. The compound of claim 1, wherein Ar is phenyl substituted by heteroaryl optionally substituted with one to three $R_2$.

19. The compound of claim 1, wherein Ar is phenyl substituted by pyrazolyl, imidazolyl, oxadiazolyl, or pyrimidinyl, each optionally substituted with one to three $R_2$.

20. The compound of claim 1, wherein $X_i$ is halogen, alkyl, alkoxy, haloalkoxy, cyano, $R_5R_6N$—, aminosulfonyl, carbamoylamino, acyl, acylamino, carboxy, alkoxycarbonyl, heteroaryl or heteroarylalkyl,
where heteroaryl or heteroarylalkyl may be optionally substituted with one to three $R_4$.

21. The compound of claim 1, wherein $X_1$ and $X_2$ are independently halogen, alkyl, alkoxy, haloalkoxy, $R_5R_6N$—, or acetamido.

22. The compound of claim 1, wherein $X_1$ and $X_2$ taken together on adjacent carbon atoms form a 4-membered bridge comprising —CH=.

23. The compound of claim 1 selected from the group consisting of:

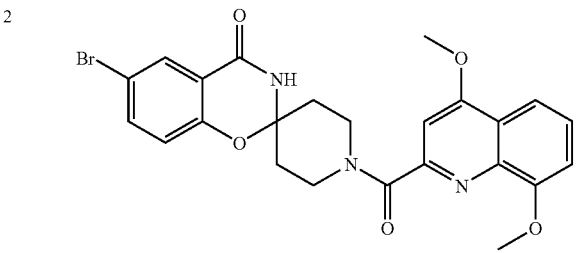

6-Bromo-1'-[4,8-dimethoxyquinolin-2-yl)carbonyl]spiro[2H-1,3-benzoxazin-2,4'-piperidin]-4-(3H)-one;

| # | Structure | Name |
|---|---|---|
| 9 | | 6-Acetamido-1'-[4,8-dimethoxyquinolin-2-yl)carbonyl]spiro[2H-1,3-benzoxazin-2,4'-piperidin]-4-(3H)-one; |
| 137 | | 1'[4,8-Dimethoxyquinolin-2-yl)carbonyl]-6-methylspiro[2H-1,3-benzoxazin-2,4'-piperidin]-4-(3H)-one; |
| 139 | | 1'-[4,8-Dimethoxyquinolin-2-yl)carbonyl]-6-ethoxyspiro[2H-1,3-benzoxazin-2,4'-piperidin]-4-(3H)-one; |
| 144 | | 6-Ethoxy-1'-[7-methoxy-3-methyl-1H-indol-2-yl)carbonyl]spiro[2H-1,3-benzoxazin-2,4'-piperidin]-4-(3H)-one; |
| 150 | | 1'-[4,8-Dimethoxyquinolin-2-yl)carbonyl]-6-methoxyspiro[2H-1,3-benzoxazin-2,4'-piperidin]-4-(3H)-one; |
| 152 | | 1'-[(4,8-Dimethoxynaphth-2-yl)carbonyl]-6-methoxyspiro[2H-1,3-benzoxazin-2,4'-piperidin]-4-(3H)-one; |

| | | |
|---|---|---|
| 153 | 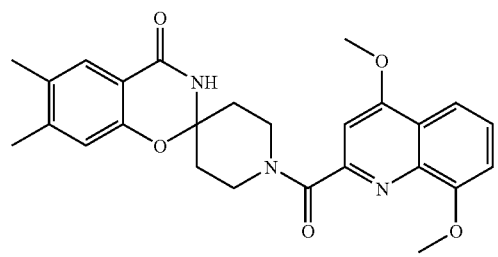 | 1'-[4,8-Dimethoxyquinolin-2-yl)carbonyl]-6,7-dimethylspiro[2H-1,3-benzoxazin-2,4'-piperidin]-4-(3H)-one; |
| 159 | 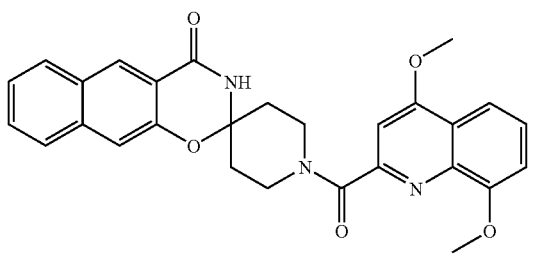 | 1'-[4,8-Dimethoxyquinolin-2-yl)carbonyl]spiro[2H-naphtho[2,3-e]-1,3-oxazin-2,4'-piperidin]-4-(3H)-one; |
| 164 | 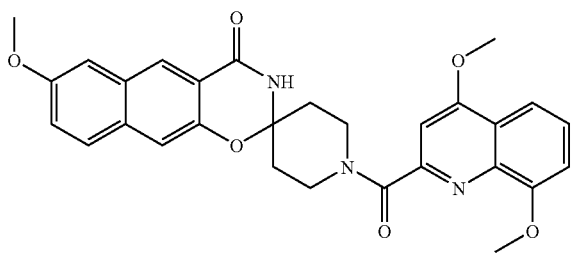 | 1'-[4,8-Dimethoxyquinolin-2-yl)carbonyl]-7-methoxyspiro[2H-naphtho[2,3-e]-1,3-oxazin-2,4'-piperidin]-4-(3H)-one; |
| 169 | 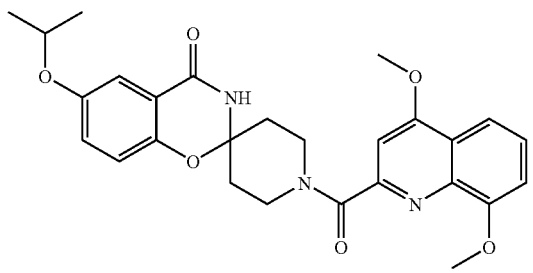 | 1'-[4,8-Dimethoxyquinolin-2-yl)carbonyl]-6-isopropoxyspiro[1,3-benzoxazin-2,4'-piperidin]-4-(3H)-one; |
| 172 | 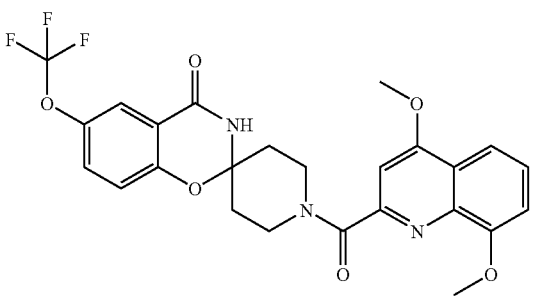 | 1'-[4,8-Dimethoxyquinolin-2-yl)carbonyl]-6-trifluoromethoxyspiro[1,3-benzoxazin-2,4'-piperidin]-4-(3H)-one; |
| 180 | 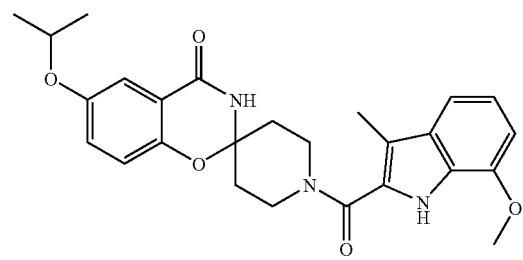 | 6-Isopropoxy-1'-[7-methoxy-3-methyl-1H-indol-2-yl)carbonyl]spiro[1,3-benzoxazin-2,4'-piperidin]-4-(3H)-one; |

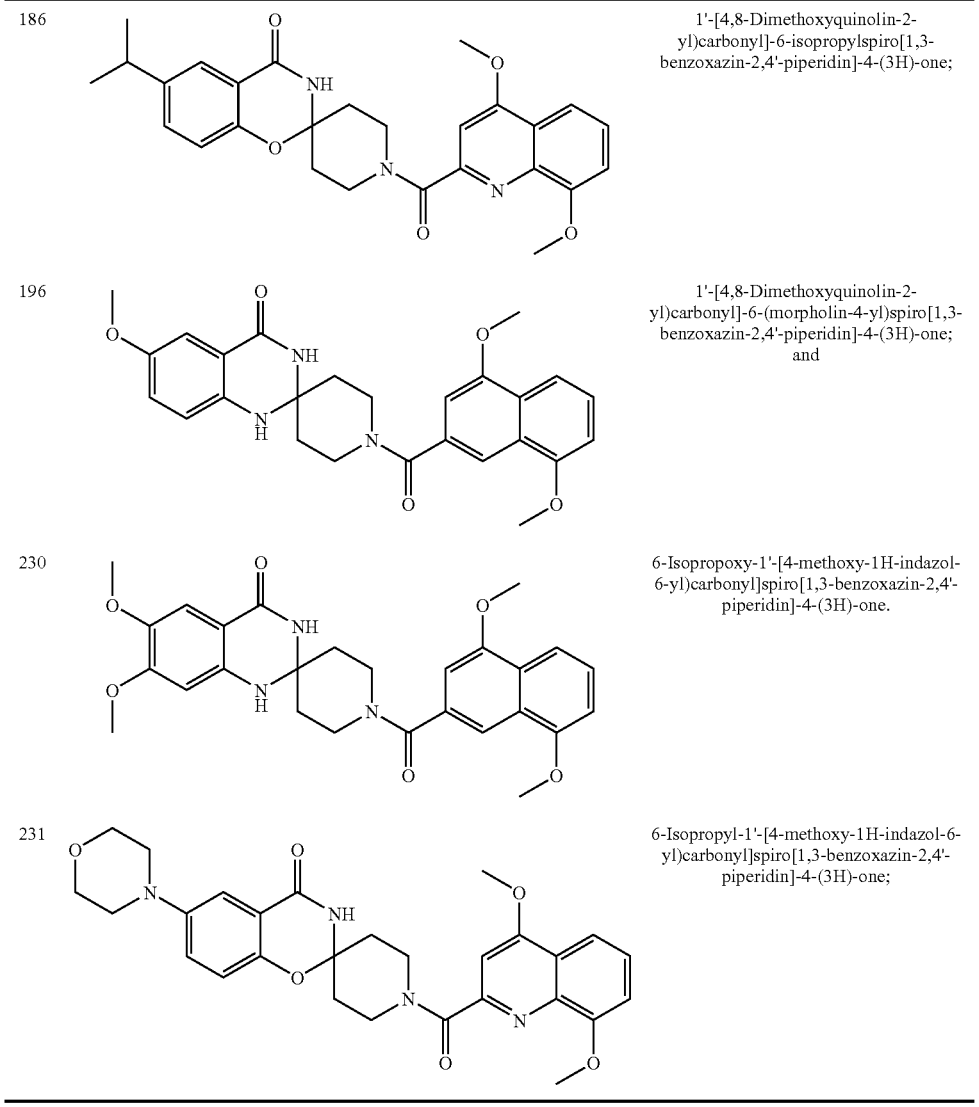

| 186 | 1'-[4,8-Dimethoxyquinolin-2-yl)carbonyl]-6-isopropylspiro[1,3-benzoxazin-2,4'-piperidin]-4-(3H)-one; |
| 196 | 1'-[4,8-Dimethoxyquinolin-2-yl)carbonyl]-6-(morpholin-4-yl)spiro[1,3-benzoxazin-2,4'-piperidin]-4-(3H)-one; and |
| 230 | 6-Isopropoxy-1'-[4-methoxy-1H-indazol-6-yl)carbonyl]spiro[1,3-benzoxazin-2,4'-piperidin]-4-(3H)-one. |
| 231 | 6-Isopropyl-1'-[4-methoxy-1H-indazol-6-yl)carbonyl]spiro[1,3-benzoxazin-2,4'-piperidin]-4-(3H)-one; |

24. The compound of claim 1, wherein the compound is 1'-[4,8-dimethoxyquinolin-2-yl) carbonyl]-6-methoxyspiro[2H-1,3-benzoxazin-2,4'-piperidin]-4-(3H)-one (compound 150).

25. The compound of claim 1, wherein the compound is 1'-[(4,8-dimethoxynaphth-2-yl)carbonyl]-6 -methoxyspiro[2H-1,3 -benzoxazin-2,4'-piperidin]-4-(3H)-one (compound 152).

26. The compound of claim 1, wherein the compound is 1'-[4,8-dimethoxyquinolin-2yl)carbonyl]-6-isopropoxyspiro[1,3 -benzoxazin-2,4'-piperidin]-4-(3H)-one (compound 169).

27. The compound of claim 1, wherein the compound is 6-isopropoxy-1'-[7-methoxy-3-methyl-1H-indol-2-yl)carbonyl]spiro[1,3-benzoxazin-2,4'-piperidin]-4-(3H)-one (compound 180).

28. The compound of claim 1, wherein the compound is 1'-[4,8-dimethoxyquinolin-2-yl)carbonyl]-6-isopropylspiro[1,3-benzoxazin-2,4'-piperidin]-4-(3H)-one (compound 186).

29. The compound of claim 1, wherein the compound is 1'-[4,8-dimethoxyquinolin-2-yl)carbonyl]-6-(morpholin-4-yl)spiro[1,3-benzoxazin-2,4'-piperidin]-4-(3H)-one (compound 196).

30. A composition which comprises in combination a compound of claim 1, or a pharmaceutically or agriculturally acceptable salt of said compound and a pharmaceutically or agriculturally acceptable carrier, vehicle or diluent.

31. A pharmaceutical combination composition comprising in combination: a therapeutically effective amount of a composition comprising a first compound, said first compound is a compound of claim 1, or a pharmaceutically acceptable salt of said compound; a second compound, said second compound being an anti-atherosclerosis agent, an anti-diabetic agent, an anti-obesity agent or a cardiovascular agent and/or optionally a pharmaceutically acceptable vehicle, diluent or carrier.

32. A method for treating obesity, an overweight condition, hypertriglyceridemia, hyperlipidemia, hypoalphalipoproteinemia, diabetes mellitus, hyperinsulinemia, impaired glucose tolerance, insulin resistance, diabetic complications, atherosclerosis, hypertension, coronary heart disease, hypercholesterolemia, diseases associated with reduced neuronal metabolism, polycystic ovary disease, breast cancer, uterine cancer, ovarian cancer, colon cancer, prostate cancer, liver cancer, endometrial cancer, loss of cognitive function caused by Mild Cognitive Impairment, cerebrovascular disease or congestive heart failure, or any combination thereof, in a subject by administering to said subject in need of such treatment a therapeutically effective amount of a compound of claim 1, or a pharmaceutically acceptable salt of said compound.

33. The method according to claim 32, wherein said subject is afflicted with atherosclerosis.

34. The method according to claim 32, wherein said subject is afflicted with diabetes mellitus.

35. The method according to claim 32, wherein said subject is afflicted with obesity.

36. The method according to claim 32, wherein said subject is afflicted with loss of cognitive function caused by reduced neuronal metabolism.

37. A method of treating a fungal infection in a subject in need thereof, comprising:
administering a compound of claim 1 or a pharmaceutically acceptable salt thereof to said subject in an amount effective to treat said fungal infection.

38. A method of controlling infestation of cultivated plants by plant pathogenic fungi, comprising:
applying a compound according to claim 1 to said plants, parts thereof or the locus thereof in an amount effective to control said plant pathogenic fungi.

* * * * *

UNITED STATES PATENT AND TRADEMARK OFFICE
CERTIFICATE OF CORRECTION

PATENT NO.        : 8,110,570 B2
APPLICATION NO.   : 12/501717
DATED             : February 7, 2012
INVENTOR(S)       : Anderson et al.

It is certified that error appears in the above-identified patent and that said Letters Patent is hereby corrected as shown below:

In the Patent:
Column 66, Compound 141, Name: Please correct "(1-methyl-1H-pyrazol-3-"
to read -- (1-methyl-1H-pyranzol-5- --

Column 100, Compound 238, Name:
Please correct "Methyl 2-{-1-14, 8-dimethoxyquinolin-2-"
to read -- Methyl 2-{-1-[4, 8-dimethoxyquinolin-2- --

Column 116, Example 11, Line 29: Please correct "MS nl/z:" to read -- MS m/z: --

Column 120, Example 47, Line 23: Please correct "[2H-1,3'-benzoxazin-2,"
to read -- [2H-1,3-benzoxazin-2, --

Column 123, Example 79, Line 26: Please correct "MS m/z: δ 477.0"
to read -- MS m/z: 477.0 --
Example 80, Line 28: Please correct "[2H-1,3'-benzoxazin-2"
to read -- [2H-1,3-benzoxazin-2 --
Example 81, Line 40: Please correct" MS m/z: δ 493.0"
to read -- MS m/z: 493.0 --

Column 124, Example 89, Line 3: Please correct "(M+H)" to read -- (M+H)$^+$ --
Example 90, Line 10: Please correct "δ 491.0" to read -- 491.0 --

Column 125, Example 102, Line 21: Please correct "(M+Na)." to read -- (M+Na)$^+$. --

Column 129, Example 138, Line 42:
Please correct "spiro[21'-1,3-benzoxazin-2,"
to read -- spiro[2H-1, 3-benzoxazin-2, --

Signed and Sealed this
Fifteenth Day of May, 2012

David J. Kappos
*Director of the United States Patent and Trademark Office*

CERTIFICATE OF CORRECTION (continued)
U.S. Pat. No. 8,110,570 B2

Column 130, Example 139, Line 55: Please correct "lithium salt. 6 MS"
to read -- lithium salt. δ MS --

Column 142, Line 6: Please correct "(Catalog No. 30-100K)"
to read -- (Catalog No. 30-1010K) --

Column 145, Line 48: Please correct "Abbott VPT™" to read -- Abbott VP™ --

In the Claims:
Column 150, Claim 20, Line 39: Please correct "wherein X<sub>i</sub> is halogen"
to read -- wherein $X_1$ is halogen --

Column 155, Claim 23, Compound 196: Please correct

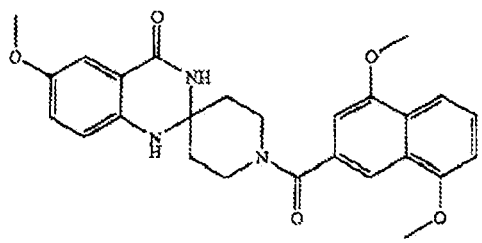

to read

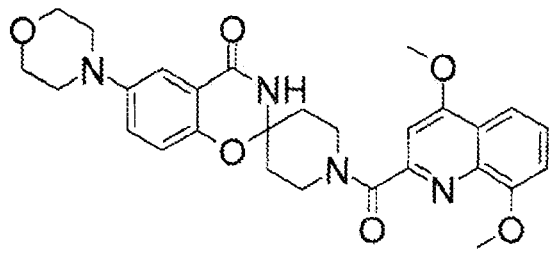

Column 155, Claim 23, Compound 230: Please correct

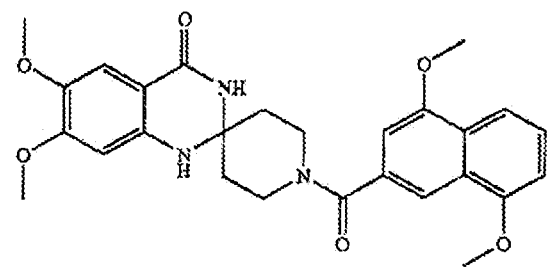

to read

CERTIFICATE OF CORRECTION (continued)
U.S. Pat. No. 8,110,570 B2

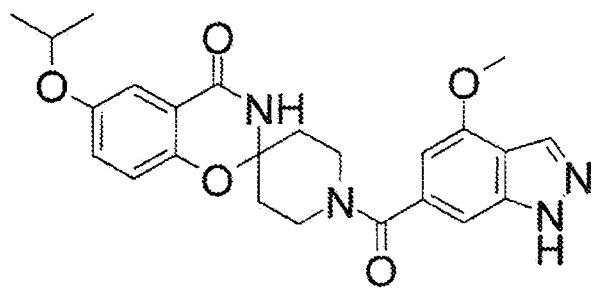

Column 155, Claim 23, Compound 231: Please correct

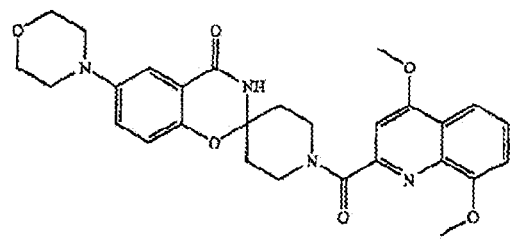

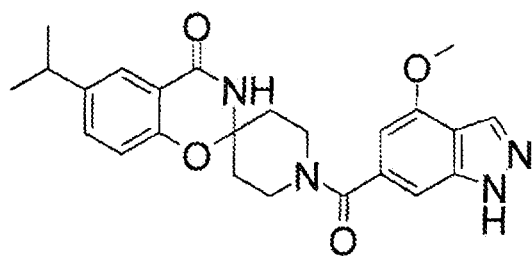

to read